(12) United States Patent
Wright et al.

(10) Patent No.: US 7,094,953 B2
(45) Date of Patent: Aug. 22, 2006

(54) PLANT RETROELEMENTS AND METHODS RELATED THERETO

(75) Inventors: David A. Wright, Boone, IA (US); Daniel F. Voytas, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 27 days.

(21) Appl. No.: 10/395,607

(22) Filed: Mar. 24, 2003

(65) Prior Publication Data

US 2004/0019928 A1   Jan. 29, 2004

Related U.S. Application Data

(63) Continuation-in-part of application No. 09/586,106, filed on Jun. 2, 2000, now Pat. No. 6,720,479, which is a continuation-in-part of application No. 09/322,478, filed on May 28, 1999, now Pat. No. 6,331,662.

(60) Provisional application No. 60/087,125, filed on May 29, 1998.

(51) Int. Cl.
*A01H 5/00* (2006.01)

(52) U.S. Cl. .................. 800/298; 435/325; 435/410; 435/419; 435/252.3; 435/320.1; 536/23.1; 536/23.72; 536/24.1; 536/23.2; 536/23.6; 800/295

(58) Field of Classification Search ................ 435/325, 435/410, 419, 252.3, 320.1; 536/23.1, 23.72, 536/24.1, 23.2, 23.6; 800/295, 298
See application file for complete search history.

(56) References Cited

U.S. PATENT DOCUMENTS

| | | | |
|---|---|---|---|
| 4,683,195 A | 7/1987 | Mullis et al. | |
| 4,873,191 A | 10/1989 | Wagner et al. | |
| 5,070,020 A | 12/1991 | Ingolia et al. | |
| 5,204,253 A | 4/1993 | Sanford et al. | |
| 5,252,726 A | 10/1993 | Wöldike | |
| 5,792,932 A | 8/1998 | Marco et al. | |
| 5,866,793 A | 2/1999 | Baga et al. | |
| 6,005,092 A | 12/1999 | Shoseyov et al. | |
| 6,013,863 A | 1/2000 | Lundquist et al. | |
| 6,054,635 A | 4/2000 | Bestwick et al. | |
| 6,184,443 B1 | 2/2001 | Pedersen et al. | |
| 6,559,359 B1 | 5/2003 | Laten | |

OTHER PUBLICATIONS

GenBank Accession No. B62585.
GenBank Accession No. D50643.
GenBank Accession No. J02798.
GenBank Accession No. J05212.
GenBank Accession No. K00821.
GenBank Accession No. L05934.
GenBank Accession No. M28156.
GenBank Accession No. M63985.
GenBank Accession No. S44893.
GenBank Accession No. U09119.
GenBank Accession No. U39944.
GenBank Accession No. U68402.
GenBank Accession No. U76670.
GenBank Accession No. U93215.
GenBank Accession No. X15121.
GenBank Accession No. Z17657.
GenBank Accession No. AB005247.
GenBank Accession No. AB005248.
GenBank Accession No. AF096096.
GenBank Accession No. AF129516.
GenBank Accession No. AF233296.
GenBank Accession No. AJ000640.
GenBank Accession No. AL161566.

Abler et al., "Isolation and characterization of a genomic sequence encoding the maize *Cat3* catalase gene," *Plant Mol. Biol.*, 1993, 22:1031-1038.

Altschul et al., "Basic Local Alignment Search Tool," *J. Mol. Biol.*, 1990, 215:403-410.

Ausubel et al., *Current Protocols in Molecular Biology*, 1993, Greene Publishing Associates (TOC only).

Bennetzen, "The contributions of retroelements to plant genome organization, function and evolution," *Trends Microbiol.*, 1996, 4:347-353.

Bezerra et al., "A corm-specific gene encodes tarin, a major globulin of taro (*Colocasia esculenta* L. Schott)," *Plant Mol. Biol.*, 1995, 28:137-144.

Bhattacharyya et al., "A *copia*-like retrotransposon Tgm*r* closely linked to the *Rps l-k* allele that confers race-specific resistance of soybean to *Phytophthora sojae*," *Plant Mol. Biol.*, 1997, 34:255-264.

Blume and Grierson, "Expression of ACC oxidase promoter-GUS fusions in tomato and *Nicotiana plumbaginifolia* regulated by developmental and environmental stimuli," *Plant J.*, 1997, 12:731-746.

Boeke and Sandmeyer, "Yeast Transposable Elements," *The Molecular and Cellular Biology of the Yeast Saccharomyces*, 1991, Broach et al. (eds.), Cold Spring Harbor Laboratory Press, Cold Spring Harbor, NY, pp. 193-261.

Boeke et al., "Metaviridae," *Virus Taxonomy: ICTV VIIth Report*, 1998, van Regenmortel et al. (eds.), Academic Press, pp. 359-367.

(Continued)

*Primary Examiner*—David Guzo
(74) *Attorney, Agent, or Firm*—Fish & Richardson P.C.

(57) ABSTRACT

The present invention provides nucleic acids, as well as vectors, cells, and plants (including plant parts, seeds, and embryos) containing the nucleic acids. In particular, molecular tools are provided in the form of nucleic acids that encode reverse transcriptases. The invention also features methods for manipulating such nucleic acids. In addition, the invention features methods to introduce nucleic acids containing retroelements or retroelement sequences into cells.

7 Claims, 12 Drawing Sheets

OTHER PUBLICATIONS

Boeke et al., "Psuedoviridae," *Virus Taxonomy: ICTV VIIth Report*, 1998, van Regenmortel et al. (eds.), Academic Press, pp. 349-357.

Bossinger and Smyth, "Initiation patterns of flower and floral organ development in *Arabidopsis thaliana*," *Development*, 1996, 122:1093-1102.

Boyko et al., "A high-density cytogenetic map of the *Aegilops tauschii* genome incorporating retrotransposons and defense-related genes: insights into cereal chromosome structure and function," *Plant Mol. Biol.*, 2002, 48:767-790.

Braiterman and Boeke, "Ty1 In Vitro Integration: Effects of Mutations in *cis* and in *trans*," *Mol. Cell. Biol.*, 1994, 14:5731-5740.

Brunak et al., "Prediction of Human mRNA Donor and Acceptor Sites from the DNA Sequence," *J. Mol. Biol.*, 1991, 220:49-65.

Bureau et al., "Transduction of a Cellular Gene by a Plant Retroelement," *Cell*, 1994, 77:479-480.

Busk et al., "Regulatory elements in vivo in the promoter of the abscisic acid responsive gene *rab17* from maize," *Plant J.*, 1997, 11:1285-1295.

Bustos et al., "Regulation of β-Glucuronidase Expression in Transgenic Tobacco Plants by an A/T-Rich, *cis*-Acting Sequence Found Upstream of a French Bean β-Phaseolin Gene," *Plant Cell*, 1989, 1:839-853.

Casal et al., "Different Phototransduction Kinetics of Phytochrome A and Phytochrome B in *Arabidopsis thaliana*," *Plant Physiol.*, 1998, 116:1533-1538.

Chapman et al., "Initiator methionine tRNA is essential for *Ty1* transposition in yeast," *Proc. Natl. Acad. Sci. USA*, 1992, 89:3236-3240.

Chavanne et al., "Structure and evolution of *Cyclops*: a novel giant retrotransposon of the *Ty3/Gypsy* family highly amplified in pea and other legume species," *Plant Mol. Biol.*, 1998, 37:363-375.

Chen et al., "Construction of a Soybean Genomic & Root cDNA Library from *Phytophthora* Resistane Line L85-3044," *Soybean Genetics Newsletter*, 1998, 25:132-135.

Choi et al., "Tissue-specific and developmental regulation of a gene encoding a low molecular weight sulfur-rich protein in soybean seeds," *Mol. Gen. Genet.*, 1995, 246:266-268.

Choi et al., "DEMETER, a DNA Glycosylase Domain Protein, Is Required for Endosperm Gene Imprinting and Seed Viability in *Arabidopsis*," *Cell*, 2002, 110:33-42.

Christou et al., "Stable transformation of soybean by electroporation and root formation from transformed callus," *Proc. Natl. Acad. Sci USA*, 1987, 84:3962-3966.

Church and Gilbert, "Genomic sequencing," *Proc. Natl. Acad. Sci. USA*, 1984, 81:1991-1995.

Concelcão and Krebbers, "A cotyledon regulatory region is responsible for the different spatial expression patterns of *Arabidopsis* 2S albumin genes," *Plant J.*, 1994, 5:493-505.

Daboussi, "Fungal transposable elements and genome evolution," *Genetica*, 1997, 100:253-260.

Dasgupta et al., "Cloning and sequencing of 5' flanking sequence from the gene encoding 2S storage protein, from two *Brassica* species," *Gene*, 1993, 133:301-302.

de Castro et al., "Spatial and Temporal Gene Expression Patterns Occur during Corm Development," *Plant Cell*, 1992, 4:1549-1559.

Devereux et al., "A comprehensive set of sequence analysis programs for the VAX," *Nucl. Acids. Res.*, 1984, 12:387-395.

Di Laurenzio et al., "The SCARECROW Gene Regulates an Asymmetric Cell Division That Is Essential for Generating the Radial Organization of the *Arabidopsis* Root," *Cell*, 1996, 86:423-433.

Dixon and Gonzales (eds.), *Plant Cell Culture: A Practical Approach*, 2nd edition, 1994, Oxford University Press (TOC only).

Doolittle et al., "Origins and Evolutionary Relationships of Retroviruses," *Quart. Rev. Biol.*, 1989, 64:1-30.

Ellis et al., "Polymorphism of insertion sites of *Ty1-copia* class retrotransposons and its use for linkage and diversity analysis in pea," *Mol. Gen. Genet.*, 1998, 260:9-19.

Enjuto et al., "Expression of the *Arabidopsis HMG2* Gene, Encoding 3-hydroxy-3-Methylglutaryl Coenzyme A Reductase, Is Restricted to Meristematic and Floral Tissues," *Plant Cell*, 1995, 7:517-527.

Ficker et al., "A promoter directing high level expression in pistils of transgenic plants," *Plant Mol. Biol.*, 1997, 35:425-431.

Ficker et al., "Multiple elements of the *StRnase* promoter from potato (*Solanum tuberosum* L.) are required for cell type-specific expression in transgenic potato and tobacco," *Mol. Gen. Genet.*, 1998, 257:132-142.

Flavell et al., "Retrotransposon-based insertion polymorphisms (RBIP) for high throughput marker analysis," *Plant J.*, 1998, 16:643-650.

Grandbastien, "Retroelements in higher plants," *TIG*, 1992, 8:103-108.

Grandbastien et al., "Tnt1, a mobile retroviral-like transposable element of tobacco isolated by plant cell genetics," *Nature*, 1989, 337:376-380.

Granger et al., "Isoloation of an *Arabidopsis* homologue of the maize homeobox *Knotted-1* gene," *Plant Mol. Biol.*, 1996, 31:373-378.

Green et al., "Binding site requirements for pea nuclear protein factor GT-1 correlate with sequences required for light-dependent transcriptional activation of the *rbcS-3A* gene," *EMBO J.*, 1988, 7:4035-4044.

Guerrero et al., "Promoter sequences from a maize pollen-specific gene direct tissue-specific transcription in tobacco," *Mol. Gen. Genet.*, 1990, 224:161-168.

Gustafson-Brown et al., "Regulation of the *Arabidopsis* Floral Homeotic Gene *APETALA1*," *Cell*, 1994, 76:131-143.

Hake et al., "Homeobox genes in the functioning of plant meristems," *Phil. Trans. R. Soc. Lond. B.*, 1995, 350:45-51.

Hansen et al., "Wound-inducible and organ-specific expression of ORF13 from *Agrobacterium rhizogenes* 8196 T-DNA in transgenic tobacco plants," *Mol. Gen. Genet.*, 1997, 254:337-343.

Hebsgaard et al., "Splice site prediction in *Arabidopsis thaliana* pre-mRNA by combining local and global sequence information," *Nucl. Acids. Res.*, 1996, 24:3439-3452.

Hirochika et al., "Retrotransposons of rice involved in mutations induced by tissue culture," *Proc. Natl. Acad. Sci. USA*, 1996, 93:7783-7788.

Hofmann and Stoffel, "A Database of Membrane Spanning Protein Segments," *Biol. Chem.*, 1993, 374:166, Abstract No. MF C-35.

Hu et al., "*Zeon-1*, a member of a new maize retrotransposon family," *Mol. Gen. Genet.*, 1995, 248:471-480.

Jin and Bennetzen, "Integration and Nonrandom Mutation of a Plasma Membrane Proton ATPase Gene Fragment within the *Bs1* Retroelement of Maize," *Plant Cell*, 1994, 6:1177-1186.

Jofuku et al., "Control of *Arabidopsis* Flower and Seed Development by the Homeotic Gene *APETALA2*," *Plant Cell*, 1994, 6:1211-1225.

Jordano et al., "A Sunflower Helianthinin Gene Upstream Sequence Ensemble Contains an Enhancer and Sites of Nuclear Protein Interaction," *Plant Cell*, 1989, 1:855-866.

Josefsson et al., "Structure of a Gene Encoding the 1.7 S Storage Protein, Napin, from *Brassica napus*," *JBL*, 1987, 262:12196-12201.

Kerstetter et al., "Sequence Analysis and Expression Patterns Divide the Maize *knotted1*-like Homeobox Genes into Two Classes," *Plant Cell*, 1994, 6:1877-1887.

Kim et al., "Nuclear protein factors binding to a class I patatin promoter region are tuber-specific and sucrose-inducible," *Plant Mol. Biol.*, 1994, 26:603-615.

Kim et al., "Retroviruses in invertebrates: The *gypsy* retrotransposon is apparently an infectious retrovirus of *Drosophila melanogaster*," *Proc. Natl. Acad. Sci. USA*, 1994, 91:1285-1289.

Koltunow et al., "Different Temporal and Spatial Gene Expression Patterns Occur during Anther Development," *Plant Cell*, 1990, 2:1201-1224.

Konieczny et al., "A Superfamily of *Arabidopsis thaliana* Retrotransposons," *Genetics*, 1991, 127:801-809.

Kulikauskas and McCormick, "Identification of the tobacco and *Arabidopsis* homologues of the pollen-expressed LAT59 gene of tomato," *Plant Mol. Biol.*, 1997, 34:809-814.

Kumagai et al., "Cytoplasmic inhibition of carotenoid biosynthesis with virus-derived RNA," *Proc. Natl. Acad. Sci. USA*, 1995, 92:1679-1683.

Kumar and Bennetzen, "Plant Retrotransposons," *Ann. Rev. Gen.*, 1999, 33:479-532.

Lee and Huang, "Genes encoding oleosins in maize kernel of inbreds Mo17 and B73," *Plant Mol. Biol.*, 1994, 26:1981-1987.

Li et al., "A novel *myb*-related gene from *Arabidopsis thaliana*," *FEBS Lett.*, 1996, 379:117-121.

Lincoln et al., "*A knotted1*-like Homeobox Gene in *Arabidopsis* Is Expressed in the Vegetative Meristem and Dramatically Alters Leaf Morphology When Overexpressed in Transgenic Plants," *Plant Cell*, 1994, 6:1859-1876.

Lo, "Transformation by Iontophoretic Microinjection of DNA: Multiple Integrations Without Tandem Insertions," *Mol. Cell. Biol.*, 1983, 3:1803-1814.

Long et al., "A member of the KNOTTED class of homeodomain proteins encoded by the *STM* gene of *Arabidopsis*," *Nature*, 1996, 379:66-69.

Lotan et al., "*Arabidosis* LEAFY COTYLEDON1 Is Sufficient to Induce Embryo Development in Vegetative Cells," *Cell*, 1998, 93:1195-1205.

Lowe and Eddy, "tRNAscan-SE: a program for improved detection of transfer RNA genes in genomic sequence," *Nucl. Acids. Res.*, 1997, 25:955-964.

Maestre et al., "mRNA retroposition in human cells: processed pseudogene formation," *EMBO J.*, 1995, 14:6333-6338.

Malik et al., "Poised for Contagion: Evolutionary Origins of the Infectious Abilities of Invertebrate Retroviruses," *Genome Res.*, 2000, 10:1307-1318.

Mandel et al., "Molecular characterization of the *Arabidopsis* floral homeotic gene *APETALA1*," *Nature*, 1992, 360:273-277.

Marquet et al., "tRNAs as primer of reverse transcriptases," *Biochimie*, 1995, 77:113-124.

Martin et al., "Identification of mutants in metabolically regulated gene expression," *Plant J.*, 1997, 11:53-62.

Matsuoka et al., "The promoters of two carboxylases in a $C_4$ plant (maize) direct cell-specific, light-regulated expression in a $C_3$ plant (rice)," *Plant J.*, 1994, 6:311-319.

Meier et al., "Elicitor-Inducible and Constitutive in Vivo DNA Footprints Indicate Novel *cis*-Acting Elements in the Promoter of a Parsley Gene Encoding Pathogenesis-Related Protein 1,"*Plant Cell*, 1991, 3:309-315.

Meier et al., "The tomato RBCS3A promoter requires integration into the chromatin for correct organ-specific regulation," *FEBS Lett.*, 1997, 415:91-95.

Meinkoth et al., "Hybridization of Nucleic Acids Immobilized on Solid Supports," *Anal. Biochem.*, 1984, 138:267-284.

Nakai and Horton, "PSORT: a program for detecting sorting signals in proteins and predicting their subcellular localization," *TIBS*, 1999, 24:34-35.

Paul et al., "The isolation and characterisation of the tapetum-specific *Arabidopsis thaliana* A9 gene," *Plant Mol. Biol.*, 1992, 19:611-622.

Pearce et al., "Rapid isolation of plant Ty1-*copia* group retrotransposon LTR sequences for molecular marker studies," *Plant J.*, 1999, 19:711-717.

Peleman et al., "Transient occurrence of extrachromosomal DNA of an *Ababidopsis thaliana* transposon-like element, *Tat1*," *Proc. Natl. Acad. Sci. USA*, 1991, 88:3618-3622.

Pearce et al., "Pea Ty1-*copia* group retrotransposons: transpositional activity and use as markers to study genetic diversity in *Pisum*," *Mol. Gen. Genet.*, 2000, 263:898-907.

Pélissier et al., "*Athlia*, a new retroelement from *Arabidopsis thaliana*," *Plant Mol. Biol.*, 1995, 29:441-452.

Peterson-Burch et al., "Retroviruses in plants?" *TIG*, 2000, 16:151-152.

Purugganan and Wessler, "Molecular evolution of *magellan*, a maize Ty3/*gypsy*-like retrotransposon," *Proc. Natl. Acad. Sci. USA*, 1994, 91:11674-11678.

Purugganan and Wessler,"Transposon signature: species-specific molecular markers that utilize a class of multiple-copy nuclear DNA," *Molecular Ecology*, 1995, 4:265-269.

Ray, "*Arabidopsis* floral homeotic gene BELL (*BEL1*) controls ovule development through negative regulation of AGAMOUS gene (AG)," *Proc. Natl. Acad. Sci. USA*, 1994, 91:5761-5765.

Reiser et al., "The *BELL1* Gene Encodes a Homeodomain Protein Involved in Pattern Formation in the *Arabidopsis* Ovule Primordium," *Cell*, 1995, 83:735-742.

Rost et al., "Taxonomy of Retroviruses," *Molecular Biology of Tumor Viruses—RNA Tumor Viruses*, 1984, 2nd edition, Weiss et al. (eds.), Cold Spring Harbor Laboratory Press, Cold Spring Harbor, NY, pp. 25-207.

Rost et al., "Transmembrane helices predicted at 95% accuracy," *Prot. Science*, 1995, 4:521-533.

Saitou and Nei, "The Neighbor-joining Method: A New Method for Reconstructing Phylogenetic Trees," *Mol. Biol. Evol.*, 1987, 4:406-425.

Sambrook et al., *Molecular Cloning, A Laboratory Manual*, 1989, Cold Spring Harbor Laboratory Press (TOC only).

SanMiguel et al., "Nested Retrotransposons in the Intergenic Regions of the Maize Genome," *Science*, 1996, 274:765-768.

Sheridan et al., "The *mac 1* Gene: Controlling the Commitment to the Meiotic Pathway in Maize," *Genetics*, 1996, 142:1009-1020.

Shiina et al., "Identification of Promoter Elements Involved in the Cytosolic $Ca^{2+}$-Mediated Photoregulation of Maize *cab*-m1 Expression," *Plant Physiol.*, 1997, 115:477-483.

Sjödahl et al., "Deletion analysis of *Brassica napus* cruciferin gene *cru 1* promoter in transformed tobacco: promoter activity during early and late stages of embryogenesis is influenced by *cis*-acting elements in partially separate regions," *Planta*, 1995, 197:264-271.

Smyth et al., "Plant retrotransposon from *Lilium henryi* is related to *Ty3* of yeast and the gypsy group of *Drosophila*," *Proc. Natl. Acad. Sci. USA*, 1989, 86:5015-5019.

Song et al., "An Env-like protein encoded by a *Drosophila* retroelement: evidence that *gypsy* is and infectious retrovirus," *Genes Dev.*, 1994, 8:2046-2057.

Su and Brown, "*Ty3/gypsy*-like Retrotransposon Sequences in Tomato," *Plasmid*, 1997, 38: 148-157.

Thompson et al., "Germ Line Transmission and Expression of a Corrected HPRT Gene Produced by Gene Targeting in Embryonic Stem Cells," *Cell*, 1989, 56:313-321.

Thompson et al., "CLUSTAL W: improving the sensitivity of progressive multiple sequence alignment through sequence weighting, position-specific gap penalties and weight matrix choice," *Nucl. Acids. Res.*, 1994, 22:4673-4680.

Thompson et al., "The CLUSTAL_X windows interface: flexible strategies for multiple sequence alignment aided by quality analysis tools," *Nucl. Acids. Res.*, 1997, 25:4876-4882.

Tinland et al., "*Agrobacterium tumefaciens* transfers single-stranded transferred DNA (T-DNA) into the plant cell nucleus," *Proc. Natl. Acad. Sci. USA*, 1994, 91:8000-8004.

Töpfer et al., "Uptake and Transient Expression of Chimeric Genes in Seed-Derived Embryos," *Plant Cell*, 1989, 1:133-139.

Treacy et al., "*Bnm 1*, a *Brassica* pollen-specific gene," *Plant Mol. Biol.*, 1997, 34:603-611.

Tsuchiya et al., "Tapetum-Specific Expression of the Gene for an Endo-β-1,3-glucanase Causes Male Sterility in Transgenic Tobacco," *Plant Cell Physiol.*, 1995, 36:487-494.

Urao et al., "Molecular cloning and characterization of a gene that encodes a MYC-related protein in *Arabidopsis*," *Plant Mol. Biol.*, 1996, 32:571-576.

Van der Putten et al., "Efficient insertion of genes into the mouse germ line via retroviral vectors," *Proc. Natl. Acad. Sci. USA*, 1985, 82:6148-6152.

Varmus and Brown, "Retroviruses," *Mobile DNA*, 1989, Berg and Howe (eds.), American Society for Microbiology, Washington, D.C., pp. 53-108.

Verbruggen et al., "Osmoregulation of a Pyrroline-5-Carboxylate Reductase Gene in *Arabidopsis thaliana*," *Plant Physiol.*, 1993, 103:771-781.

Verdaguer, "Isolation and expression in transgenic tobacco and rice plants, of the cassava vein mosaic virus (CVMV) promoter," *Plant Mol. Biol.*, 1996, 31:1129-1139.

Vicient et al., "*Envelope*-Class Retrovirus-Like Elements Are Widespread, Transcribed and Spliced, and Insertionally Polymorphic in Plants," *Genome Res.*, 2001, 11:2041-2049.

von Heijne, "A new method for predicting signal sequence cleavage sites," *Nucl. Acids Res.*, 1986, 14:4683-4690.

Voytas, "Retroelements in Genome Organization," *Science*, 1996, 274:737-738.

Voytas et al., "The Structure, Distribution and Evolution of the Ta1 Retrotransposable Element Family of *Arabidopsis thaliana*," *Genetics*, 1990, 126:713-721.

Voytas and Ausubel, "A copia-like transposable element family in *Arabidopsis thaliana*,"*Nature*, 1988, 336:242-244.

Voytas and Naylor, "Rapid flux in plant genomes," *Nature Genetics*, 1998, 20:6-7.

Wakeley et al., "A maize pectin methylesterase-like gene, ZmC5, specifically expressed in pollen," *Plant Mol. Biol.*, 1998, 37:187-192.

Wakayama et al., "Full-term development of mice from enucleated oocytes injected with cumulus cell nuclei," *Nature*, 1998, 394:369-374.

Wessler et al., "LTR-retrotransposons and MITEs: important players in the evolution of plant genomes," *Curr. Opin. Genet. Dev.*, 1995, 5:814-821.

Weterings et al., "Regional Localization of Suspensor mRNAs during Early Embryo Development," *Plant Cell*, 2001, 13:2409-2425.

White et al., "Retrotransposons in the flanking regions of normal plant genes: A role for *copia*-like elements in the evolution of gene structure and expression," *Proc. Natl. Acad. Sci. USA*, 1994, 91:11792-11796.

Wright and Voytas, "*Athila4* of *Arabidopsis* and *Calypso* of Soybean Define a Lineage of Endogenous Plant Retroviruses," *Genome Res.*, 2001, 12:122-131.

Wilmut et al., "Viable offspring derived from fetal and adult mammalian cells," *Nature*, 1997, 385:810-813.

Wright et al., "Multiple Non-LTR Retrotransposons in the Genome of *Arabidopsis thaliana*," *Genetics*, 1996, 142:569-578.

Xiong and Eickbush, "Origin and evolution of retroelements based upon their reverse transcriptase sequences," *EMBO J.*, 1990, 9:3353-3362.

Yamamoto et al., "Characterization of *cis*Acting Sequences Regulating Root-Specific Gene Expression in Tobacco," *Plant Cell*, 1991, 3:371-382.

Yu and Wise, "An anchored AFLP—and retrotransposon-based map of diploid *Avena*," *Genome*, 2000, 43:736-749.

Zambryski, "Chronicles from the *Agrobacterium*-Plant Cell DNA Transfer Story," *Ann. Rev. Plant Mol.*, 1992, 43:465-490.

Zhang et al., "DNA Sequences That Activate Isocitrate Lyase Gene Expresion during Late Embryogenesis and during Postgerminative Growth," *Plant Physiol.*, 1996, 110:1069-1079.

Vershinin et al., "LINEs and *gypsy*-like retrotransposons in *Hordeum* species," *Plant Molecular Biology*, 2002, 49:1-14.

Figure 1
*Alignment of RT amino acid sequences (SEQ ID NOs:201-335, top to bottom)*

```
                       Domain 1                                          Domain 2
              [....10....20....30........40...].50....60
                         ***      **********
will8-2      1:LEVGLIYPISD.SAWVSSNZVVPKKGGMTVIHNDKNDLIPTQTIIRWQMCIDYHK.LNDV: 57
hark5        1:LEAGLIYLISD.SAWVSPVHVVPKKGGKTVVRNEKNDLILTRTVTGWRMCIDYRK.LNDA: 58
Calypso7-1   1:LEAGLVYPISD.SAWVSPVQVVPKKGGMTVIRNEKNDLIPTRTVTGWRMCIDYRK.LNDA: 58
will2        1:LEAGLIYPISD.SAWVSPVQVVPKKEGKTVIKDEKDELISTRTITGWRMCIDYQK.LNDA: 58
hark5-1      1:LEAGLIYPISD.SAWVSPVQVVPKKEGKTVIKDEKDELISTRTITGWRMCIDYQK.LNDA: 58
L859-6       1:LEAGLIYPISD.SAWVSPMQVVPKKGGMTVIKNDKDELISTRTVTGWRMCIDYRK.LNDA: 58
Calypso4-1   1:ZEAGLIYPSSD.SAWVSLVQVVPKKGGMTVIKNDKDELISIRTVTGWRMCIDYRK.LNDA: 57
hark2        1:LEADLIYPISD.STWVSPVQVVPEKGGMTVIKNDKDELISTRTVTGWRMCIDYRK.LNDA: 58
Calypso5-1   1:LEAGLIHPISD.SAWVSPVQVVLKKCGMTVIKNDKDELISTRTVTGWRMCIDYRK.LNNA: 58
will3        1:LEAGLIYPISD.SSWVSPVQVVPKKGGMTVVKNDRNELIPTRRVTRWRMCIDYRK.LNEA: 58
L859-3       1:LEAGLIYLISD.SSZVSPVHVALKKGGMTVIKNDRDELIPTRIVTGWRMGIDYKK.LNEA: 57
Calypso6-1   1:LEAGFIYPISD.NSWVSPVQVVPKKCGMAVIRNDRNELIPTRTVTGWRMCVDYRK.LNEA: 58
will8-3      1:LEVGLIYLISD.SAWVSLVQVAPKKCGMTVVQNERNDLIPTRTVTGZRMCIDYCK.LNEA: 57
L858-2       1:LEVGLIYLISD.SAWVSLVQVAPKKCGMTVVQNERNDLIPTRTVTGZRMCIDYCK.LNEA: 57
Calypso3-1   1:LEVCLIYPISD.NAWVSPVQVVPKKGGMTVVQNERNDLIPTRTVTGWRMCIDYHK.LNEA: 58
Calypso1-1   1:LEAGFIYPISD.SAWVSPVQVVPKKGGMTVVRNERNDLIPTRTATGWWMCIDYRK.LNEA: 58
L852         1:LEAGLIYPISN.STZVSPVQVVPKKGGMTVVQNEKNDLIPTRTVTSWRICIDYRK.LNEA: 57
Calypso2-1   1:LEAGLIYPFSN.SAWVSPVQVVPKKGEMTVVRNEKNDLIPRRTITGWRMCINYRK.LNEA: 58
L859-2       1:LEVGLIYPISD.SAWVSPVLVVSKKEGMTVIRNEKNDLIPTRTVTSWKLCIDYRK.LNEA: 58
Cyclops-2    1:LDARMIYPISD.SPWVSPVHVVPKKGGNTVIRNDKDELIPTKVATGWRMCIEYRR.LNTA: 58
Cyclops-1    1:LDARMIYPISD.SPWVSPVHVVPKKGGNTVIRNDKDELIPTKVATGWRMCIEYRR.LNTA: 58
pea9-1       1:LDAGMIYPISD.SPWVSPVHVVPKKGGITVIRNDKDELIPTKVETGWRMCIDYRR.LNTA: 58
pea8-1       1:LDAGMIYPISD.SPWVSPVHVVPKKGGMTVIRNDKDELIPTKVATGWRICIDYRQ.LNTA: 58
favabean1    1:LDAGMIYPISD.SSWVSPIHVMPKKGGTTVIKNEKNELIPTRTVTGWZVCIDYRR.LNLA: 57
fababean2    1:LDAGMIYPISE.SSZVSPIHVVPNKGGTIVIKNEKNZLIPSRTVTGWZVCIVIEK.IEPA: 55
pea1         1:LDSGMIYPISD.SSWVSPVHVVPKKGGTSVILNEKNELIPTRTVTGWRVCIDHRR.LNTA: 58
tob2-2       1:LDVGVVYPISD.SSWTSPVQCVPKKVGMTVVKNSKNELIPTRTITGWRVCMDYRK.LNKV: 58
tob5-3       1:LDVGVVYPIFD.SSWTLPVQYVPKKGGMTVVTNVKNELIPTRTVTGWRVCMDYHK.LNKV: 58
tob4-1       1:LDVGVVYPISD.SSCISPVQCVPKKGGMTVVANSQNGLIPTRIVTGWKVCMDYRK.LNKV: 58
tob1         1:LDAGVIYPIYD.SSZTSPVQCVPKKGGMTVVTNEKNELIPTRMVTGWRVCMDYRK.LNKL: 57
tom4-10      1:LDARVIYPIAD.SSWVCLVQCVPKKGGMTVVPNEKNELVRMRPVTGWRVCMDYRK.LNSZ: 57
tom10-16     1:LDAGVIYPISD.SSWVCPIQCVPKKGGMTVVPNKKNELVLMRPVTGGWVCMDYRK.LNAW: 58
tom4-4       1:LDTGIVZPISD.NKZVSPVQCEPKKGDITVITNEKNELIPTMIVTZWRICMDYRK.LNEA: 55
pot8-8       1:LDAGIVYQISD.SKGVYPIZFVPKKCSMTVITNEKNELIPTRTVTGWRICMDYMK.LNEA: 57
pot8-3       1:LDVGIVYPISE.SKWVSPVZCVPKKRGMPVITNEKNELIPTRTVTGWRICMDYRK.LNEA: 57
pot8-4       1:LDAGIVYPISD.SKWVSPVQCVPKKGGMTVITNEKNELIPTRTVTGWRICMDYRK.LNEA: 58
pot8-5       1:SDAGIVYPIYD.IKWISPVHCVPKKGGMTIITNEKKELISARTVIEWHIZMDYRR.LNEA: 57
tom10-4      1:LDAGIVYPISD.NKWVSLVQCVPKKGGMAMITNENNEFIPTSTVTRWRICMNYTK.LNEA: 58
pot8-10      1:LDTGIVYPISD.NKWASPVQCVPKKGGMTVVTNEKNELIPTRTVTGWRLCMDYRK.LNEA: 58
pot5-1       1:LDARIVYPISD.SKWVSPVKCVPKKGRMTVLTNEKNEVIPTRTVTGZRICMDYMK.LNDA: 57
syc4-2       1:LEVGVIYLISN.SNWVSPVQVVAPKKTGITVVKNQNDELVPTHVQNGWWVCINYRK.LNVI: 58
syc4-7       1:LEVGVIYPISD.SNWVSPVQVVPKKTGITVVKNQNDELVPTRVQNGWQVCIDYIK.LNVV: 58
syc2-3       1:LKVZVIYPIZD.RNWVSPVQVVPKKIGITVVKNZNDELVPTSVQNGWRVCIDYRK.LNVV: 55
cot5-3       1:LDDGMIYPISN.SNWVSPVHIVPKKTSATVIENSAGEIVPTRVQNGWRVCIDYRK.LNSL: 58
cot8-6       1:LDSGMIYPISD.NNWVSPVHIVPKKTGVTVIENSAGEMVPTZVRNGRRVCIDYRK.LNSL: 57
cot8-7       1:LDAGMIYSIFD.SDWVSWVHVVPKKTGVTVVKNSSGELVPTRVQNRWRVCIDYRK.LNAA: 58
Diaspora     1:LQAGIIYPISD.SQWVSPVQVVPKKTGLTVIKNEKEELIPTRVQNNWRVCIHYRR.LNQV: 58
TfcII#1      1:LAADIIYPISD.SRWVSPIHVVPKKTGTTLVKTSDDELVPQRVANSWRVCVDYRR.LNAN: 58
TfcII#2      1:LAADIIYPISD.SRWVSPIHVVPKKTGTTLVKTSDDELVPQRVANSWRVCVDYRR.LNAN: 58
TfcII#3      1:LAADIIYLISD.SRWVSPIHVVPKKTGTTLVKTSDDELVPQRVANSWRVCVDYRZ.LNAN: 57
syc4-3       1:LDVGIIYPIFY.SNZVSPTQVVPKNSGVTVVKNANDELIPNRLTIGWRVCINYKK.LNSV: 57
hau7-2       1:LDAGVIYPISD.STWVSPVHCVPKKGGMTVVKNSKDELIPTRTITGHRKCIDYRK.LNAA: 58
Athila6-1    1:LDAGVIYPISD.STWVSPVHYVPKKGGMTVVKNSKDELIPTRTITGHRMCIDYRK.LNAA: 58
f18p14       1:LDASVIYPISD.STWVSPVHCVPIKGGMTVIKYSKDELLPTRTITGHRICIDYKK.LNAA: 58
hau8-4       1:LDAGVIYPISD.RTWVSPVHCVPKKGGMTVVKNEKDELIPTRTITGHRMCIDYRK.LNAA: 58
Athila4-1    1:LDAGVIYPISD.STWVSPVHCVPKKGGMTVVKNEKDELIPTRTITGHRMCIDYRK.LNAA: 58
Athila4-3    1:LDAGVIYPISD.STWVSPVHCVPKKDGMIVVKNEKDELIPTRTITGHRMCIDYRK.LNAA: 58
Athila4-4    1:LDAGVIYPISD.STWVSPVHCVPKKDGMTVVKNEKDELIPTRTITGHRMCIDYRK.LNAA: 58
Athila4-2    1:LDAGVIYPISD.STWVSPVHCVPKKGGMTVVKNEKDELIPTRTITGHRMCIDYRK.LNAA: 58
```

Figure 1

Domain 1                                                    Domain 2

```
                  ....10....20....30....40....50....60
                           ***   **********
t13e11       1:VDAGVKYPISE.STWISLVHCVPKKGGMTVVKNEKNELI.TRTITWHRMCIDYRK.LNVA: 57
f7b19        1:LDAGVIYPISD.SIWVSPMHCVPKKGGMTVVKNZKDELIPTRAITSHRVCIDYRK.LNAA: 57
t13d4        1:LDADIIYPISD.STWVSPVHCVPKKRGMTVVKNDLDELIPTRTIIGHRMCIDYRK.LNAA: 58
t24g23Ath9-1 1:LDADIIYPISD.CTWVSAVHCVPKKGGMTVVIKNDHDELIPTRTITGHRMCIDYRK.LNAA: 58
t16i21       1:LDVDIIYPISD.STWVSPVHCVSKKGGMIVVKNDLDELIPARTITGHKMCIDYRK.LNAA: 58
La8-1        1:LDAGIIYPISD.STWVSPVHVVPKKGGVTVVKNDNDELIPTRTITGHRMCIDYRK.LNAA: 58
La9-6        1:LDAGIIYPISD.STWVSPVHVVPKKGGVTVVKNDNDELIPTRTITGHRMCIDYRK.LNAA: 58
Athila1-1    1:LDAGIIYPISD.STWVSPVHVVPKKGGVTVVKNDNDELIPTRTITGHRMCIDYRK.LNAA: 58
La9-7        1:LDAGIIYPISD.STWVSPVHVVPKKGGVTVVKNDIDELIPTRTIMGHRMCIDYRK.LNAA: 58
La9-9        1:LDAGIIYPISD.STWVSPVHVVPKKGGVTVVKNDIDELIPTRTIMGHRMCIDYRK.LNAA: 58
hau8-3       1:LEAGIIYPISD.SSWVSPVHVVPKKEGVTEVKNEIDELIPTRTITGHWMCIDYRK.LNAA: 58
f23m2Ath5-2  1:LEAGIIYSISD.SSWVSPVHVVPKKEGVTEVKNEIDELIPTRTITGHWMCIDYRK.LNAA: 58
t17a11       1:LEAGIIYPILD.SSZVSPVHVVPKKGGVTVVKNEKDELIPTRTIIGHRMCIDYRK.LNAA: 57
La9-5        1:LEAGIIYPISD.SSWVSPVHVVPKKGGVTIVKNEEDEMIHTRTITCHRMCIDYZK.LNAA: 57
bar7         1:LEEGIIYPVAH.SDWVSPVHCIPKKGGITVVPNDKDELIPZRIITTGYRMVIDFRK.LNKA: 57
bar2-12      1:LEAGIIYPVAH.NDWVSPVHCVPKKGCITVVPNDKDELIPHRIITGYRMVIDFRK.MNKA: 58
bar2-19      1:LDEGIIYHVAH.SDWVSPVHSVPKKGGITVVPNDKDELIPQRIITGYRMVIDFRK.LNKA: 58
bar2-4       1:LEAGIIYRVAH.SDWLSRVHCVPKKGGITVVPNDKDELIPQRTITGYRMVIDFRK.LNKA: 58
Baggy2       1:LEAGIIYPVAH.SDWVSPVHCVPKKGGITVVPNDKNELIPHRIVTGYRMVIDFRK.LNKA: 58
rye3-4       1:PEAGIIYPVAD.SQWVSHVHCVPKKGGMTVVPNDKHELIPQRIVTGYRMVIDFRK.LNKA: 58
rye4-4       1:LEAGIIYPVAD.SQWVSHVHYVPKKGGMTVVPNDKDELIPQRIVTGYRMVSDFRK.LNKA: 58
rye5-2       1:LEAGINYPIAD.SQRVSPVHCVPKKGGMTVVPKDKDEFIPQRIVTGYRMVIDFRK.LNKA: 58
rye5-4       1:LEAGIIYPVAD.SQWVSPVHCVPKKGGMTVVPNDKDELISQRIVTGYRMVIDFRK.LNKA: 58
wheat3-1     1:LEVGIIYPVAD.SQWVSPVHCVPKKGGITVVPNDKDELIPQRIITGYRMVIDFRK.LNKA: 58
wheat8-5     1:LEAGIIYPVAE.SQWVSPVHCVPKKGGITVVPNDKDELIPQRIITGYRMVIDFRK.LNKA: 58
wheat8-2     1:LEAGIIYPVVD.SQWVSPVHCVLKKGGITVVPNDKDELIPQRIITGYRMVIDFRK.LNKA: 58
wheat5-3     1:LEAGIIYPVAD.SKWVIPVHVKKGGITVVPNDKDELIPQRTITGYRMVIDFRK.LNKA: 58
wheat8-11    1:LEAGITYPVAD.SEWVSPLHCVPKKGGITVVLNDKDELIPQIIITGYRMVIDFHK.LNKA: 58
oat6-1       1:MDAGIIYPIAD.SEWVSHVHCVPKKGGITVVPNDNDELIPQRIVVGYRMCIDFRK.VNKV: 58
oat6-8       1:LDVGIIYPIAD.SEWVSLVHCVPKKGGITVVPNDNDELIPQRIVVGYRMCIDFRK.VNKV: 58
oat6-7       1:LDAGIIYPIAD.SQWVSLVHCVPKKGGITVVPNEDNELIPQRVVVYRMCIDFRR.INKV: 58
rice1        1:LYARIIYLVPY.SEWVSPVQVVPKKGGMTAVANAQNELIPQRTVTGWRMCIDYRK.LNKA: 58
RiceAthila   1:LHARIIYLVPY.SEWVSPVQVVPKKGGMTAVANAQNELIPQRTVTGWRMCIDYRK.LNKA: 58
rice2-10     1:LHARIIYPVPY.SERVSPVQVVPKKGGMAVVANAQNELITQQTVTGWRMCIDYRK.LNKA: 58
rice5-2      1:LHAEIIYPVPY.REWVSPVZVMPKKGRMTVIANAQNELIPQRTVTGWRMCIDYMK.LNKA: 57
rice2-17     1:LHAGIIYITVPC.SEWVSTVQVGPKMGZMTVVANAQNKLIPQPTITGWRMCIDYRK.LNKA: 57
sorg4-3      1:YHAGIIYPVPH.SEWVSPVQVVPKKGGMTVVRNEKNELIPQRIVTGWRMCIDYQK.LNTA: 58
sorg5-6      1:YHAGIIYPVPH.SEWVSPVQVVPKKEGMTVVRNEKNELIPQRIVTRWRMCIDYRK.LNKA: 58
sorg5-4      1:LHTRIIYLVPH.SEWVSTVQVVPKKGGMSVVRNEKNEFIPQQTVTGWRMCIDYQK.LNKA: 58
sorg5-2      1:LHAGIIYPVPH.SEWVSPVQVVPKKGGMTVIINEKNELIPQRTVTGWQMCIDYRK.LNKA: 58
sorg5-8      1:LHAGIIYLVPH.SEWVSPVQVVPKKGGMTIIMNEKNELIPQRTVTVWRMCIDYRK.LNKA: 58
sorg5-5      1:LHAEIIYHVPH.SEWVSPVQVVPKKGGMIVVTNEKNELIPQRTVTGWRMCIDYRK.INKA: 58
Tat4-1       1:LGAGSIVEKY.PEWLANPVVVKKK........N........GKLRVCIDFTD.LNKA: 40
f26h6        1:LDAGSIVEVRY.PDWLRNPVVVKKK........N........GKWRVCIDFTD.LNKA: 40
Rire2        1:IAAGFIKEVLH.PDWLANPVLVRKK........T........GQWRMCVDYTD.LNKS: 40
Grand1-4     1:VAAGFIREVLH.PEWLANPVLVLKK........NK.......VDWRMCVDYTD.LNKH: 41
Vulgar       1:LAANFVREVHH.SEWLANVVMVPKK........D........KSLRMCIDFKH.VNKV: 40
Cinful       1:LSAGVIREVKY.PEWLANTVMVKKA........N........GKWRMCIDFTD.LNKA: 40
Mag          1:LAAGVIKPVDH.SDWATPLVVVRKADG...............GLRICADYKVTLNKV: 41
SURL         1:ERLDVITPVDEPTDWVSSLVVVMKKNG...............QLRVCLDPRD.LNRA: 41
Mdg1         1:IKDGIVEQSIS..EYNSPLLLVPKK.........S...LPNSEEKRWRLVVDYRQ.INKK: 45
412          1:IKDKIVEPSVS..QYNSPLLLVPKK.........S...SPNSDKKKWRLVIDYRQ.INKK: 45
Cft-1        1:LAKGWIRRSTS..SAGTPCMFVPKANG............KLRLVQDYRK.LNEI: 39
boty         1:LAKGWIRESAS..QVASPTMWVPKKDG............PDRLVVDYRK.LNTL: 39
Skippy       1:IRKGYIRPSKS..SAGFPVMFVPKPNSN...........KLRLVVDYRQ.LNEI: 40
Maggy        1:LKKGFIRPSSS..SVASPVLFVKKQGG............GLRFCVDYRA.LNNI: 39
Grasshopper  1:MDKGWIRASSS..SAAAPVLMVRKASG............GWRLCVDYRA.LNSI: 39
Tf1          1:LKSGILRESKA..INACPVMFVPKKEG............TLRMVVDYKP.LNKY: 39
Tma1-1       1:LSKGFIRPSTS..PWEAPVLFVKKKDG............SFRLCIDYRR.LNRV: 39
Tma3-1       1:LGKRFIRPSTS..PWRAPMLFMKKKDG............SFRLCIDYRG.LNQV: 39
Del1         1:LNKGFIRGSTS..PWGAHVLFDPKKDD............SKRMCIDYZK.LNSV: 38
```

Figure 1

```
              Domain 1                                              Domain 2
         . . . .10 . . . .20 . . . .30 . . . .40 . . . .50 . . . .60
                        ***            **********
Reina    1:LEQGVIQHSSS..PFASPVLLVKKKDG................EWRLCVDYRR.LNAH: 39
IFG7     1:LEAGIIQPSQS..SFSDPVVLVHKKDG................SWCMCPDYRE.LNKL: 39
Ty3      1:LDNKFIVPSKS..PCSSPVVLVPKKDG................TFRLCVDYRT.LNKA: 39
Tom      1:LEQGLIRESNS..PYNSPTWVVPKK.....PDASGK.......AKYRVVIDYRK.LNEI: 44
297      1:LNQGLIRESNS..PYNSPTWVVPKK.....PDASGA.......NKYRVVIDYRK.LNEI: 44
17.6     1:LNQGIIRTSNS..PYNSPIWVVPKK.....QDASGK.......QKFRIVIDYRK.LNEI: 44
TED      1:LDQGIIRPSDS..AWSSPIWVVPKK.....IDASGK.......QKWRLVVDFRK.LNEK: 44
Gypsy    1:LKDGIIRPSRS..PYNSPTWVVDKKG.....TDAFGN.......PNKRLVIDFRK.LNEK: 45
Yoyo     1:LEDGIIRPSRS..PYNSPVWIVDKK.....PDSLGN.......KQYRLVIDYRK.LNSV: 44
Ulysses  1:LKLGIIEESDS..PWSNRTTVVMRP..................GKNRFCLDARK.LNSV: 38
Woot     1:LDLGVIKREAS..PYASPMTVGKKK.........D........GTVRICLDARM.INSK: 39
Cer1     1:LNQKVIRESKS..PWSSPVVLVKKKDG................SIRMCIDYRK.VNKV: 39
HIV1     1:GKISKIGP.EN..PYNTPVFAIKKKDS................TKWRKLVDFRE.LNKR: 39
RSV      1:LQLGHIEPSLS..CWNTPVFVIR.KAS................GSYRLLHDLRA.VNAK: 39
MuMLV    1:LDQGILVPCQS..PWNTPLLPVKKPGT................NDYRPVQDLRE.VNKR: 40
```

Figure 1

```
              Domain 2                    Domain 3                    Domain 4
             .....70....|....80....90....100....110.|...120
             ****       ****|*          *******      ****|
will8-2     58:TKKDHFPLPFMDQMLERLA.GQAFYCFLDGYSGYNQIAVHLKDQEKTTIICPF......G:110
hark5       59:IKKDHFPLPFIDQMLERLA.SQSFYYFLDEYSRYNQIAIHPKDQEKTAFTCPF......G:111
Calypso7-1  59:TRKDHFPLPFMDQMLERLA.GQSFYCFLDGYSGYDQIVVDLNDQEKTAFTRPF......G:111
will2       59:TRKDHYPLPFMDQMLERLA.GQSYYCFLDGYSGYNQIDVDPKDQEKTAFTYPF......G:111
hark5-1     59:TRKDHYPLPFMDQMLERLA.GQSYYCFLDGYSGYNQIDVDPKDQEKTAFTYPF......G:111
L859-6      59:TRKDHYPLPFMGHMLERLV.GQSYYCFLDGYSGYNQIVVDPKDQEKTAFTYPF......G:111
Calypso4-1  58:TRKDHYPLPFMDQMLERLV.GZSYYCFLDEYSGYNZIVVDPKDQEKTAFTYPF......G:108
hark2       59:TQKDHYSLPFMDQMLERLA.GQSYYCFLNGYSGYNQIVVDPKDQEKTAFTCLF......G:111
Calypso5-1  59:TWKDHYPLPFMDHMLERLA.RQSYYCFLDGYSSYNZIAIDIKDQEKTTFTFPF......G:110
will3       59:TRKDHYPLPFMDQMLKRLA.RQSFYRFLDGYSGYNQIAVDPQDQEKTAFTCPF......S:111
L859-3      58:TRKDHYPLPFMDQMLERLA.GQSSYYLLDGYSGYNQIAVDPQDQEKTAFTCPF......G:110
Calypso6-1  59:TRKDHYPLPFMDQMLERLA.GQSFYYFLDGYSGYN.....P....SWITCPF......G:101
will8-3     58:TRKDHFPLPFMDQMLERLA.GQAYYCFLDRYSGYNQIAVDPRDQEKMAFTCPF......G:110
L858-2      58:TRKDHFPLPFMDQMLERLA.GQAYYCFLDRYSGYNQIAVDPRDQEKMAFTCPF......G:110
Calypso3-1  59:TRKDHFPLPFMDQMLERLA.GQAYYCFLDGYSGYNQIAVDPIDQEKTVFTCPF......G:111
Calypso1-1  59:TQKDHFPLPFMDZMLERLA.GQAYYCFLDGYSGYNQIAVDPRDQEKTAFTCPF......G:110
L852        58:TRKDHFPLPFMDQMLERLA.GQAYYCFLDGYSRYNQIAVDPRDQEKTTFTCPF......G:110
Calypso2-1  59:TRKDHFPLLFMDQMLERLV.GQAYYYFLDGYSGYNQIAVDPRDQEKAAFTCPF......G:111
L859-2      59:TRKDHFPLPFMDQMLERLA.GHAYYCFLDAYFGYNQIVVDPKDQEKMAFTCPF......G:111
Cyclops-2   59:TRKDHFPLPFMDQMLERLS.GQQYYCFLDGYSGYNQIAVDPADHZKTAFTCPF......G:110
Cyclops-1   59:TRKDHFPLPFMDQMLERLS.GQQYYCFLDGYSGYNQIAVDPADHZKTAFTCPF......G:110
pea9-1      59:TRKDHFPLPFMDQMLERLS.GQQYYCFLDGYSGYNQIAVDPADHEKTAFTCPF......G:111
pea8-1      59:TRKDHFPLPFMDQMLERLS.GQQYYCFLDGYSGYNQIAVDPVDHEKTAFTCPF......G:111
favabean1   58:TRKDHFPLPFIDQMLERLA.DHEYYCFLDGYSGYNQIAVVPEDQEKTTFTCPF......G:110
fababean2   56:TRKDHFPLPFIDQMLERLA.DHEYYCFLDGYSGYNQIAVVPEDQEKTTFTCPF......G:108
pea1        59:TRKDHFPLPFIDQMLERLA.GHEYYCFLDGYSGYNQIVVAPEDQEKTAFTCPY......G:111
tob2-2      59:TCKDHFPLPFLDQMLDRLA.GRAFYCFLDEYSGYNQILLIAPEDPEKTTFTCPY......G:111
tob5-3      59:TRKDHFPLPFLDQMLDRLA.GCAFYCFLDGYSGCNKILIAPKDQEKTTFTCTY......G:111
tob4-1      59:TRKDHFPLPFLDQMLDRLA.GRAFYCFLDGYSGYNQIFITPEDQEKTTFTCPY......G:111
tob1        58:TRKDHFPFPFLDQMLDRLA.CRAFYCFLDVZSGYSQIFIAPZDHEKTTFTCPY......G:108
tom4-10     58:TEKDYFHMPFMDQMLDRLA.GKGWYCFLDGYSGYNQISIAPEDQEKTTFTCPY......G:110
tom10-16    59:TEKDHFPMPFMDQMLDRLA.EKGWYCFLDGZSGYNZISIAPEDQEKTTFTCPY......G:109
tom4-4      56:TRKDHYPVPFIDQMLDRLA.GEZYYCFLNGYLRYNQIVISPKDZEKTTFTCPY......G:106
pot8-8      58:TRKDHYPIHFIDQMLDKLA.EZKYYCFLACYSRYNQFLLAPQDQEETTFTCPY......G:109
pot8-3      58:TRKDHCPVPFIDQMLDRLV.GQEYYCFLEGYSGYNQIAVAPEDQEKTTFTCLY......G:110
pot8-4      59:TRKDHYPVPFIDQMLDRLA.GQEYYCFLDGYSGYNQIVIAPEDQGKTTFTCLY......G:111
pot8-5      58:TRKEHYPVPFIDQMLDRFI.GQEYYCFLDGYSGYNQIVIAPZDKEKTTFTSLY......G:109
tom10-4     59:TRKNHYPILFIDYMLDRLA.GQEYYCFLDYZSGYNZILIAPEDQEKTTFTCPY......G:109
pot8-10     59:TRKDHYSVPFIDQMLDRLA.GQEYYCFLDGYSRYNZIVIAPEDQENTTFTCPY......G:110
pot5-1      58:TRKDHYPVPFIDKILDRLA.GHEYYCFLGVYSGVYNQIVIAIEDZVKTTFTCSY......G:109
syc4-2      59:TCKDHFPLPFIDKMLERLA.GHSYYCFLDGYLGYFQIAITSEDQEKMIFKCPF......G:111
syc4-7      59:TRKDHFPLPFIDQMFERLA.GHSYYCFLDGYSCYFZIAITPEDQEKTTFTCPF......G:110
syc2-3      56:TRKDHFPLPFIDQMLERLV.GHSYYCFLDGYSSYFQIVITPEDZEKTTFTCPF......G:107
cot5-3      59:TRKDHFPLPFIDQMLERLA.GKSHYCCLDGYZGFFQIPVAPEDQEKTMFTCPF......G:110
cot8-6      58:TRKDHFPLLFIDQMLEHLA.RKSHYCCLDGYSGFFQIPMALKDQEKMTFTCPF......G:110
cot8-7      59:TRNDHFPLPFIDQMLERLA.NKTHYCCLDGYSGLFQIPVAPEDQDKTTFTCPF......G:111
Diaspora    59:TKKDHFPLPFIDQILECLA.GKSHYCFLDGFSGYMQITTIALEDQEKTTFTCLF......G:111
TfcII#1     59:TRKDHFPLPFIDSMLERLA.GNVYYCFLDGYSGYNQIHTAPEDQEKTTFTCPF......G:111
TfcII#2     59:TRKDHFPLPFIDSMLERLA.GNMYYCFLDGYSGYNQIHTAPEDQEKTTFTCPF......G:111
TfcII#3     58:TRKDHFPLPFIDSMLERLA.GNMYYCFLDGYSGYNQIHTAPEDQEKTTFTCPF......G:110
syc4-3      58:TRKDHFPLPFMDZILERVA.GHKFYYFLYGYSRYNZIETAPEDZENTTFTCPF......G:107
hau7-2      59:SRKDHFPLPFIDQMLERLA.NHPYYCFLDGYSGFFQIPIHPNDQEKTTFTCPY......G:111
Athila6-1   59:SRKDHFPLPFIDQMLERLA.NHPYYCFLDGYSGFFQIPIHPNDQEKTTFTCPY......G:111
f18p14      59:TRKDLFPLPFIDQMLKRLA.NHPYYCFLDGYSGFFQIPIHPNDQEKTTFTCPC......G:111
hau8-4      59:SRKDHFPLPFIDQMLERLA.NHPYYCLLDGYSGFFQIPIHPNDQEKTTFTCPY......G:111
Athila4-1   59:SRKDHFPLPFIDQMLERLA.NHPYYCFLDGYSGFFQIPIHPNDQEKTTFTCPY......G:111
Athila4-3   59:SRKDHFPLPFIDQMLERLA.NHPYYCFLDGYSGFFQIPIHPNDQEKTTFTCPY......G:111
Athila4-4   59:SRKDHFPLPFIDQMLERLA.NHPYYCFLDGYNGFFQIPIHPNDQEKTTFTCPY......G:111
Athila4-2   59:SRKDHFPLPFIDQMLERLA.KYPYYCFLDGYSGFFQIPIHPNDQEKTTFRCPY......G:111
```

Figure 1

```
                    Domain 2                    Domain 3                  Domain 4
                 . . . .70 . . .|.80 . . . .90 . . .100 . . .110 .|. . 120
                 ****           ** *|*         *******              ****|
t13e11        58:SRKDHFPLPFIDQMLERLA.NHPYYCFFDEYSGFFQIPTHPNDQEKTTFTCPY......G:110
f7b19         58:SKKDHFPLPFIDQMLERLA.NHPYYCFLDGYSGFFQIPIHPTDQZKTTFTCPY......G:109
t13d4         59:TRKDHFPLPFIDQMLERLA.NHVYYCFLDGYSGFFQIATHPNDQEKTTFTCPY......G:111
t24g23Ath9-1  59:TRKDHLPLPFIDQMLERLA.NHVYYCFLDGYSGFFQIATHPNDQEKTTFNCPY......G:111
t16i21        59:TRKDHFPLPFIDQMLERLA.NHVYYCFLDGYSGFFQIAIHPNDQEKTTFTCPN......G:111
La8-1         59:SRKDHFPSPFIDQMLERLA.NHTHYCFLDGYSGFFQIPIHPNDQEKTTFTCPC......G:111
La9-6         59:SRKDHFPLPFIDQMLERLA.NHTHYCFLDGYSGFFQIPIHPNDQEKTTFTCPC......G:111
Athila1-1     59:SRKDHFPLPFIDQMLERLA.NHTHYCFLDGYSGFFQIPIHPNDQEKTTFTCPY......G:111
La9-7         59:SRKDQFPLLFIDQMLERLA.NHTHYCFLGGYSGFFQIPIHPNDQEKTTFTCPY......G:111
La9-9         59:SRKDQFPLLFIDQMLERLA.NHTHYCFLDGYSGFFQIPIHPNDQEETTFTCPY......G:111
hau8-3        59:TRKDHFPLPFIDHMLERLA.NHKYYCFLDGYSGFFQIPIHPDDQEKZTFTCPY......G:110
f23m2Ath5-2   59:TRKDHFPLPFIDHMLERLA.NHKYYCFLDGYSGFFQILIHPDDQEKZTFTCPY......G:110
t17a11        58:TKKDHFALPFIDQMLERLE.NHKYYCFLDGYSGFFQIPIHPDDQEK...........:102
La9-5         58:TRKDHFSVPFIDQMLERLA.NHKYYFLDGYSGFFZIPIHPDDZEKMTFTCPY......G:108
bar7          58:TRKDHYPLPFIDQMLERLS.KHTHFLFLDGYTGFSQIPVAQFDQEKTTLTZHF......G:109
bar2-12       59:TRKEHYPLPFSDQMLERLS.KHTHFCFLDGYSSFSQILVAQSDQEKTTFTYPF......G:111
bar2-19       59:TRKDHYPLPFIDHMLERLS.KLTHFCFLDGYSSFSQIPVAQSDQEKTTFTCPF......G:111
bar2-4        59:TRKDHYPLPFIDQMRERLS.KHTHFCFLNGYFGFSQIPVAQSDQEKTTFTCPF......G:111
Baggy2        59:TRKDHYPLPFIDKMLERLS.KNTHFCFLDGYSGFSQISAAQSDQEKTTFTCPF......G:111
rye3-4        59:TKKDHYPLPFIDQMLDRLS.KHTHFCFLDGYYGFSQIPVSKGDQEKTTFTCPF......G:111
rye4-4        59:TKKDHYPLPFIDQMLERLS.KHTHFFFLDGYSGFSQIPVSKGDQEKTTFTCTF......G:111
rye5-2        59:TMKDHYPLPFIDQMPDRLS.KHTHFCFLDGYSGFSQIPLSKGDQEKTTFTCPF......G:111
rye5-4        59:TKKDQYPLPFIDQMLERLS.KHTHFCFLDGYSSFSQIPMSKGDKEKTTFTCPF......G:111
wheat3-1      59:TKRDHYPLPFIDQILERLC.KHTHYCFQDGYPGFSQIPVSAKDQSKTTFTCPF......G:111
wheat8-5      59:TKKDHYPLPFIDQMLERLC.KHTHYCFLDGYSGFSQIPVSAKDQSKTTFTCPF......G:111
wheat8-2      59:TKKDHYPLPFIDQMLERLC.KHTHYCFLDGYSGFSQIPVSAKDQSKTTFTCPF......G:111
wheat5-3      59:TKKYHYPLPFIDQMLERLS.KHTHYCFLDGYSGFSQIPVSAKDQSKTTFTCPF......G:111
wheat8-11     59:TKKDHYPLPLIDQILERLS.KHTHFCFLDGYTGFSQIPVSVKDQSKTTFTCPF......G:111
oat6-1        59:TKKDHYPLPFIDQMLERFS.KKTHFCFLDGYSGFSQIVVKQQDQEKTTFTCPY......G:111
oat6-8        59:TKKDHYPLPFIDQMLERLS.KKTHFCFLDGYSSFSQIAVKQQDQEKTTFTCPY......G:111
oat6-7        59:TRKDHYPLPFIDQMLERLS.KKTHFCFLDGHSGFSQIVVKAQDQEKTTFTCPY......G:111
rice1         59:TKKDHFPLPFIDEMLERLA.NHSFFCFLDGYSGYHQIPIHPDDQEKTTFTCPY......G:111
RiceAthila    59:TKKNHFPLPFVDEMLERLA.NHSFFCFLDGYSGYHQIPIHPENZSKTTFTCPY......G:110
rice2-10      59:TKKDHFPLPFIVEMLERLA.NHSFFCFLDGYFGYHQIPIHPEDZSKTTFTCPY......G:110
rice5-2       58:TKKDHFPLPFIDEMLERLA.NHSFFRFLDGYSRYDQIPIHPEDQSKTTFTCSY......D:110
rice2-17      58:TKEDHFPLPFIDEMLERMT.NHSFFCFLDGYSGYHQIPIRPEDQSKTTFTCPY......G:110
sorg4-3       59:TKKDNFPLPFIDEMLERLA.NHSFFCFLDGYSGYHQIPIHPDDQEKTTFTCPY......G:111
sorg5-6       59:TKKDHFPLPFIDEMLEWLA.NHSFFCFLDGYSGYHQIPIHPDDQEKTTFTCPY......Z:110
sorg5-4       59:TRKDHFPLPFIDEMLZWLT.NHSFFCFLEGYSRYHQIPIHHDDQSKTTFTZPY......G:109
sorg5-2       59:TRKDHFPLPFIDEMLERLA.NHSFFCFLDGYSGYHQIPIHPDDQSKTTFTCPY......G:111
sorg5-8       59:TREDHFPLPFIDEMLEWLA.NHSFFCFLDGYZGYHQIPIHPDDQSKTTFTCPY......G:110
sorg5-5       59:TRKDHFPLPFIDEMLERLA.NHSFFCFLDGZLGYHQIPINLDDQSKTTFPCPH......G:110
Tat4-1        41:CPKDSFPLPHIDRMVEATT.GNELLSFMDAFSGYNQIPMHKDDQEKTSFITDR......G: 93
f26h6         41:CPKDSFPLPHIDRLVEATA.GNELLSFMDAFSGYNQILMHQNDREKTVFITDQ......G: 93
Rire2         41:CPKDPFGLPRIDQVVDSTA.GCELLSFLDCYSGYHQIRLKESDCLKTSFITPF......G: 93
Grand1-4      42:CPKDPFGLPRIDQVVDSTA.GCSMLSFLDCYSWYHQISLAKEDEEKTAFITPF......G: 94
Vulgar        41:SPKDHFPLPRIDQIVDSTA.GCERLSFLDAYSGYHQIRLYGPDELKTAFITPF......G: 93
Cinful        41:CPKDEFPLPRIDSLVDATA.SSELMSLLDCYSGYHQIWMKREDEPKTSFITPS......G: 93
Mag           42:LAIDRFPVPKMEDLFSNLS.GNKFFTKLDLSQAYNQIVLSERSSEYTVINTHR......G: 94
SURL          42:IKREHYQLPSRAEITAHFA.GAKYFSKLDASSGFWQIQLDDESSKLCTFITPY......G: 94
Mdg1          46:LLADKFPLPRIEDILDQLG.RAKYFSCLDLMSGFHQIELDERSRNITSFSTST......G: 98
412           46:LLADKFPLPRIDDILDQLG.RAKYFSCLDLMSGFHQIELDEGSRDITSFSTSN......G: 98
Cft-1         40:TIKNRYPLPNIEEAQDRLT.GSDWYTKIDLRDAFYAIRMAEGEEWKTAFRTRY......G: 92
boty          40:TKKDRYPLPLATELRDRLG.GRTIFTKMDLRNGYHLIRMKEGEEWKTAFRTKY......G: 92
Skippy        41:TEKDRTSLPLITELKDRLF.GKKWFTALDLKSAYNLIRIKEADEWKTAFRTKY......G: 93
Maggy         40:TVKDRYPLPLVRETLNNLA.GMKFFSKIDIVSAFNNIRIKKGEEYLTAFRTRF......G: 92
Grasshopper   40:TMQDRYPLPLIKETIRSLT.GARWFTKVDVRAAFHKLRIAEGDEHLTAFRTRF......G: 92
Tf1           40:VKPNIYPLPLIEQLLAKIQ.GSTIFTKLDLKSAYHLIRVRKGDEHKLAFRCPR......G: 92
Tma1-1        40:TVKNKYPLPRIDELLDQLT.GATCFSKIDLTSGYHQIKIAEADVRKTAFRTTY......G: 92
Tma3-1        40:TVKNKYPLPRIDELLDQLR.GATCFSKIDLTSDYHQIPIAEADVKPKTAFRTRY.....G: 92
Del1          39:TVKNKYPLPRIDDLFDQLN.GAZYFSKIDLRFRYHQLRIRAZDIPKTAFRTRY......G: 89
```

Figure 1

|  | Domain 2 | Domain 3 | Domain 4 |
|---|---|---|---|

```
                . . . .70 . . .|.80 . . .90 . . .100 . . .110 .|. .120
                ****            ****|*      *******             ****|
Reina      40: TVKNRYPMPVFDEIVDELC.GTKIFTKLDHRSGYHQIRIKEGDEFKTAFQTHN......G: 92
IFG7       40: TIKDKFPIPVIDELLDELH.GSIYFTKLDLRSGYHQIRMKTEDIPKTTERTHE......G: 92
Ty3        40: TISDPFPLPRIDNLLSRIG.NAQIFTTLDLHSGYHQIPMEPKDRYKTAFVTPS......G: 92
Tom        45: TIPDRFPIPNMDEILGKLG.KCQYFTTIDLARGFHQIEMDSESIQKTAFSTKR......G: 97
297        45: TIPDRYPIPNMDEILGKLG.KCQYFTTIDLAKGFHQIEMDEESISKTAFSTKS......G: 97
17.6       45: TVGDRHPIPNMDEILGKLG.RCNYFTTIDLAKGFHQIEMDPESVSKTAFSTKH......G: 97
TED        45: TIDDKYPIPNISDVLDKLG.KCQYFTTLDLASGFYQVEMDPQDISKTAFNVEH......G: 97
Gypsy      46: TIPDRYPMPSIPMILANLG.KAKFFTTLDLKSGYHQIYLAEHDREKTSFSVNG......G: 98
Yoyo       45: TIADRYPIPEINEVLSHLG.SNTFFSVIDLKSGFHQIPLKNSDIEKTAFSINN......E: 97
Ulysses    39: TVKDAYPLPCIEGILSRST.RLILSLASTLSSRSGNRDGGEEQGVYGVYCTRR......P: 91
Woot       40: MIADCESPPAADELLRRFH.EIRYMSTIDLRSSYWQIPLSPESRQYTAFLYNG......R: 92
Cer1       40: VKNNAHPLPNIEATLQSLA.GKKLYTVFDMIAGFWQIPLDEKSKEITAFAIGS......E: 92
HIV1       40: TQDFW.EVQLGIPHPAGLK.KKKSVTVLDVGDAYFSVPLDEDFRKYTAFTIPSINNETPG: 97
RSV        40: LVPFG.AVQQGAPVLSALP.RGWPLMVLDLKDCFFSIPLAEQDREAFAFTLPSVNNQAPA: 97
MuMLV      41: VEDIHPTVPNPYNLLSGLPPSHQWYTVLDLKDAFFCLRLHPTSQPLFAFEWRDPEMGISG:100
```

Figure 1

```
                      Domain 4                              Domain 5         Domain 6
              . . . 130 . . . 140 . . . 150 . . .    160 . . . 170 . . . 180
                      ******                              *****
will8-2    110:.VFAYRQMSFELCNAPTTFZRFMMAIFADLVEK....CIEVFMNDFSIFGS.SFYHCLSN:163
hark5      111:.VFAYRRMPFELCNAPATFZRHMLAIFANMVEK....CIEVFIDDFSVFGP.SFVCCLTN:164
Calypso7-1 111:.VFAYRRMPFNLCNGPATFQRCMMAIFADMVEK....YIEVFMDDFFVFGS.SFDCCLAN:165
will2      111:.VFAYRRMPFGLCNAPATFQRCMMTIFSDMVEK....ZIEVFMDDFSIFGP.SFEGCLSN:164
hark5-1    111:.VFAYRRMPFGLCNAPATFQRCMMTIFSDMVEK....ZIEVFMDDVSIFGP.SFEGCLSN:164
L859-6     111:.VFAYQCMPFGLCNAPATFQRCMMAIFSDMVEI....CIEVFMDDFSIFGP.SFEGCLSN:165
Calypso4-1 108:.VFAYRHMPFGLCNAPATFQRCIMAIFSDMVEK....CIELFMDDFSIFGP.SFKGCLLN:162
hark2      111:.VFAYKRMHFGLCNAPATTCQRCMMTIFSGIVEK....CTELFMDDFSIFGP.SFEGYLSN:165
Calypso5-1 110:.VFAYRCMPFGLCNALATFQRCMMAIFSDMVEK....CIEVFMDDFSVFGP.SFDGCLSN:164
will3      111:.VFAYRMPFGLCNASTTFQRCMMAIFDDMVEK....CIEVFMDDFSFFGA.SFGNCLAN:165
L859-3     110:.VFAYRRMSFGLCNAPTTFQRCMMAIFADMVKK....CIEVFMDDFSVFGA.SFENCLAN:164
Calypso6-1 101:.VFAYRRMSFGLCNVLATFQRCMMAIFAVMVEK....CFEVFMDDFSVFGA.SFENCLAN:155
will8-3    110:.VFAYRRMSFRLCNAPATFQRCMLAIFSDMVEK....SIEVFMDEFSIFGP.LFDSCLRN:164
L858-2     110:.VFAYRRMSFRLCNAPATFQRCVLAIFSDMVEK....SIEVFMDEFSIFGP.LFDSCLRN:164
Calypso3-1 111:.VFAYRRMSFGLCNVPATFQRCMLTIFSDMVEK....SIEVFMDDFSVFGP.SFDSCLRN:165
Calypso1-1 110:.VFAYRRMSFGLCNALAIFQRCMLAIFSDMVEK....SIEVFMDDFWIFGP.SFDNYLRN:164
L852       110:.VFAYRRMPFGLCNAPATFQRCMLAIFSDMVEK....NIEVFMDDFSVFGP.SFDSCLRN:164
Calypso2-1 111:.VFAYRRMPFGLCNAPATFQRFMLAIFSDMVZK....SIEVFMDDFWVFGP.SFNS.LRN:163
L859-2     111:.VFAYRRIPFGLCNAPTTFQMCMLAIFADIVEK....SIEVFMDDFSVFVP.SLESCLKK:165
Cyclops-2  110:.VFAYRKMSFGLCNAPTTFQRCVQAIFADLNEK....TMEVFMDDFSVFGV.SFSLCLAN:164
Cyclops-1  110:.VFAYRKMSFGLCNAPTTFQRCVQAIFADLIEK....TMEVFMDDFSVFGG.SFSLCLAN:164
pea9-1     111:.VFAYRKMPFGLCNAPATFQRCVQAIFVDLIEK....TMEVFMDDFSVFGG.SFSLCLAN:165
pea8-1     111:.VFAYRKMPFGLCNAPATFQRCVLAIFADLIEK....TMDVFMDDFSVFGG.TFSLCLAN:165
favabean1  110:.IFSYRRIPFGLCNAPATFQRCMQSIFADMLEK....YMEVFMDDFSVFGK.SFDNCLSN:164
fababean2  108:.IFSYRRIPFWLC.MPCYLSKMHASLFADMLEK....YMEVFMDDFSVFGK.SFDNCLNN:161
pea1       111:.TFAYRRMPFGLCNAPATFQRCMTSIFSDMLEK....YMKVFMDDFSVFGS.SFDNCLAN:165
tob2-2     111:.TFVFSRMPFRLCNAPATFQRCMMAIFSYMVKD....IFEVFMDDFSVVGH.SFDECLKN:165
tob5-3     111:.TFVFSRMSFGLCNAPTTFZRCMMAIFTYMVED....ILEVFMDDFSVVGD.ZFDECLKN:163
tob4-1     111:.TFAFSRMPFGLCNAPTTFZRYMMAIFTDMVED....ILEVFMDDFSVVGD.SFDECLNN:164
tob1       108:.TFAYKRMPFGLCNALANFYRCMMAIFTDMVKD....YLKVFMDDFSMVGD.SFDDCLEN:162
tom4-10    110:.TFAFRRMSFGLCNAPATFQRWMMSIFSDMMED....TIEVFMDDFSVVGD.SFERCLSN:164
tom10-16   109:.TFALKRMSFGLCNAPATFHRCKMLIFFDMVDD....TIDAFMDDFSLVGE.SFERCLNH:163
tom4-4     106:.TYAFKKIPFGLCZNASATFQZCMMAIFHDMVED....FVEIFMNDFSVFGD.SFDMCLEN:158
pot8-8     109:.TYAFKRMSFGLCNAPTTFQRCIRAIFHDMVED....FVEIFMDDFSVFGZ.SFERCLEN:162
pot8-3     110:.TYAFKZLPFGLCNAPATFQRZMMAIFHDMVED....FVEIFMDDFSVFRE.SFDRCLEN:162
pot8-4     111:.TYVSKRMSFGLCNAPSIFQRCMMAIFHDKVED....FMEIFMDDFSVFGE.SFDRCLEN:165
pot8-5     109:.TYAFKRMSFGPCNAPTTFQRCMTAIFHDMVKY....FVEIFMDEFLVFGE.SFDTCLEY:163
tom10-4    109:.TYAFKRMPFGLCNALSNFQRCMMTIFHDMVEY....FEDIFMDDFLVFWE.SFDRCLEN:163
pot8-10    110:.TYAFKRLPFGLCNAPTLFQRCMMAIFHDMVED....FVKVYMDDFSVFGE.SFELCLSN:164
pot5-1     109:.TYAFKHMPFGLCNALATFQRCMLAIFHDMVED....FVEVFMDDFLVFGE.SFELCLTN:163
syc4-2     111:.TFAYRHMPFGLCNAPTTFZRCMVSIFSDYIEN....IIEVFMDDFTVYGD.SFDNCLHN:164
syc4-7     110:.TFSYRCMPFGLCNAPATFQRCMVSIFSDYIEN....IIEVFMDDFIVYED.SFDNCLHN:164
syc2-3     107:.TFAYRCMPFGLCNAPTTFQRCMVSIFSYYIEN....IIEVFMDDFIVYGD.SFNNFLHN:161
cot5-3     110:.TFSYRRMPFGLCNAPASFHRCMVSIFSDYVDK....IIEVFMDDFTVYGE.SFEVSLTN:164
cot8-6     110:.MFAYRRMSFRLCNAPTMFQRCMISIFFDYVKK....IIEVFMDEFTVYSE.SFEVYLSN:164
cot8-7     111:.TFAYRRMSFGLCNAPATFQRCMVSIFSDYVEK....IIEFFMDDFTVYGN.SFNECLDN:165
Diaspora   111:.TFAYRRMSFGLCNAPGTFQRCMISIFSDFLEN....CIEEFMDDFTVYGS.SFDGCLDS:165
TfcII#1    111:.TFAYRRMPFGLCNAPATFQRCMVSIFQDMNER....YLEVFMDDFSVHGD.SFQTCLDN:165
TfcII#2    111:.TFAYRRMPFGLCNAPATFQRCMVSIFQDMNER....YLEVFMDDFSVHGD.SFQTCLDN:165
TfcII#3    110:.TFAYRRMPFGLCNAPATFQRCMVSIFQDMNER....YLEVFMDDFSVHGD.SFQTCLDN:164
syc4-3     107:.TFAYRRMSFGLCNALATFZRCMLSIFSDMVEH....FLEVFMDDFFVFGN.SFDDCLHN:160
hau7-2     111:.TFAYKRMPFGLCNAPATFQRCMTSISSDLIEE....MVEVFMDDFSVYGS.SFSSCLLN:165
Athila6-1  111:.TFAYKRMPFGLCNAPATFQRCMTSIFSDLIEE....MVEVFMDDFSVYGS.SFSSCLLN:165
f18p14     111:.TFAYKRMPFGLCNAPATFQRYMTSIFSDLIKE....MVEVFMNDFSVYGS.SFSSCLLN:165
hau8-4     111:.TFAYKRMPFGLCNAPATFQRCMTSIFSDLIEE....MVEVFMDDFSVYGP.SFSSCLLN:165
Athila4-1  111:.TFAYKRMPFGLCNAPATFQRCMTSIFSDLIKE....MVEVFMDDFSVYGP.SFSSCLLN:165
Athila4-3  111:.TFAYKRMPFGLCNAPATFQRCMTSIFSDLIKE....MVEVFMDDFSVYGP.SFSSCLLN:165
Athila4-4  111:.TFAYKRMPFGLCNAPATFQRCMTSIFSDLIEE....MVEVFMDDFSVYGP.SFSSCLLN:165
Athila4-2  111:.TFAYKRMPFGLCNAPATFRRCMTSIFSDLIEE....MVEVFMDDFSVYGP.SFSSCLLN:165
```

Figure 1

|  | | Domain 4 | | Domain 5 | Domain 6 |
|---|---|---|---|---|---|
| | | . . . 130 . . . 140 . . . 150 . . . | | 160 . . . 170 . . | 180 |
| | | ******* | | ***** | |

```
t13e11       110:..TFAYKRMAFGLCNAPATFQRCMTSIFSDLIEE....IVEVFMDDFSGYSP.SFSSCLLN:164
f7b19        109:..TFAYKRMPFGLCNNPTTFQRCMTFIFLDLIEE....IVEVFMDDFSVYGP.SFSSCLLN:163
t13d4        111:..TFAYKRMPFGLCNAPGTFQRSMTSIFSDFIEE....IMEVFMDDFSVYGS.SFSSCLLN:165
t24g23At9-   1111:..TFAYKRMPFGLCNAPGTFQRSMTSIFSDFIEE....IMEVFMDDFSVYGS.SFSSCLLN:165
t16i21       111:..TFAYKRMSFGLCNAPGTFQRSMTSIFSDFIEE....IMEVFMDDF....S.GFSSCLLN:161
La8-1        111:..TFAYRRMPFGLCNAPATFQRCMMSIFSDLIEN....VVEVLMDDFSVYGD.SFASCLSN:165
La9-6        111:..TFAYRRMPFGLCNAPATFQRCMMSIFSDLIEN....VVEVLMDDFSVYGD.SFASCLSN:165
Athila1-1    111:..TFAYRRMPFGLCNAPATFQRCMMSIFSDLIEN....VVEVFMDDFSVYGD.SFASCLSN:165
La9-7        111:..TFAYRRMPFGLCNAPATFQRCMMSIFSDLIEN....VVKVFMDDFSVYGD.SFASCLSN:165
La9-9        111:..TFAYRRMPFGLCNAPATFQRCMMSIFSDLIEN....VVKVFMDDFSVYGD.SFASCLSN:165
hau8-3       110:..TVAYRRMPFGLCNAPATFQRGMMSIFTDMIED....IMEVFMDDFSVYGS.LFEDCLEN:164
f23m2Ath5-   2110:..TVAYRRMPFGLCNAPATFQRGMMSIFTDMIED....IMEVFMDDFSVYGS.LFEDCLEN:164
t17a11       102:...TTYQRMPFSLCNAPATFQRGMMSIFTDMIED....IMEVFVDDFSVYGS.SFEDCLEN:155
La9-5        108:..TFAYRRMPFGLCNAPTTFQIGMMSIFTNMIED....IMEVFMDEFSVYGS.SFEDSLEN:162
bar7         109:..TFAYIRMPFGLCNAPATFQRCMMAIFSDFCEK....IVNVFMDNFSVYGC.SFDDCLNN:163
bar2-12      111:..TFAYRRMPFGLCNAPATFQRCMMAIFSDFCEK....FVEVFMDDFSVYGS.SFDDCLNN:165
bar2-19      111:..TFAYRRMPFGLCNAPATFQRCMMAIFSNFCEN....IVEVFMDDFSVYGS.SFDDCLSN:165
bar2-4       111:..TFAYRRMTFGLCNAPASFQRCMMAIFPDFCEK....IVEVFMDDFSIYGS.SFDDCLSN:165
Baggy2       111:..TFAYRRMPFGLCNAPATFQRCMMAISSDFCEK....IIEVFMDDFSVYGS.SFDDYLSN:165
rye3-4       111:..TFAYRRMPFGLCNAPATFQRCMMAILSDFZEK....IVEVFMDDFSVYGT.SFDDYLSN:164
rye4-4       111:..TFAYRRMPFGLCNAPATFQRCMMAIFSDFCEK....IVEVFMDDFSVYGT.SFDDCLSN:165
rye5-2       111:..TFAYRGMPFGLCNAPATFQRCMIVIFSVFFEK....IVEVFMDDFSVYGT.SFDDCLSN:165
rye5-4       111:..TFAYRRMPFGLCNASATFQTCMMAILYDFCER....IVDVFMDDFCIYET.SFDDCLSN:165
wheat3-1     111:..TFAYRCMPFGLCNAPATFQRCMMAIFSDFCEK....ICEVFMDDFSVYGS.SFDDCLSN:165
wheat8-5     111:..TFAYRRMPFGLCNAPSTFQRCMMAIFSDFCEK....ICEVFMDEFSVYGS.SFDDCLSN:165
wheat8-2     111:..TFGYRRMPFDLCNAPATFQICMMAIFSDFCEK....ICEVFMDDFSVYGS.SYDDCLSN:165
wheat5-3     111:..TFAYRRMPFGLCNAPATFQRYMMAILSDFCEK....ICEVFMDDSSIYGS.SFDDCLSN:165
wheat8-11    111:..TFAYRLMPFGLCNAPTSFQRCMMAIFSVFCEN....ICEVFMDDFSVYGS.SFDDCLSN:165
oat6-1       111:..TYAYRCMPFGLCNAPSTFLRCMSAIFHGFCEE....IVEVFMDDFSVYGT.SFDNCLHN:165
oat6-8       111:..TFAYRRMPIGLCNAPATFQRCMSAIFHGFCEE....IVEVFMDDFSVYGT.SFDNCLHN:165
oat6-7       111:..TYDYRRMPFGLCNAPATFQRCMSAIFHGFCEE....IVEVFMDDFSVYGT.SFDNCLHN:165
rice1        111:..TYAYRRMPFGLCNTPASFQRCMMSIFSDMIED....IMEVFMDDFSVYGK.TLGHCLQN:165
RiceAthila   110:..TYAYCRMSFGLCNAPASFQRCMMSIFSDMIED....IMEVFMNDFSVYRK.TFGHCLQN:164
rice2-10     110:..TYAYHRMSFGLCNAPASFQRCMMSIFSDMIED....IMEVFMDDFSVYGK.TFGHCLQN:164
rice5-2      110:..TYAYRRMSFGLCNAPASFQRCMMSIFSDMIKD....IMEVFMHDFSIYGK.TSGHCLQN:164
rice2-17     110:..TYAYRRMSFGLCNAPASFQRCMLSIFSDMIED....IMKVFMDDFSVYGK.TFGHCLZN:163
sorg4-3      111:..TYAZRRMSFGLCNAPASFQRCMMSIFSDMIEK....IMEVFMDDFTVYGK.TFDHCLEN:164
sorg5-6      110:..TYAYZRMSFGLCNALASFQRCMMSIFSDMIEK....IMEVFMDDFTVYGK.TFDHCLEN:163
sorg5-4      109:..TYAYRRMSFRLCNAPASFQRCMMSIFSNMIEK....IMEVFTDDFTVYGK.TFDDCLEN:163
sorg5-2      111:..TYAYRRMSFGLCNAPASFQRCMMSIFSDMIEE....IMEVFMDDFSVYGK.AFDSCLEN:165
sorg5-8      110:..TYAYRRMSFGLCNALASFQRCMMSIFSDMIEE....IMEVFMDDFSVYGK.TFDSCLKN:164
sorg5-5      110:..TYAYRRMSFGLCNAPASFQRCMMSVFSNMIEE....IMEIFMDDFSVYGK.TFDSCLEN:164
Tat4-1       93:..TYCYKVMPFGLKNAGARYQRLVNQMFAPQLGK....TMEVYIDDMLVKSK.KSADHIEH:147
f26h6        93:..TYCYKVMPFGLKNAGATYPRLVNQMFTDQLDH....SMEVYIDDMLVKSL.RAEEHITH:147
Rire2        93:..AYCYVTMPFGLKNAGATYQRMIQRCESTQIGR....NVEAYVDDVVVKTK.QKDDLISD:147
Grand1-4     94:..AFCYTSMSFGLKNGRATYQRAIQTCLANHWGK....RVEAYVDDVVIKIE.NSENFIED:148
Vulgar       93:..CFCYITMPFGLKNAGATFMRMIQKCLLDQIGR....NVEAYMDDIVVKSR.KGSNLLTD:147
Cinful       93:..TYCYLRMPEGLKNAGGSFSRMTAKVLQSQIGR....NVLTYVDDIIVKST.KQENHIAD:147
Mag          94:..LFKYSRLVYGLASSPGIFQKLMVNMFKNVPN.....VVVFYDDILIRNQ.DLDSHLKS:146
SURL         94:..RYKFLRLPFGICSAPEVYHKIVHQMFAHIPG....VNTMMDDVIVWGT.TQQEHDNR:146
Mdg1         98:..AYRYTRLPFGLKIAPNSFQRMMTLAFSGLTPS....QAFLYMDDLVVIGC.SEKHMLKN:152
412          98:..SYRFTRLPFGLKIAPNSFQRMMTIAFSGIEPS....QAFLYMDDLIVIGC.SEKHMLKN:152
Cft-1        92:..LYEFLVMPMGLTNAPASCQDLVNETLRDLLDV....CVVAYMDDILVYTKGSLQEHTKQ:147
boty         92:..LYEYQVMPFGLTNAPATFMRLMNNVLSQYLDT....CCICYLDDILVYSN.NKVQHIKD:146
Skippy       93:..LFEYLVMPFGLTNAPAVFQRMITNVLREYLDI....FVVCYLDDILIFSD.TEEEHTEH:147
Maggy        92:..LYESLVMPFGLTGAPATFQRYINDSLREYLDV....FCTAYLDDILIYSR.TRTEHEEH:146
Grasshopper  92:..LFEWLVCPFGLAGAPATFQRYVNGVLGDTLGD....YASAYLDDILIYSSGSKSDHWSK:147
Tf1          92:..VFEYLVMPYGISTAPAHFQYFINTILGEAKES....HVVCYMDDILIHSK.SESEHVKH:146
Tma1-1       92:..HFEFVVMPFGLTNAPAAFMRLMNSVFQEFLDE....FVIIFIDDILVYSK.SPEEHEVH:146
Tma3-1       92:..HFEFVVMPFGLTNAPAAFMRLMNSVFQEFLDE....FVIIFIDDILVYSK.SPEEHEVH:146
Del1         89:..HYEFLVMPFGLTNVPTAFMNLMNRVFREYLDK....FIVVEVDYVLIYSR.TQKDHEHH:143
```

Figure 1 –

```
                       Domain 4                           Domain 5        Domain 6
              . . . 130 . . . 140 . . . 150 . . . 160 . . . 170 . . . 180
                    * * * * * *                      * * * * *
Reina      92:.HYEYRVMPFGLTGAPATFQDFMNKILTPFLRK....CVVVFLDDVLIYSR.DMEEHVLQ:146
IFG7       92:.HYEFFVMPFGLTNTPSTFQGLMNSIFKPFLRK....FVLVFFDDILIYNK.SWKDHVEH:146
Ty3        92:.KYEYTVMPFGLVNAPSTFARYMADTFRDLR......FVNVYLDDILIFSE.SPEEHWKH:144
Tom        97:.HYEYVRMPFGLRNAPATFQRCMNNILRPLINK....HCLVYLDDMIIFST.SLDEHLNS:151
297        97:.HYEYLRMPFGLRNAPATFQRCMNNILRPLLNK....HCLVYLDDIIIFST.SLTEHLNS:151
17.6       97:.HYEYLRMPFGLKNAPATFQRCMNDILRPLLNK....HCLVYLDDIIVFST.SLDEHLQS:151
TED        97:.HEEFLRMPMGLKNSPSTFQRVMDNVLRGLQNN....ICLVYLDDIIVYST.SLQEHLEN:151
Gypsy      98:.KYEFCRLPFGLRNASSIFQRALDDVLREQIGK....ICYVYVDDVIIFSE.NESDHVRH:152
Yoyo       97:.KYEFTRLPFGLKNAPSIFQRTLDDILRDYIGQ....CCYVYIDDITIFSR.NEKEHSTH:151
Ulysses    91:.LYQFRHMPFGLCNAAQHF.EAHDKVIPANLRS....NVFVYLDDLLIISA.DFPTHLKY:144
Woot       92:.SYTYQVLPFGLKTAVGSFSRAMDVVLGTEVRE....FVVNYIDDLLVASE.TLNEHLEH:146
Cerl       92:.LFEWNVLPFGLVISPALFQGTMEEIIGDLLGV....CAFVYVDDLLIASK.DMEQHLQD:146
HIV1       98:IRYQYNVLPQGWKGSPAIFQSSMTKILEPFRKQNPDIVIYQYMDDLYVGSDLEIGQHRTK:157
RSV        98:RRFQWKVLPQGMTCSPTICQLVVGQVLEPLRLKHPSLCMLHYMDDLLLAASSHDGLEAAG:157
MuMLV     100:.QLTWTRLPQGFKNSPTLFDEALHRDLADFRIQHPDLILLQYVDDLLLAATSELDCQQGT:159
```

Figure 1

|  |  | Domain 6 | Domain 7 |  |
|---|---|---|---|---|
|  |  | ...190....200.| |. .210 . .| |  |
|  |  | **********| * ******| |  |
| will8-2 | 164: | LELVLQRCAETNLLMNWEKCHFMVQEGIVLGHKI | :197 |
| hark5 | 165: | LELVLKYCEETNLVLNWEKCHFMVQEGIMLGHKI | :198 |
| Calypso7-1 | 166: | LERILQZCEETNLVLNWENFHFMVQERIVLGHKI | :198 |
| will2 | 165: | LERVLKRREESKLVLNWEKCHFMVQEGIVLGHKI | :198 |
| hark5-1 | 165: | LERVLKRREESKLVLNWEKCHFMVQEGIVLGHKI | :198 |
| L859-6 | 166: | LEKVLKRCEESNLVLNWKKCHFMVQEGIMLGHKI | :199 |
| Calypso4-1 | 163: | LERVLQRCEESNLVLNWEKFHFMVQEGIVLGHKI | :196 |
| hark2 | 166: | LERVLQRCEESNLVLNWEKCHFMVQEGIVLGHKI | :199 |
| Calypso5-1 | 165: | LERVFZRCEESNLVLNWEKCHFMVQEGIVLGHKI | :197 |
| will3 | 166: | LEKVLQRCEKSNLVLNWEKCHFMVQEGIVLGHKI | :199 |
| L859-3 | 165: | LEKVLQRYEESNLVLNWEKCHFMVQEGIMLGHKI | :198 |
| Calypso6-1 | 156: | LEKVLQRCEETNLVLNREKCNFMVQEGIVLGHKI | :189 |
| will8-3 | 165: | LEMVLQRCVZTNLVLNZEKCHFMVREGIVMGHNI | :196 |
| L858-2 | 165: | LEMVLQRCVZTNLVLNZEKCHFMVREGIVMDHNI | :196 |
| Calypso3-1 | 166: | LEMVLQRCVETNLVLNWEKCHFMVREGIVLGHKI | :199 |
| Calypso1-1 | 165: | LEMVLQRCVZTNLVLNWEKCHFMVREGIVLSHKI | :197 |
| L852 | 165: | LEMVLZRCVETNLVLNWEKCHFMVREGIVLSHKI | :197 |
| Calypso2-1 | 164: | LEMVLZSZVETNLVLNWEKCHFMVQEGIVLGHKI | :195 |
| L859-2 | 166: | LEMVLQRCVETNLVLNWEKCHFMVREGIVLGHKI | :199 |
| Cyclops-2 | 165: | LKTVLERCVKTNLVLNWZKCHFMVTEGIVLGHKV | :197 |
| Cyclops-1 | 165: | LKTVLERCVKTNLVLNWEKCHFMVTEGIVLGYKV | :198 |
| pea9-1 | 166: | LKTVLERCVKTNLVLNWEKCHFMVTEGIVLGHKV | :199 |
| pea8-1 | 166: | LKTVLERCVKTNLVLNWEKCHFMVTEGIVLGHKV | :199 |
| favabean1 | 165: | LALVLERCQESNLILNWEKCHFMVREGIVLGHKI | :198 |
| fababean2 | 162: | LSLFLRKFPEDHLILNWEKCHFIVREGIVLGHKI | :195 |
| pea1 | 166: | LSLVLQRCQETNLVLNWEKCHFMVQEGIVLGHKI | :199 |
| tob2-2 | 166: | LDRVLAHCEETNLVLMWEKCHFMVEEGINLWHKI | :199 |
| tob5-3 | 164: | LDRVLARCEEANLVLNWEKCHFMVEEGIVLSHKI | :197 |
| tob4-1 | 165: | LDRVLAHCKETNLVLNWEKCHFMVEEGIVLGHKI | :198 |
| tob1 | 163: | LDKVLARYEETNLVLNWEKCHFMIEEGIVLGHKI | :196 |
| tom4-10 | 165: | LSEVLKRCEDCNLVLNWEKCHFMVKEGIVLGHRI | :198 |
| tom10-16 | 164: | LSDVLKRCEDCNLVLNWEKCHFMVKKGIVLGHRI | :197 |
| tom4-4 | 159: | LDSVLASCEETNLFLNWEZZQFLVKEGIMLGHKV | :190 |
| pot8-8 | 163: | FDRVLAVCEETNFFLNWEKCHFLVKEGIVLGHKV | :196 |
| pot8-3 | 163: | WDRVLARCEETNLILNWKKCHFLVNEGIVLGHKV | :196 |
| pot8-4 | 166: | LDRVLARCEETNFVLNWEKCHFLVKECIVLGHKV | :199 |
| pot8-5 | 164: | LDNVLARCEETNPVLNWEKCHFLVKKGIVLGHKV | :197 |
| tom10-4 | 164: | LNRLLARCEQTNLVLNWEKCHFLVKEGNFSGHKV | :197 |
| pot8-10 | 165: | RDRVLTRCEETNLVLNWEKCHFLVREGIMLGQKI | :198 |
| pot5-1 | 164: | FDRFLARCEETNLVINZZKCHFLVREGIVLGHKI | :195 |
| syc4-2 | 165: | LTLVIQRCIETNLVLNSZKCHFMVEQGIVLGHVV | :197 |
| syc4-7 | 165: | LTLVFZRCIETNLVLNFEKCHVMVEZGIVLGHVV | :196 |
| syc2-3 | 162: | LTLVLQRCIETNLVLNYEKCHFMVEQGIVLGHVI | :195 |
| cot5-3 | 165: | LAKILERCLEFNLVLNYEKCHFMVDKGLVLGHII | :198 |
| cot8-6 | 165: | LEKFLERCLEFNLVLNYENCYLMVDKGLVLGHII | :198 |
| cot8-7 | 166: | LAKILQRCLEFNLVLNYEKCHFMVDKGLILGHIV | :199 |
| Diaspora | 166: | LEKVLNRRIETNLVLNFEKCHFMVEGIVLGHII | :199 |
| TfcII#1 | 166: | LESVLSRCVEKNLVLNWEKCHFMVQHGIVLGHII | :199 |
| TfcII#2 | 166: | LESVLSRCVEKNLVLNWEKCHFMVQHGIVLGHII | :199 |
| TfcII#3 | 165: | LESVLSRCVEKNLVLNWEKCHFMVQHGIVLGHII | :198 |
| syc4-3 | 161: | LKKVLNRCEEKNIILNZEKCHFMVSKRIVLGHIV | :193 |
| hau7-2 | 166: | LCRVLKRCEETNLVLNWEKCHFMVREGIVLGHKI | :199 |
| Athila6-1 | 166: | LCRVLKRCEETNLVLNWEKCHFMVREGIVLGHKI | :199 |
| f18p14 | 166: | LCRVLKRCEETNLVLNWEKCQFMVREGIVLGHKI | :199 |
| hau8-4 | 166: | LGRVLTRCEETNLVLNWEKCHFMVKEGIVLGHKI | :199 |
| Athila4-1 | 166: | LGRVLTRCEETNLVLNWEKCHFMVKEGIVLDHKI | :199 |
| Athila4-3 | 166: | LGRVLTRCEETNLVLNWEKCHFMVKEGIVLGHKI | :199 |
| Athila4-4 | 166: | LGRVLTRCEETNLVLNWEKCHFMVKEGIVLGHKI | :199 |
| Athila4-2 | 166: | LGRVLTRCEETNLVLNWEKCHFMVKEGIVLGHKI | :199 |

Figure 1

```
                              Domain 6              Domain 7
                     . . . 190 . . . 200 . . . 210 . .
                                 **********|*  ******
t13e11            165:LGRVLTRCKETNLVLNWEKCHFMVKEGIVLGHKI:198
f7b19             164:LGRVLTRCKETNLVHNWEKCHFMVKEGIVLVHKI:197
t13d4             166:LCRVLERCEETNLVLNWEKCHFMVQEGIVLGHKI:199
t24g23Athila9-1   166:LCRVLERCEETNLVLNWEKCHFMVQEGIVLGHKI:199
t16i21            162:LCRVLERCEETNLVLNWEKCHFMVHEGIVLGHKI:195
La8-1             166:LCRVLKRCEETNLVLNWEKCHFMVRDGIVLGHKI:199
La9-6             166:LCRVLKRCEETNLVLNWEKCHFMVRDGIVLGHKI:199
Athila1-1         166:LCRVLKRCEETNLVLNWEKCHCMVRDGIVLGHKI:199
La9-7             166:LCRVLKRCZETNLVLNWEKZHFMVRDGIVLGHKI:197
La9-9             166:LCRVLKRCZETNLVLNWEKZHFMVRDGIVLGHKI:197
hau8-3            165:HCKVLARCEEKHLVLNWEKCHFRVQDGIVLGHRI:198
f23m2Athila5-2    165:LYKVLARCEEKHLVLNWEKCHFRVQDGIVLGHRI:198
t17a11            156:LYKVLARCEEKHLVLNWEKCHFMVQNGIVLGHRI:189
La9-5             163:LCKVLARCEEEHLVFNWEKCHLMVQDGIILGHKI:196
bar7              164:VDRVLQRCKDTNVVLNWEKCHFMVNEGIVLGHKI:197
bar2-12           166:LDRVLQRCKDTNLVLNWEKCHFMVNEGIVLGHKI:199
bar2-19           166:LDRVLQRCKDTNLVLNGEKCHFMVNEGIVLGHKI:199
bar2-4            166:LDRVLQRCKDTNLFLNWKKCHFMVNDGIVLGHKF:199
Baggy2            166:LDRVLQRCKDTNLVLNWEKCHFMVNEGIVLGHKI:199
rye3-4            165:NDRVLQRCEDTNLVLNWEKCHFMVNEGIVLGQKI:198
rye4-4            166:LDRVLQRCEDTNLVLNCEKCHFMVNEGIVLGHKI:199
rye5-2            166:LDRVLQRCEDTNLVLNWEKCHFMVNEGIFLGHKI:199
rye5-4            166:LDRVLQRCEETNLVLNWEKSHFMVNEGIVLGHKI:199
wheat3-1          166:LDRVLQRCEETNLVLNWEKCHFMVNEGIVLGHKV:199
wheat8-5          166:PDRVLQRCEETNLVLNWEKCHFMVNEGIVLGHKV:199
wheat8-2          166:LNRVLQRCEETNLVLNWEKCHFMVNEGIVLGHKV:199
wheat5-3          166:LDRVLQRCEETYLVLNWEKCQFMVNEGIVLGHKV:199
wheat8-11         166:LDRVLQRCEDTSLILNWEKCHFMVNEGIVLGHKI:199
oat6-1            166:LDKVLQRCEGTNLVLNWEKCHFMVNEGIVLGHKV:199
oat6-8            166:LDKVLQRCEETNIVLNWEKFHFMVNEGIVLGHKV:199
oat6-7            166:LDKFLQRFEETNLVLNWEKCHFMVNEGIVLGHKI:199
rice1             166:LDKVLQRCQEKDLVLNWEKCHFMVCEGIVLGHRV:199
RiceAthila        165:LDKVLERYQEKDLVLNWEKCHFMVCEGIVLGHRV:198
rice2-10          165:LDKVLQRCQEKDLVLNWEKZHFMVREGIVLGHRV:197
rice5-2           165:LDKILQRCQEKDLVLNWEKCHFMVREGIVLSHRV:198
rice2-17          164:LDKVLQRCQENDLVFNWEKCHFMVREGIVLGHRV:197
sorg4-3           165:LDRVLQRCEEKHLILNWEKCHFMVQEGIVLGHKV:198
sorg5-6           164:LDRVLQRCEENHLILNWEKCHFMVQEGIVLGHKV:197
sorg5-4           164:LDKVLQLCEGKHLIVNZEKCHFMVREGIVLGHKV:196
sorg5-2           166:LDKVLQSCEEKHLILNWEKCHFMVREGIVLGHLV:199
sorg5-8           165:LDKVLQRCEEKHLVLNWEKCHFMVREGIVLGHLV:198
sorg5-5           165:LDRVLQRCEEKYLVLNWKKCHFMVREGIVLGHLV:198
Tat4-1            148:LTACFETLNKYNMKLNPAKCSFGVTSGEFLGYIV:181
f26h6             148:LRQCFQVLNRYNMKLNPSKCTFGVTSGEFLGYLV:181
Rire2             148:LEETFASIRAFRMKLNPEKCTFGVPSGKLLGFMV:181
Grand1-4          149:LQLVFNSLRRYRWKLNPEKCVFGVPAGKLLGFIV:182
Vulgar            148:LAETFANLRRYDIKLNPAKCSFGVPSGKLLDFFV:181
Cinful            148:LQETFASFRQAGLKLNPEKCVFGVKKGKFLGCLV:181
Mag               147:IKEVLDILERYGLKIKRSKCEFMVTEVRYLGFII:180
SURL              147:LREVLSIARRMNLKLNKDKCEFSVKKLTFIGDLI:180
Mdg1              153:LTDVFKLCRQHNLKLHPEKCTFFMKEVTYLGHKC:186
412               153:LTEVFGKCREYNLKLHPEKCSFFMHEVTFLGHKC:186
Cft-1             148:VQDVFERLTKSGFKTAPEKCEFHKKEVKFLGFII:181
boty              147:VSNILESLSKADLLCKPSKCEFHVTETEFLGFTV:180
Skippy            148:VHKVLKALQDANMLVEPTKSHFHQSQVTYLGHET:181
Maggy             147:LKLVLEALRKAGLYANAAKCEFFVTETKFLGLLV:180
Grasshopper       148:VTRVLDKLAAAGLNLDLDKSAFAVKEVKYLGFIV:181
Tf1               147:VKDVLQKLKNANLIINQAKCEFHQSQVKFIGYHI:180
Tma1-1            147:LRRVMEKLREEKLFAKLSKCSFWQREMGFLGHIV:180
Tma3-1            147:LRRVKEKLREQKLFAKLSKCSFWQREMGFLGHIV:180
De11              144:LRISLQLLRNNQLYAKLSKCEFWMEKVKFLGHVV:177
```

Figure 1

```
                        Domain 6           Domain 7
                 ... 190 ... 200 . . . 210 . .
                        *********** *  *****
Reina     147:VKQVFQKLKDHQLKLKLSKCRFAQTTLEFLGHII:180
IFG7      147:VDRVLQLLEEKKLYAKRSKCFFVLQEVEYLGHIV:180
Ty3       145:LDTVLERLKNENLIVKKKKCKFASEETEFLGYSI:178
Tom       152:LQLVFEKLSESNLKLQLDKCEFLKKEATFLGHIV:185
297       152:IQLVFTKLADANLKLQLDKCEFLKKEANFLGHIV:185
17.6      152:LGLVFEKLAKANLKLQLDKCEFLKQETTFLGHVL:185
TED       152:LERVFQRLRESNFKIQMDKSEFLKLETAYLGHII:185
Gypsy     153:IDTVLKCLIDANMRVSQEKTRFFKESVEYLGFIV:186
Yoyo      152:LKNIFTTLEKANMKVQLDKCKFFEKEVEFLGFIV:185
Ulysses   145:LELVAECLRNANLTIGMAKSKFLFRNLNYLGFIQ:178
Woot      147:LRQVFEKLKQARMTINLEKSNFIQKEVKFLGHIL:180
Cer1      147:VKEALTRIRKSGMKLRASKCHIAKKEVEYLGHKV:180
HIV1      158:IEELRQHLLRWGLTTPDKKHQK.EPPFLWMGYEL:190
RSV       157:.EEVISTLERAGFTISPDKVQR.EPGVQYLGYKL:189
MuMLV     159:.RALLQTLGNLGYRASAKKAQICQKQVKYLGYLL:192
```

PLANT RETROELEMENTS AND METHODS RELATED THERETO

CROSS-REFERENCE TO RELATED APPLICATIONS

This application is a continuation in part of U.S. patent application Ser. No. 09/586,106 filed on Jun. 2, 2000, now U.S. Pat. No. 6,720,479, which is a continuation in part of U.S. patent application Ser. No. 09/322,478 filed on May 28, 1999, now U.S. Pat. No. 6,331,662, which claims priority to U.S. Provisional Patent Application Ser. No. 60/087,125 filed on May 29, 1998. These are hereby incorporated by reference in their entirety for all purposes.

STATEMENT AS TO FEDERALLY SPONSORED RESEARCH

The present invention was funded, in part, by the United States Department of Agriculture, Contract Number 98-CRHF-0-6019 (USDA/CSREES Project number IOW03120). The United States Government may have certain rights in the invention.

FIELD OF THE INVENTION

The present invention provides plant retroelements and methods related to plant retroelements.

BACKGROUND OF THE INVENTION

Eukaryotic retrotransposons are divided into two distinct classes of elements based on their structures: the long terminal repeat (LTR) retrotransposons and the LINE-like or non-LTR elements. See, Doolittle et al. (1989) *Quart. Rev. Biol.* 64:1–30; and Xiong and Eickbush (1990) *EMBO J.* 9:3353–3362. These element classes are related by the fact that each must undergo reverse transcription of an RNA intermediate to replicate, and each generally encodes its own reverse transcriptase. The LTR retrotransposons replicate by a mechanism resembling that of the retroviruses. See, Boeke and Sandmeyer (1991) *Yeast transposable elements*, in *The Molecular and Cellular Biology of the Yeast Saccharomyces*, ed. Broach, Jones, and Pringle, pp. 193–261 (Cold Spring Harbor Laboratory, Cold Spring Harbor, N.Y.). LTR retrotransposons typically use a specific tRNA to prime reverse transcription, and a linear cDNA is synthesized through a series of template transfers that require redundant LTR sequences at each end of the mRNA. This process occurs within a virus-like particle formed from proteins encoded by the retrotransposon mRNA. After reverse transcription, an integration complex is organized that directs the resulting cDNA to a new site in the genome of the host cell.

Phylogenetic analyses based on reverse transcriptase amino acid sequences have separated the LTR retrotransposons into two families: the Ty3/gypsy retrotransposons (*Metaviridae*), and the Ty1/copia elements (*Pseudoviridae*). See, Boeke et al. (1998) *Metaviridae*, in *Virus Taxonomy: ICTV VIIth Report*, ed. Murphy (Springer-Verlag, NY); and Boeke et al. (1998) *Pseudoviridae*, in *Virus Taxonomy: ICTV VIIth Report*, ed. Murphy (Springer Verlag, NY); Xiong and Eickbush supra. Although distinct, Ty3/gypsy elements are more closely related to retroviruses than to Ty1/copia elements. Ty3/gypsy elements share a similar genetic organization with the retroviruses, principally in the order of integrase and reverse transcriptase in their pol genes. Reverse transcriptase precedes integrase in the Ty3/gypsy elements, and this order is reversed for the Ty1/copia elements. In addition, some Ty3/gypsy elements have an extra open reading frame (ORF) encoding a polypeptide that is similar to retroviral envelope (env) proteins, which is required for viral infectivity. The *Drosophila melanogaster* gypsy retrotransposons encode an env-like ORF and can be transmitted between cells. See, Kim et al. (1994) *Proc. Natl. Acad. Sci. USA* 91:1285–1289; and Song et al. (1994) *Genes Dev.* 8:2046–2057. The retroviruses and the Ty3/gypsy retrotransposons that encode envelope-like proteins make up two distinct lineages of infectious LTR retroelements. The Ty3/gypsy elements have been further divided into two genera, the metaviruses and the errantiviruses, the latter including all elements with env-like genes. See, Boeke et al. *Metaviridae* (supra).

Retrotransposons have been extremely successful in plants. See, e.g., Bennetzen (1996) *Trends Microbiol.* 4:347–353; and Voytas (1996) *Genetics* 142:569–578. The enormous size of many plant genomes allows a great tolerance for repetitive DNA, a substantial proportion of which appears to be composed of retrotransposons. Because of their abundance, retrotransposons have undoubtedly influenced plant gene evolution. Retrotransposons can cause mutations in coding sequences (Grandbastien et al. (1989) *Nature* 337:376–380; Hirochika et al. (1996) *Proc. Natl. Acad. Sci. USA* 93:7783–7788; and Purugganan and Wessler (1994) *Proc. Natl. Acad. Sci. USA* 91:11674–11678), and the promoter regions of some plant genes contain relics of retrotransposon insertions that contribute transcriptional regulatory sequences. See, White et al. (1994) *Proc. Natl. Acad. Sci. USA* 91:11792–11796. Retrotransposons also can generate gene duplications, as repetitive retrotransposon sequences provide substrates for unequal crossing over. Such an event is thought to have caused a zein gene duplication in maize (White et al., supra). Cellular mRNAs occasionally are reverse transcribed, and the resultant cDNA recombines into the genome to give rise to new genes or, more frequently, cDNA pseudogenes. See, Maestre et al. (1995) *EMBO J.* 14:6333–6338. The transduction of gene sequences during reverse transcription, which produced the oncogenic retroviruses, also has been documented for a plant retrotransposon (Bureau et al. (1994) *Cell* 77:479–480; and Jin and Bennetzen (1994) *Plant Cell* 6:1177 1186). A maize Bs1 insertion in Adh1 carries part of an ATPase gene and is the only known example of a retrotransposon-mediated gene transduction event.

Plant genomes can encode representatives of the two major lineages of LTR retrotransposons that have been identified in other eukaryotes. Among these are numerous examples of Ty1/copia elements (see, e.g., Konieczny et al. (1991) *Genetics* 127:801–809; Voytas and Ausubel (1988) *Nature* 336:242–244; and Voytas et al. (1990) *Genetics* 126:713–721). Also prevalent are Ty3/gypsy elements that are member of the genus *Metaviridae* (Smyth et al. 1989 *Proc. Natl. Acad. Sci. USA* 86:5015–5019; Purugganan and Wessler (1994) *Proc. Natl. Acad. Sci. USA* 91:11674–11678; and Su and Brown (1997) *Plasmid* 38:148–157). As stated above, some metaviruses, including plant metaviruses, contain an envelope gene characteristic of the retroviruses. It has been suggested that the envelope gene may be required for cell-to-cell transmission of plant metaviruses (Bennetzen, supra). The uncertainty, however, has been described with respect to Cyclops, a retroelement identified from pea: "Since genes encoding ENV functions are very heterogeneous at the sequence level and difficult to identify by homology even between retroviruses, the possibility cannot be completely excluded at the present time that the 3' ORF of Cyclops is, in fact, an env gene and, hence, Cyclops is a retrovirus or a descendant of one." Chavanne et al. (1998) *Plant Mol. Biol.* 37:363–375.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY

The present invention provides nucleic acids, as well as vectors, cells, and plants (including plant parts, seeds, and embryos) containing the nucleic acids. In particular, molecular tools are provided in the form of nucleic acids that are retroelements or that contain retroelement sequences. The invention also features methods for manipulating such nucleic acids. For example, the invention features methods to introduce nucleic acids containing retroelements or retroelement sequences into cells, especially retroelements carrying at least one agronomically significant characteristic. Specifically, the invention provides a method to transfer agronomically significant characteristics to plants, in which a helper cell line that expresses gag, pol, and env sequences is used to enable transfer of a secondary construct that carries an agronomically significant characteristic and has retroelement sequences that allow for replication and integration.

In one aspect, the invention features an isolated nucleic acid molecule containing a nucleotide sequence selected from the group consisting of: (a) a sequence having at least 60% identity to a nucleotide sequence of one or more of the even-numbered SEQ ID NOs from SEQ ID NO:42 to SEQ ID NO:164; (b) a sequence encoding a polypeptide with an amino acid sequence having at least 60% identity to an amino acid sequence of one or more of the odd-numbered SEQ ID NOs from SEQ ID NO:43 to SEQ ID NO:165; (c) a sequence that is an allelic variant of (a) or (b); and (d) a sequence that is fully complementary to a nucleotide sequence of (a), (b), or (c). The invention also features a stably transformed cell containing the isolated nucleic acid molecule. The cell can be a plant cell or a helper cell expressing gag, pol, and env genes. The invention also features a transgenic seed containing the nucleic acid molecule. The nucleic acid molecule can further contain a regulatory element operably linked to the nucleotide sequence.

In another aspect, the invention features an isolated nucleic acid molecule containing a nucleotide sequence that encodes a reverse transcriptase. The reverse transcriptase can contain any two of the following amino acid motifs: (a) Trp-Val-Ser within reverse transcriptase domain 1; (b) Thr-Val/Ile-Val/Ile-Xaa-Xaa-Xaa-Xaa-Xaa-Asp/Glu-Leu-Val/Ile (SEQ ID NO:191) between reverse transcriptase domains 1 and 2; (c) Thr/Ser-Arg/Lys-Arg/Lys-Asp-His (SEQ ID NO:192) within reverse transcriptase domain 2; (d) Met-Leu-Asp/Glu-Arg-Leu (SEQ ID NO:193) spanning the boundary between reverse transcriptase domains 2 and 3; (e) Cys-Phe-Leu-Asp-Gly-Tyr-Ser (SEQ ID NO:194) within reverse transcriptase domain 3; (f) Phe-Thr-Cys-Pro (SEQ ID NO:195) within reverse transcriptase domain 3; (g) Phe-Gly-Leu-Cys-Asn-Ala-Pro (SEQ ID NO:196) within reverse transcriptase domain 4; (h) Phe-Met-Asp-Asp-Phe (SEQ ID NO:197) within reverse transcriptase domain 5; (i) Leu-Val/Ile-Leu-Asn-Trp-Glu-Lys-Cys-His-Phe-Met-Val/Ile (SEQ ID NO:198) spanning the boundary between reverse transcriptase domains 6 and 7; and (j) Gly-Leu-Ile-Val-Leu-Gly-His (SEQ ID NO:200) within reverse transcriptase domain 7. The invention also features a stably transformed cell containing the isolated nucleic acid molecule. The stably transformed cell can be a plant cell, a helper cell expressing gag, pol, and env genes, or a prokaryotic cell. The invention also features a transgenic seed containing the nucleic acid molecule. The isolated nucleic acid molecule can further contain a regulatory element operably linked to the nucleotide sequence. Furthermore, the invention features an isolated reverse transcriptase. The isolated reverse transcriptase can contain any two of the amino acid motifs described above.

In another aspect, the invention features an Athila retrotransposon containing an open reading frame that has no substantial sequence similarity to retrotransposon gag or pol open reading frames. The open reading frame can be positioned downstream from an Athila integrase open reading frame.

In another aspect, the invention provides isolated nucleic acid molecules encoding at least a portion of a plant retroelement and containing a nucleotide sequence selected from the group consisting of:

(a) a sequence that is a plant retroelement primer binding site having at least 95% identity to SEQ ID NO:2;

(b) a sequence that is at least a portion of a plant retroelement envelope sequence having at least 50% identity to SEQ ID NO:5;

(c) a sequence that is at least a portion of a plant retroelement gag sequence having at least 50% identity to SEQ ID NO:7;

(d) a sequence that is at least a portion of a plant retroelement integrase sequence having at least 70% identity to SEQ ID NO:9;

(e) a sequence that is at least a portion of a plant retroelement reverse transcriptase sequence having at least 70% identity to SEQ ID NO:11;

(f) a sequence that is at least a portion of a plant retroelement protease sequence having at least 50% identity to SEQ ID NO:13;

(g) a sequence that is at least a portion of a plant retroelement RNaseH sequence having at least 70% identity to SEQ ID NO:15;

(h) a sequence that is at least a portion of a plant retroelement sequence having at least 50% identity to SEQ ID NO:17;

(i) a sequence of SEQ ID NO:2, SEQ ID NO:5, SEQ ID NO:7, SEQ ID NO:9, SEQ ID NO:11, SEQ ID NO:13, SEQ ID NO:15, or SEQ ID NO:17;

(j) a sequence that encodes an amino acid sequence that is at least a portion of a plant retroelement envelope amino acid sequence having at least 30% identity to SEQ ID NO:6;

(k) a sequence that encodes an amino acid sequence that is at least a portion of a plant retroelement gag amino acid sequence having at least 30% identity to SEQ ID NO:8;

(l) a sequence that encodes an amino acid sequence that is at least a portion of a plant retroelement integrase amino acid sequence having at least 75% identity to SEQ ID NO:10;

(m) a sequence that encodes an amino acid sequence that is at least a portion of a plant retroelement reverse transcriptase amino acid sequence having at least 79% identity to SEQ ID NO:12;

(n) a sequence that encodes an amino acid sequence that is at least a portion of a plant retroelement protease amino acid sequence having at least 55% identity to SEQ ID NO:14;

(o) a sequence that encodes an amino acid sequence that is at least a portion of a plant retroelement RNaseH amino acid sequence having at least 90% identity to SEQ ID NO:16;

(p) a sequence that encodes an amino acid sequence that is at least a portion of a plant retroelement amino acid sequence having at least 40% identity to SEQ ID NO: 18;

(q) a sequence that encodes a polypeptide with an amino acid sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18;

(r) a sequence that is an allelic variant of an amino acid sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18; and (s) a sequence fully complementary to a nucleotide sequence of (a), (b), (c), (d), (e), (f), (g), (h), (i), (j), (k), (l), (m), (n), (o), (p), (q), or (r).

Seeds and plants containing the nucleic acids described above also are provided. Nucleic acid molecules as described above that further contain gag, pol, and env genes with adenine-thymidine-guanidine as the gag gene start codon also are provided. Furthermore, nucleic acids that contain gag, pol, and env genes with adenine-thymidine-guanidine as the gag gene start codon, and further contain SEQ ID NO:4 also are provided.

The invention also provides plant envelope nucleic acid sequences, as well as constructs, cells, seeds, embryos, and plants containing such nucleic acid sequences. In particular, the invention features isolated nucleic acid molecules encoding at least a portion of a plant envelope amino acid sequence and containing a nucleotide sequence selected from the group consisting of:

(a) a sequence having at least 90% identity to SEQ ID NO:5;

(b) the sequence of SEQ ID NO:5;

(c) a sequence encoding a polypeptide with an amino acid sequence having at least 85% identity to SEQ ID NO:6;

(d) a sequence encoding a polypeptide with the amino acid sequence of SEQ ID NO:6;

(e) a sequence that is an allelic variant of SEQ ID NO:6; and (f) a sequence that is fully complementary to a nucleic acid sequence of (a), (b), (c), (d), or (e).

The invention also provides plant integrase nucleic acid sequences, as well as constructs, cells, seeds, embryos, and plants containing such nucleic acid sequences. In particular, the invention features isolated nucleic acid molecules encoding at least a portion of a plant integrase amino acid sequence and containing a nucleotide sequence selected from the group consisting of:

(a) a sequence having at least 90% identity to SEQ ID NO:9;

(b) the sequence of SEQ ID NO:9;

(c) a sequence encoding a polypeptide with an amino acid sequence having at least 85% identity to SEQ ID NO:10;

(d) a sequence encoding a polypeptide with the amino acid sequence of SEQ ID NO:10;

(e) a sequence that is an allelic variant of SEQ ID NO:10; and (f) a sequence that is fully complementary to a nucleic acid sequence of (a), (b), (c), (d), or (e).

The invention also provides plant reverse transcriptase nucleic acid sequences, as well as constructs, cells, seeds, embryos, and plants containing such nucleic acid sequences. In particular, the invention features isolated nucleic acid molecules encoding at least a portion of a plant reverse transcriptase amino acid sequence and containing a nucleotide sequence selected from the group consisting of:

(a) a sequence having at least 90% identity to SEQ ID NO:11;

(b) the sequence of SEQ ID NO:11;

(c) a sequence encoding a polypeptide with an amino acid sequence having at least 85% identity to SEQ ID NO:12;

(d) a sequence encoding a polypeptide with the amino acid sequence of SEQ ID NO:12;

(e) a sequence that is an allelic variant of SEQ ID NO:12; and (f) a sequence that is fully complementary to a nucleic acid sequence of (a), (b), (c), (d), or (e).

The invention also provides plant RNaseH nucleic acid sequences, as well as constructs, cells, seeds, embryos, and plants containing such nucleic acid sequences. In particular, the invention features isolated nucleic acid molecules encoding at least a portion of a plant RNaseH amino acid sequence and containing a nucleotide sequence selected from the group consisting of:

(a) a sequence having at least 90% identity to SEQ ID NO:15;

(b) the sequence of SEQ ID NO:15;

(c) a sequence encoding a polypeptide with an amino acid sequence having at least 95% identity to SEQ ID NO:16;

(d) a sequence encoding a polypeptide with the amino acid sequence of SEQ ID NO:16;

(e) a sequence that is an allelic variant of SEQ ID NO:16; and (f) a sequence that is fully complementary to a nucleic acid sequence of (a), (b), (c), (d), or (e).

The invention also provides plant retroelement nucleic acid sequences, as well as constructs, cells, seeds, embryos, and plants containing such nucleic acid sequences. In particular, the invention features isolated nucleic acid molecules encoding at least a portion of a plant retroelement amino acid sequence and containing a nucleotide sequence selected from the group consisting of:

(a) a sequence having at least 95% identity to a nucleic acid sequence of SEQ ID NO:2, SEQ ID NO:5, SEQ ID NO:7, SEQ ID NO:9, SEQ ID NO:11, SEQ ID NO:13, SEQ ID NO:15, or SEQ ID NO:17;

(b) a sequence of SEQ ID NO:2, SEQ ID NO:5, SEQ ID NO:7, SEQ ID NO:9, SEQ ID NO:11, SEQ ID NO:13, SEQ ID NO:15, or SEQ ID NO:17;

(c) a sequence encoding a polypeptide with an amino acid sequence having at least 90% identity to an amino acid sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18;

(d) a sequence encoding a polypeptide with an amino acid sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18;

(e) a sequence that is an allelic variant of an amino acid sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18; and (f) a sequence that is fully complementary to a nucleic acid sequence of (a), (b), (c), (d), or (e).

The invention also provides isolated nucleic acid molecules encoding at least a portion of a plant retroelement reverse transcriptase and containing a nucleotide sequence selected from the group consisting of:

(a) a sequence having at least 85% identity to a nucleic acid sequence of one or more of the even-numbered SEQ ID NOs from SEQ ID NO:42 to SEQ ID NO:164;

(b) a sequence encoding a polypeptide with an amino acid sequence having at least 85% identity to an amino acid sequence of one or more of the odd-numbered SEQ ID NOs from SEQ ID NO:43 through SEQ ID NO:165;

(c) a sequence that is an allelic variant of a nucleic acid sequence of (a) or (b); and (d) a sequence that is fully complementary to a nucleic acid sequence of (a) or (b).

The invention also features nucleic acid molecules such as those described above, which further contain gag, pol, and env genes and have adenine-thymidine-guanidine as the gag gene start codon. In addition, the nucleic acid molecules described herein can further contain SEQ ID NO:5. In particular, the invention features isolated nucleic acid molecules encoding at least a portion of a plant envelope sequence and containing a nucleotide sequence selected from the group consisting of:

(a) a sequence having at least 90% identity to SEQ ID NO:5;

(b) a sequence encoding a polypeptide with an amino acid sequence having at least 85% identity to SEQ ID NO:6;

(c) a sequence that is an allelic variant of SEQ ID NO:5; and (d) a sequence that is fully complementary to a nucleic acid sequence of (a), (b), or (c).

The invention also features isolated nucleic acid molecules encoding at least a portion of a plant retroelement reverse transcriptase and containing a nucleotide sequence selected from the group consisting of:

(a) a sequence having at least 95% identity to a nucleic acid sequence of one or more of the even-numbered SEQ ID NOs from SEQ ID NO:42 to SEQ ID NO:164;

(b) a sequence encoding a polypeptide with an amino acid sequence having at least 95% identity to an amino acid sequence of one or more of the odd-numbered SEQ ID NOs from SEQ ID NO:43 through SEQ ID NO:165;

(c) a sequence that is an allelic variant of a nucleic acid sequence of (a) or (b); and (d) a sequence that is fully complementary to a nucleic acid sequence of (a) or (b).

The nucleic acid molecules described above can further contain gag, pol, and env genes, with adenine-thymidine-guanidine as the gag gene start codon. In addition, the invention provides nucleic acid molecules that further contain SEQ ID NO:5.

The invention also features isolated nucleic acid molecules encoding at least a portion of a plant retroelement reverse transcriptase and containing a nucleotide sequence selected from the group consisting of:

(a) a sequence of one or more of the even-numbered SEQ ID NOs from SEQ ID NO:42 to SEQ ID NO:164;

(b) a sequence encoding a polypeptide with an amino acid sequence of one or more of the odd-numbered SEQ ID NOs from SEQ ID NO:43 through SEQ ID NO:165;

(c) a sequence that is an allelic variant of a nucleic acid sequence of (a) or (b); and (d) a sequence that is fully complementary to a nucleic acid sequence of (a) or (b).

The invention also features plant retroelements containing the nucleic acid sequences described herein. Plant cells containing the plant retroelement nucleic acid molecules also are provided, as are plant retroelement proteins encoded by the nucleic acid molecules.

The invention also features plant retroelement nucleic acid sequences containing specialized signals, as well as constructs, cells, seeds, embryos, and plants containing such nucleic acid sequences. In particular, the invention provides isolated nucleic acid molecules containing a nucleotide sequence selected from the group consisting of:

(a) a sequence having at least 95% identity to SEQ ID NO:2;

(b) the sequence of SEQ ID NO:2;

(c) a sequence encoding a polypeptide with the amino acid sequence of SEQ ID NO:4; and (d) a sequence that is fully complementary to a nucleic acid sequence of (a), (b), or (c).

Seeds and plants containing the nucleic acid molecules described herein also are provided, as are nucleic acids that further contain gag, pol, and env genes and have adenine-thymidine-guanidine as the gag gene start codon. In addition, the nucleic acids provided herein can further contain SEQ ID NO:5. The invention also provides methods to impart agronomically significant characteristics to a plant cell. Such methods can involve contacting at least one plant cell with a nucleic acid molecule of the invention, under conditions sufficient to allow the nucleic acid molecule to enter the cell.

Nucleic acid molecules of the invention also can contain at least one nucleic acid sequence that imparts an agronomically significant characteristic. Agronomically significant characteristics can include, without limitation, those selected from the group consisting of: male sterility, self-incompatibility, foreign organism resistance, improved biosynthetic pathways, environmental tolerance, photosynthetic pathways, nutrient content, fruit ripening, oil biosynthesis, pigment biosynthesis, seed formation, starch metabolism, salt tolerance, cold/frost tolerance, drought tolerance, tolerance to anaerobic conditions, protein content, carbohydrate content (e.g., sugar and starch content), amino acid content, and fatty acid content.

In another aspect, the invention features seeds and plants containing the nucleic acid molecules provided herein. Suitable plants include, for example, soybean, maize, sugar cane, beet, tobacco, wheat, barley, poppy, rape, sunflower, alfalfa, sorghum, rose, carnation, gerbera, carrot, tomato, lettuce, chicory, pepper, melon, cabbage, oat, rye, cotton, flax, potato, pine, walnut, citrus fruits, hemp, oak, rice, petunia, orchids, *Arabidopsis*, broccoli, cauliflower, Brussels sprouts, onion, garlic, leek, squash, pumpkin, celery, peas, beans, strawberries, grapes, apples, pears, peaches, banana, palm, cocoa, cucumber, pineapple, apricot, plum, sugar beet, lawn grasses, maple, triticale, safflower, peanut, and olive.

In another aspect, the invention features methods for transferring a nucleic acid molecule into a plant cell. The methods can involve contacting a plant cell with a nucleic acid molecule of the present invention, under conditions sufficient to allow the nucleic acid molecule to enter the at least one plant cell. In particular, the invention provides methods to impart agronomically significant characteristics to at least one plant cell. Such methods can involve contacting at least one plant cell with a plant retroelement nucleic acid molecule encoding an agronomically significant characteristic such as those described above, under conditions sufficient to allow the nucleic acid molecule to enter the cell.

The nucleic acid molecules of the invention can be transmissible either to all plants or to a limited set of plants, such as a species. For example, plant viruses in general only infect a narrow host range or may infect a single species, and the present sequences can be genetically engineered to be similar. However, if a broad host range is desirable, those features that cause specificity can be removed, or can be overridden by the feature of broad transmissibility. The present invention is drawn to both of these embodiments, as well as to other variations.

By "agronomically significant" it is meant any trait of a plant that is recognized by members of the agricultural industry as desirable. Agronomically significant characteristics can include, for example, male sterility, self-incompatibility, foreign organism resistance, improved biosynthetic pathways, environmental tolerance, photosynthetic pathways, nutrient content, fruit ripening, oil biosynthesis, pigment biosynthesis, seed formation, starch metabolism, salt tolerance, cold/frost tolerance, drought tolerance, tolerance to anaerobic conditions, protein content, carbohydrate content, amino acid content, and fatty acid content.

"Fragment" is meant to refer to any subset of the referent nucleic acid molecule.

By "plant" it is meant one or more plant seed, plant embryo, plant part or whole plant. The plant may be an angiosperm (monocot or dicot), gymnosperm, man-made or naturally occurring.

By "proteins" it is meant any compounds that comprise amino acids, including peptides, polypeptides, fusion proteins, etc.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e. combinations) of two or more of the compounds.

According to the present invention, an isolated, or biologically pure, protein or nucleic acid molecule is a compound that has been removed from its natural milieu. An "isolated nucleic acid" refers to a nucleic acid that is separated from the other nucleic acid molecules by which it is naturally flanked in the genome, including nucleic acids that normally flank one or both sides of a retroelement nucleic acid sequence in a plant genome. An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., any, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid. As such, "isolated" and "biologically pure" do not necessarily reflect the extent to that the compound has been purified. An isolated compound of the present invention can be obtained from its natural source, can be produced using molecular biology techniques or can be produced by chemical synthesis.

Lastly, "more than" and "greater than" are interchangeable, and when used to modify a percent identity, i.e. "more than 90% identity", mean any increment to 100%, so long as the increment were greater than the percentage specifically named. In the example of "more than 90% identity", the term would include, among all other possibilities, 90.00001, 93.7, 98.04 and 99.0827 and 100%.

Unless otherwise defined, all technical and scientific terms used herein have the same meaning as commonly understood by one of ordinary skill in the art to that this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

The following is a summary of the sequence listing, provided as a convenient reference.

| SEQ ID NO | Description |
|---|---|
| 1 | Specialized primer binding site version 1 |
| 2 | Specialized primer binding site version 2 |
| 3 | Specialized polypurine tract |
| 4 | Targeting sequence |
| 5 | NA generic envelope |
| 6 | AA of 5 |
| 7 | NA of generic gag |
| 8 | AA of 7 |
| 9 | NA of generic integrase |
| 10 | AA of 9 |
| 11 | NA of generic reverse transcriptase |
| 12 | AA of 11 |
| 13 | Generic protease |
| 14 | AA of 13 |
| 15 | Generic RNaseH |
| 16 | AA of 15 |
| 17 | Generic retroelement |
| 18 | AA of 17 |
| 19 | NA calypso 1-1 |
| 20 | NA calypso 1-2 |
| 21 | NA calypso 1-3 |
| 22 | NA calypso 2-1 |
| 23 | NA calypso 2-2 |
| 24 | NA athila env |
| 25 | NA cyclops env |
| 26 | NA athila integrase |
| 27 | NA athila reverse transcriptase |
| 28 | NA athila RNaseH |
| 29 | NA cyclops reverse transcriptase |
| 30 | NA cyclops RNaseH |
| 31 | NA cyclops integrase |
| 32 | NA calypso envelope |
| 33 | NA calypso RNaseH |
| 34 | NA calypso reverse transcriptase |
| 35 | NA calypso integrase |
| 36 | Primer binding site A |
| 37 | Primer binding site B |
| 38 | Primer binding site minimum |

| SEQ ID NO | Description |
|---|---|
| 39 | Primer binding site extended |
| 40 | Polypurine tract A |
| 41 | Polypurine tract B |
| 42 | Tobacco1 RT DNA |
| 43 | Tobacco1 RT AA |
| 44 | Tobacco2-2 RT DNA |
| 45 | Tobacco2-2 RT AA |
| 46 | Tobacco4-1 RT DNA |
| 47 | Tobacco4-1 RT AA |
| 48 | Tobacco5-3 RT DNA |
| 49 | Tobacco5-3 RT AA |
| 50 | Rice1 RT DNA |
| 51 | Rice1 RT AA |
| 52 | Rice2-10 RT DNA |
| 53 | Rice2-10 RT AA |
| 54 | Rice2-17 RT DNA |
| 55 | Rice2-17 RT AA |
| 56 | Rice5-2 RT DNA |
| 57 | Rice5-2 RT AA |
| 58 | Barley2-4 RT DNA |
| 59 | Barley2-4 RT AA |
| 60 | Barley2-12 RT DNA |
| 61 | Barley2-12 RT AA |
| 62 | Barley2-19 RT DNA |
| 63 | Barley2-19 RT AA |
| 64 | Barley7 RT DNA |
| 65 | Barley7 RT AA |
| 66 | Oat6-1 RT DNA |
| 67 | Oat6-1 RT AA |
| 68 | Oat6-7 RT DNA |
| 69 | Oat6-7 RT AA |
| 70 | Oat6-8 RT DNA |
| 71 | Oat6-8 RT AA |
| 72 | Rye5-2 RT DNA |
| 73 | Rye5-2 RT AA |
| 74 | Rye3-4 RT DNA |
| 75 | Rye3-4 RT AA |
| 76 | Rye4-4 RT DNA |
| 77 | Rye4-4 RT AA |
| 78 | Rye5-4 RT DNA |
| 79 | Rye5-4 RT AA |
| 80 | Wheat3-1 RT DNA |
| 81 | Wheat3-1 RT AA |
| 82 | Wheat5-3 RT DNA |
| 83 | Wheat5-3 RT AA |
| 84 | Wheat8-2 RT DNA |
| 85 | Wheat8-2 RT AA |
| 86 | Wheat8-5 RT DNA |
| 87 | Wheat8-5 RT AA |
| 88 | Wheat8-11 RT DNA |
| 89 | Wheat8-11 RT AA |
| 90 | Cotton5-3 RT DNA |
| 91 | Cotton5-3 RT AA |
| 92 | Cotton8-6 RT DNA |
| 93 | Cotton8-6 RT AA |
| 94 | Cotton8-7 RT DNA |
| 95 | Cotton8-7 RT AA |
| 96 | Tomato4-4 RT DNA |
| 97 | Tomato4-4 RT AA |
| 98 | Tomato4-10 RT DNA |
| 99 | Tomato4-10 RT AA |
| 100 | Tomato10-4 RT DNA |
| 101 | Tomato10-4 RT AA |
| 102 | Tomato10-16 RT DNA |
| 103 | Tomato10-16 RT AA |
| 104 | Potato5-1 RT DNA |
| 105 | Potato5-1 RT AA |
| 106 | Potato8-3 RT DNA |
| 107 | Potato8-3 RT AA |
| 108 | Potato8-4 RT DNA |
| 109 | Potato8-4 RT AA |
| 110 | Potato8-5 RT DNA |
| 111 | Potato8-5 RT AA |
| 112 | Potato8-8 RT DNA |
| 113 | Potato8-8 RT AA |
| 114 | Potato8-10 RT DNA |
| 115 | Potato8-10 RT AA |
| 116 | Sycamore2-3 RT DNA |
| 117 | Sycamore2-3 RT AA |
| 118 | Sycamore4-2 RT DNA |
| 119 | Sycamore4-2 RT AA |
| 120 | Sycamore4-3 RT DNA |
| 121 | Sycamore4-3 RT AA |
| 122 | Sycamore4-7 RT DNA |
| 123 | Sycamore4-7 RT AA |
| 124 | Sorghum4-3 RT DNA |
| 125 | Sorghum4-3 RT AA |
| 126 | Sorghum5-2 RT DNA |
| 127 | Sorghum5-2 RT AA |
| 128 | Sorghum5-4 RT DNA |
| 129 | Sorghum5-4 RT AA |
| 130 | Sorghum5-5 RT DNA |
| 131 | Sorghum5-5 RT AA |
| 132 | Sorghum5-6 RT DNA |
| 133 | Sorghum5-6 RT AA |
| 134 | Sorghum5-8 RT DNA |
| 135 | Sorghum5-8 RT AA |
| 136 | L85 Soybean8-2 RT DNA |
| 137 | L85 Soybean8-2 RT AA |
| 138 | L85 Soybean2 RT DNA |
| 139 | L85 Soybean2 RT AA |
| 140 | L85 Soybean9-2 RT DNA |
| 141 | L85 Soybean9-2 RT AA |
| 142 | L85 Soybean9-3 RT DNA |
| 143 | L85 Soybean9-3 RT AA |
| 144 | L85 Soybean9-6 RT DNA |
| 145 | L85 Soybean9-6 RT AA |
| 146 | Williams Soybean8-2 RT DNA |
| 147 | Williams Soybean8-2 RT AA |
| 148 | Williams Soybean8-3 RT DNA |
| 149 | Williams Soybean8-3 RT AA |
| 150 | Williams Soybean2 RT DNA |
| 151 | Williams Soybean2 RT AA |
| 152 | Williams Soybean3 RT DNA |
| 153 | Williams Soybean3 RT AA |
| 154 | Hark Soybean2 RT DNA |
| 155 | Hark Soybean2 RT AA |
| 156 | Hark Soybean5-1 RT DNA |
| 157 | Hark Soybean5-1 RT AA |
| 158 | Hark Soybean5 RT DNA |
| 159 | Hark Soybean5 RT AA |
| 160 | Pea1 RT DNA |
| 161 | Pea1 RT AA |
| 162 | Pea8-1 RT DNA |
| 163 | Pea8-1 RT AA |
| 164 | Pea9-1 RT DNA |
| 165 | Pea9-1 RT AA |
| 166 | 5' RT primer |
| 167 | N terminal RT sequence |
| 168 | 3' RT primer |
| 169 | C-terminal RT sequence |
| 170 | Tat1 primer DVO158 |
| 171 | Tat1 primer DVO159 |
| 172 | LTR primer DVO354 |
| 173 | LTR primer DVO355 |
| 174 | Primer DVO405 |
| 175 | Primer DVO385 |
| 176 | Primer DVO371 |
| 177 | Potential PPT in phage clones |
| 178 | Zinc finger characteristic |
| 179 | Protease characteristic |
| 180 | Conserved retrovirus-like RT motif |
| 181 | Conserved retrovirus-like RT motif |
| 182 | Conserved retrovirus-like RT motif |
| 183 | Conserved retrovirus-like RT motif |
| 184 | Conserved retrovirus-like RT motif |
| 185 | Conserved retrovirus-like integrase motif |
| 186 | Conserved retrovirus-like integrase motif |
| 187 | Conserved retrovirus-like integrase motif |
| 188 | PPT |
| 189 | Calypso amino-terminal consensus |
| 190 | Cyclops2 amino-terminal sequence |
| 191 | Invariant sequence |
| 192 | Invariant sequence |

-continued

| SEQ ID NO | Description |
|---|---|
| 193 | Invariant sequence |
| 194 | Invariant sequence |
| 195 | Invariant sequence |
| 196 | Invariant sequence |
| 197 | Invariant sequence |
| 198 | Invariant sequence |
| 199 | Invariant sequence |
| 200 | Invariant sequence |
| 201 | will8-2 RT |
| 202 | hark5 RT |
| 203 | Calypso7-1 RT |
| 204 | will2 RT |
| 205 | hark5-1 RT |
| 206 | L859-6 RT |
| 207 | Calypso4-1 RT |
| 208 | hark2 RT |
| 209 | Calypso5-1 RT |
| 210 | will3 RT |
| 211 | L859-3 RT |
| 212 | Calypso6-1 RT |
| 213 | will8-3 RT |
| 214 | L858-2 RT |
| 215 | Calypso3-1 RT |
| 216 | Calypso1-1 RT |
| 217 | L852 RT |
| 218 | Calypso2-1 RT |
| 219 | L859-2 RT |
| 220 | Cyclops-2 RT |
| 221 | Cyclops-1 RT |
| 222 | pea9-1 RT |
| 223 | pea8-1 RT |
| 224 | favabean1 RT |
| 225 | favabean2 RT |
| 226 | pea1 RT |
| 227 | tob2-2 RT |
| 228 | tob5-3 RT |
| 229 | tob4-1 RT |
| 230 | tob1 RT |
| 231 | tom4-10 RT |
| 232 | tom10-16 RT |
| 233 | tom4-4 RT |
| 234 | pot8-8 RT |
| 235 | pot8-3 RT |
| 236 | pot8-4 RT |
| 237 | pot8-5 RT |
| 238 | tom10-4 RT |
| 239 | pot8-10 RT |
| 240 | pot5-1 RT |
| 241 | syc4-2 RT |
| 242 | syc4-7 RT |
| 243 | syc2-3 RT |
| 244 | cot5-3 RT |
| 245 | cot8-6 RT |
| 246 | cot8-7 RT |
| 247 | Diaspora RT |
| 248 | TfcII#1 RT |
| 249 | TfcII#2 RT |
| 250 | TfcII#3 RT |
| 251 | syc4-3 RT |
| 252 | hau7-2 RT |
| 253 | Athila6-1 RT |
| 254 | f18p14 RT |
| 255 | hau8-4 RT |
| 256 | Athila4-1 RT |
| 257 | Athila4-3 RT |
| 258 | Athila4-4 RT |
| 259 | Athila4-2 RT |
| 260 | t13e11 RT |
| 261 | f7b19 RT |
| 262 | t13d4 RT |
| 263 | t24g23Athila9-1 RT |
| 264 | t16i21 RT |
| 265 | La8-1 RT |
| 266 | La9-6 RT |
| 267 | Athila1-1 |
| 268 | La9-7 |
| 269 | La9-9 |
| 270 | hau8-3 RT |
| 271 | f23m2Athila5-2 RT |
| 272 | t17a11 RT |
| 273 | La9-5 RT |
| 274 | bar7 RT |
| 275 | bar2-12 RT |
| 276 | bar2-19 RT |
| 277 | bar2-4 RT |
| 278 | Baggy2 RT |
| 279 | rye3-4 RT |
| 280 | rye4-4 RT |
| 281 | rye5-2 RT |
| 282 | rye5-4 RT |
| 283 | wheat3-1 RT |
| 284 | wheat8-5 RT |
| 285 | wheat8-2 RT |
| 286 | wheat5-3 RT |
| 287 | wheat8-11 RT |
| 288 | oat6-1 RT |
| 289 | oat6-8 RT |
| 290 | oat6-7 RT |
| 291 | rice1 RT |
| 292 | RiceAthila RT |
| 293 | rice2-10 RT |
| 294 | rice5-2 RT |
| 295 | rice2-17 RT |
| 296 | sorg4-3 RT |
| 297 | sorg5-6 RT |
| 298 | sorg5-4 RT |
| 299 | sorg5-2 RT |
| 300 | sorg5-8 RT |
| 301 | sorg5-5 RT |
| 302 | Tat4-1 RT |
| 303 | f26h6 RT |
| 304 | Rire2 RT |
| 305 | Grand1-4 RT |
| 306 | Vulgar RT |
| 307 | Cinful RT |
| 308 | Mag RT |
| 309 | SURL RT |
| 310 | Mdg1 RT |
| 311 | 412 RT |
| 312 | Cft-1 RT |
| 313 | boty RT |
| 314 | Skippy RT |
| 315 | Maggy RT |
| 316 | Grasshopper RT |
| 317 | Tf1 RT |
| 318 | Tma1-1 RT |
| 319 | Tma3-1 RT |
| 320 | Del1 RT |
| 321 | Reina RT |
| 322 | IFG7 RT |
| 323 | Ty3 RT |
| 324 | Tom RT |
| 325 | 297 RT |
| 326 | 17.6 RT |
| 327 | TED RT |
| 328 | Gypsy RT |
| 329 | Yoyo RT |
| 330 | Ulysses RT |
| 331 | Woot RT |
| 332 | Cer1 RT |
| 333 | HIV1 RT |
| 334 | RSV RT |
| 335 | MuMLV RT |

DESCRIPTION OF DRAWINGS

FIG. 1 is an alignment of reverse transcriptase sequences (SEQ ID NOS: 201 to 335, top to bottom). Shaded regions indicate identical or similar amino acids. Asterisks indicate invariant motifs identified by the alignment.

DETAILED DESCRIPTION

The present invention provides nucleic acids, as well as vectors, cells, and plants (including plant parts, seeds, and embryos) containing the nucleic acids. In particular, molecular tools are provided in the form of nucleic acids that are retroelements or that contain retroelement sequences. The invention also features methods for manipulating such nucleic acids. For example, the invention features methods to introduce nucleic acids containing retroelements or retroelement sequences into cells, especially retroelements carrying at least one agronomically significant characteristic.

1. Nucleic Acid Molecules

The invention provides isolated nucleic acid molecules. The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be a sense strand or an antisense strand. In addition, a nucleic acid can be circular or linear.

The invention provides nucleic acid molecules having nucleotide sequences with a specified percent identity to the nucleotide sequences provided in the sequence listing. For example, a nucleic acid molecule of the invention can contain a nucleotide sequence that is at least 60% identical (e.g., 60%, 62%, 65%, 70%, 75%, 80%, 85%, 90%, 95%, or 100% identical) to one or more of the nucleic acid sequences of SEQ ID NO:1 to SEQ ID NO:165. Furthermore, the isolated nucleic acid molecules provided herein typically are at least 15 nucleotides in length, and can be up to about 30 kilobases in length. An isolated nucleic acid molecule thus can be, for example, 15, 20, 25, 30, 50, 100, 200, 500, 1000, 2500, 5000, 10000, 20000, or about 30000 nucleotides in length.

The nucleic acid molecules provided herein can contain plant retroelement sequences. Such sequences can include, for example, a retroelement LTR, polypurine tract (PPT), primer binding site (PBS), gag gene, pol gene, and/or env gene, or portions of a pol gene (e.g., an integrase, RNaseH, or reverse transcriptase gene). An isolated nucleic acid molecule provided by the present invention can be, for example, a nucleic acid molecule encoding at least a portion of a plant retroelement reverse transcriptase. Such a nucleic acid molecule can contain a nucleotide sequence selected from the group consisting of:

(a) a sequence having at least 85% identity to a nucleic acid sequence of one or more of the even-numbered SEQ ID NOs from SEQ ID NO:42 to SEQ ID NO:164;

(b) a sequence encoding a polypeptide with an amino acid sequence having at least 85% identity to an amino acid sequence of one or more of the odd-numbered SEQ ID NOs from SEQ ID NO:43 to SEQ ID NO:165;

(c) a sequence that is an allelic variant of a nucleic acid sequence of (a) or (b); and (d) a sequence that is fully complementary to a nucleic acid sequence of (a), (b), or (c).

Such isolated nucleic acid molecules further can contain gag, pol, and env genes that have adenine-thymidine-guanidine as the gag gene start codon. In addition, such nucleic acid molecules also can contain SEQ ID NO:5 or sequences homologous to SEQ ID NO:5. The invention thus provides isolated nucleic acid molecules encoding at least a portion of a plant envelope sequence and containing a nucleic acid sequence selected from the group consisting of:

(a) a sequence having at least 90% identity to SEQ ID NO:5;

(b) a sequence encoding a polypeptide with an amino acid sequence having at least 85% identity to SEQ ID NO:6;

(c) a sequence that is an allelic variant of SEQ ID NO:5; and (d) a sequence that is fully complementary to a nucleic acid sequence of (a), (b) or (c).

Isolated nucleic acid molecules of the invention also can encode at least a portion of a plant retroelement reverse transcriptase and contain a nucleic acid sequence selected from the group consisting of:

(a) a sequence having at least 95% identity to a nucleic acid sequence of one or more of the even-numbered SEQ IDNOs from SEQ ID NO:42 to SEQ ID NO:164;

(b) a sequence encoding a polypeptide with an amino acid sequence having at least 95% identity to an amino acid sequence of one or more of the odd-numbered SEQ ID NOs from SEQ ID NO:43 to SEQ ID NO:165;

(c) a sequence that is an allelic variant of a nucleic acid sequence of (a) or (b); and (d) a sequence that is fully complementary to a nucleic acid sequence of (a), (b), or (c).

In some embodiments, isolated nucleic acid molecules provided herein can encode at least a portion of a plant retroelement reverse transcriptase and can contain a nucleic acid sequence selected from the group consisting of:

(a) a sequence having at least 60% identity to a nucleic acid sequence of one or more of the even-numbered SEQ ID NOs from SEQ ID NO:42 to SEQ ID NO:164;

(b) a sequence encoding a polypeptide with an amino acid sequence having at least 60% identity to an amino acid sequence of one or more of the odd-numbered SEQ ID NOs from SEQ ID NO:43 to SEQ ID NO:165;

(c) a sequence that is an allelic variant of a nucleic acid sequence of (a) or (b); and (d) a sequence that is fully complementary to a nucleic acid sequence of (a), (b), or (c).

Furthermore, an isolated nucleic acid molecule can encode at least a portion of a plant retroelement reverse transcriptase and can contain a nucleic acid sequence selected from the group consisting of:

(a) a sequence of one or more of the even-numbered SEQ ID NOs from SEQ ID NO:42 to SEQ ID NO:164;

(b) a sequence encoding a polypeptide with an amino acid sequence of one or more of the odd-numbered SEQ ID NOs from SEQ ID NO:43 through SEQ ID NO:165;

(c) a sequence that is an allelic variant of a nucleic acid sequence of (a) or (b); and (d) a nucleic acid sequence fully complementary to a nucleic acid sequence of (a), (b), or (c).

The invention provides isolated nucleic acid molecules that contain a nucleotide sequence having (1) a length, and (2) a percent identity to an identified nucleotide sequence over that length. The invention also provides isolated nucleic acid molecules that contain a nucleotide sequence encoding a polypeptide that contains an amino acid sequence having (1) a length, and (2) a percent identity to an identified amino acid sequence over that length. Typically, the identified nucleic acid or amino acid sequence is a sequence referenced by a particular sequence identification number, and the nucleic acid or amino acid sequence being compared to the identified sequence is referred to as the target sequence. For example, an identified sequence can be the sequence set forth in SEQ ID NO:42.

A length and percent identity over that length for any nucleic acid or amino acid sequence is determined as follows. First, a nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library as well as at Fish & Richardson's web site (World Wide Web at fr.com/blast) or the U.S. government's National Center for Biotechnology Information web site (World Wide Web at ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to the sequence set forth in SEQ ID NO:42, (2) the Bl2seq program presents 775 nucleotides from the target sequence aligned with a region of the sequence set forth in SEQ ID NO:42 where the first and last nucleotides of that 775 nucleotide region are matches, and (3) the number of matches over those 775 aligned nucleotides is 700, then the 1000 nucleotide target sequence contains a length of 775 and a percent identity over that length of 90.3 (i.e., 700÷775×100=90.3).

It will be appreciated that a single nucleic acid or amino acid target sequence that aligns with an identified sequence can have many different lengths with each length having its own percent identity.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The nucleic acid molecules described herein can further contain at least one nucleic acid sequence encoding an agronomically significant characteristic. Useful agronomically significant characteristics can include, for example: male sterility, self-incompatibility, foreign organism resistance, improved biosynthetic pathways, environmental tolerance, photosynthetic pathways, nutrient content, fruit ripening, oil biosynthesis, pigment biosynthesis, seed formation, starch metabolism, salt tolerance, cold/frost tolerance, drought tolerance, tolerance to anaerobic conditions, protein content, carbohydrate content (e.g., sugar and starch content), amino acid content, and fatty acid content.

Recombinant molecules of the present invention also can contain secretory signals (e.g., signal segment nucleic acid sequences) to enable an expressed protein to be secreted from the cell that produces the protein. Furthermore, recombinant nucleic acid molecules can contain fusion sequences that lead to the expression of nucleic acid molecules of the present invention as fusion proteins. Recombinant molecules also can include intervening and/or untranslated sequences surrounding and/or within the nucleic acid sequences of nucleic acid molecules of the present invention.

Included within the scope of the present invention, with particular regard to the nucleic acids above, are allelic variants, degenerate sequences and homologues. As used herein, the term "allelic variant" refers to a full-length gene or partial sequence of a full-length gene that has a nucleotide sequence that is similar but not identical to that of the reference gene. Such sequence differences can be due to natural variations caused by, for example, mutation or recombination. Allelic variants can encode polypeptides with amino acid sequences that vary from the amino acid sequence encoded by the reference gene. An allelic variant typically encodes a protein having an activity similar to that of the protein encoded by the gene to which it is being compared. Allelic variants also can contain alterations in the 5' or 3' untranslated regions of the gene (e.g., in regulatory control regions).

The present invention includes variants that arise during laboratory manipulation, such as, but not limited to, variants produced during polymerase chain reaction amplification or site directed mutagenesis. There is a substantial amount of redundancy in the various codons that code for specific amino acids. Therefore, this invention also is directed to those nucleic acid sequences containing alternative codons that code for the eventual translation of the identical amino acid. Also included within the scope of the invention are mutations either in the nucleic acid sequence or in the translated protein that do not substantially alter the ultimate physical properties of the expressed protein. For example, substitution of valine for leucine, arginine for lysine, or asparagines for glutamine may not cause a change in functionality of the polypeptide.

The nucleic acid molecules provided herein typically encode plant retroelement polypeptides. For example, a nucleic acid molecule of the invention can encode a reverse transcriptase polypeptide having the amino acid sequence of one or more of the odd-numbered SEQ ID NOs from SEQ ID NO:43 to SEQ ID NO:165. Alternatively, a nucleic acid molecule can encode a reverse transcriptase that is an allelic variant of one or more of the odd-numbered SEQ ID NOs from SEQ ID NO:43 to SEQ ID NO:165. Furthermore, a nucleic acid molecule can encode a reverse transcriptase polypeptide that contains two or more amino acid sequences that are conserved (i.e., "invariant") among the odd-numbered SEQ ID NOs from SEQ ID NO:43 to SEQ ID NO:165. The conserved nucleic acid sequences are contiguous and reside within or between one of the seven amino acid sequence domains that define reverse transcriptases (Xiong and Eickbush, supra). For example, a nucleic acid molecule provided herein can encode a reverse transcriptase containing the amino acid sequence Trp-Val-Ser within reverse transcriptase domain 1; the amino acid sequence Thr-Val/Ile-Val/Ile-Xaa-Xaa-Xaa-Xaa-Xaa-Asp/Glu-Leu-Val/Ile (SEQ ID NO:191) between reverse transcriptase domains 1 and 2; the amino acid sequence Thr/Ser-Arg/Lys-Arg/Lys-Asp-His (SEQ ID NO:192) within reverse transcriptase domain 2; and/or the amino acid sequence Met-Leu-Asp/Glu-Arg-Leu (SEQ ID NO:193) spanning the boundary between reverse transcriptase domains 2 and 3. For example, the amino acid sequence Met-Leu-Asp/Glu can be present within reverse transcriptase domain 2, the Arg can be between domains 2 and 3, and the Leu can be within domain 3. Furthermore, a nucleic acid molecule provided herein can encode a reverse transcriptase containing the amino acid sequence the amino acid sequence Cys-Phe-Leu-Asp-Gly-Tyr-Ser (SEQ ID NO:194) within reverse transcriptase domain 3; the amino acid sequence Phe-Thr-Cys-Pro (SEQ ID NO:195) within reverse transcriptase domain 3; the amino acid sequence Phe-Gly-Leu-Cys-Asn-Ala-Pro (SEQ ID NO:196) within reverse transcriptase domain 4; the amino acid sequence Phe-Met-Asp-Asp-Phe (SEQ ID NO:197) within reverse transcriptase domain 5; the amino acid sequence Leu-Val/Ile-Leu-Asn-Trp-Glu-Lys-Cys-His-Phe-Met-Val/Ile (SEQ ID NO:198) spanning the boundary between reverse transcriptase domains 6 and 7 (e.g., with the amino acid sequence Leu-Val/Ile-Leu-Asn-Trp-Glu-Lys-Cys-His-Phe (SEQ ID NO:199) within domain 6, the Met between domains 6 and 7, and the Val/Ile within domain 7); and/or the amino acid sequence Gly-Leu/Ile-Val-Leu-Gly-His (SEQ ID NO:200) within reverse transcriptase domain 7.

Knowing the nucleic acid sequences of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain similar nucleic acid molecules from other species. Such nucleic acid molecules can be obtained in a variety to of ways including screening appropriate expression libraries of DNA; and PCR amplification of appropriate libraries of DNA using oligonucleotide primers of the present invention. Libraries to screen or from which to amplify nucleic acid molecules can include cDNA libraries as well as genomic DNA libraries. Similarly, DNA sources to screen or from which to amplify nucleic acid molecules can include adult cDNA and genomic DNA. Techniques to clone and amplify genes are disclosed, for example, in Sambrook et al. (1989) *Molecular Cloning. A Laboratory Manual* (Cold Spring Harbor Laboratory Press).

Recombination constructs can be made using the starting materials above or with additional materials, using methods well-known in the art. In general, the sequences can be manipulated to have ligase-compatible ends, and incubated with ligase to generate full constructs. For example, restriction enzymes can be chosen on the basis of their ability to cut at an acceptable site in both sequence to be ligated, or a linker can be added to adapt the sequence end(s) to be compatible. The methods for conducting these types of molecular manipulations are well known in the art, and are described in detail in Sambrook et al., supra; and Ausubel et al. (1993) *Current Protocols in Molecular Biology* (Greene Publishing Associates, Inc.). The methods described herein according to Tinland et al. (1994) *Proc. Natl. Acad. Sci. USA* 91:8000–8004 also can be used.

The invention also provides vectors containing the nucleic acid molecules described herein. Such vectors can be, without limitation, viral vectors, plasmids, phage, and cosmids. For example, vectors can be of viral origin (e.g., paramyxovirus vectors, SV40 vectors, molecular conjugate vectors, or vectors derived from adenovirus, adeno-associated virus, herpes virus, lentivirus, retrovirus, parvovirus, or Sindbis virus) or of non-viral origin (e.g., vectors from bacteria or yeast). An isolated nucleic acid encoding a plant retroelement polypeptide can be inserted into a vector such that the polypeptide is expressed. For example, a nucleic acid provided herein can be inserted into an expression vector. "Expression vectors" can contain one or more regulatory elements (e.g., a sequence that controls and regulates the transcription and/or translation of another sequence. Such regulatory elements can include, for example, promoter sequences, enhancer sequences, response elements, protein recognition sites, or inducible elements that modulate expression of a nucleic acid sequence.

Nucleic acid constructs of the invention can contain one or more regulatory elements operably linked to a nucleic acid coding sequence. As used herein, "operably linked" refers to positioning of a regulatory element in a construct relative to a nucleic acid coding sequence in such a way as to permit or facilitate expression of the encoded polypeptide. The choice of element(s) that can be included depends upon several factors, including, but not limited to, replication efficiency, selectability, inducibility, desired expression level, and cell or tissue specificity.

Expression vectors of the present invention can contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention can include transcription control sequences. Transcription control sequences are sequences that control the initiation, elongation and termination of transcription. Particularly important transcription control sequences are those that control transcription initiation, such as promoter, enhancer, operator and repressor sequences. Suitable transcription control sequences include any transcription control sequences that can function in at least one of the recombinant cells of the present invention.

A variety of transcription control sequences are known to those skilled in the art. Useful transcription control sequences can include those that function in bacterial, yeast, insect and mammalian cells, such as, without limitation, tac, lac, trp, trc, oxy-pro, omp/lpp, rrnB, bacteriophage lambda (such as lambda pL and lambda pR and fusions that include such promoters), bacteriophage T7, T7lac, bacteriophage T3, bacteriophage SP6, bacteriophage SP01, metallothionein, alphamating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxyirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Suitable transcription control sequences also can include tissue-specific promoters and enhancers, as well as lymphokine-inducible promoters (e.g., promoters inducible by interferons or interleukins). Transcription control sequences of the present invention can also include naturally occurring transcription control sequences naturally associated with plants.

The following promoters can be particularly useful in early expression of the present sequences: Ogs4B (Tsuchiya et al. (1994) *Plant Cell Physiol.* 36:487; TA29 (Koltunow et al. (1990) *Plant Cell* 2:1201; and A3 and A9 (Paul et al. (1992) *Plant Mol. Biol.* 19:611). In order to then constitutively express the sequences described above, the construct optionally can contain, for example, a 35S promoter.

Other suitable regulatory elements include promoters that initiate transcription only, or predominantly, in certain cell types. For example, promoters specific to plant vegetative tissues such as ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory elements. In other embodiments, a promoter specific to a reproductive tissue (e.g., fruit, ovule, seed, pollen, pistils, female gametophyte, egg cell, central cell, nucellus, suspensor, synergid cell, flowers, embryonic tissue, embryo, zygote, endosperm, integument, seed coat or pollen) is used. A cell type or tissue-specific promoter can drive expression of operably linked sequences in tissues other than the target tissue. Thus, as used herein a cell type or tissue-specific promoter is one that drives expression preferentially in the target tissue, but also can lead to some expression in other cell types or tissues as well. Methods for identifying and characterizing promoter regions in plant genomic DNA include, for example, those described in the following references: Jordano et al. (1989) *Plant Cell* 1:855–866; Bustos et al. (1989) *Plant Cell* 1:839–854; Green et al. (1988) *EMBO J.* 7:4035–4044; Meier et al. (1991) *Plant Cell* 3:309–316; and Zhang et al. (1996) *Plant Physio.* 110:1069–1079.

Reproductive tissue promoters include, for example, those derived from the following seed-genes: zygote and embryo LEC1 (Lotan (1998) *Cell* 93:1195–1205); suspensor G564 (Weterings (2001) *Plant Cell* 13:2409–2425); maize MAC1 (Sheridan (1996) *Genetics* 142:1009–1020); maize Cat3 (GenBank No. L05934; Abler (1993) *Plant Mol. Biol.* 22:10131–1038); *Arabidopsis* viviparous-l (GenBank No. U93215); *Arabidopsis* atmyc1 (Urao (1996) *Plant Mol. Biol.* 32:571–57; Conceicao (1994) *Plant* 5:493–505); and Brassica napus napin gene family, including napA (GenBank No. J02798; Josefsson (1987) *JBL* 26:12196–1301; and Sjodahl (1995) *Planta* 197:264–271). Other examples of reproductive tissue-specific promoters include those derived from the pollen genes described in, for example: Guerrero (1990) *Mol. Gen. Genet.* 224:161–168; Wakeley (1998) *Plant Mol. Biol.* 37:187–192; Ficker (1998) *Mol. Gen. Genet.* 257: 132–142; Kulikauskas (1997) *Plant Mol. Biol.* 34:809–814; and Treacy (1997) *Plant Mol. Biol.* 34:603–611. Still other suitable reproductive tissue promoters include those derived from the following embryo genes: *Brassica napus* 2s storage protein (Dasgupta (1993) *Gene* 133:301–302); *Arabidopsis* 2s storage protein (GenBank No. AL161566); soybean β-conglycinin (GenBank No. S44893); *Brassica napus* oleosin 20 kD gene (GenBank No. M63985); soybean oleosin A (GenBank No. U09118); soybean oleosin B (GenBank No. U09119); soybean lectin1 (GenBank K00821); soybean Kunitz trypsin inhibitor 3 (GenBank No. AF233296); soybean glycinin1 (GenBank No. X15121); *Arabidopsis* oleosin (GenBank No. Z17657); maize oleosin 18 kD (GenBank No. J05212; Lee (1994) *Plant Mol. Biol.* 26:1981–1987); and the gene encoding low molecular weight sulfur rich protein from soybean (Choi (1995) *Mol. Gen. Genet.* 246:266–268). Other examples of reproductive tissue promoters include those derived from the following endosperm genes: *Arabidopsis* Fie (GenBank No. AF129516); *Arabidopsis* Mea; *Arabidopsis* Fis2 (GenBank No. AF096096); rice Glu1 (GenBank No. M28156); and rice 26 kDa globulin (GenBank No. D50643). Further examples of reproductive tissue promoters include those derived from the following genes: ovule BEL1 (Reiser (1995) *Cell* 83:735–742; Ray (1994) *Proc. Natl. Acad. Sci. USA* 91:5761–5765; and GenBank No. U39944); central cell FIE (GenBank No. AF129516); flower primordia *Arabidopsis* APETALA1 (a.k.a. AP1; Gustafson-Brown (1994) *Cell* 76:131–143; Mandrel (1992) *Nature* 360:273–277); flower *Arabidopsis* AP2 (Jofuku (1994) *Plant Cell* 6:1211–1225); *Arabidopsis* flower ufo, expressed at the junction between sepal and petal primordia (Bossinger (1996) *Development* 122:1093–1102); fruit-specific tomato E8; a tomato gene expressed during fruit ripening, senescence and abscission of leaves and flowers (Blume (1997) *Plant J.* 12:731–746); pistil-specific potato SK2 (Ficker (1997) *Plant Mol. Biol.* 35:425–431); *Arabidopsis* DMC1 (GenBank No. U76670); and *Arabidopsis* DMT1 (Choi (2002) *Cell* 110:33–42).

Suitable vegetative tissue promoters include, for example, those derived from the following genes: pea Blec4, active in epidermal tissue of vegetative and floral shoot apices of transgenic alfalfa; potato storage protein patatin gene (Kim (1994) *Plant Mol. Biol.* 26:603–615; Martin (1997) *Plant J.*, 11:53–62); root *Agrobacterium rhizogenes* ORF13 (Hansen (1997) *Mol. Gen. Genet.* 254:337–343); genes active during taro corm development (Bezerra (1995) *Plant Mol. Biol.* 28:137–144); de Castro (1992) *Plant Cell* 4:1549–1559); root meristem and immature central cylinder tobacco gene TobRB7 (Yamamoto (1991) *Plant Cell* 3:371–382); ribulose biphosphate carboxylase genes RBCS1, RBCS2, and RBCS3A expressed in tomato leaves (Meier (1997) *FEBS Lett.* 415:91–95); ribulose biphosphate carboxylase genes expressed in leaf blade and leaf sheath mesophyll cells (Matsuoka (1994) *Plant J.* 6:311–319); leaf chlorophyll a/b binding protein (Shiina (1997) *Plant Physiol.* 115:477–483; Casal (1998) *Plant Physiol.* 116:1533–1538); *Arabidopsis* Atmyb5, expressed in developing leaf trichomes, stipules, in epidermal cells on the margins of young rosette and cauline leaves, and in immature seeds between fertilization and the 16 cell stage of embryo development and persists beyond the heart stage (Li (1996) *FEBS Lett.* 379:117–121); a maize leaf-specific gene described by Busk (1997) *Plant J.* 11:1285–1295; "SHOOTMERISTEMLESS" and "SCARECROW" genes active in developing shoot or root apical meristems (Di Laurenzio (1996) *Cell* 86:423–433; Long (1996) *Nature* 379:66–69); 3-hydroxy-3-methylglutaryl coenzyme A reductase HMG2, expressed in meristematic tissue, and floral reductase HMG2, expressed in meristematic and floral (e.g., secretory zone of the stigma, mature pollen grains, gynoecium vascular tissue, and fertilized ovules) tissues (Enjuto (1995) *Plant Cell* 7:517–527); meristem kn1-related genes from maize and other species (Granger (1996) *Plant Mol. Biol.* 31:373–378; Kerstetter (1994) *Plant Cell* 6:1877–1887; Hake (1995) *Philos. Trans. R. Soc. Lond. B. Biol. Sci.* 350:45–51; Lincoln (1994) *Plant Cell* 6:1859–1876); and constitutive Cauliflower mosaic virus 35S.

Other examples of suitable plant promoters include those described in U.S. Pat. Nos. 6,184,443, 6,054,635, 6,005,092, 5,866,793, and 5,792,932, for example.

Cell type or tissue-specific promoters derived from viruses also can be suitable regulatory elements. Such viral promoters include, for example, the tobamovirus subgenomic promoter (Kumagai (1995) *Proc. Natl. Acad. Sci. USA* 92:1679–1683); the phloem-specific tungro bacilliform virus (RTBV) promoter; the cassaya vein mosaic virus (CVMV) promoter, expressed most strongly in vascular elements, leaf mesophyll cells, and root tips (Verdaguer (1996) *Plant. Mol. Biol.* 31:1129–1139).

Vectors can be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.), for example. Vectors that can be used to transfer the sequences disclosed herein into plant cells or plant parts can be particularly useful.

The present invention includes nucleic acid molecules that are oligonucleotides, as well as nucleic acid molecules that contain entire retroelement nucleotide sequences. Thus, nucleic acid molecules of the invention can range in length from about 10 nucleotides to more than 10,000 nucleotides. Oligonucleotides, for example, can be between about 10 and about 30 nucleotides in length (e.g., 10, 11, 12, 13, 14, 15, 17, 19, 20, 22, 24, 26, 28, or 30 nucleotides in length). Oligonucleotides of the present invention can be RNA, DNA, or derivatives of either. The minimum size of such oligonucleotides typically is the size required for formation of a stable hybrid between an oligonucleotide and a complementary sequence within a nucleic acid molecule of the present invention, under stringent hybridization conditions. The present invention includes oligonucleotides that can be used as probes to identify nucleic acid molecules, primers to produce nucleic acid molecules or therapeutic reagents, for example. Stringent hybridization conditions are those experimental parameters that allow an individual skilled in the art to identify significant similarities between heterologous nucleic acid molecules. These conditions are well known to those skilled in the art. See, e.g., Sambrook et al., supra, and Meinkoth et al. (1984) *Anal. Biochem.* 138:267–284.

Recombinant DNA technologies can be used to improve expression of transformed nucleic acid molecules by manipulating, for example, the number of copies of the nucleic acid molecules within a host cell, the efficiency with that those nucleic acid molecules are transcribed, the efficiency with that those nucleic acid molecules are transcribed, the efficiency with that the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgamo sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Nucleic acid molecules within the scope of the invention can be obtained using any method including, without limitation, common molecular cloning and chemical nucleic acid synthesis techniques. For example, PCR can be used to construct nucleic acid molecules that contain plant retroelement sequences. PCR refers to a procedure or technique in which target nucleic acid is amplified in a manner similar to that described in U.S. Pat. No. 4,683,195, and subsequent modifications of the procedure described therein.

The invention also provides isolated plant retroelements containing the nucleic acid molecules described herein, as well as plant cells containing the nucleic acid molecules described herein. The invention features both plants and plant parts (e.g., seeds) containing the nucleic acid molecules and polypeptides provided herein. Suitable plants can include those selected from the group consisting of: soybean, maize, sugar cane, beet, tobacco, wheat, barley, poppy, rape, sunflower, alfalfa, sorghum, rose, carnation, gerbera, carrot, tomato, lettuce, chicory, pepper, melon, cabbage, oat, rye, cotton, flax, potato, pine, walnut, citrus fruit (e.g., orange and grapefruit), hemp, oak, rice, petunia, orchids, *Arabidopsis*, broccoli, cauliflower, Brussels sprouts, onion, garlic, leek, squash, pumpkin, celery, pea, bean, strawberries, grapes, apples, pears, peaches, banana, palm, cocoa, cucumber, pineapple, apricot, plum, sugar beet, lawn grasses, maple, triticale, safflower, peanut, and olive.

Nucleic acids of the present invention can be transferred to cells according to the methods of the present invention, as well as using any suitable means known in the art. The transformed cells can be induced to form transformed plants via organogenesis or embryogenesis, according to the procedures of Dixon (1987) *Plant Cell Culture: A Practical Approach* (IRL Press, Oxford).

Any seed, embryo, plant or plant part is amenable to the methods provided herein. Agronomically significant seeds, embryos, plants or plant parts are particularly useful. For example, soybean, maize, sugar cane, beet, tobacco, wheat, barley, poppy, rape, sunflower, alfalfa, sorghum, rose, carnation, gerbera, carrot, tomato, lettuce, chicory, pepper, melon, cabbage, oat, rye, cotton, flax, potato, pine, walnut, citrus (including oranges, grapefruit etc.), hemp, oak, rice, petunia, orchids, *Arabidopsis*, broccoli, cauliflower, Brussels sprouts, onion, garlic, leek, squash, pumpkin, celery, pea, bean (including various legumes), strawberries, grapes, apples, pears, peaches, banana, palm, cocoa, cucumber, pineapple, apricot, plum, sugar beet, lawn grasses, maple, triticale, safflower, peanut, and olive are among the useful seeds, embryos plants or plant parts. Particularly useful are: soybean, tobacco and maize seeds, embryos, plants or plant parts. However, *Arabidopsis* seeds, embryos, plants or plant parts are also useful, since *Arabidopsis* is an excellent system for study of plant genetics.

2. Polypeptides

The invention provides polypeptides encoded by the nucleic acid molecules described herein. As used herein, a "polypeptide" refers to a chain of amino acid residues, regardless of post-translational modification (e.g., phosphorylation or glycosylation). Polypeptides of the invention can be plant retroelement polypeptides. Polypeptides of the invention typically have amino acid sequences that are at least 60% (e.g., 61%, 65%, 70%, 75%, 80%, 85%, 90%, 95%, 99%, or 100%) identical to the sequences set forth in one or more of the amino acid sequences of SEQ ID NO:1 to SEQ ID NO:165 (e.g., the odd-numbered SEQ ID NOs from SEQ ID NO:43 to SEQ ID NO:165).

Plant retroelement polypeptides of the invention can contain at least one amino acid substitution relative to the corresponding wild type polypeptides (e.g., the odd-numbered SEQ ID NOs from SEQ ID NO:43 to SEQ ID NO:165). Such amino acid substitutions typically are located at positions that are not required for or are minimally involved in reverse transcriptase function. Amino acid substitutions can be conservative or non-conservative. Conservative amino acid substitutions replace an amino acid with an amino acid of the same class, whereas non-conservative amino acid substitutions replace an amino acid with an amino acid of a different class. Examples of conservative substitutions include amino acid substitutions within the following groups: (1) glycine and alanine; (2) valine, isoleucine, and leucine; (3) aspartic acid and glutamic acid; (4) asparagine, glutamine, serine, and threonine; (5) lysine, histidine, and arginine; and (6) phenylalanine and tyrosine.

Non-conservative amino acid substitutions may replace an amino acid of one class with an amino acid of a different class. Non-conservative substitutions can make a substantial change in the charge or hydrophobicity of the gene product. Non-conservative amino acid substitutions also can make a substantial change in the bulk of the residue side chain, e.g., substituting an alanine residue for an isoleucine residue. Examples of non-conservative substitutions include the substitution of a basic amino acid for a non-polar amino acid or a polar amino acid for an acidic amino acid.

Polypeptides of the invention can be any plant retroelement polypeptide. A polypeptide can be, for example, a gag, pol, env, RNaseH, invertase, or reverse transcriptase polypeptide. Such polypeptides can contain a portion or all of one or more of the amino acid sequences provided herein. For example, a plant retroelement polypeptide can be a reverse transcriptase polypeptide having the amino acid sequence of one or more of the odd-numbered SEQ ID NOs from SEQ ID NO:43 to SEQ ID NO:165. Alternatively, a reverse transcriptase polypeptide can be an allelic variant of one or more of the odd-numbered SEQ ID NOs from SEQ ID NO:43 to SEQ ID NO:165. Furthermore, a reverse transcriptase polypeptide can contain two or more particular sequences that are conserved (i.e., "invariant") among the odd-numbered SEQ ID NOs from SEQ ID NO:43 to SEQ ID NO:165. The conserved amino acid sequences are contiguous and reside within or between one of the seven amino acid sequence domains that define reverse transcriptases (Xiong and Eickbush, supra). For example, a reverse transcriptase can contain the amino acid sequence Tip-Val-Ser within reverse transcriptase domain 1; the amino acid sequence Trp-Val-Ser within reverse transcriptase domain 1; the amino acid sequence Thr-Val/Ile-Val/Ile-Xaa-Xaa-Xaa-Xaa-Xaa-Asp/Glu-Leu-Val/Ile (SEQ ID NO:191) between reverse transcriptase domains 1 and 2; the amino acid sequence Thr/Ser-Arg/Lys-Arg/Lys-Asp-His (SEQ ID NO:192) within reverse transcriptase domain 2; and/or the amino acid sequence Met-Leu-Asp/Glu-Arg-Leu (SEQ ID NO:193) spanning the boundary between reverse transcriptase domains 2 and 3. For example, the amino acid sequence Met-Leu-Asp/Glu can be present within reverse transcriptase domain 2, the Arg can be between domains 2 and 3, and the Leu can be within domain 3. Furthermore, a nucleic acid molecule provided herein can encode a reverse transcriptase containing the amino acid sequence the amino acid sequence Cys-Phe-Leu-Asp-Gly-Tyr-Ser (SEQ ID NO:194) within reverse transcriptase domain 3; the amino acid sequence Phe-Thr-Cys-Pro (SEQ ID NO:195) within reverse transcriptase domain 3; the amino acid sequence Phe-Gly-Leu-Cys-Asn-Ala-Pro (SEQ ID NO:196) within reverse transcriptase domain 4; the amino acid sequence Phe-Met-Asp-Asp-Phe (SEQ ID NO:197) within reverse transcriptase domain 5; the amino acid sequence Leu-Val/Ile-Leu-Asn-Trp-Glu-Lys-Cys-His-Phe-Met-Val/Ile (SEQ ID NO:198) spanning the boundary between reverse transcriptase domains 6 and 7 (e.g., with the amino acid sequence Leu-Val/Ile-Leu-Asn-Trp-Glu-Lys-Cys-His-Phe (SEQ ID NO:199) within domain 6, the Met between domains 6 and 7, and the Val/Ile within domain 7); and/or the amino acid sequence Gly-Leu/Ile-Val-Leu-Gly-His (SEQ ID NO:200) within reverse transcriptase domain 7.

As used herein, "reverse transcriptase" refers to a polypeptide having enzymatic activity that catalyzes the incorporation of deoxynucleotides into a nucleic acid molecule, using RNA as a template. For example, a reverse transcriptase can catalyze the incorporation of deoxynucleotides into a cDNA molecule, using mRNA as a template and oligo(dT) as a primer. A reverse transcriptase polypeptide can be identified by measuring its enzymatic activity. Typically, one "unit" of a reverse transcriptase can catalyze the incorporation of 1 mmol dNTP into acid- (e.g., trichloroacetic acid-) precipitatable material in 10 minutes. As such, reverse transcriptase polypeptides such as those containing the sequences specified above can be used to prepare double-stranded nucleic acid molecules from RNA molecules. Reverse transcriptase polypeptides are further defined as amino acid sequences having the seven conserved amino acid sequence domains that characterize all known reverse transcriptases (Xiong and Eickbush, supra). These seven amino acid sequence domains can be identified using a standard amino acid sequence alignment program (e.g. ClustalX; see, Thompson et al. (1997) *Nucl. Acids Res.* 24:4876–4882). Input data for alignments can include amino acid sequences for reverse transcriptases from characterized retrotransposons, as well as retroelement and reverse transcriptase amino acid sequences such as those described above. Alignment can be performed using default parameters, and the seven conserved domains can be identified in by comparison to the domains identified in the alignment of Xiong and Eickbush, supra.

Plant retroelement polypeptides can be produced by a number of different methods. For example, polypeptides can be obtained by extraction from viruses, isolated cells, tissues, and plant fluids. Polypeptides also can be produced by chemical synthesis. Alternatively, polypeptides of the invention can be produced by standard recombinant technology using heterologous expression vectors encoding retroelement polypeptides. Expression vectors can be introduced into host cells (e.g., by transformation or transfection) for expression of the encoded polypeptide, which then can be purified. Expression systems that can be used for small or large scale production of plant retroelement polypeptides include, without limitation, microorganisms such as bacteria (e.g., *E. coli* and *B. subtilis*) transformed with recombinant bacteriophage DNA, plasmid DNA, or cosmid DNA expression vectors containing the nucleic acid molecules of the invention, and yeast (e.g., *S. cerevisiae*) transformed with recombinant yeast expression vectors containing the nucleic acid molecules of the invention. Useful expression systems also include insect cell systems infected with recombinant virus expression vectors (e.g., baculovirus) containing the nucleic acid molecules of the invention, and plant cell systems infected with recombinant virus expression vectors (e.g., tobacco mosaic virus) or transformed with recombinant plasmid expression vectors (e.g., Ti plasmid) containing the nucleic acid molecules of the invention. Plant retroelement polypeptides also can be produced using mammalian expression systems, which include cells (e.g., primary cells or immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids of the invention.

3. Host Cells—Eukaryotic Organisms

The term "host" or "host cell" includes not only prokaryotes, such as *E. coli*, but also eukaryotic cells such as fungus, insect, plant, and animal cells. Animal cells include, for example, COS cells and HeLa cells. Fungal cells include yeast cells, such as *Saccharomyces cereviseae* cells. Host cells containing a nucleic acid (e.g., a vector) of the present invention can be used for such purposes as propagating a vector, producing a nucleic acid (e.g., DNA, RNA, or antisense RNA), or expressing a polypeptide or a fragment thereof.

Host cells can be transformed with a DNA molecule (e.g., a vector) using techniques known to those of ordinary skill in the art, such as, without limitation, calcium phosphate or lithium acetate precipitation, electroporation, lipofection and particle bombardment. Other useful methods include, for example, infective, vector-containing bacterial strains (such as *Agrobacterium rhizogenes* and *Agrobacterium tumefaciens*) according to Zambryski (1992) *Ann. Rev. Plant Mol. Biol.* 43:465; pollen-tube transformation (Zhon-xun et al. (1989) *Plant Cell* 1:133); polyethylene glycol or electroporation transformation (Christou et al. (1987) *Proc. Nat. Acad. Sci. USA* 84:3662); and bilistic processes (Yang and Christou (1994) *Particle Bombardment Technology for Gene Transfer*).

As used herein, the term "transformed" is meant to encompass any suitable method for introducing a nucleic acid molecule into a host cell (e.g., transformation, transfection, transduction, or infection). A host cell can be transformed using any of the methods disclosed herein, for example. Furthermore, host cells that integrate an introduced nucleic acid sequence into their genome are called stably transformed cells. Stably transformed cells typically retain the introduced nucleic acid sequence with each cell division. Cells that contain introduced nucleic acid sequences that are not integrated into the genome are called transiently transformed cells. Transiently transformed cells typically lose at least a portion of the introduced nucleic acid sequence with each cell division. Thus, transformed cells can be either transiently and/or stably transformed.

Plants: Among the eukaryotic organisms featured in the invention are plants containing an exogenous nucleic acid that encodes a polypeptide of the invention.

Accordingly, a method according to the invention comprises making a plant having a nucleic acid construct described herein. Techniques for introducing exogenous nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants can be entered into a breeding program, e.g., to introduce a nucleic acid encoding a polypeptide into other lines, to transfer the nucleic acid to other species or for further selection of other desirable traits. Alternatively, transgenic plants can be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds (i.e., transgenic seeds) produced by a transgenic plant can be grown and then selfed (or outcrossed and selfed) to obtain seeds homozygous for the nucleic acid encoding a novel polypeptide.

Polypeptides of the invention can be expressed in plants in a cell- or tissue-specific manner according to the regulatory elements included within a particular nucleic acid construct present in the plant. Suitable cells, tissues and organs in which to express a polypeptide of the invention include, without limitation, egg cell, central cell, synergid cell, zygote, ovule primordia, nucellus, integuments, endothelium, female gametophyte cells, embryo, axis, cotyledons, suspensor, endosperm, seed coat, ground meristem, vascular bundle, cambium, phloem, cortex, shoot or root apical meristems, lateral shoot or root meristems, floral meristem, leaf primordia, leaf mesophyll cells, and leaf epidermal cells, e.g., epidermal cells involved in forming the cuticular layer. Also suitable are cells and tissues grown in liquid media or on semi-solid media.

Fungi: Other eukaryotic organisms featured in the invention are fungi containing an exogenous nucleic acid that encodes a chimeric polypeptide of the invention.

Accordingly, a method according to the invention comprises introducing a nucleic acid construct as described herein into a fungus. Techniques for introducing exogenous nucleic acids into many fungi are known in the art, e.g., U.S. Pat. Nos. 5,252,726 and 5,070,020. Transformed fungi can be cultured by techniques known to those skilled in the art. Such fungi can be used to introduce a nucleic acid encoding a polypeptide into other fungal strains, to transfer the nucleic acid to other species or for further selection of other desirable traits.

A suitable group of fungi with which to practice the invention include fission yeast and budding yeast, such as *Saccharomyces cereviseae*, *S. pombe*, *S. carlsbergeris* and *Candida albicans*. Filamentous fungi such as *Aspergillus* spp. and *Penicillium* spp. are also useful.

Animals: Other eukaryotic host cells featured in the invention are animals cells (e.g., cells from insects such as mosquitoes and flies, fish, and mammals such as rodents, bovines and porcines, including cell lines such as Chinese hamster ovary cells, HeLa cells, and COS cells) that contain an exogenous nucleic acid that encodes a polypeptide of the invention (e.g., a nucleic acid molecule encoding a polypeptide having the amino acid sequence of one or more one of the odd-numbered SEQ ID NOs from SEQ ID NO:43 to SEQ ID NO:165). In some embodiments, the animal cells are within transgenic animals. A variety of techniques known in the art can be used to generate such transgenic animals. Such techniques typically involve generating a plurality of animals whose genomes can be screened for the presence or absence of the transgene. For example, a transgene can be introduced into a non-human mammal by pronuclear microinjection (U.S. Pat. No. 4,873,191), retrovirus mediated gene transfer into germ lines (Van der Putten et al. (1985) *Proc. Natl. Acad. Sci. USA* 82:6148), gene targeting into embryonic stem cells (Thompson et al. (1989) *Cell* 56:313), electroporation of embryos (Lo (1983) *Mol. Cell. Biol.* 3:1803), and transformation of somatic cells in vitro followed by nuclear transplantation (Wilmut et al. (1997) *Nature* 385:810–813; and Wakayama et al. (1998) *Nature* 394:369–374). When using mice to make a transgenic animal, suitable genetic backgrounds for use in making founder lines include, without limitation, C57B6, SJL/J, FVB/N, 129SV, BALB/C, C3H, and hybrids thereof.

The invention also provides methods to transfer nucleic acid molecules into host cells (e.g., prokaryotic, fungal, plant, and animal cells). Such methods can involve contacting a host cell with a nucleic acid molecule of the present invention, under conditions sufficient to allow the nucleic acid molecule to enter the cell. In particular, the invention provides methods to impart agronomically significant characteristics to plant cells, by contacting a plant cell with a nucleic acid molecule encoding an agronomically significant characteristic, under conditions sufficient to allow the nucleic acid molecule to enter the cell. Useful agronomically significant characteristics include, for example, those selected from the group consisting of: male sterility, self-incompatibility, foreign organism resistance, improved biosynthetic pathways, environmental tolerance, photosynthetic pathways, nutrient content, fruit ripening, oil biosynthesis, pigment biosynthesis, seed formation, starch metabolism, salt tolerance, cold/frost tolerance, drought tolerance, tolerance to anaerobic conditions, protein content, carbohydrate content, amino acid content, and fatty acid content.

Cultured cell lines: In some embodiments, host cells can be cultured cell lines. Cultured helper cell lines that express gag, pol, and env genes can be particularly useful. In some embodiments, a cell line can be transformed with a retroelement vector containing LTR sequences flanking a PPT, a PBS, and a nucleotide sequence of interest (e.g., a nucleotide sequence encoding an agronomically significant characteristic).

The following paragraph is designed to elaborate on the best mode and is not indicative of the sole means for making and carrying out the present invention. This paragraph is not intended to be limiting. The best way to make the present nucleic acids is to clone the nucleic acids from the respective organisms or amplify them from genomic cDNA by the polymerase chain reaction using appropriate primers. The best way to make the present retroelements is to assemble the nucleic acids using standard cloning procedures. Transcriptional controls can be manipulated by inserting enhancers in or near the 5' LTR. Marker genes or genes of interest can be inserted within the retroelement.

In these new aspects of the invention, it is understood that the materials and methods described previously are useful in obtaining the present materials. Moreover, the discussion as to scope and usefulness of the invention, including the percent identities, retroelement uses and constructs, plants transfected, methods for improving crops, etc. are applicable for the present new aspects as well. For instance, combination of the previously disclosed materials with the present materials are certainly within the scope of the present disclosure.

The invention will be further described in the following examples, which do not limit the scope of the invention described in the claims.

EXAMPLES

Example 1

Characterizing the *Arabidopsis* Retroelements ("Tat" and "Athila" Elements)

Plant material and Southern hybridizations: The *Arabidopsis* Information Service supplied the following seed stocks (Kranz and Kirchheim (1987) *Arabidopsis Inform. Serv.* 24): Col-0, La-0, Kas-1, Co-4, Sei-0, Mv-0, L1-0, Cvi-0, Fi-3, Ba-1, Hau-0, Aa-0, Ms-0, Ag-0, Ge-0, No-0 and Mh-0. Genomic DNA was extracted using Qiagen genomic tips and protocols supplied by Qiagen (Valencia, Calif.). For Southern hybridizations, the resulting DNA was digested with EcoRI, electrophoresed on 0.8% agarose and transferred to Gene Screen Plus membranes using the manufacturer's alkaline transfer protocol (Perkin Elmer™ Life Sciences, Boston, Mass.). All hybridizations were performed as described by Church and Gilbert (1984) *Proc. Natl. Acad. Sci. USA* 81:1991–1995.

Library screening, probe preparation and PCR: Tat1 clones were obtained by screening a Landsberg erecta (La-0) 1 phage library (Voytas et al. (1990) supra), using a probe derived by PCR amplification of La-0 DNA. The primers for probe amplification were based on the three published Tat1 sequences (DVO158, 5'-GGGATCCGCAATTAGAATCT-3' (SEQ ID NO:170); DVO159, 5'-CGAATTCGGTCCACT-TCGGA-3' (SEQ ID NO:171)). See, Peleman et al. (1991) *Proc. Natl. Acad. Sci. USA* 88:3618–3622. Subsequent probes were restriction fragments of cloned Tat1 elements, and all probes were radiolabeled by random priming (Promega). Long PCR was performed using the Expand Long Template PCR System (Boehringer Mannheim) with LTR-specific primers DVO354 (5'-CCACAAGATTCTAAT-TGCGGATTC-3'; SEQ ID NO:172) and DVO355 (5'-CCGAAATGGACCGAACCCGACATC-3'; SEQ ID NO:173). The protocol used was for PCR amplification of DNA up to 15 kb in length. The following PCR primers were used to confirm the structure of Tat1–3: DVO405 (5'-TTTCCAGGCTCTTGACGAGATTTG-3'; SEQ ID NO:174) for the 3' non-coding region, DVO385 (5'-CGACTCGAGCTCCATAGCGATG-3'; SEQ ID NO:175) for the second ORF of Tat1–3 (note that the seventh base was changed from an A to a G to generate XhoI and SalI restriction sites) and DVO371 (5'-CGGATTGGGC-CGAAATGGACCGAA-3'; SEQ ID NO:176) for the 3' LTR.

DNA sequencing: Clones were sequenced either by the DNA sequencing facility at Iowa State University or with the fmol sequencing kit (Promega). DNA from the λ phage clones was initially subcloned into the vector pBluescript II KS⁻ and transformed into the *E. coli* host strain XL1 Blue (Stratagene). Ausubel et al, supra. Subclones in the vector pMOB were used for transposon mutagenesis with the TN 1000 sequencing kit (Gold Biotechnologies). Transposon-specific primers were used for DNA sequencing reactions.

Sequence analysis: Sequence analysis was performed using the GCG software package (Devereux et al. (1984) *Nucl. Acids Res.* 12:387–395), DNA Strider 1.2 (Marck (1991) DNA Strider 1.2, Gif-sur-Yvette, France), the BLAST search tool (Altschul et al. (1990) *J. Mol. Biol.* 215:403–410) and the tRNAscan-SE 1.1 program (Lowe and Eddy (1997) *Nucl. Acids Res.* 25:955–964). Phylogenetic relationships were determined by the neighbor-joining distance algorithm using Phylip (Felsenstein (1993) PHYLIP (Phylogeny Inference Package), Department of Genetics, University of Washington, Seattle; Saitou and Nei (1987) *Mol. Biol. Evol.* 4:406–425) and were based on reverse transcriptase amino acid sequence that had been aligned with ClustalW1.7. Thompson et al. (1994) *Nucl. Acids Res.* 22:4673–4680. Transmembrane helices were identified using the PHDhtm program. Rost et al. (1995) *Port. Science* 4:521–533. All DNA sequences have been submitted to the DDBS/EMBL/GenBank databases under the accession numbers X12345, X23456, X34567 and X45678.

Tat1 is a retrotransposon: Tat1 insertions share features with retrotransposon solo LTRs. We reasoned that if Tat1 is a retrotransposon, then there should be full-length elements in the genome consisting of two Tat1 sequences flanking an internal retrotransposon coding region. To test this hypothesis, additional Tat1 elements were isolated by screening a Landsberg (La-0) genomic DNA library with a Tat1 probe. Twenty-one 1 phage clones were isolated and Southern analysis revealed two clones (pDW42 and pDW99) each with two copies of Tat1 (data not shown). The two Tat1 elements in each clone were sequenced, along with the intervening DNA. All Tat1 sequences shared >89% nucleotide identity to the previously characterized Tat1a–Tat1c elements. Peleman et al., supra. In clone pDW99, the 5' and 3' Tat1 sequences were 433 bases in length and only differed at two base positions. These Tat1 sequences also had conserved features of LTRs, including the dinucleotide end-sequences (5' TG-CA 3') that were part of 12 base inverted terminal repeats. If the two Tat1 elements in clone pDW99 were retrotransposon LTRs, then both, along with the intervening DNA, should be flanked by a target site duplication. A putative five base target site duplication (TATGT) was present immediately adjacent to the 5' and 3' Tat1 elements, supporting the hypothesis that they and the intervening DNA inserted as a single unit. In clone pDW42, the 5' Tat1 was 432 bases in length and shared 98% nucleotide sequence identity to the 3' Tat1. The last ~74 bases of the 3' Tat1 was truncated during library construction and lies adjacent to one phage arm. A target site duplication, therefore, could not be identified in this clone.

DNA sequences were analyzed for potential coding information between the 5' and 3' Tat1 elements. Nearly identical ORFs of 424 and 405 amino acids were found encoded between the Tat1 sequences in PDW42 and pDW99, respectively. The derived amino acid sequences of these ORFs were used to search the DNA sequence database with the BLAST search tool, and significant similarity was found to the *Zea mays* retrotransposable element Zeon-1 (p=4.4×10⁻⁸). Hu et al. (1995) *Mol. Gen. Genet.* 248:471–480. The ORFs have ~44% similarity across their entirety to the 628 amino acid ORF encoded by Zeon-1 (see below). The Zeon-1 ORF includes a zinc finger motif characteristic of retrotransposon gag protein RNA binding domains. Although the Tat1 ORFs do not include the zinc finger motif, the degree of similarity suggests that they are part of a related gag protein.

If the Tat1 sequences in pDW42 and pDW99 defined retrotransposon insertions, a PBS would be predicted to lie adjacent to the 5' Tat1 elements in both clones. The putative Tat1 PBS shares similarity with the PBSs of Zeon-1 and another maize retrotransposon called Cinful (see below), but it is not complementary to an initiator methionine tRNA as is the case for most plant retrotransposons. Additionally, a possible polypurine tract (PPT), the primer for second strand cDNA synthesis, was observed one base upstream of the 3' Tat1 sequence in both phage clones (5'-GAGGACT-TGGGGGGCAAA-3'; SEQ ID NO:177). We concluded from the available evidence that Tat1 is a retrotransposon, and we have designated the 3960 base insertion in pDW42 as Tat1-1 and the 3879 base insertion in pDW99 as Tat1-2. It is apparent that both Tat1-2 and Tat1-2 are non-funtional. Their ORFs are truncated with respect to the coding information found in transposition-competent retrotransposons, and they lack obvious pol motifs.

In light of our findings, the previously reported Tat1 sequences can be reinterpreted. Tat1 a and Tat1b, which are flanked by putative target site duplications, are solo LTRs. Tat1c, the only element without a target site duplication, is actually the 5' LTR and part of the coding sequence for a larger Tat1 element.

Copy number of Tat1 among *A. thaliana* ecotypes: To estimate Tat1 copy number, the 5' LTR, gag and the 3' non-coding region were used as separate probes in Southern hybridizations. The Southern filters contained genomic DNA from 17 ecotypes representing wild populations of *A. thaliana* from around the world. This collection of ecotypes had previously been used to evaluate retrotransposon population dynamics. Konieczny et al., supra; Voytas et al. (1990) supra; Wright et al. (1996) *Genetics* 142:569–578. Based on the hybridization with the gag probe, element copy number ranges from two to approximately ten copies per ecotype. The copy number of the LTRs is higher, likely due to the presence of two LTRs flanking full-length elements or solo LTRs scattered throughout the genome. The Tat1 copy number contrasts with the copy numbers (typically less than three per ecotype) observed for 28 other *A. thaliana* retrotransposon families. In addition, the Tat1-hybridizing restriction fragments are highly polymorphic among strains. This degree of polymorphism, coupled with the high copy number, suggested that Tat1 has been active in transposition since the separation of the ecotypes. The Tat1 3' non-coding region contains DNA sequences from elsewhere in the genome: In an attempt to identify a complete and functional Tat1 element, LTR-specific primers were used in PCR reactions optimized for amplification of large DNA fragments. Most full-length retrotransposable elements are between five and six kb in length. DNAs from al 17 ecotypes were used as templates, and each gave amplification products of ~3.2 kb, the size predicted for Tat1-1 and Tat1-2 (data not shown). In La-0, however, a 3.8 kb PCR product was also recovered. This PCR product was cloned, sequenced and called Tat1-3. This insertion is expected to be about 4.6 Kb in total length if the LTR sequences are included.

Tat1-3 differed from Tat1-1 and Tat1-2 in that it had two ORFs separated by stop codons and a 477 base insertion in the 3' non-coding region. The first ORF (365 amino acids) was similar to but shorter than the ORFs of the other Tat1 elements. The sequences constituting the second ORF (188 amino acids) were not present in the other Tat1 insertions and were not related to other sequences in the DNA databases. Database searches with the 477 base insertion in the 3' non-coding region, however, revealed three regions of similarity to other genomic sequences. A region of 113 bases matched a region of 26 bp repeats in the 5' untranslated sequence of the AT-P5C1 mRNA, which encodes pyrroline-5-carboxylate reductase (p=2.1e-19). Verbruggen et al. (1993) *Plant Physiol.* 103: 771–781. In addition, 50 bases appear to be a remnant of another retrotransposon related to Tat1. These 50 bases are 71% identical to the 3' end of the Tat1-3 LTR and the putative primer binding site. The putative primer binding site, however, is more closely related to those of other plant retrotransposons such as Huck-2 (Sanmiguel et al. (1996) Science 274: 765–768). Finally, sequences in the remainder of the insertion showed significant similarity to a region on chromosome 5. To confirm that Tat1-3 was not a PCR artifact, two additional primer pairs were used in separate amplifications. Both amplifications gave PCR products of the predicted sizes, which were cloned and confirmed to be Tat1-3 by DNA sequencing.

PCR amplification with the additional primer pairs also yielded a product 0.8 kb longer than that expected for Tat1-3. This product was cloned, sequenced and found to be another Tat1 element, designated Tat 1-4. This element has sequences similar to a Tat1 LTR, polypurine tract and the second ORF of Tat1-3. In Tat1-4, 1182 bases of DNA are found in the 3' non-coding region at the position corresponding to the 477 base insertion in Tat1-3. This region does not match any sequences in the DNA databases.

Other Tat1-like elements in *A. thaliana*: A BLAST search of DNA sequences generated by the *A. thaliana* genome project identified two more solo LTRs similar to Tat1. All share similarities throughout, but most strikingly, they are very well conserved at the 5' and 3' ends where it is expected integrase would bind. Braiterman and Boeke (1994) *Mol. Cell. Biol.* 14:5731–5740. These conserved end-sequences suggests that the integrases encoded by full-length elements are also related, and that the LTRs have evolved under functional constraints; that is, they are not simply degenerate Tat1 LTRs. The two new LTRs are designated as Tat2-1 and Tat3-1. Tat2-1 is 418 bases long, is flanked by a five base target site duplication (CTATT) and is ~63% identical to the Tat1-2 5'LTR. Tat3-1 is 463 bases long and is also flanked by a target site duplication (ATATT). Tat3-1 is ~53% identical to the Tat1-2 5' LTR.

Tat1 and Athila are related to Ty3/gypsy retrotransposons: Further analysis of data from the *A. thaliana* genome project revealed two slightly degenerate retrotransposons with similarity to the Tat1 ORF. These elements were identified within the sequence of the P1 phage clones MXA21 (Accession AB005247; bases 54,977–66,874) and MX110 (Accession AB005248; bases 24,125–35,848). Each has two LTRs, a putative PBS, and long ORFs between their LTRs. The genetic organization of these elements is depicted in FIGS. 5A and 6A. Amino acid sequence analysis indicated the presence of an RNA binding domain that defines gag in both elements. This region is followed by conserved reverse transcriptase, RNaseH, and integrase amino acid sequence domains characteristic of pol (data not shown). Classification of eukaryotic retrotransposons into the Ty1/copia elements (*Pseudoviridae*) and Ty3/gypsy elements (*Metaviridae*) is based on pol gene structure. Boeke et al. *Metaviridae*, supra; Boeke et al. *Pseudoviridae*, supra. The domain order of the pol genes (reverse transcriptase precedes integrase) and similarities among their encoded reverse transcriptases (see below) identifies these elements as the first full-length *A. thaliana* Ty3/gypsy elements.

Because the characterized Tat1 insertions do not encode pol genes, this element family could not be classified. However, the amino acid sequence of the Tat1-2 ORF is 51% similar to the gag region of the MXA21 retrotransposon. Since plant retrotransposons within the Ty1/copia or Ty3/gypsy families, even those with highly similar pol genes, share little amino acid sequence similarity in their gag regions, Tat1 is likely a Ty3/gypsy element. This conclusion is further supported by the report that the Tat-like Zcon-1 retrotransposon is very similar to a *Z. mays* Ty3/gypsy element called cinful (Bennetzen, supra); however, only the 5' LTR and putative primer binding site (PBS) sequences are available in the sequence database for analysis (Accession No. U68402). Because of the extent of similarity to Tat1, we have named the MXA21 insertion Tat4-1.

The gag region of the MX110 element is 62% similar ($p=1.1 \times 10^{-193}$) to the first ORF of Athila, which has previously been unclassified (Pelissier et al. (1995) *Plant Mol. Biol.* 29:441–452). This implies that Athila is also a Ty3/gypsy element, and we have designated the MX110 insertion as Athila1-1. Our classification of Athila as a Ty3/gypsy element is further supported by the observation that the Athila gag amino acid sequence shares significant similarity to the gag protein encoded by the Cyclops-2 Ty3/gypsy retrotransposon of pea (Accession AJ000640; $p=1.1 \times 10^{-46}$; data not shown). Further analysis of the available *A. thaliana* genome sequences identified three additional Athila homologs. They include an additional Athila1 element, designated Athila1-2, and two more distantly related Athila-like elements, designated Athila2-1 and Athila3-1.

In addition to similarities among their gag amino acid sequences, the Tat elements have short LTRs (<550 bp) and long 3' non-coding regions (>2 kb). In contrast, the Athila-like elements have long LTRs (>1.2 kb) and are very large retrotransposons (>11 kb). One additional feature to note about both the Athila-like and Tat-like elements is the high degree of sequence degeneracy of their internal coding regions. This contrasts with the near sequence identity of their 5' and 3' LTRs, which is typically greater than 95%. Because a single template is used in the synthesis of both LTRs, LTR sequences are usually identical at the time of integration. The degree of sequence similarity between the LTRs suggests that most elements integrated relatively recently. The polymorphisms observed in the internal domains of these insertions, therefore, may have been present in their progenitors, and these elements may have been replicated in trans.

A novel, conserved coding region in Athila elements: A surprising feature of Athila1-1 is the presence of an additional ORF after integrase. Like gag, this ORF shares significant similarity across its entirety ($p=3.8 \times 10^{-8}$) to the second ORF of Athila. This ORF is also encoded by the Athila2-1 and Athila3-1 elements, although it is somewhat more degenerate. The presence of this coding sequence among these divergent retrotransposons suggests that it plays a functional role in the element replication cycle. However, the ORF shows no similarity to retrotransposon gag or pol genes. The retroviruses and some Ty3/gypsy retrotransposons encode an env gene after integrase. Although not well-conserved in primary sequence, both viral and retrotransposon envelope proteins share some structural similarities. They are typically translated from spliced mRNAs and the primary translation product encodes a signal peptide and a transmembrane domain near the C-terminus. All four families of Athila elements encode a domain near the center of the ORF that is strongly predicted to be a transmembrane region (70%–90% confidence, depending on the element analyzed). See, Rost et al., supra. Two retrotransposons, Athila and Athila2-1, also have a hydrophobic transmembrane domain near the 5' end of their env-like ORFs, which may serve as a secretory signal sequence. Von Heijne (1986) *Nucl. Acids Res.* 14:4683–4690.

Two lineages of plant Ty3/gypsy retrotransposons: Relationships among Ty3/gypsy retrotransposons from *A.*

*thaliana* and other organisms were assessed by constructing a neighbor-joining tree of their reverse transcriptase amino acid sequences. Including in the analysis were reverse transcriptases from two additional families of *A. thaliana* Ty3/gypsy elements that we identified from the unannotated genome sequence data (designated Tma elements; Tma1-1 and Tma3-1); two other Tma element families were identified in the genome sequence that did not encode complete reverse transcriptases (Tma2-1 and Tma4-1; Table 1). Also included in the phylogenetic analyses were reverse transcriptases from a faba bean retrotransposon and the cyclops-2 element from pea. The plant Ty3/gypsy group retrotransposons resolved into two lineages: One was made up of dell from lily, the IFG7 retrotransposon from pine, reina from *Z. mays*, and Tma1-1 and Tma3-1. This group of elements formed a single branch closely related to numerous fungal retrotransposons (branch 1). The second branch (branch 2) was well-separated from all other known Ty3/gypsy group elements, and was further resolved into two lineages: Athila1-1, cyclops-2 and the faba bean reverse transcriptase formed one lineage (the Athila branch), and Tat4-1 and Grande1-4 from *Zea diploperennis* formed a separate, distinct branch (the Tat branch).

Primer binding sites: Most plant Ty1/copia retrotransposons as well as the branch 1 Ty3/gypsy elements have PBSs complementary to the 3'-end of an initiator methionine tRNA. This is not the case for any of the branch 2 Ty3/gypsy elements. We compared the putative PBSs of Tat-branch and Athila-branch elements to known plant tRNA genes as well as to the 11 tRNA genes that had been identified to date in sequences generated by the *A. thaliana* genome project. In addition, we searched the unannotated *A. thaliana* genome sequences and identified 30 more *A. thaliana* tRNA genes using the program tRNAscan-SE (Lowe and Eddy (1997) *Nucl. Acids Res.* 25:955–964). The PBS of Tat1 is complementary to 10 bases at the 3' end of the asparagines tRNA for the AAC codon; these 10 bases are followed by a two base mismatch and six additional bases of perfect complementarity. The Tat4-1 PBS is complementary to 20 bases at the 3' end of the arginine tRNA for the AGG codon with one mismatch 10 bases from the 3' end; Huck-2, Grande-zm1, Grande1-4, and the retrotransposon-like insertion in the 3' non-coding region of Tat1-3 all have 20-base perfect complementarity to this tRNA. The PBS of Athila1-1 is perfectly complementary to 15 bases at the 3' end of the aspartic acid tRNA for the GAC codon, and Athila and Athila2-1 have 13 bases of complementarity to this tRNA. At this time there is no known plant tRNA complementary to the PBS of Zeon-1, which has the same PBS as the maize retrotransposon cinful. As more tRNA sequences become available, a candidate primer may be identified for these elements.

Example 2

Characterizing the *Pisum sativum* Retroelement ("Cyclops" Element) env Gene

After identifying the retroelement elements in *A. thaliana*, the element called Cyclops2 from *Pisum sativum* (Chavanne et al., supra) was examined. Comparison of this element to the Athila-like elements both in size and amino acid and nucleotide sequence composition was made. Cyclops2 also encodes an open reading frame (ORF) in the position corresponding to the env-like gene of the Athila elements. This Cyclops2 ORF was examined using the same methods used to characterize the Athila group env-like genes (see Example 1). The Cyclops2 ORF was found to have a potential splice site at its N-terminus and transmembrane domains at the N-terminus, the central region and the C-terminus. Based on the presence of these features, it was concluded that Cyclops2 is a retrovirus-like retroelement that encodes on env-like gene.

Example 3

Obtaining the Soybean Retroelements ("Calypso" Elements)

Library Screening and Southern Hybridization: A soybean genomic lambda phage library (line L85–3044) was initially screened with a reverse transcriptase probe under low stringency conditions (50° C. with a 1% SDS wash; Church and Gilbert supra). The library was previously described (Chen et al. (1998) *Soybean Genetics Newsletter* 25:132–134). The probe was obtained by PCR amplification of genomic *P. sativum* DNA using primers based on the reverse transcriptase of Cyclops2 (DVO701 and DVO702). All probes were radio-labeled using random primers and protocols supplied by Promega. For Southern hybridizations, DNA was digested, electrophoresed on 0.8% agarose gels, and transferred to Gene Screen Plus membranes using the manufacturer's alkaline transfer protocol (Perkin Elmer™ Life Sciences). All high stringency hybridizations were as described by Church and Gilbert, supra.

DNA sequencing: Lambda phage clones were subcloned into the vector pBluescript KSII— and transformed into the *E. coli* host strain XL1 Blue (Stratagene) as described by Ausubel et al., supra. Subclones were sequenced by primer walking at the Iowa State University DNA sequencing facility.

Sequence Analysis: DNA Sequence analysis was performed using the GCG software package (Devereux et al., supra), DNA Strider 1.2 (Marck (1991) DNA Strider 1.2, Gif-sur-Yvette, France) and the BLAST search tool (Altschul et al., supra). Phylogenetic relationships were determined by the neighbor-joining distance algorithm (Saitou and Nei, supra) using PAUP v4.0 beta 1 (Swofford (1993) Illinois Natural History Survey, Champaign, IL.) and were based on reverse transcriptase amino acid sequences that had been aligned with ClustalX v1.63 b (Thompson et al., supra). Transmembrane helices were identified using the PHDhtm program and TMPred (Rost et al., supra; and Hofmann and Stoffel (1993) *Biol. Chem.* 374:166).

Retrovirus-like elements in Glycine max. Soybean retrovirus-like elements were identified by a low stringency (50° C.) screen of a soybean lambda library using a reverse transcriptase probe. The probe was based on a sequence from Cyclops2 (Chavanne et al., supra). The screen produced 63 λ clones that appeared to contain a retrovirus-like reverse transcriptase based on hybridization to the probe. Thirty-five of these putative elements were sequenced to varying degrees and 24 encoded readily identifiable retrovirus-like sequences. Most of the elements were distantly related and had premature stop codons, frame shifts, deletions or insertions. A related group of three elements and another related pair were completely sequenced and analyzed. The three elements in the first group are referred to as Calypso1-1, Calypso1-2, and Calypso1-3. The elements in the second pair are referred to as Calypso2-1 and Calypso2-2. The remaining soybean retrovirus-like elements will be given the Calypso name and a sequential designator number based on their family grouping.

The Calypso retrovirus-like elements had the same overall structure and sequence homology as the previously described Athila and Cyclops elements. The elements were about 12 kb in length; they had a 5' LTR, a Primer Binding Site (PBS), a gag protein, a pol protein, a spacer, an env-like protein, another spacer region, a Polypurine Tract (PPT) and a 3' LTR. The LTRs varied from about 1.3 to about 1.5 kb in length, and characteristically began with TG and ended with CA. The PBS was similar to that used by the Athila and Cyclops elements; it is 4 to 6 bases past the 5' LTR and matches the 3' end of a soybean aspartic acid tRNA for 18 to 19 bases with 1 mismatch. The fact that the sequences of the Calypso primer binding sites are shared with the *A. thaliana* and *P. sativum* retrovirus-like elements, indicates that this sequence is a unique marker for envelope-encoding retroelements. The gag protein extends ~850 amino acids and encodes a zinc finger domain (characterized by the amino acid motif CxxCxxxHxxxxC; SEQ ID NO:178) and a protease domain (characterized by the amino acid motif LIDLGA (SEQ ID NO:179)). These domains are located at approximately the same positions within gag as in other retroelements. The approximately 600 amino acid reverse transcriptase region follows gag and has the conserved plant retrovirus-like motifs that approximate the following amino acids: KTAF (SEQ ID NO:180), MP/SFGLCNA (SEQ ID NO:181), V/I/MEVFMDDFS/WV/I (SEQ ID NO:182), FELMCDASDYAI/VGAVLGQR (SEQ ID NO:183), and YATT/IEKEL/MLAIVF/YAL/FEKFR/KSYLI/VGSR/KV (SEQ ID NO:184), respectively. The approximately 450 amino acid integrase domain has the plant retrovirus-like integrase motifs that approximate HCHxSxxGGH30xCDxCQR (SEQ ID NO:185) for the Zn finger as well as two other motifs that approximate WGIDFI/V/MGP (SEQ ID NO:186), and PYHPQTxGQA/VE (SEQ ID NO:187). After integrase, there is a ~0.7 kb spacer then a ~450 amino acid env-like protein coding region. The env-like protein of the Calypso elements is well conserved through most of the ORF but conservation decreases toward the C-terminus. The conservation includes 2 or 3 presumed transmembrane domains and a putative RNA splice site acceptor. The coding sequence for the env-like protein is followed by a ~2 kb spacer and then a polypurine tract with the approximate sequence ATTTGGGGG/AANNT (SEQ ID NO:188). The 3' LTR starts immediately after the final T of the PPT.

Calypso elements are abundant and heterogeneous: The Calypso elements appear to be abundant in the soybean genome. High stringency Southern blots of soybean DNA probed with reverse transcriptase, gag or env-like sequences produced smeared hybridization patterns, suggesting that the elements are abundant and heterogeneous. Their heterogeneity was also supported by DNA sequence analysis, which revealed a maximum of 93% nucleotide identity among elements, and most elements averaged ~88% nucleotide identify. This identity can be region-specific or dispersed over the element's entirety. For example, reverse transcriptase, integrase and envelope-like coding regions may be well conserved, whereas the LTR, gag and spacer regions may have very little sequence conservation.

Phylogenetic analysis of Calypso reverse transcriptase: The reverse transcriptase of retroelements is the preferred protein for assessment of phylogenetic relationships (Xiong and Eickbush, supra). This is due to the high degree of amino acid sequence conservation found in reverse transcriptase proteins from many sources. The Calypso retrovirus-like elements were compared to previously described Ty3/gypsy and retrovirus-like elements from plants, fungi and invertebrate animals. The Calypso elements formed a distinct group with other plant retrovirus-like elements from *A. thaliana* and *P. sativum* and Faba bean. This group did not include plant Ty3/gypsy elements that are members of the metavirus genus. This indicates that the plant retrovirus-like elements from these four plant species are closely related and form a new element group that may be present in all or most plant species.

The Calypso reverse transcriptase and integrase are well-conserved: Frame shifts in the retrovirus-like elements were repaired through sequence comparison between the retrovirus-like elements from *A. thaliana, P. sativum* and *G. max*. Restoration typically involved an insertion or deletion of a single nucleotide or a single nucleotide substitution. When the edited ORFs of seven plant retrovirus-like elements from three species were compared, it was found that the gag domain had very little conservation. The amino acid sequence around the protease domain was reasonably conserved (~50%) but the reverse transcriptase and integrase domains were highly conserved (~70%).

The env-like ORF of Calypso is well-conserved: Animal retrovirus env proteins share little in common. They are however cleaved into two functional units that consist of the surface (SU) and transmembrane (TM) peptides. The SU peptide contains a transmembrane secretory signal at the N-terminus. The TM peptide has two transmembrane domains, one at the N-terminus, which functions in membrane fusion, and another near the C-terminus, which acts as an anchor site. The retrovirus env protein is expressed from an RNA that is spliced near the beginning of the env ORF. There are currently nine Athila group elements from *A. thaliana* that have an identifiable env-like ORF. Alignment of the env-like amino acid sequence shows that there are five subgroups of env-like proteins in the Athila family. Three are distinct, four are closely related and another pair is closely related. As a whole, these env-like sequences share limited homology over the entire length of the ORF, but within subgroups, they share high homology (data not shown). Some of the Athila env-like proteins have an apparent secretory peptide and a central transmembrane domain, suggesting that they may have an env-like function.

Among the Calypso elements, seven have been characterized that encode env-like ORFs. These env-like ORFs form four families that have a high degree of overall sequence similarity beginning at the first methionine and continuing for three quarters of the ORF; sequence similarity falls off dramatically near the C-terminus. The amino acid sequence at the first methionine has the consensus sequence QMASR/KKRR/KA (SEQ ID NO:189), which appears to be a nuclear targeting signal, however, the program PSORT only predicts a 0.300 confidence level for this targeting role (Nakai and Horton (1999) *Trends Biochem. Sci.* 24:34–36). A similar sequence (ASKKRK; SEQ ID NO:190) is found at the same position in the env-like ORF of Cyclops2, suggesting that it serves a similar purpose. No other potential targeting peptide stands out from the sequence that has been analyzed so far. There is a conserved region that is predicted to be a transmembrane domain near the center of the Calypso env-like protein and a second transmembrane domain located at variable positions near the C-terminus. These may be the fusion and anchor functions of a TM peptide. It should also be noted that five of the seven ORFs are predicted to have a transmembrane domain that is just before and includes the first methionine. This N-terminal transmembrane domain may be a secretory signal of an SU peptide. The program Tmpred estimates these transmembrane domains to be significant based on a score >500

(Hofmann and Stoffel, supra). These three transmembrane domains are found in the Cyclops2 env-like protein at similar locations but at a reduced significance score. Another feature of the Calypso env-like ORF is the conserved splice site that is predicted to be at the first methionine by the program NetGene2 v. 2.4 with a confidence level of 1.00 (Hebsgaard et al. (1996) *Nucl. Acids Res.* 24:3439–3452); and Brunak et al. (1991) *J. Mol. Biol.* 220:49–65). There are other less preferred putative splice sites in the region, but only the splice site near the methionine is optimally placed and conserved in all seven env-like ORFs.

Example 4

Obtaining "Generic" Plant Retroelements

ClustalX v1.63b (Thompson et al., supra) was used to align nucleotide sequences of Calypso1-1, Calypso1-2 and Calypso1-3. A consensus sequence was generated from the ClustalX output. The consensus sequence file was then translated and compared using ClustalX to amino acid sequences of retrovirus-like elements from soybean, pea (Cyclops2) and *A. thaliana* (Athila-like elements) using the GCG computer software package (Devereux et al., supra). For coding regions encompassing protease, reverse transcriptase and integrase, a new consensus sequence was generated that best matched the coding information in all elements. This second consensus sequence forms the protease, reverse transcriptase and integrase genes of the generic element. The gag gene of the generic element is a consensus sequence generated by editing elements between Calypso1-1 and Calypso2-2. The env gene is a consensus sequence based on env gene sequence alignments of all Calypso elements. All non-coding regions for the generic element were obtained from Calypso1-2, with the exception of the LTRs, which were taken from Calypso1-1.

A generic retroelement will be constructed by first generating a DNA sequence that approximates the sequence of the generic element. An element that closely matches the consensus—for example, Calypso1-1—will be modified by PCR-based site-directed mutagenesis (Ausubel et al., supra). Modifications will be sequentially introduced into the starting element until it conforms to the sequence of the generic element.

The generic element will be modified so that it will be expressed at high levels in plant cells. This will be accomplished by inserting an enhancer—such as the cauliflower mosaic virus 35S enhancer—into the 5' LTR. To monitor replication, a maker gene will be inserted into the virus between the end of the coding region for the env gene and the polypurine tract. The marker gene may encode resistance to an herbicide or antibiotic. The modified generic element will then be introduced into plant cells by standard means of plant transformation.

Example 5

Obtaining a Library of Reverse Transcriptase Sequences

The degenerate oligos DVO1197 (5' GTG-CGN-AAR-GAR-GTN-NTN-AAR-YT 3' (SEQ ID NO:166) for the N terminal amino acid sequence VRKEVLKL (SEQ ID NO:167)) and DVO1198 (5' AAC-YTT-NGW-RAA-RTC-YTT-DAT-RAA 3' (SEQ ID NO:168) for the C terminal amino acid sequence VKSFDKIF (SEQ ID NO:169)) were used to amplify the Xiong/Eickbush plant retroelement reverse transcriptase domain from genomic DNA of the following plants: New sequences were obtained from *Nicotiana tabacum* (Tobacco), *Platanus occidentalis* (sycamore), *Gossypium hirsutum* (cotton), *Lycopersicon esculentum* (tomato), *Solanum tuberosum* (potato), *Oryza sativa* (rice), *Triticum aestivum* (wheat), *Hordeum vulgare* (barley), *Sorghum bicolor* (sorghum), *Avena sativa* (oat), *Secale cereale* (rye). No sequence was obtained for *Pinus coulteri* (big-cone pine), *Zea mays* (corn), *Zea mays* subspecies Parviglumis (teosinte), and a Tripsacum species. A positive control for PCR was used to obtain previously known sequences from: *Arabidopsis thaliana*, *Pisum sativum* (pea) and three varieties (Hard 89, L85 and Williams) of *Glycine max* (soybean).

The conditions for PCR were as follows: 50 µL reactions were set up with 5 µL of Promega Taq enzyme buffer, 1 µL of Taq enzyme, 5 µL of Promega 25 mM magnesium chloride, 100 ng genomic DNA, 5 µL of 2.5 mM Promega dNTP (deoxynucleotide mixture) and 7.5 µL of each oligo from a 20 pmol/µL solution. The reaction volume was brought to 50 µL with deionized water. PCR was done with a 92° C. melting temperature for 2 minutes for the first cycle and 20 seconds for each cycle thereafter, 50° C. annealing temperature for 30 seconds and 72° C. extension for 1 minute 30 seconds. There was a total of thirty cycles. Based on known sequence data, a 762 base pair band was expected for each PCR reaction.

The PCR reactions were run out on a 0.8% agarose gel, the approximately sized 762 based pair band was excised for each species and ligated to a T-vector pBLUESCRIPT II KS-. The ligations were transformed into the *E. coli* strain XL1 BLUE, selected and sequenced. The results are in the Sequence Listing, at SEQ ID NOS:42 through 165, with the even-numbered sequences in that range being the DNA sequences identified, and the odd-numbered 3sequences being the amino acid sequences deduced from the DNA sequences.

Example 6

Identifying Invariant Regions within the Reverse Transcriptase Polypeptides

The amino acid sequences obtained through the PCR survey (Example 5) were analyzed to determine whether they contain conserved amino acid signatures that distinguish them from previously characterized reverse transcriptases. To accomplish this, reverse transcriptase amino acid sequences were obtained from characterized retrotransposons and retroviruses. These include Tat4-1, f26h6, Rire2, Grand1-4, Vulgar, Cinful, Mag, SURL, Mdg1, 412, Cft-1, boty, Skippy, Maggy, Grasshopper, Tf1, Tma1-1, Tma3-1, Del1, Reina, IFG7, Ty3, Tom, 297, 17.6, TED, Gypsy, Yoyo, Ulysses, Woot, Cer1, HIV1, RSV, and MuMLV. The boundaries of these reverse transcriptase amino acid sequences were as defined by Xiong and Eickbush, supra. The characterized reverse transcriptases then were compared to the derived amino acid sequences of the PCR products obtained from the survey of plant genomes (portions of the odd-numbered sequences from SEQ ID NO:43 to SEQ ID NO:165 within the boundaries defined by Xiong and Eickbush; SEQ ID NOS are as indicated in FIG. 1). The alignment was prepared using the program ClustalX with default parameters (Thompson et al. (1997) *Nucl. Acids Res.* 24:4876–4882). The result of the alignment is presented in FIG. 1. The seven conserved amino acid sequence domains were identified by comparing the alignment of the characterized retrotransposon and retroviral reverse transcriptase sequences in FIG. 1 to the alignment published by Xiong and Eickbush, supra. Several nearly invariant amino acid motifs were identified that distinguish the derived reverse transcriptase amino acid sequences from the other retrotransposon and retroviral reverse transcriptases. These invariant motifs are defined as SEQ ID NOs:191 to 200, and are indicated by asterisks in FIG. 1.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a nucleotide sequence that encodes a reverse transcriptase, said reverse transcriptase comprising the following amino acid motifs:
   (a) Thr-Val/Ile-Val/Ile-Xaa-Xaa-Xaa-Xaa-Xaa-Asp/Glu-Leu-Val/Ile (SEQ ID NO:191) between reverse transcriptase domains 1 and 2; and
   (b) Phe-Met-Asp-Asp-Phe (SEQ ID NO:197) within reverse transcriptase domain 5.

2. A stably transformed cell comprising the isolated nucleic acid molecule of claim 1.

3. A transgenic seed comprising the nucleic acid molecule of claim 1.

4. The isolated nucleic acid molecule of claim 1, further comprising a regulatory element operably linked to said nucleotide sequence.

5. The stably transformed cell of claim 2, wherein said cell is a plant cell.

6. The stably transformed cell of claim 2, wherein said cell is a helper cell expressing gag, pol, and env genes.

7. The stably transformed cell of claim 2, wherein said cell is a prokaryotic cell.

* * * * *

SEQUENCE LISTING

```
<160> NUMBER OF SEQ ID NOS: 200

<210> SEQ ID NO 1
<211> LENGTH: 18
<212> TYPE: DNA
<213> ORGANISM: Glycine max

<400> SEQUENCE: 1
tggcgccgtt gccaattg                                              18

<210> SEQ ID NO 2
<211> LENGTH: 18
<212> TYPE: DNA
<213> ORGANISM: Glycine max

<400> SEQUENCE: 2
tggcgccgtt gtcgggga                                              18

<210> SEQ ID NO 3
<211> LENGTH: 6
<212> TYPE: DNA
<213> ORGANISM: Glycine max

<400> SEQUENCE: 3 ttgggg                                                            6

<210> SEQ ID NO 4
<211> LENGTH: 7
<212> TYPE: PRT
<213> ORGANISM: Artificial Sequence
<220> FEATURE:
<223> OTHER INFORMATION: Plant Retroelement Sequence

<400> SEQUENCE: 4

Met Ala Ser Arg Lys Arg Lys
 1               5

<210> SEQ ID NO 5
<211> LENGTH: 1263
<212> TYPE: DNA
<213> ORGANISM: Artificial Sequence
<220> FEATURE:
<223> OTHER INFORMATION: Plant Retroelement Sequence

<400> SEQUENCE: 5
atggcctccc gtaaacgcaa agctgtgccc acacccgggg aagcgtccaa ctgggactct    60
tcacgtttca ctttcgagat tgcttggcac agataccagg atagcattca gctccggaac   120
atccttccag agaggaatgt agagcttgga ccagggatgt tgatgagtt cctgcaggaa    180 ctccagaggc tcagatggga ccaggttctg acccgacttc cagagaagtg gattgatgtt   240
```

-continued

```
gctctggtga aggagtttta ctccaaccta tatgatccag aggaccacag tccgaagttt    300
tggagtgttc gaggacaggt tgtgagattt gatgctgaga cgattaatga tttcctcgac    360
accccggtca tcttggcaga gggagaggat tatccagcct actctcagta cctcagcact    420
cctccagacc atgatgccat cctttccgct ctgtgtactc caggggacg atttgttctg     480 aatgttgata gtgccccctg gaagctgctg cggaaggatc tgatgacgct cgcgcagaca    540
tggagtgtgc tctcttattt taaccttgca ctgacttttc acacttctga tattaatgtt    600
gacagggccc gactcaatta tggcttggtg atgaagatgg acctggacgt gggcagcctc    660
atttctcttc agatcagtca gatcgcccag tccatcactt ccaggcttgg gttcccagcg    720
ttgatcacaa cactgtgtga gattcagggg gttgtctctg atacctgat ttttgagtca     780 ctcagtcctg tgatcaacct tgcctacatt aagaagaact gctggaaccc tgccgatcca    840
tctatcacat ttcaggggac ccgccgcacg cgcaccagag cttcggcgtc ggcatctgag    900
gctcctcttc catcccagca tccttctcag ccttttccc agagaccacg gcctccactt     960
ctatccacct cagcacctcc atacatgcat ggacagatgc tcaggtcctt gtaccagggt   1020
cagcagatca tcattcagaa cctgtatcga ttgtccctac atttgcagat ggatctgcca   1080
ctcatgactc cggaggccta tcgtcagcag gtcgccaagc taggagacca gccctccact   1140 gacaggggg aagagccttc tggagccgct gctactgagg atcctgccgt tgatgaagac    1200
ctcatagctg acttggctgg cgctgattgg agcccatggg cagacttggg cagaggcagc   1260
tga                                                                 1263
```

<210> SEQ ID NO 6
<211> LENGTH: 421
<212> TYPE: PRT
<213> ORGANISM: Artificial Sequence
<220> FEATURE:
<223> OTHER INFORMATION: Plant Retroelement Sequence

<400> SEQUENCE: 6

```
Met Ala Ser Arg Lys Arg Lys Ala Val Pro Thr Pro Gly Glu Ala Ser
  1               5                  10                  15

Asn Trp Asp Ser Ser Arg Phe Thr Phe Glu Ile Ala Trp His Arg Tyr
             20                  25                  30

Gln Asp Ser Ile Gln Leu Arg Asn Ile Leu Pro Glu Arg Asn Val Glu
         35                  40                  45

Leu Gly Pro Gly Met Phe Asp Glu Phe Leu Gln Glu Leu Gln Arg Leu
     50                  55                  60

Arg Trp Asp Gln Val Leu Thr Arg Leu Pro Glu Lys Trp Ile Asp Val
 65                  70                  75                  80

Ala Leu Val Lys Glu Phe Tyr Ser Asn Leu Tyr Asp Pro Glu Asp His
                 85                  90                  95

Ser Pro Lys Phe Trp Ser Val Arg Gly Gln Val Val Arg Phe Asp Ala
            100                 105                 110

Glu Thr Ile Asn Asp Phe Leu Asp Thr Pro Val Ile Leu Ala Glu Gly
        115                 120                 125

Glu Asp Tyr Pro Ala Tyr Ser Gln Tyr Leu Ser Thr Pro Asp His
    130                 135                 140

Asp Ala Ile Leu Ser Ala Leu Cys Thr Pro Gly Gly Arg Phe Val Leu
145                 150                 155                 160

Asn Val Asp Ser Ala Pro Trp Lys Leu Leu Arg Lys Asp Leu Met Thr
                165                 170                 175
```

```
Leu Ala Gln Thr Trp Ser Val Leu Ser Tyr Phe Asn Leu Ala Leu Thr
            180                 185                 190

Phe His Thr Ser Asp Ile Asn Val Asp Arg Ala Arg Leu Asn Tyr Gly
            195                 200                 205

Leu Val Met Lys Met Asp Leu Asp Val Gly Ser Leu Ile Ser Leu Gln
            210                 215                 220

Ile Ser Gln Ile Ala Gln Ser Ile Thr Ser Arg Leu Gly Phe Pro Ala
225                 230                 235                 240

Leu Ile Thr Thr Leu Cys Glu Ile Gln Gly Val Val Ser Asp Thr Leu
                245                 250                 255

Ile Phe Glu Ser Leu Ser Pro Val Ile Asn Leu Ala Tyr Ile Lys Lys
            260                 265                 270

Asn Cys Trp Asn Pro Ala Asp Pro Ser Ile Thr Phe Gln Gly Thr Arg
            275                 280                 285

Arg Thr Arg Thr Arg Ala Ser Ala Ser Ala Ser Glu Ala Pro Leu Pro
            290                 295                 300

Ser Gln His Pro Ser Gln Pro Phe Ser Gln Arg Pro Arg Pro Leu
305                 310                 315                 320

Leu Ser Thr Ser Ala Pro Pro Tyr Met His Gly Gln Met Leu Arg Ser
                325                 330                 335

Leu Tyr Gln Gly Gln Gln Ile Ile Ile Gln Asn Leu Tyr Arg Leu Ser
            340                 345                 350

Leu His Leu Gln Met Asp Leu Pro Leu Met Thr Pro Glu Ala Tyr Arg
            355                 360                 365

Gln Gln Val Ala Lys Leu Gly Asp Gln Pro Ser Thr Asp Arg Gly Glu
            370                 375                 380

Glu Pro Ser Gly Ala Ala Ala Thr Glu Asp Pro Ala Val Asp Glu Asp
385                 390                 395                 400

Leu Ile Ala Asp Leu Ala Gly Ala Asp Trp Ser Pro Trp Ala Asp Leu
                405                 410                 415

Gly Arg Gly Ser Glx
            420

<210> SEQ ID NO 7
<211> LENGTH: 1596
<212> TYPE: DNA
<213> ORGANISM: Artificial Sequence
<220> FEATURE:
<223> OTHER INFORMATION: Plant Retroelement Sequence

<400> SEQUENCE: 7
atgcgaggta gaactgcatc tggagacgtt gttcctatta acttagaaat tgaagctacg      60
tgtcggcgta caacgctgc aagaagaaga agggagcaag acatagaagg aagtagttac     120
acctcacctc ctccttctcc aaattatgct cagatggacg gggaaccggc acaaagagtc     180
acactagagg acttctctaa taccaccact cctcagttct ttacaagtat cacaaggccg     240
gaagtccaag cagatctcct tactcaaggg aacctcttcc atggtcttcc aaatgaagat     300
ccatatgcgc atctagcctc atacatagag atatgcagca ccgttaaaat cgccggagtt     360
ccaaaagatg cgatactcct taacctcttt tccttttccc tagcaggaga ggcaaaaaga     420
tggttgcact cctttaaagg caatagctta agaacatggg aagaagtagt ggaaaaattc     480
ttaaagaagt atttcccaga gtcaaagacc gtcgaacgaa agatggagat ttcttatttc     540
catcaatttc tggatgaatc ccttagcgaa gcactagacc atttccacgg attgctaaga     600
```

-continued

```
aaaacaccaa cacacagata cagcgagcca gtacaactaa acatattcat cgatgacttg      660
caactcttaa tcgaaacagc tactagaggg aagatcaagc tgaagactcc cgaagaagcg      720
atggagctcg tcgagaacat ggcggctagc gatcaagcaa tccttcatga tcacacttat      780
gttcccacaa aaagaagcct cttggagctt agcacgcagg acgcaacttt ggtacaaaac      840
aagctgttga cgaggcagat agaagccctc atcgaaaccc tcagcaagct gcctcaacaa      900
ttacaagcga taagttcttc ccactcttct gttttgcagg tagaagaatg ccccacatgc      960
agagggacac atgagcctgg acaatgtgca agccaacaag cccctctcg tgaagtaaat     1020 tatataggca tactaaatcg ttacggattt cagggctaca accagggaaa tccatctgga     1080
ttcaatcaag gggcaacaag atttaatcac gagccaccgg ggtttaatca aggaagaaac     1140
ttcatgcaag gctcaagttg gacgaataaa ggaaatcaat ataaggagca aggaaccaa      1200 ccaccatacc agccaccata ccagcaccct agccaaggtc cgaatcagca gaaaagccc      1260 accaaaatag gaactgct gctgcaattc atcaaggaga caagatcaca tcaaaagagc       1320
acggatgcag ccattcggaa tctagaagtt caaatgggcc aactggcgca tgacaaagcc     1380
gaacggccca ctagaacttt cggtgctaac atggagagaa gaaccccaag gaaggataaa     1440
gcagtactga ctagagggca gagaagagcg caggaggagg gtaaggttga aggagaagac     1500
tggccagaag aaggaaggac agagaagaca gaagaagaag agaaggtggc agaagaacct     1560
aagcgtacca agagccagag agcaagggaa gccaag                                1596
```

<210> SEQ ID NO 8
<211> LENGTH: 532
<212> TYPE: PRT
<213> ORGANISM: Artificial Sequence
<220> FEATURE:
<223> OTHER INFORMATION: Plant Retroelement Sequence

<400> SEQUENCE: 8

```
Met Arg Gly Arg Thr Ala Ser Gly Asp Val Val Pro Ile Asn Leu Glu
 1               5                  10                  15

Ile Glu Ala Thr Cys Arg Arg Asn Asn Ala Ala Arg Arg Arg Arg Glu
            20                  25                  30

Gln Asp Ile Glu Gly Ser Ser Tyr Thr Ser Pro Pro Ser Pro Asn
        35                  40                  45

Tyr Ala Gln Met Asp Gly Glu Pro Ala Gln Arg Val Thr Leu Glu Asp
    50                  55                  60

Phe Ser Asn Thr Thr Thr Pro Gln Phe Thr Ser Ile Thr Arg Pro
65                  70                  75                  80

Glu Val Gln Ala Asp Leu Leu Thr Gln Gly Asn Leu Phe His Gly Leu
                85                  90                  95

Pro Asn Glu Asp Pro Tyr Ala His Leu Ala Ser Tyr Ile Glu Ile Cys
            100                 105                 110

Ser Thr Val Lys Ile Ala Gly Val Pro Lys Asp Ala Ile Leu Leu Asn
        115                 120                 125

Leu Phe Ser Phe Ser Leu Ala Gly Glu Ala Lys Arg Trp Leu His Ser
    130                 135                 140

Phe Lys Gly Asn Ser Leu Arg Thr Trp Glu Glu Val Val Glu Lys Phe
145                 150                 155                 160

Leu Lys Lys Tyr Phe Pro Glu Ser Lys Thr Val Glu Arg Lys Met Glu
                165                 170                 175

Ile Ser Tyr Phe His Gln Phe Leu Asp Glu Ser Leu Ser Glu Ala Leu
            180                 185                 190
```

```
Asp His Phe His Gly Leu Leu Arg Lys Thr Pro Thr His Arg Tyr Ser
        195                 200                 205

Glu Pro Val Gln Leu Asn Ile Phe Ile Asp Asp Leu Gln Leu Leu Ile
        210                 215                 220

Glu Thr Ala Thr Arg Gly Lys Ile Lys Leu Lys Thr Pro Glu Glu Ala
225                 230                 235                 240

Met Glu Leu Val Glu Asn Met Ala Ala Ser Asp Gln Ala Ile Leu His
            245                 250                 255

Asp His Thr Tyr Val Pro Thr Lys Arg Ser Leu Leu Glu Leu Ser Thr
                260                 265                 270

Gln Asp Ala Thr Leu Val Gln Asn Lys Leu Leu Thr Arg Gln Ile Glu
            275                 280                 285

Ala Leu Ile Glu Thr Leu Ser Lys Leu Pro Gln Gln Leu Gln Ala Ile
            290                 295                 300

Ser Ser Ser His Ser Ser Val Leu Gln Val Glu Glu Cys Pro Thr Cys
305                 310                 315                 320

Arg Gly Thr His Glu Pro Gly Gln Cys Ala Ser Gln Gln Asp Pro Ser
                325                 330                 335

Arg Glu Val Asn Tyr Ile Gly Ile Leu Asn Arg Tyr Gly Phe Gln Gly
            340                 345                 350

Tyr Asn Gln Gly Asn Pro Ser Gly Phe Asn Gln Gly Ala Thr Arg Phe
            355                 360                 365

Asn His Glu Pro Pro Gly Phe Asn Gln Gly Arg Asn Phe Met Gln Gly
        370                 375                 380

Ser Ser Trp Thr Asn Lys Gly Asn Gln Tyr Lys Glu Gln Arg Asn Gln
385                 390                 395                 400

Pro Pro Tyr Gln Pro Pro Tyr Gln His Pro Ser Gln Gly Pro Asn Gln
                405                 410                 415

Gln Glu Lys Pro Thr Lys Ile Glu Glu Leu Leu Leu Gln Phe Ile Lys
            420                 425                 430

Glu Thr Arg Ser His Gln Lys Ser Thr Asp Ala Ala Ile Arg Asn Leu
            435                 440                 445

Glu Val Gln Met Gly Gln Leu Ala His Asp Lys Ala Glu Arg Pro Thr
450                 455                 460

Arg Thr Phe Gly Ala Asn Met Glu Arg Arg Thr Pro Arg Lys Asp Lys
465                 470                 475                 480

Ala Val Leu Thr Arg Gly Gln Arg Arg Ala Gln Glu Glu Gly Lys Val
                485                 490                 495

Glu Gly Glu Asp Trp Pro Glu Glu Gly Arg Thr Glu Lys Thr Glu Glu
            500                 505                 510

Glu Glu Lys Val Ala Glu Glu Pro Lys Arg Thr Lys Ser Gln Arg Ala
            515                 520                 525

Arg Glu Ala Lys
        530

<210> SEQ ID NO 9
<211> LENGTH: 603
<212> TYPE: DNA
<213> ORGANISM: Artificial Sequence
<220> FEATURE:
<223> OTHER INFORMATION: Plant Retroelement Sequence

<400> SEQUENCE: 9
tgtgataaat gccagagaac agggggata tctcgaagaa atgagatgcc tttgcagaat    60
```

```
atcatggaag tagagatctt tgactgttgg ggcatagact tcatggggcc ttttccttcg    120
tcatacggga atgtctacat cttggtagct gtggattacg tctccaaatg ggtggaagcc    180
atagccacgc caaaggacga tgccagggta gtgatcaaat ttctgaagaa gaacattttt    240
tcccgttttg gagtcccacg agccttgatt agtgatagg gaacgcactt ctgcaacaat    300
cagttgaaga agtcctgga gcactataat gtccgacata aggtggccac accttatcac    360
cctcagacaa atgccaagc agaaatttct aacagggagc tcaagcgaat cctggaaaag    420
acagttgcat caacaagaaa ggattggtcc ttgaagctcg atgatgctct ctgggcctat    480
aggacagcgt tcaagactcc catcggctta tcaccatttc agctagtgta tgggaaggca    540
tgtcatttac cagtggagct ggagtacaaa gcatattggg ctctcaagtt gctcaacttt    600
gac                                                                 603
```

```
<210> SEQ ID NO 10
<211> LENGTH: 201
<212> TYPE: PRT
<213> ORGANISM: Artificial Sequence
<220> FEATURE:
<223> OTHER INFORMATION: Plant Retroelement Sequence

<400> SEQUENCE: 10

Cys Asp Lys Cys Gln Arg Thr Gly Gly Ile Ser Arg Arg Asn Glu Met
 1               5                  10                  15

Pro Leu Gln Asn Ile Met Glu Val Glu Ile Phe Asp Cys Trp Gly Ile
            20                  25                  30

Asp Phe Met Gly Pro Phe Pro Ser Ser Tyr Gly Asn Val Tyr Ile Leu
        35                  40                  45

Val Ala Val Asp Tyr Val Ser Lys Trp Val Glu Ala Ile Ala Thr Pro
    50                  55                  60

Lys Asp Asp Ala Arg Val Val Ile Lys Phe Leu Lys Lys Asn Ile Phe
65                  70                  75                  80

Ser Arg Phe Gly Val Pro Arg Ala Leu Ile Ser Asp Arg Gly Thr His
                85                  90                  95

Phe Cys Asn Asn Gln Leu Lys Lys Val Leu Glu His Tyr Asn Val Arg
            100                 105                 110

His Lys Val Ala Thr Pro Tyr His Pro Gln Thr Asn Gly Gln Ala Glu
        115                 120                 125

Ile Ser Asn Arg Glu Leu Lys Arg Ile Leu Glu Lys Thr Val Ala Ser
    130                 135                 140

Thr Arg Lys Asp Trp Ser Leu Lys Leu Asp Asp Ala Leu Trp Ala Tyr
145                 150                 155                 160

Arg Thr Ala Phe Lys Thr Pro Ile Gly Leu Ser Pro Phe Gln Leu Val
                165                 170                 175

Tyr Gly Lys Ala Cys His Leu Pro Val Glu Leu Glu Tyr Lys Ala Tyr
            180                 185                 190

Trp Ala Leu Lys Leu Leu Asn Phe Asp
        195                 200

<210> SEQ ID NO 11
<211> LENGTH: 600
<212> TYPE: DNA
<213> ORGANISM: Artificial Sequence
<220> FEATURE:
<223> OTHER INFORMATION: Plant Retroelement Sequence

<400> SEQUENCE: 11
```

```
ttggaggctg ggctcatata ccccatctct gacagcgctt gggtaagccc agtacaggtg    60
gttcccaaga aggtggaat gacagtggta cgagatgaga ggaatgactt gataccaaca   120
cgaactgtca ctggttggcg aatgtgtatc gactatcgca agctgaatga agccacacgg   180
aaggaccatt tcccttacc tttcatggat cagatgctgg agagacttgc agggcaggca   240
tactactgtt tcttggatgg atactcggga tacaaccaga tcgcggtaga ccccagagat   300
caggagaaga cggcctttac atgcccccttt ggcgtctttg cttacagaag gatgccattc   360
gggttatgta atgcaccagc cacatttcag aggtgcatgc tggccatttt ttcagacatg   420
gtggagaaaa gcatcgaggt atttatggac gacttctcgg tttttggacc ctcatttgac   480
agctgtttga ggaacctaga gagggtactt cagaggtgcg aagagactaa cttggtactg   540
aattgggaaa agtgtcattt catggttcga gagggcatag tcctaggcca caagatctca   600
```

<210> SEQ ID NO 12
<211> LENGTH: 200
<212> TYPE: PRT
<213> ORGANISM: Artificial Sequence
<220> FEATURE:
<223> OTHER INFORMATION: Plant Retroelement Sequence

<400> SEQUENCE: 12

```
Leu Glu Ala Gly Leu Ile Tyr Pro Ile Ser Asp Ser Ala Trp Val Ser
  1               5                  10                  15

Pro Val Gln Val Val Pro Lys Lys Gly Gly Met Thr Val Val Arg Asp
                 20                  25                  30

Glu Arg Asn Asp Leu Ile Pro Thr Arg Thr Val Thr Gly Trp Arg Met
             35                  40                  45

Cys Ile Asp Tyr Arg Lys Leu Asn Glu Ala Thr Arg Lys Asp His Phe
         50                  55                  60

Pro Leu Pro Phe Met Asp Gln Met Leu Glu Arg Leu Ala Gly Gln Ala
 65                  70                  75                  80

Tyr Tyr Cys Phe Leu Asp Gly Tyr Ser Gly Tyr Asn Gln Ile Ala Val
                 85                  90                  95

Asp Pro Arg Asp Gln Glu Lys Thr Ala Phe Thr Cys Pro Phe Gly Val
            100                 105                 110

Phe Ala Tyr Arg Arg Met Pro Phe Gly Leu Cys Asn Ala Pro Ala Thr
            115                 120                 125

Phe Gln Arg Cys Met Leu Ala Ile Phe Ser Asp Met Val Glu Lys Ser
        130                 135                 140

Ile Glu Val Phe Met Asp Asp Phe Ser Val Phe Gly Pro Ser Phe Asp
145                 150                 155                 160

Ser Cys Leu Arg Asn Leu Glu Arg Val Leu Gln Arg Cys Glu Glu Thr
                165                 170                 175

Asn Leu Val Leu Asn Trp Glu Lys Cys His Phe Met Val Arg Glu Gly
            180                 185                 190

Ile Val Leu Gly His Lys Ile Ser
        195                 200
```

<210> SEQ ID NO 13
<211> LENGTH: 858
<212> TYPE: DNA
<213> ORGANISM: Artificial Sequence
<220> FEATURE:
<223> OTHER INFORMATION: Plant Retroelement Sequence

<400> SEQUENCE: 13

```
aaggaagaac cactagccct tccacaggat ctcccatatc ctatggcacc caccaagaag      60
aacaaggagc gttactttgc acgtttcttg gaaatattca aagggttaga aatcactatg     120
yccattcggg aagccttaca gcagatgccc ctctactcca aatttatgaa agacatcctc     180
accaagaagg ggaagtatat tgacaacgag aatattgtgg taggaggcaa ttgcagtgcg     240
ataatacaaa ggattctacc caagaagttt aaagaccccg gaagtgttac catcccgtgc     300
accattggga aggaagccgt aaacaaggcc ctcattgatc taggagcaag tatcaatctg     360
atgcccttgt caatgtgcaa agaattggg  aatttgaaga tagatcccac caagatgacg     420
cttcaactgg cagaccgctc aatcacaagg ccatatgggg tggtagaaga tgtcctggtc     480
aaggtacgcc acttcacttt tccggtggac tttgttatca tggatatcga agaagacact     540
gagattcccc ttatcttagg cagacccttc atgctgactg ccaactgtgt ggtggatatg     600
gggaaaggga acttagagtt gactattgat aatcagaaga tcacctttga ccttatcaag     660
gcaatgaagt acccacagga gggttggaag tgcttcagaa tagaggagat tgatgaggaa     720
gatgtcagtt ttctcgagac accaaagact tcgctagaaa aagcaatggt aaatcattta     780
gactgtctaa ccagtgaaga ggaagaagat ctgaaggctt gcttggaaaa cttggatcaa     840
gaagacagta ttcctgag                                                   858

<210> SEQ ID NO 14
<211> LENGTH: 286
<212> TYPE: PRT
<213> ORGANISM: Artificial Sequence
<220> FEATURE:
<223> OTHER INFORMATION: Plant Retroelement Sequence

<400> SEQUENCE: 14

Lys Glu Glu Pro Leu Ala Leu Pro Gln Asp Leu Pro Tyr Pro Met Ala
 1               5                  10                  15

Pro Thr Lys Lys Asn Lys Glu Arg Tyr Phe Ala Arg Phe Leu Glu Ile
            20                  25                  30

Phe Lys Gly Leu Glu Ile Thr Met Pro Phe Gly Glu Ala Leu Gln Gln
        35                  40                  45

Met Pro Leu Tyr Ser Lys Phe Met Lys Asp Ile Leu Thr Lys Lys Gly
    50                  55                  60

Lys Tyr Ile Asp Asn Glu Asn Ile Val Val Gly Gly Asn Cys Ser Ala
65                  70                  75                  80

Ile Ile Gln Arg Ile Leu Pro Lys Lys Phe Lys Asp Pro Gly Ser Val
                85                  90                  95

Thr Ile Pro Cys Thr Ile Gly Lys Glu Ala Val Asn Lys Ala Leu Ile
            100                 105                 110

Asp Leu Gly Ala Ser Ile Asn Leu Met Pro Leu Ser Met Cys Lys Arg
        115                 120                 125

Ile Gly Asn Leu Lys Ile Asp Pro Thr Lys Met Thr Leu Gln Leu Ala
    130                 135                 140

Asp Arg Ser Ile Thr Arg Pro Tyr Gly Val Val Glu Asp Val Leu Val
145                 150                 155                 160

Lys Val Arg His Phe Thr Phe Pro Val Asp Phe Val Ile Met Asp Ile
                165                 170                 175

Glu Glu Asp Thr Glu Ile Pro Leu Ile Leu Gly Arg Pro Phe Met Leu
            180                 185                 190

Thr Ala Asn Cys Val Val Asp Met Gly Lys Gly Asn Leu Glu Leu Thr
        195                 200                 205
```

```
Ile Asp Asn Gln Lys Ile Thr Phe Asp Leu Ile Lys Ala Met Lys Tyr
    210                 215                 220

Pro Gln Glu Gly Trp Lys Cys Phe Arg Ile Glu Glu Ile Asp Glu Glu
225                 230                 235                 240

Asp Val Ser Phe Leu Glu Thr Pro Lys Thr Ser Leu Glu Lys Ala Met
                245                 250                 255

Val Asn His Leu Asp Cys Leu Thr Ser Glu Glu Glu Asp Leu Lys
            260                 265                 270

Ala Cys Leu Glu Asn Leu Asp Gln Glu Asp Ser Ile Pro Glu
        275                 280                 285

<210> SEQ ID NO 15
<211> LENGTH: 192
<212> TYPE: DNA
<213> ORGANISM: Artificial Sequence
<220> FEATURE:
<223> OTHER INFORMATION: Plant Retroelement Sequence

<400> SEQUENCE: 15
tttgaactaa tgtgtgatgc cagtgattat gcagtaggag cagttttggg acagaggaaa      60
gacaaggtat ttcacgccat ctattatgct agcaaggtcc tgaatgaagc acagttgaat     120
tatgcaacca cagaaaagga gatgctagcc attgtctttg ccttggagaa gttcaggtca     180
tacttgatag gg                                                         192

<210> SEQ ID NO 16
<211> LENGTH: 64
<212> TYPE: PRT
<213> ORGANISM: Artificial Sequence
<220> FEATURE:
<223> OTHER INFORMATION: Plant Retroelement Sequence

<400> SEQUENCE: 16

Phe Glu Leu Met Cys Asp Ala Ser Asp Tyr Ala Val Gly Ala Val Leu
1               5                   10                  15

Gly Gln Arg Lys Asp Lys Val Phe His Ala Ile Tyr Tyr Ala Ser Lys
            20                  25                  30

Val Leu Asn Glu Ala Gln Leu Asn Tyr Ala Thr Thr Glu Lys Glu Met
        35                  40                  45

Leu Ala Ile Val Phe Ala Leu Glu Lys Phe Arg Ser Tyr Leu Ile Gly
    50                  55                  60

<210> SEQ ID NO 17
<211> LENGTH: 12286
<212> TYPE: DNA
<213> ORGANISM: Artificial Sequence
<220> FEATURE:
<223> OTHER INFORMATION: Plant Retroelement Sequence

<400> SEQUENCE: 17
tgataactgc taaataattg tgaattaata gtagaaaatt agtcaaattt tggcttaaaa      60
ttaattattt agcagttatt tgtgattaaa agttagaaaa gcaattaagt tgaattttg     120 gccatagata tgaaaactga aggtacaaca agcaaaaggc agcagaaagt gaagaaaaag     180
aataaaatct gaagcagacc cagcccaaca cgcgccctta gcgcgcgtca cgcgctaagc     240
ttgcaaggca gcacaggcac taagcgaggc gttaagcacg aagatgcagg attcgttacg     300
tgcgctaagc gcgaggcaca cgctaagcgc gcgatccaac agaagcacac gctaagcctg     360
cagcatgcgc taagcgcgcc tacgaaggcc caaagcccat ttctacacct ataaatagag     420
```

-continued

```
atccaagcca agggagaatg tacaccttgc ctcagagcac ttctctcagc attccaagct      480
tgagctctcc cttttctctc tatattcttt gcttttatta tccattcttt ctttcacccc      540
agttgtaaag cccctcaatg gccatgagtg gttaatcccc tagctacggc ctggtaggcc      600
taaaaagcca atgatgtatg gtgtacttca agagttatca atgcaaagag gattcattcc      660
aggttttatg ttctaattct ttccttttta tcttgcattt atgtcttaaa tttctgttgg      720
gttttattcg ctcgggagag ggtatttcct aataagggtt taagaagtaa tgcatgcatc      780
agttttaggg gttatacgct tggtaaaggg taacacctaa tagaacaaat taagaaaagg      840
atcgtcgggc tagcattgct aggcatagaa tgatggccca atgcccatgc atttagcaac      900
atctagaatt taaccttaat gcatttttaat tattgaatct tcacaaaggc atttgggaga      960
taggtagtta aaataggctt gtcatcgtga ggcatcaagg gcaagtaaaa ttaatagatg     1020
tgggtagaac taattcaact gcattggtaa tgaacatcat aaattcattc atcgtaggcc     1080
aattaggttt gtccggtctt ggcattttca tcaattgtct tcctaaatta tttgatctaa     1140
tagcaacaat ttattcttat gcctattcct gttttttacta tttactttta cttacaaatt     1200
gaagagtatt caataaagtg caataaaatc cctatggaaa cgatactcgg acttccgaga     1260
attactactt agaacgattt ggtacacttg tcaaacacct caacaagttt ttggcgccgt     1320
tgtcggggat tttgttctcg cacttaattg ccatactata ttagtttgta agcttaattc     1380
ttcttttctt ggctcattct tttattattc tttactttac tttttcttct atcctttctt     1440
tcttctccca taaattgcac gggtagtgcc tttttgtttt tatgcgaggt agaactgcat     1500
ctggagacgt tgttcctatt aacttagaaa ttgaagctac gtgtcggcgt aacaacgctg     1560
caagaagaag aagggagcaa gacatagaag gaagtagtta cacctcacct cctccttctc     1620
caaattatgc tcagatggac ggggaaccgg cacaaagagt cacactagag gacttctcta     1680
ataccaccac tcctcagttc tttacaagta tcacaaggcc ggaagtccaa gcagatctcc     1740
ttactcaagg gaacctcttc catggtcttc caaatgaaga tccatatgcg catctagcct     1800
catacataga gatatgcagc accgttaaaa tcgccggagt tccaaaagat gcgatactcc     1860
ttaacctctt ttcctttcc ctagcaggag aggcaaaaag atggttgcac tcctttaaag     1920
gcaatagctt aagaacatgg gaagaagtag tggaaaaatt cttaaagaag tatttcccag     1980
agtcaaagac cgtcgaacga aagatggaga tttcttattt ccatcaattt ctggatgaat     2040
cccttagcga agcactagac catttccacg gattgctaag aaaaacacca acacacagat     2100
acagcgagcc agtacaacta aacatattca tcgatgactt gcaactctta atcgaaacag     2160
ctactagagg gaagatcaag ctgaagactc ccgaagaagc gatggagctc gtcgagaaca     2220
tggcggctag cgatcaagca atccttcatg atcacactta tgttcccaca aaaagaagcc     2280
tcttggagct tagcacgcag gacgcaactt tggtacaaaa caagctgttg acgaggcaga     2340 tagaagcccct catcgaaacc ctcagcaagc tgcctcaaca attacaagcg ataagttctt     2400
cccactcttc tgttttgcag gtagaagaat gccccacatg cagagggaca catgagcctg     2460
gacaatgtgc aagccaacaa gacccctctc gtgaagtaaa ttatataggc atactaaatc     2520
gttacggatt tcagggctac aaccagggaa atccatctgg attcaatcaa ggggcaacaa     2580
gatttaatca cgagccaccg gggtttaatc aaggaagaaa cttcatgcaa ggctcaagtt     2640
ggacgaataa aggaaatcaa tataaggagc aaaggaacca accaccatac cagccaccat     2700
accagcaccc tagccaaggt ccgaatcagc aagaaaagcc caccaaaata gaggaactgc     2760
tgctgcaatt catcaaggag acaagatcac atcaaaagag cacggatgca gccattcgga     2820
```

-continued

| | |
|---|---|
| atctagaagt tcaaatgggc caactggcgc atgacaaagc cgaacggccc actagaactt | 2880 |
| tcggtgctaa catggagaga agaaccccaa ggaaggataa agcagtactg actagagggc | 2940 |
| agagaagagc gcaggaggag ggtaaggttg aaggagaaga ctggccagaa gaaggaagga | 3000 |
| cagagaagac agaagaagaa gagaaggtgg cagaagaacc taagcgtacc aagagccaga | 3060 |
| gagcaaggga agccaagaag gaagaaccac tagcccttcc acaggatctc ccatatccta | 3120 |
| tggcacccac caagaagaac aaggagcgtt actttgcacg tttcttggaa atattcaaag | 3180 |
| ggttagaaat cactatgcca ttcggggaag ccttacagca gatgccctc tactccaaat | 3240 |
| ttatgaaaga catcctcacc aagaagggga agtatattga caacgagaat attgtggtag | 3300 |
| gaggcaattg cagtgcgata atacaaagga ttctacccaa gaagtttaaa gaccccggaa | 3360 |
| gtgttaccat cccgtgcacc attgggaagg aagccgtaaa caaggccctc attgatctag | 3420 |
| gagcaagtat caatctgatg cccttgtcaa tgtgcaaaag aattgggaat ttgaagatag | 3480 |
| atcccaccaa gatgacgctt caactggcag accgctcaat cacaaggcca tatgggtgg | 3540 |
| tagaagatgt cctggtcaag gtacgccact tcacttttcc ggtggacttt gttatcatgg | 3600 |
| atatcgaaga agacactgag attccccta tcttaggcag acccttcatg ctgactgcca | 3660 |
| actgtgtggt ggatatgggg aaagggaact tagagttgac tattgataat cagaagatca | 3720 |
| cctttgacct tatcaaggca atgaagtacc cacaggaggg ttggaagtgc ttcagaatag | 3780 |
| aggagattga tgaggaagat gtcagtttt tcgagacacc aaaagacttcg ctagaaaaag | 3840 |
| caatggtaaa tcatttagac tgtctaacca gtgaagagga agaagatctg aaggcttgct | 3900 |
| tggaaaactt ggatcaagaa gacagtattc ctgagggaga agccaatttc gaggagctag | 3960 |
| agaaggaagt tccgtctgag aagccgaaga tagagttgaa gatattgcct gatcatctga | 4020 |
| agtatgtgtt cttggaggaa gataaaccta tagtgatcag taacgcactc acaacagagg | 4080 |
| aggaaaatag gttggtagat gtcctcaaga aacacaggga agcaattgga tggcacatat | 4140 |
| cggatctcaa ggaaattagc cctgcttact gcatgcacag gataatgatg gaagaggact | 4200 |
| acaagccagt ccgacaaccc cagaggcggc tgaatccaac aatgaaggaa gaggtaagaa | 4260 |
| aggaggtact caagctcttg gaggctgggc tcatataccc catctctgac agcgcttggg | 4320 |
| taagcccagt acaggtggtt cccaagaaag gtggaatgac agtggtacga gatgagagga | 4380 |
| atgacttgat accaacacga actgtcactg gttggcgaat gtgtatcgac tatcgcaagc | 4440 |
| tgaatgaagc cacacggaag gaccatttcc ccttaccttt catggatcag atgctggaga | 4500 |
| gacttgcagg gcaggcatac tactgtttct tggatggata ctcgggatac aaccagatcg | 4560 |
| cggtagaccc cagagatcag gagaagacg ccttttacatg cccctttggc gtctttgctt | 4620 |
| acagaaggat gccattcggg ttatgtaatg caccagccac atttcagagg tgcatgctgg | 4680 |
| ccatttttc agacatggtg gagaaaagca tcgaggtatt tatggacgac ttctcggttt | 4740 |
| ttggaccctc atttgacagc tgtttgagga acctagagag ggtacttcag aggtgcgaag | 4800 |
| agactaactt ggtactgaat tgggaaaagt gtcatttcat ggttcgagag gcatagtcc | 4860 |
| taggccacaa gatctcagcc agagggattg aggttgatcg ggcaaagata gacgtcatcg | 4920 |
| agaagctgcc accaccactg aatgttaaag gggttagaag tttcttaggg catgcaggtt | 4980 |
| tctacaggag gtttatcaag gacttctcga agattgccag gccccttaagc aatctgttga | 5040 |
| ataaagacgt ggcttttgtg tttgatgaag aatgtttagc agcatttcaa tcactgaaga | 5100 |
| ataagctcgt cactgcaccc gtaatgattg cacccgactg gaataaagat tttgaactaa | 5160 |

-continued

```
tgtgtgatgc cagtgattat gcagtaggag cagttttggg acagaggaaa gacaaggtat    5220
ttcacgccat ctattatgct agcaaggtcc tgaatgaagc acagttgaat tatgcaacca    5280
cagaaaagga gatgctagcc attgtctttg ccttggagaa gttcaggtca tacttgatag    5340
ggtcgagggt catcatttac acagatcatg ctgccatcaa gcacctgctc gccaaaacag    5400
actcaaagcc gaggttgatt agatgggtcc tgctgttaca agaatttgac atcatcatca    5460
aggacaagaa aggatccgag aatgtggtag ccaatcatct atctcgatta aagaatgaag    5520
aagtcaccaa ggaagaacca gaggtaaaag gtgaatttcc tgatgagttt cttttgcagg    5580
ttaccgaaag accttggttt gcagacatgg ctaactacaa agccacggga gtcattccag    5640
aggagtttaa ttggagtcag aggaagaaat tcttgcacga tgcacgcttc tatgtgtggg    5700
atgatcctca tttgttcaag gcaggagcag ataatttatt aaggagatgc gtcacaaagg    5760
aggaagcacg gagcattctt tggcactgcc acagttcacc ctatggcgga caccacagtg    5820
gggacagaac agcagcaaaa gtgctacaat caggttttt ctggccctct atttttaaag    5880
atgctcacga gtttgtgcgt tgttgtgata aatgccagag aacagggggg atatctcgaa    5940
gaaatgagat gcctttgcag aatatcatgg aagtagagat cttttgactgt tggggcatag    6000 acttcatggg gccttttcct tcgtcatacg ggaatgtcta catcttggta gctgtggatt    6060
acgtctccaa atgggtggaa gccatagcca cgccaaagga cgatgccagg gtagtgatca    6120
aatttctgaa gaagaacatt ttttcccgtt ttggagtccc acgagccttg attagtgata    6180
ggggaacgca cttctgcaac aatcagttga agaaagtcct ggagcactat aatgtccgac    6240
ataaggtggc cacaccttat caccctcaga caaatggcca agcagaaatt tctaacaggg    6300
agctcaagcg aatcctggaa aagacagttg catcaacaag aaaggattgg tccttgaagc    6360
tcgatgatgc tctctgggcc tataggacag cgttcaagac tcccatcggc ttatcaccat    6420
ttcagctagt gtatgggaag gcatgtcatt taccagtgga gctggagtac aaagcatatt    6480
gggctctcaa gttgctcaac tttgacaaca acgcatgcgg ggaaaagagg aagctacagc    6540
tgctggaatt agaagagatg agactgaatg cctacgagtc atccaaaatt tacaaggaaa    6600
agatgaaggc atatcatgac aagaagctac tgaggaaaga attccagcca gggcagcagg    6660
tattactctt taactcaagg ctaaggctat tcccaggtaa gctgaagtcc aagtggtcag    6720
ggccattcat aatcaaagaa gtcagaccttt acggagcagt agaattggtg gaccctagag    6780
aagaggactt tgagaagaaa tggatcgtca atggacagcg cttgaagcct tataacggag    6840
gacaactaga gcgattgacg accatcatct acttaaatga cccttgagaa ggcctactgt    6900
ctagctaaag acaataaact aagcgctggt tgggaggcaa cccaacatat tttgtaaaaa    6960
tgtagttatc tttattctat gtaaaaaaaa aaaaaagcc caataggtgc aaataggaaa    7020
caggaggtgc aaaaagcaaa ggcccaacag gtgaagacaa caataggagg ggtgccaata    7080
gcaaaactga agtgggctgc acgaagccac gcgcccaatt cttggtctttt tcacacaaaa    7140 caatcactaa cgaaggtaaa gaattgctttt gtatggatgt tgttatgaat gcacaggtaa    7200
cagcacgcta agccctgctc gacgcttagc caatgaagac ggattgaagg ccataacgac    7260
gagctcgtta agcgtgacga agcacgctaa gcaggcgcct gacaggacga gaaagcaaag    7320
cgcgcgctta gccggcactt ccgcgctaag cgcgctcatg aacatcactg aacgcgctaa    7380
acgtgtgcca gaggcgctaa acgcgtgcca gaggcgctaa acgcgtgcat tagtcacagc    7440
aggatggtgc taagcgcggg gttgggcctc agggcccatc aaccctcgca ccttacttgt    7500
tgcaccccta tttctactat tcccactccc ttctaatttc ttttttgcacc cccttcttt    7560
```

-continued

```
actgactgca cctctatttt gattactttt tgcacccccc ctgattgcta acttcagact   7620
atctttcttg ttttttgttt ttttggtttt ttggtcagat ggcctcccgt aaacgcaaag   7680
ctgtgcccac acccggggaa gcgtccaact gggactcttc acgtttcact ttcgagattg   7740
cttggcacag ataccaggat agcattcagc tccggaacat ccttccagag aggaatgtag   7800
agcttggacc agggatgttt gatgagttcc tgcaggaact ccagaggctc agatgggacc   7860
aggttctgac ccgacttcca gagaagtgga ttgatgttgc tctggtgaag gagttttact   7920
ccaacctata tgatccagag gaccacagtc cgaagttttg gagtgttcga ggacaggttg   7980
tgagatttga tgctgagacg attaatgatt tcctcgacac cccggtcatc ttggcagagg   8040
gagaggatta tccagcctac tctcagtacc tcagcactcc tccagaccat gatgccatcc   8100
tttccgctct gtgtactcca gggggacgat tgttctgaa tgttgatagt gcccctgga    8160
agctgctgcg gaaggatctg atgacgctcg cgcagacatg gagtgtgctc tcttatttta   8220
accttgcact gacttttcac acttctgata ttaatgttga cagggcccga ctcaattatg   8280
gcttggtgat gaagatggac ctggacgtgg gcagcctcat ttctcttcag atcagtcaga   8340
tcgcccagtc catcacttcc aggcttgggt tcccagcgtt gatcacaaca ctgtgtgaga   8400
ttcaggggt tgtctctgat accctgattt ttgagtcact cagtcctgtg atcaaccttg    8460
cctacattaa gaagaactgc tggaaccctg ccgatccatc tatcacatt cagggggccc    8520
gccgcacgcg caccagagct tcggcgtcgg catctgaggc tcctcttcca tcccagcatc   8580
cttctcagcc ttttttcccag agaccacggc ctccacttct atccacctca gcacctccat  8640
acatgcatgg acagatgctc aggtccttgt accagggtca gcagatcatc attcagaacc   8700
tgtatcgatt gtccctacat ttgcagatgg atctgccact catgactccg gaggcctatc   8760
gtcagcaggt cgccaagcta ggagaccagc cctccactga caggggggaa gagccttctg   8820
gagccgctgc tactgaggat cctgccgttg atgaagacct catagctgac ttggctggcg   8880
ctgattggag cccatgggca gacttgggca gaggcagctg atcttatgct ttaatgtttt   8940
cttttatatt atgtttgtgt tctcttttat gttttatgtt atgtttttat gtagtctgtt   9000
tggtaattaa aaagaggtag tagtaaaaat attagtattt cagtatgtgt tttctgagta   9060
ataagtgcat gataactcaa gcaatcataa ttctttagct tgttcagaaa ggttcaacac   9120
ttgagatgcc actgatcctt ggagaaacac tggttctgga agcaaaagtc aggtcaagaa   9180
atggaacatg aatagcacag agtggaaagg ttagcttgat ggaacaaggt cataactggt   9240
acgccgaata cttgtttaag tccctgtgag catggttgtc aaactctaga gtcaactcat   9300
agactctcat gagtttaaga gtttacttca gtcccgcgag ttgactcgga agcaaactcg   9360
cttttgagca aactcgtgga ctcggagtga actcatgtaa actcgtaaga gtctacgagt   9420
tgactctaga gtttgacaac catgcataag tgttcaaaat taaagcattt aaataattaa   9480
aaaaagcaca aatgtcttca aagaagcatg ttcaatcctc taataggatc atcttcatga   9540
atatcatcac tttcatcatc atctccatct ccatcatcat catcaaggtc ttcctcagat   9600
tgtgcatcat cattaggttc cacaaagatt aaattatcta gatcaaaagc ttaaaataga   9660
tatcaaatat gctatattag aaatagttaa aacttaaaat aatacacaag caaattttaa   9720
atatgagaaa gttcagaaat tatacctttt cttggtgtta ttaaagtttc attttatctt   9780
ctcttttgca ttttccatct cctcacatat gaaaagcata attctattga atttcagtaa   9840
caagtttgat ccaactccaa cattgtaagg tcagttgttg tgttttgtaa tagactaata   9900
```

-continued

```
tgaagtatga agtatgaact atgaacttat tgtcatctgt ttgcaaattg gtgcattttg      9960
aatatattta cttattatcc attttttttt ttttacgaag tagactctca cgagtctgcg     10020
tagactctcg atatcgataa ccttgccgat gagagtgtga acttaattgt gagagaaaat     10080
gcctattttt aagttcctgg ttttgcatca ttcttagacg gttagaatag ttacttaagg     10140
tggatatgat caaggccatg tttgtttgtt tacctactta gccaaaaagc caacctaaca     10200
tagtttracc ccttgcaccc atgattgagc caactgatta ttttgaatta accttgagcc     10260
aattaaacaa aatcctgacc ttttaggatt ttaagagagt aaaaatgggt tataaaggtc     10320
ttaatttggg ggattttggg aaataggtag ccaagacaat aagtacagca cacaaagtag     10380
gacacctttt acaaacagta ggcccaattt cgaaaaaaaa atgaaaagaa tttaataaag     10440
ggcagaaaca aagagcaag agaggtgtca aagaaaagt gttgtgggga aataaagggg     10500
ctaagtaaaa aggcctaggc agaattggaa attttttgttc tcttttaatc ctaacttrga     10560
atttccaaga aaaccatga ttttttgtaa gccaggcccc gatacaagcc ataaagtcc      10620 ttagtgatcc accaaaggta actagagata actgtaactg agatgaaatg caaaattttg     10680
aagtgttact tgcaggttgt tatcaaattg caaacactaa actaggcact tgtgagcaga     10740
gggaaacacc agccttgtga ggaaagtaag gcaagccaaa tttgattgag ttccagatga     10800
ctaactgatt caattcttct gttgtaatgc tttcatttta agatgttgac agatgcagaa     10860
aggaccagtg aaagaaggag gaactgagcc attgatagtg ttggaatatt taagaacttg     10920
cttgagaatt tacttgtttt tggttttctt ggggacaagc aaagtttcat ttggggaatt     10980
ttgataactg ctaaataatt gtgaattaat agtagaaaat tagtcaaatt ttggcttaaa     11040
attaattatt tagcagttat ttgtgattaa aagttagaaa agcaattaag ttgaattttt     11100
ggccatagat atgaaaactg aagtacaac aagcaaaagg cagcagaaag tgaagaaaaa     11160
gaataaaatc tgaagcagac ccagcccaac acgcgccctt agcgcgcgtc acgcgctaag     11220
cttgcaaggc agcacaggca ctaagcgagg cgttaagcac gaagatgcag gattcgttac     11280
gtgcgctaag cgcgaggcac acgctaagcg cgcgatccaa cagaagcaca cgctaagcct     11340
gcagcatgcg ctaagcgcgc ctacgaaggc ccaaagccca tttctacacc tataaataga     11400
gatccaagcc aagggagaat gtacaccttg cctcagagca cttctctcag cattccaagc     11460
ttgagctctc ccttttctct ctatattctt tgcttttatt atccattctt tctttcaccc     11520
cagttgtaaa gcccctcaat ggccatgagt ggttaatccc ctagctacgg cctggtaggc     11580
ctaaaaagcc aatgatgtat ggtgtacttc aagagttatc aatgcaaaga ggattcattc     11640
caggttttat gttctaattc tttccttttt atcttgcatt tatgtcttaa atttctgttg     11700
ggttttattc gctcgggaga gggtatttcc taataagggt ttaagaagta atgcatgcat     11760
cagttttagg ggttatacgc ttggtaaagg gtaacaccta atagaacaaa ttaagaaaag     11820
gatcgtcggg ctagcattgc taggcataga atgatggccc aatgcccatg catttagcaa     11880
catctagaat ttaaccttaa tgcatttttaa ttattgaatc ttcacaaagg catttgggag     11940
ataggtagtt aaaataggct tgtcatcgtg aggcatcaag ggcaagtaaa attaatagat     12000
gtgggtagaa ctaattcaac tgcattggta atgaacatca taaattcatt catcgtaggc     12060
caattaggtt tgtccggtct tggcattttc atcaattgtc ttcctaaatt atttgatcta     12120
atagcaacaa tttattctta tgcctattcc tgttttact atttactttt acttacaaat     12180
tgaagagtat tcaataaagt gcaataaaat ccctatggaa acgatactcg gacttccgag     12240
aattactact tagaacgatt tggtacactt gtcaaacacc tcaaca                    12286
```

```
<210> SEQ ID NO 18
<211> LENGTH: 1802
<212> TYPE: PRT
<213> ORGANISM: Artificial Sequence
<220> FEATURE:
<223> OTHER INFORMATION: Plant Retroelement Sequence

<400> SEQUENCE: 18
```

Met Arg Gly Arg Thr Ala Ser Gly Asp Val Pro Ile Asn Leu Glu
1               5                   10                  15

Ile Glu Ala Thr Cys Arg Arg Asn Asn Ala Ala Arg Arg Arg Glu
                20                  25                  30

Gln Asp Ile Glu Gly Ser Ser Tyr Thr Ser Pro Pro Ser Pro Asn
            35                  40                  45

Tyr Ala Gln Met Asp Gly Glu Pro Ala Gln Arg Val Thr Leu Glu Asp
    50                  55                  60

Phe Ser Asn Thr Thr Thr Pro Gln Phe Phe Thr Ser Ile Thr Arg Pro
65                  70                  75                  80

Glu Val Gln Ala Asp Leu Leu Thr Gln Gly Asn Leu Phe His Gly Leu
                85                  90                  95

Pro Asn Glu Asp Pro Tyr Ala His Leu Ala Ser Tyr Ile Glu Ile Cys
            100                 105                 110

Ser Thr Val Lys Ile Ala Gly Val Pro Lys Asp Ala Ile Leu Leu Asn
            115                 120                 125

Leu Phe Ser Phe Ser Leu Ala Gly Glu Ala Lys Arg Trp Leu His Ser
    130                 135                 140

Phe Lys Gly Asn Ser Leu Arg Thr Trp Glu Glu Val Val Glu Lys Phe
145                 150                 155                 160

Leu Lys Lys Tyr Phe Pro Glu Ser Lys Thr Val Glu Arg Lys Met Glu
                165                 170                 175

Ile Ser Tyr Phe His Gln Phe Leu Asp Glu Ser Leu Ser Glu Ala Leu
            180                 185                 190

Asp His Phe His Gly Leu Leu Arg Lys Thr Pro Thr His Arg Tyr Ser
        195                 200                 205

Glu Pro Val Gln Leu Asn Ile Phe Ile Asp Asp Leu Gln Leu Leu Ile
    210                 215                 220

Glu Thr Ala Thr Arg Gly Lys Ile Lys Leu Lys Thr Pro Glu Glu Ala
225                 230                 235                 240

Met Glu Leu Val Glu Asn Met Ala Ala Ser Asp Gln Ala Ile Leu His
                245                 250                 255

Asp His Thr Tyr Val Pro Thr Lys Arg Ser Leu Leu Glu Leu Ser Thr
            260                 265                 270

Gln Asp Ala Thr Leu Val Gln Asn Lys Leu Leu Thr Arg Gln Ile Glu
        275                 280                 285

Ala Leu Ile Glu Thr Leu Ser Lys Leu Pro Gln Gln Leu Gln Ala Ile
    290                 295                 300

Ser Ser His Ser Ser Val Leu Gln Val Glu Cys Pro Thr Cys
305                 310                 315                 320

Arg Gly Thr His Glu Pro Gly Gln Cys Ala Ser Gln Asp Pro Ser
                325                 330                 335

Arg Glu Val Asn Tyr Ile Gly Ile Leu Asn Arg Tyr Gly Phe Gln Gly
            340                 345                 350

Tyr Asn Gln Gly Asn Pro Ser Gly Phe Asn Gln Gly Ala Thr Arg Phe
        355                 360                 365

```
Asn His Glu Pro Pro Gly Phe Asn Gln Gly Arg Asn Phe Met Gln Gly
    370                 375                 380

Ser Ser Trp Thr Asn Lys Gly Asn Gln Tyr Lys Glu Gln Arg Asn Gln
385                 390                 395                 400

Pro Pro Tyr Gln Pro Tyr Gln His Pro Ser Gln Gly Pro Asn Gln
            405                 410                 415

Gln Glu Lys Pro Thr Lys Ile Glu Glu Leu Leu Leu Gln Phe Ile Lys
            420                 425                 430

Glu Thr Arg Ser His Gln Lys Ser Thr Asp Ala Ala Ile Arg Asn Leu
            435                 440                 445

Glu Val Gln Met Gly Gln Leu Ala His Asp Lys Ala Glu Arg Pro Thr
    450                 455                 460

Arg Thr Phe Gly Ala Asn Met Glu Arg Arg Thr Pro Arg Lys Asp Lys
465                 470                 475                 480

Ala Val Leu Thr Arg Gly Gln Arg Arg Ala Gln Glu Glu Gly Lys Val
            485                 490                 495

Glu Gly Glu Asp Trp Pro Glu Glu Gly Arg Thr Glu Lys Thr Glu Glu
            500                 505                 510

Glu Glu Lys Val Ala Glu Pro Lys Arg Thr Lys Ser Gln Arg Ala
    515                 520                 525

Arg Glu Ala Lys Lys Glu Pro Leu Ala Leu Pro Gln Asp Leu Pro
    530                 535                 540

Tyr Pro Met Ala Pro Thr Lys Lys Asn Lys Glu Arg Tyr Phe Ala Arg
545                 550                 555                 560

Phe Leu Glu Ile Phe Lys Gly Leu Glu Ile Thr Met Pro Phe Gly Glu
            565                 570                 575

Ala Leu Gln Gln Met Pro Leu Tyr Ser Lys Phe Met Lys Asp Ile Leu
            580                 585                 590

Thr Lys Lys Gly Lys Tyr Ile Asp Asn Glu Asn Ile Val Val Gly Gly
            595                 600                 605

Asn Cys Ser Ala Ile Ile Gln Arg Ile Leu Pro Lys Lys Phe Lys Asp
    610                 615                 620

Pro Gly Ser Val Thr Ile Pro Cys Thr Ile Gly Lys Glu Ala Val Asn
625                 630                 635                 640

Lys Ala Leu Ile Asp Leu Gly Ala Ser Ile Asn Leu Met Pro Leu Ser
            645                 650                 655

Met Cys Lys Arg Ile Gly Asn Leu Lys Ile Asp Pro Thr Lys Met Thr
            660                 665                 670

Leu Gln Leu Ala Asp Arg Ser Ile Thr Arg Pro Tyr Gly Val Val Glu
            675                 680                 685

Asp Val Leu Val Lys Val Arg His Phe Thr Phe Pro Val Asp Phe Val
    690                 695                 700

Ile Met Asp Ile Glu Glu Asp Thr Glu Ile Pro Leu Ile Leu Gly Arg
705                 710                 715                 720

Pro Phe Met Leu Thr Ala Asn Cys Val Val Asp Met Gly Lys Gly Asn
            725                 730                 735

Leu Glu Leu Thr Ile Asp Asn Gln Lys Ile Thr Phe Asp Leu Ile Lys
            740                 745                 750

Ala Met Lys Tyr Pro Gln Glu Gly Trp Lys Cys Phe Arg Ile Glu Glu
            755                 760                 765

Ile Asp Glu Glu Asp Val Ser Phe Leu Glu Thr Pro Lys Thr Ser Leu
770                 775                 780
```

-continued

```
Glu Lys Ala Met Val Asn His Leu Asp Cys Leu Thr Ser Glu Glu Glu
785                 790                 795                 800

Glu Asp Leu Lys Ala Cys Leu Glu Asn Leu Asp Gln Glu Asp Ser Ile
                805                 810                 815

Pro Glu Gly Glu Ala Asn Phe Glu Glu Leu Lys Glu Val Pro Ser
            820                 825                 830

Glu Lys Pro Lys Ile Glu Leu Lys Ile Leu Pro Asp His Leu Lys Tyr
                835                 840                 845

Val Phe Leu Glu Glu Asp Lys Pro Ile Val Ile Ser Asn Ala Leu Thr
850                 855                 860

Thr Glu Glu Glu Asn Arg Leu Val Asp Val Leu Lys Lys His Arg Glu
865                 870                 875                 880

Ala Ile Gly Trp His Ile Ser Asp Leu Lys Glu Ile Ser Pro Ala Tyr
                885                 890                 895

Cys Met His Arg Ile Met Met Glu Glu Asp Tyr Lys Pro Val Arg Gln
                900                 905                 910

Pro Gln Arg Arg Leu Asn Pro Thr Met Lys Glu Glu Val Arg Lys Glu
            915                 920                 925

Val Leu Lys Leu Leu Glu Ala Gly Leu Ile Tyr Pro Ile Ser Asp Ser
930                 935                 940

Ala Trp Val Ser Pro Val Gln Val Val Pro Lys Lys Gly Gly Met Thr
945                 950                 955                 960

Val Val Arg Asp Glu Arg Asn Asp Leu Ile Pro Thr Arg Thr Val Thr
                965                 970                 975

Gly Trp Arg Met Cys Ile Asp Tyr Arg Lys Leu Asn Glu Ala Thr Arg
            980                 985                 990

Lys Asp His Phe Pro Leu Pro Phe Met Asp Gln Met Leu Glu Arg Leu
                995                 1000                1005

Ala Gly Gln Ala Tyr Tyr Cys Phe Leu Asp Gly Tyr Ser Gly Tyr Asn
            1010                1015                1020

Gln Ile Ala Val Asp Pro Arg Asp Gln Glu Lys Thr Ala Phe Thr Cys
1025                1030                1035                1040

Pro Phe Gly Val Phe Ala Tyr Arg Arg Met Pro Phe Gly Leu Cys Asn
                1045                1050                1055

Ala Pro Ala Thr Phe Gln Arg Cys Met Leu Ala Ile Phe Ser Asp Met
                1060                1065                1070

Val Glu Lys Ser Ile Glu Val Phe Met Asp Asp Phe Ser Val Phe Gly
            1075                1080                1085

Pro Ser Phe Asp Ser Cys Leu Arg Asn Leu Glu Arg Val Leu Gln Arg
            1090                1095                1100

Cys Glu Glu Thr Asn Leu Val Leu Asn Trp Glu Lys Cys His Phe Met
1105                1110                1115                1120

Val Arg Glu Gly Ile Val Leu Gly His Lys Ile Ser Ala Arg Gly Ile
                1125                1130                1135

Glu Val Asp Arg Ala Lys Ile Asp Val Ile Glu Lys Leu Pro Pro Pro
                1140                1145                1150

Leu Asn Val Lys Gly Val Arg Ser Phe Leu Gly His Ala Gly Phe Tyr
                1155                1160                1165

Arg Arg Phe Ile Lys Asp Phe Ser Lys Ile Ala Arg Pro Leu Ser Asn
            1170                1175                1180

Leu Leu Asn Lys Asp Val Ala Phe Val Phe Asp Glu Glu Cys Leu Ala
1185                1190                1195                1200

Ala Phe Gln Ser Leu Lys Asn Lys Leu Val Thr Ala Pro Val Met Ile
```

-continued

```
                  1205                1210                1215
Ala Pro Asp Trp Asn Lys Asp Phe Glu Leu Met Cys Asp Ala Ser Asp
            1220                1225                1230
Tyr Ala Val Gly Ala Val Leu Gly Gln Arg Lys Asp Lys Val Phe His
            1235                1240                1245
Ala Ile Tyr Tyr Ala Ser Lys Val Leu Asn Glu Ala Gln Leu Asn Tyr
            1250                1255                1260
Ala Thr Thr Glu Lys Glu Met Leu Ala Ile Val Phe Ala Leu Glu Lys
1265                1270                1275                1280
Phe Arg Ser Tyr Leu Ile Gly Ser Arg Val Ile Ile Tyr Thr Asp His
                1285                1290                1295
Ala Ala Ile Lys His Leu Leu Ala Lys Thr Asp Ser Lys Pro Arg Leu
            1300                1305                1310
Ile Arg Trp Val Leu Leu Leu Gln Glu Phe Asp Ile Ile Ile Lys Asp
            1315                1320                1325
Lys Lys Gly Ser Glu Asn Val Val Ala Asn His Leu Ser Arg Leu Lys
            1330                1335                1340
Asn Glu Glu Val Thr Lys Glu Pro Glu Val Lys Gly Glu Phe Pro
1345                1350                1355                1360
Asp Glu Phe Leu Leu Gln Val Thr Glu Arg Pro Trp Phe Ala Asp Met
                1365                1370                1375
Ala Asn Tyr Lys Ala Thr Gly Val Ile Pro Glu Glu Phe Asn Trp Ser
            1380                1385                1390
Gln Arg Lys Lys Phe Leu His Asp Ala Arg Phe Tyr Val Trp Asp Asp
            1395                1400                1405
Pro His Leu Phe Lys Ala Gly Ala Asp Asn Leu Leu Arg Arg Cys Val
            1410                1415                1420
Thr Lys Glu Glu Ala Arg Ser Ile Leu Trp His Cys His Ser Ser Pro
1425                1430                1435                1440
Tyr Gly Gly His His Ser Gly Asp Arg Thr Ala Ala Lys Val Leu Gln
                1445                1450                1455
Ser Gly Phe Phe Trp Pro Ser Ile Phe Lys Asp Ala His Glu Phe Val
            1460                1465                1470
Arg Cys Cys Asp Lys Cys Gln Arg Thr Gly Gly Ile Ser Arg Arg Asn
            1475                1480                1485
Glu Met Pro Leu Gln Asn Ile Met Glu Val Glu Ile Phe Asp Cys Trp
            1490                1495                1500
Gly Ile Asp Phe Met Gly Pro Phe Pro Ser Ser Tyr Gly Asn Val Tyr
1505                1510                1515                1520
Ile Leu Val Ala Val Asp Tyr Val Ser Lys Trp Val Glu Ala Ile Ala
                1525                1530                1535
Thr Pro Lys Asp Asp Ala Arg Val Val Ile Lys Phe Leu Lys Lys Asn
            1540                1545                1550
Ile Phe Ser Arg Phe Gly Val Pro Arg Ala Leu Ile Ser Asp Arg Gly
            1555                1560                1565
Thr His Phe Cys Asn Asn Gln Leu Lys Lys Val Leu Glu His Tyr Asn
            1570                1575                1580
Val Arg His Lys Val Ala Thr Pro Tyr His Pro Gln Thr Asn Gly Gln
1585                1590                1595                1600
Ala Glu Ile Ser Asn Arg Glu Leu Lys Arg Ile Leu Glu Lys Thr Val
                1605                1610                1615
Ala Ser Thr Arg Lys Asp Trp Ser Leu Lys Leu Asp Asp Ala Leu Trp
            1620                1625                1630
```

-continued

```
Ala Tyr Arg Thr Ala Phe Lys Thr Pro Ile Gly Leu Ser Pro Phe Gln
    1635                1640                1645
Leu Val Tyr Gly Lys Ala Cys His Leu Pro Val Glu Leu Glu Tyr Lys
        1650                1655                1660
Ala Tyr Trp Ala Leu Lys Leu Leu Asn Phe Asp Asn Asn Ala Cys Gly
1665                1670                1675                1680
Glu Lys Arg Lys Leu Gln Leu Leu Glu Leu Glu Met Arg Leu Asn
            1685                1690                1695
Ala Tyr Glu Ser Ser Lys Ile Tyr Lys Glu Lys Met Lys Ala Tyr His
        1700                1705                1710
Asp Lys Lys Leu Leu Arg Lys Glu Phe Gln Pro Gly Gln Gln Val Leu
        1715                1720                1725
Leu Phe Asn Ser Arg Leu Arg Leu Phe Pro Gly Lys Leu Lys Ser Lys
        1730                1735                1740
Trp Ser Gly Pro Phe Ile Ile Lys Glu Val Arg Pro Tyr Gly Ala Val
1745                1750                1755                1760
Glu Leu Val Asp Pro Arg Glu Glu Asp Phe Glu Lys Lys Trp Ile Val
            1765                1770                1775
Asn Gly Gln Arg Leu Lys Pro Tyr Asn Gly Gly Gln Leu Glu Arg Leu
            1780                1785                1790
Thr Thr Ile Ile Tyr Leu Asn Asp Pro Glx
        1795                1800

<210> SEQ ID NO 19
<211> LENGTH: 9829
<212> TYPE: DNA
<213> ORGANISM: Glycine max

<400> SEQUENCE: 19
tgataactgc taaataattg tgaattaata gtagaaaatt agtcaaattt tggcttaaaa      60
ttaattattt agcagttatt tgtgattaaa agttagaaaa gcaattaagt tgaattttttg    120 gccatagata tgaaaactga aggtacaaca agcaaaaggc agcagaaagt gaagaaaaag    180
aataaaatct gaagcagacc cagcccaaca cgcgccctta gcgcgcgtca cgcgctaagc    240
ttgcaaggca gcacaggcac taagcgaggc gttaagcacg aagatgcagg attcgttacg    300
tgcgctaagc gcgaggcaca cgctaagcgc gcgatccaac agaagcacac gctaagcctg    360
cagcatgcgc taagcgcgcc tacgaaggcc caaagcccat ttctacacct ataaatagag    420
atccaagcca agggagaatg tacaccttgc ctcagagcac ttctctcagc attccaagct    480
tgagctctcc cttttctctc tatattcttt gctttatta tccattcttt ctttcacccc      540
agttgtaaag cccctcaatg gccatgagtg gttaatcccc tagctacggc ctggtaggcc    600
taaaagccaa atgatgtatg gtgtacttca agagttatca atgcaaagag gattcattcc    660
aggttttatg ttctaattct ttccttttta tcttgcattt atgtcttaaa tttctgttgg    720
gttttattcg ctcgggagag ggtatttcct aataagggtt taagaagtaa tgcatgcatc    780
agttttaggg gttatacgct tggtaaaggg taacacctaa tagaacaaat taagaaaagg    840
atcgtcgggc tagcattgct aggcatagaa tgatggccca atgcccatgc atttagcaac    900
atctagaatt taaccttaat gcattttaat tattgaatct tcacaaaggc atttgggaga    960
taggtagtta aaataggctt gtcatcgtga ggcatcaagg gcaagtaaaa ttaatagatg    1020
tgggtagaac taattcaact gcattggtaa tgaacatcat aaattcattc atcgtaggcc    1080
aattaggttt gtccggtctt ggcattttca tcaattgtct tcctaaatta tttgatctaa    1140
```

```
tagcaacaat ttattcttat gcctattcct gttttacta tttacttta   cttacaaatt   1200 gaagagtatt caataaagtg caataaaatc cctatggaaa cgatactcgg acttccgaga   1260
attactactt agaacgattt ggtacacttg tcaaacacct caacaagttt ttggcgccgt   1320
tgtcggggat tttgttctcg cacttaattg ccatactata ttagtttgta agcttaattc   1380 ttctttctt  ggctcattct tttattattc tttactttac tttttcttct atcctttctt   1440
tcttctccca taaattgcac gggtagtgcc tttttgtttt tatacgaggt agaactgcat   1500
ctggagacgt tgttcctatt aacttagaaa ttgaagctac gtgtcggcgt aacaacgctg   1560
caagaagaag aagggagcaa gacatagaag gaagtagtta cacctcacct cctccttctc   1620
caaattatgc tcagtggac  ggggaaccgg cacaaagagt cacactagag gacttctcta   1680
ataccaccac tcctcagttc tttacaagta tcacaaggcc ggaagtccaa gcagatctcc   1740
tactcaaggg aacctcttcc atggtcttcc aaatgaagat ccatatgcgc atctagcctc   1800
atacatagag atatgcagca ccgttaaaat cgccggagtt ccaaaagatg cgatactcct   1860
taacctcttt tccttttccc tagcaggaga ggcaaaaaga tggttgcact cctttaaagg   1920
caatagctta agaacatggg aagaagtagt ggaaaaattc ttaaagaagt atttcccaga   1980
gtcaaagacc gtcgaacgaa agatggagat ttcttatttc catcaatttc tggatgaatc   2040
ccttagcgaa gcactagacc atttccacgg attgctaaga aaaacaccaa cacacagata   2100
cagcgagcca gtacaactaa acatattcat cgatgacttg caaccttaat cgaaacagct   2160
actagaggga agatcaagct gaagactccc gaagaagcga tggagctcgt cgagaacatg   2220
gcggctagcg atcaagcaat ccttcatgat cacacttatg ttcccacaaa agaagcctc   2280 ttggagctta gcacgcagga cgcaactttg gtacaaaaca agctgttgac gaggcagata   2340
gaagccctca tcgaaaccct cagcaagctg cctcaacaat tacaagcgat aagttcttcc   2400
cactcttctg ttttgcaggt agaagaatgc cccacatgca gagggacaca tgagcctgga   2460
caatgtgcaa gccaacaaga cccctctcgt gaagtaaatt atataggcat actaaatcgt   2520 tacggattt  agggctacaa ccagggaaat ccatctggat tcaatcaagg ggcaacaaga   2580
tttaatcacg agccaccggg gtttaatcaa ggaagaaact tcatgcaagg ctcaagttgg   2640
acgaataaag gaaatcaata taaggagcaa aggaaccaac caccatacca gccaccatac   2700
cagcacccta gccaaggtcc gaatcagcaa gaaaagccca ccaaaataga ggaactgctg   2760
ctgcaattca tcaaggagac aagatcacat caaaagagca cggatgcagc cattcggaat   2820
ctagaagttc aaatgggcca actggcgcat gacaaagccg aacggcccac tagaactttc   2880
ggtgctaaca tggagaagaa ccccaaggaa gaatgaaaag cagtactgac ttgagggcag   2940
agaagagcgc aggaggaggg taaggttgaa ggagaagact ggccagaaga aggaaggaca   3000
gagaagacag aagaagaaga gaaggtggca tcaccaccta agaccaagag ccagagagca   3060
agggaagcca agaaggaaga accactagcc cttccacagg atctcccata tcttatggca   3120
cccaccaaga gaacaagga  gcgttacttt agacgtttct tggaaatatt caaagggtta   3180
gaaatcacta tgccattcgg ggaagcctta cagcagatgc ccctctactc caaatttatg   3240
aaagacatcc tcaccaagaa ggggaagtat attgacaacg agaatattgt ggtaggaggc   3300
aattgcagtg cgataataca aaggaagcta cccaagaagt ttaaagaccc cggaagtgtt   3360
accatcccgt gcaccattgg gaaggaagcc gtaaacaagg ccctcattga tctaagagca   3420
agtatcaatc tgatgcccctt gtcaatgtgc aaaagaattg ggaatttgaa gatagatccc   3480
```

| | |
|---|---|
| accaagatga cgcttcaact ggcagaccgc tcaatcacaa ggccatatgg ggtggtagaa | 3540 |
| gatgtcctgg tcaaggtacg ccacttcact tttccggtgg acttttttat catggatatc | 3600 |
| gaagaagaca ctgagattcc ccttatctta ggcagaccct tcatgctgac tgccaactgt | 3660 |
| gtggtggata tggggaatgg gaacttagag ttgactattg ataatcagaa gatcaccttt | 3720 |
| gaccttatca aggcaatgaa gtacccacag gagggttgga agtgcttcag aatagaggag | 3780 |
| attgatgagg aagatgtcag ttttctcgag acaccataga cttcgctaga aaaagcaatg | 3840 |
| gtaaatgctt tagactgtct aaccagtgaa gaggaagaag atctgaaggc ttgcttggaa | 3900 |
| aacttggatc aagaagacag tattcctgag ggagaagcca atttcgagac gctagagaag | 3960 |
| gaagttccgt ctgagaagaa gaagatagag ttgaagatat tgcctaatca tttgaagtat | 4020 |
| gtgttcttgg aggaagataa gcctatagtg atcagtaatg cactcacaac agaggaagaa | 4080 |
| aataggttgg tagacgtcct aaagaaacac agggaagcaa ttggatggca catatcggat | 4140 |
| ctcaggaatt agccctgcct actgcatgca catgataatg atggaagagg actacaagcc | 4200 |
| agtccgacaa ccctagaggc ggctgaatcc aacaatgaag gaagaggtaa gaaaggaggt | 4260 |
| gctcaagctt ttggaggctg ggttcatata ccccatctct gatagcgctt gggtaagtcc | 4320 |
| agtacaggtg gttcctaaga aaggcggaat gacagtggta cgaaatgaga ggaatgactt | 4380 |
| gataccaaca cgaactgcca ctggttggtg gatgtgtatc gactatcgca agttgaatga | 4440 |
| agccacacag aaggaccatt tcccctttacc tttcatggat tagatgctgg aaaggcttgc | 4500 |
| agggcaggca tactactgct tttggatgga tattcaggat acaaccagat cgcggtagac | 4560 |
| cccagagatc aggagaagac ggcctttaca tgccccttcg gcgtctttgc ttacagaagg | 4620 |
| atgtcattcg ggttatgtaa cgcactagcc atatttcaga ggtgcatgct agccattttt | 4680 |
| tcagacatgg tggagaagag catcgaggta tttatggacg acttctggat ttttggaccc | 4740 |
| tcatttgaca actatttgag gaacctagag atggtactac agaggtgcgt atagactaac | 4800 |
| ttggtactaa attgggaaaa gtgtcatttc atggttcgag agggcatagt cctgagccac | 4860 |
| aagatctcag ccagagggat tgaggttgat cagacaaaga tagacgtcat tgagaagttg | 4920 |
| ccgccaccaa tgaatgttaa aggtgtcaga agtttcttag ggcatgcagg tttctacagg | 4980 |
| aggtccatca aggacttctc gaagattgcc aggcccttaa gcaatctgtt gaataaggat | 5040 |
| gtggctttta agtttgatga agaatgttca gcagcatttt tagacactaa agaataagct | 5100 |
| caccactgca ccagtaatga ttgcaccaga ctggaataaa gatttttgaac taatgtgtga | 5160 |
| tgccagtgat tatgcagtag gagcagtttt gggacagagg cacgacaagg tatttcacgc | 5220 |
| catctattat gctagtaagg tccttaataa agcataacta aattatgcga ccacagaaaa | 5280 |
| gcagatgcta gccattgtct tttccttgga gaagttcagg tcgtacttga tagggtcgag | 5340 |
| ggtcaccatt ttcacaaatc atgctgccat caagcacttg ctcgccaaaa cagactcaaa | 5400 |
| gctgaggttg attagatggg tcctgctgat acaagaattt gacatcatca tcaaggacaa | 5460 |
| taaaggatcc aagaatgtgg tagccaatca tttatcctga ttaaagaatg aagaagtcac | 5520 |
| caaggaagaa ccagaggtaa aaggagaatt tcctgatgaa tttcttttgt aggttaccac | 5580 |
| cagaccttgg tttgcagaga tggctaacta caaagccaca ggagtcattc cagaggagtt | 5640 |
| taattggagt cagaggaaga aattcttgca tgatgcacgc ttctatgtgt gggataatcc | 5700 |
| tcatttgttt agggcaggag ctgataatct attaaggaga tgcgtcacaa aggaggaagc | 5760 |
| acagagcatt ctttggcact gccacagttc accctatggc ggacaccaca gtggggacag | 5820 |
| aacagcagca aaagtgctac aatcaggttt tttctggcct tctattttta aagatgctta | 5880 |

```
cgagtttgtg cgttgttgtg ataaatgcca gagaacaggg gggatatctc gaaggatgga   5940
gatgcctttg cagaatatca tggaagtaga gatctttgac tgttgggggca tagacttcat   6000 ggggcctctt ccttcttcat acgagaatgt ttacatcctg gtagctgtgg attacgtctc   6060
caaatgggtg gaggccatag ccattccaaa agacgatgcc agggtagtga taaaatttct   6120
gaagaagaac atcttttccc attttggagt cccatgagcc ttgattagtg atggggaacg   6180
cacttctgca ataatcagtt gaagaaagtc ctggagcact ataatgtaag acataaggtg   6240
gccacacctt atcaccctca gacaaatggc caagtagaaa tttctaacaa agagctcaag   6300
cgaatcctgg agaagacagt tgcatcatca agaaagaatt gggccttgaa gctcgatgat   6360
actctttggg cctacagggc agcattcaaa actcccatcg gcttatcacc gtttcagcta   6420
gtgtatggga aggcatgtca tttaccagtg gagctggagc acaaagcata ttaggctctc   6480
gagttactca actttgataa caacgcatgc ggagaaaaga ggaagctaca gttgctggaa   6540
ttagaagaga tgagactgaa tgcctacgag tcatccaaaa tttacaacca aaagatgaag   6600
gcatatcatg acaagaagct acagaggaaa gaattccaac catggcagca ggtattactc   6660
tttaaatcaa ggctaaggct attcccaggt aagctgaagt ccaagtggtt agggccgttc   6720
ataatcaatg aagtcagacc tcacggagca gtagaattgg gggacccctag agaagagaac   6780 tttgagaaga aatggatcgt caatggacaa cgcttaaagc tttataacga aggacaacta   6840
gagcgattga cgaccatcat ctacttgaat gacccttgag gaggcctagt gtctagctaa   6900
agacaataaa ctaagcgctg gttgggaggc aacccaacat attttgtaaa aatgtagtca   6960
tttttctgta ttccttcaaa aaaaagggga aaagcccaat aggtgcaaat agaaaacagc   7020
aggtgcagaa agtaaagacc cagtaggtga agtcagcaat aggaggggtg ccaatagaag   7080
aagcgaagtg ggctgcacga agccacgcgc atctaggcgc taagcgccta ggtatatttt   7140 caattttaa attttaaaaa ttctgaggga accaagggga cgcttccctt ggtatgctta   7200
gcgaccagat gcgcgctaag cgcgcgaacc ataaattgct ggacagtttt caaaactgtc   7260 ccaccccctca gctgcccttt tgtatttaa atttcaacca cctcattttt ttttctcttc   7320
tgcgcactcc cactccctat accctttttc tctacatttc ctctaaactt actcgcctcc   7380
ctgtgcctct tcacgtagtt tttacgaaaa taggtgagat tgggaatctg gactgttgct   7440
gtaatacttt gcaggtacca tcacgctaag ccctacacaa aggcttagcg agaaaaagaa   7500
acatagaaag gaagaaagaa gcatgcgcta agcctgcgcc agacaggaca agaaaacaca   7560
gcatgcgttt agccggcacc tcgtgctaag cgcgctcatg agactcagtg aacgcgctaa   7620
gcatggggct gggccttagg gcccatcagc cctcgtgcct tactttctgc ccctctcttt   7680
tcactaacta cactcccttc tgaatttctt tttgcaccct cctctattac taaccacaat   7740
ctatttttcc gtcttgtttc tttgttttt tcagatggcc tccgcaaaac gccgagctgt   7800
gcccacacct ggggaagcat caagctggga ctcttcccgc ttcacctcgg agatcatttg   7860
gcatagatac caggataaca ttcagctccg gaacattctt ctggagagga atgtcgagct   7920
cacacccagg atgtttgatg agttcctcca ggagctccag aggtgcagat gggaccaggt   7980
gttaacccga cttccagaga agaggattga tgtcgctctg gtgaaggagt tttactccaa   8040
cttatatgat ccagaggacc atagtccaaa gttttgtagg gttcaaggac aggtcatgtg   8100
gtttgatgca gagacgatta acgacttcct tgacacccca gtcatcctgg cagatgtaga   8160
ggagtaccca gcctactctc agtaccctcc g cactcctccc gatcatgatg ccatcctctc   8220
```

```
cactttgtgt actccagggg gacggtttgt tctgaatgtt gatggtgccc cctagaagtt    8280
gctgcggaag gatctgacga cactcgctca gacatagagt gtcctttctt attttaacct    8340
tgttcttact tctcacactt ctgatattaa tgttgacagg gcccgtctca tatatggctt    8400
ggtgatgaag atggacctgg acgtggacag ttttatttcc cagcaaatca gtcagatcgc    8460
ccaatccaac acatccaggc tcgggttccc agcgttgatc acggcactgt gtgacattca    8520
gggggttgtt tctaacaccc tgattttga gttactcaat cctatgatta accttgcgta     8580
cattacacta ctaaaaaaaa gctattttac gacgcgcgtt ccacatcgtt tctgccaaaa    8640
atgtcgtaat aggagtagcg gtggcaattc cgtaaataag tgagcatttt atgtgccatg    8700
tgcatggcgc gtgacacatt caacgacgtt ggccatgggt gcccgtcttt gtaggtggcg    8760
cgctggtaac ttaagacggt gcacttaaaa acatcgtcgt tgaaattttg aatttcgaag    8820
acgttgctct taagccaccg tcgttaaggt tgatgtatat aatgttgtaa tttgcgctat    8880
ttcgtgaaca ctcgctcgag ctcccgcttc cctgtgtgtc tgaaatttct gtgtactgtg    8940
acctcgccat gacttgtggc gtttgcccac accccgtca cctcgtccgg catctcgtct     9000
tgtggtggca ccgccgaagc cagtgagtac ccctttttgg aggggtcgta acacggctgt    9060
gttttgaagg taaggttgtg cgaagatttg atgctccata gttgttactt gctctgagtt    9120
tttcttttag tgatgtatct tttaccccctc tttcagtgct tcttccctca gaatttgatt    9180
gccggtatta gaaccccact attcatcagg tccaaacaag cttaaatcat ggtaaatgta    9240
cttcttgaca aatccaacat ttgcaaggtg gtttgacata tgagaaatag cttttaaccta    9300
atgttcttaa atttattatg aagctctcta gcgattacga aaatctctca atatcttctc    9360
tctctgtctc acatgcatca ctgtaagata ggtgtcaaaa agaaaggatt gaagttaaat    9420
ttaaacctaa tgttttgaaa tgaaggaaaa aaagaaagag attaatgacg ctagggaact    9480
tgaatgaaga aagagaaagg aacataatta gtccttgaa ctgattgggg tggggagtgt     9540
ggcacgaaac ataatttcta gttctatgga tttattcgtg acactgtggt aggaccaagc    9600
aaactctgcc cccagagtgc gcagtgtctt gcagtctgag aggttctttt gttgggctag    9660
tttgaggaat tcttcattgc agggttgagc acggtggcca atggccaagg agagaaaaga    9720
cagtactgtc aaaatggtta atggtaagat gagtgaagat gacatgtttt tttgttgtct    9780
ctttgtgtgt ttccttttgg tgggaaaatg tgatgcatag agagatcga                9829
```

<210> SEQ ID NO 20
<211> LENGTH: 12571
<212> TYPE: DNA
<213> ORGANISM: Glycine max

<400> SEQUENCE: 20

```
gatcttaaat tcttaaactt tgataacagt gcatacggag agaagagaaa gttgcagtta      60
ctggaactcg aagaaatgag gttgaacgct tacgaatcat ctaggattta caagcagaag    120
gtaaaggcgt atcatgataa gaaattacaa aagaaagaat tccagccagg gcagcaagta    180
ctactcttca actccaggtt gagattattc acaggaaagc tgaagtcaaa gtggtcagga    240
tcgttcatta ttaaggaaat cagacctcac ggagcggtag aattggtgga ccctcgagaa    300
gaaaattatg agaagaaatg gatcgtcaac ggacaacgct aaaaatttta caatggagga    360
caactagaga agttgacgac catcatgcat ttaaaagatt cttgaaagaa gccctatgtc    420
tagctaaaga cattaaacta agcgctggtt gggaggcaac ccaacatact tatgtaaggt    480
atttataagt atttatattc tgtctttatt atattttgca gttgttattt caggttaaaa    540
```

-continued

```
gaaaaaacag gggccctccg gactcgcacc agagtatcaa cgtccatatc tgaggcaccc      600
cctacttctc agccttccgc tccatcacct actgatcttc atgctcagat gttgcggtct      660
attcacacag gacaggagac ccttatggag aacatgcaca agctgtcctt tcatctacat      720
atggatccac cactgatcac tccataggtc tatcgtcagc gggtcgtctg ccatgagac       780
cagctctcca ctgacagggg ggaagagccc tctggagatg ctgcagttga tgaagacctc      840
atagcagact tggctagtgc tgattggggt ccatgggcag atttgggagg cggcacagga      900
cactggtttt attttttcttg atgttttttgt ttatgtttaa tgtttatgtt ttatgtcttt    960
```

```
cgggagaggg taaagcctaa ttaggggtaa ggaatgaata cttgaatcta ttttaagggt    2940
tagtccattc gggagagggt aaagcttaat agaacaataa aaggaagaaa ttatcgggtt    3000
atcattagag ggttttcctt ccaggttctt ttatctgctt ttctttctta ttctgcatct    3060
cagtctttat tttctgttag tctttagtcc actcgggaga gggtaaagcc taattaaggg    3120
taaggaatga ttgcgtgaat ctgttttaag ggttagttca ctcaggagag ggtaacgctt    3180
aatagaacaa taaagaaaa aaatcacagg gttagcattg acccgatgcc catactttag    3240
caaacatata gaatttaatc ttaatgcatc ttagttattg agtctttgca aagggcattt    3300
ggaagatagg taattaaggt aggcttgtca tcatgaggca tcaggggcaa gtagatggat    3360
agatgtgggg cagaatcagt tcactggtat tgataacaga caaatcttga atccatatat    3420
ctaggctgat tagactttt aggttttagc aatttatta tatagatttt attccctatt    3480
ttattgtttg aagtttctta ttctattgtt gggttttctt agaagtagct attccttatt    3540
ttactgttgg gttttcttag aaatagttat tccttattgt tgggtttctt agaagtagtt    3600
attccttatt ttactgttgg gttttattag gagtacttat cccctgttta ggagtaggta    3660
tttaggctta ttagatttag taatatttta tagactttat tctttatta ttgcttgagt    3720 ttcctttaat ttagaagtag ctgcttagat ttaaattact ttatctttat cctttaatct    3780
tatctttaaa tcttttatct tttccttatc ttatcttta tctttcttta tcttttattt    3840
caaatttctt atcccttgct agatttaaat tgcatttaat tttatacact aaatttacaa    3900
tttgcaaact aaaagtact tcacataagt gcaacaaaat ccctatggta cgatactcga    3960
cttaccgaga gattattact acgagcgatt tggtacactt gccaaagagc taacaaagat    4020
attgcctgat catctaaagt atgtgttctt ggaggaagat aaacctatag taatcagtaa    4080
cgcactcaca acaaaggagg aaaataggtt ggttgatgtc ctcaagaaat acagggaagc    4140
aattggatgg catatatcgg atctcaagga aattagccct gcttactaca tgcacagaat    4200
aatgatggaa gagaactaca agccagtccg acaaccccag aggcggctga atccaacaat    4260
gaaggaagag gtaagaaagg aggtactcaa gctcttggag gctgggctca tatacccctt    4320
ctctaacagt gcttgggtaa gcccagtaca ggtggttccc aagaaaggtg aaatgacagt    4380
ggtacgaaat gagaagaatg acttgatacc cagacgaact atcactggtt ggcgaatgtg    4440
tatcaactat cgcaagctga atgaagccac acgaaaggac catttcccct acttttcat    4500 ggatcagatg ctagagagac ttgtagggca ggcatactac tatttcttgg atggatactc    4560
gggatataat cagatcgcgg tggaccccag agatcaagag aaggcggcct ttacatgccc    4620
ttttggcgtt tttgcttata gaaggatgcc attcgggtta tgtaatgcac cagccacatt    4680
tcagaggttc atgctggcca ttttttcaga catggtgtag aaaagcattg aggtatttat    4740
ggacgacttc tgggttttg gaccctcatt taacagtttg aggaacctag atggtact    4800 ttagagttga gtagagacta acttggtact gaactgggaa agtgtcact tcatggttca    4860 agagggcatc gtcctaggcc acaagatctc agcaagaggg attgaggtcg atcgggcaaa    4920
gatagacgtc atcgagaagc tgccaccacc actgaatgtt aaaggggtta gaagtttctt    4980
agggcatgca ggtttctaca agaggtttat caaggacttc tcaaagattg ccaggcccct    5040
aagtaacctg ttgaataaag acatggtttt caagtttgat gaagaatgtt caacagcatt    5100
ccaatcattg aagaataagc ttaccactgc acctgtaatg attgcacccg actggaataa    5160
agattttgaa ctaatgtgtg atgccaatga ttatgcagta ggagcagttc tgggatagag    5220
gcacgacaag gtatttcacg ccatctatta tgctagcaag gtcctgaatg aagcatagtt    5280
```

-continued

| | |
|---|---|
| gaattatgca accatagaaa aggagatgct agccattgtc tttgccttgg agaaattcaa | 5340 |
| gtcatacttg ataggggtga gggtcaccat tttcacagat catgctgcca tcaagcacct | 5400 |
| gcttgccata acagactcaa aaccgaggtt gattagatgg gtcctactgt tacaagaatt | 5460 |
| tgacatcatc atcaaggaca agaaaggatc cgagaatgtg gtagccaatc atctatctcg | 5520 |
| attgaagaat gaagaagtca ccaaggaaga accagaggta aaaggtgaat tcctgatga | 5580 |
| gtttcttttg caggttaccg ctagatcttg gtttgcagac atggccaatt acaaagccac | 5640 |
| gggagtcatt ccagaggagc ttaattggag tcaaaggaag aaattcttgc acaatgcacg | 5700 |
| cttctatgtg tgggatgatc ctcatctgtt caaggcagga gcagataatt tactaaggag | 5760 |
| atgcgtcaca aaggaggaag cacggagcat tctttggcac tgccacagtt caccctatgg | 5820 |
| cggtcaccac agtggggaca gaacagcagc aaaagtgcta caatcaggtt ttttctggcc | 5880 |
| ctctattttt aaagatgctc acgagtttgt gcgttgttgt gataaatgcc aaagaacagg | 5940 |
| ggggatatct cgaagaaatg agatgccttt gcaaaatatc atggaagtag agatctttga | 6000 |
| ctgttggggc atagacttca tcgggcccct gccttcgtta tatggaaatg tctacatctt | 6060 |
| ggtagttgtg gattacgtct ccaaatgggt ggaagtcata gctacgccaa aggatgatgc | 6120 |
| caaggtagta atcaaatttc tgaagaagaa cattttttcc cgttttggag tcccacgagc | 6180 |
| cttgattagt gataggggaa cgcacttctg caacaatcag ttgaagaaag tcttggagca | 6240 |
| ctataatgtc cgacataagg tggccacacc ttatcatcct cagacaaatg gccaagcaga | 6300 |
| aatctctaac agggagctca aggcgaatct tggaaaagac aattgcatca tcaagaaagg | 6360 |
| attgggcctt gaagctcgat gatactctct tggcctatag ggcagcgttc aagactctca | 6420 |
| tcggcttatc gccatttcag ctagtgtatg ggaaggcatg ccatttacca gtggagctag | 6480 |
| agcacaaagc atattgggct ctcaagttgc tcaacttcga caacaacgca tgcggggaaa | 6540 |
| agaggaagct acagatgttg gaattagaag agatgagact gaatgcctac gagtcatcca | 6600 |
| gaatttacaa gcaaaagatg aaggcatatc atgataaaaa gctacagagg aaagaattcc | 6660 |
| atccagggaa gcaggtatta ctcttttaact cgaggctaag gctattccca ggtaagctga | 6720 |
| agtccaagtg gtcaaggcca tttatcataa aagaagtcag acctcatgga gcagtagaat | 6780 |
| tggtggaccc ttgagaagag aactttaaga agaaatggat cgtcaatcga cagcgcttga | 6840 |
| agccctacaa cggaggacaa ctcgagcgat tgacgaccat catctactta aatgatcctt | 6900 |
| gagaaggcct actgtctagc taaagacaat aaactaagca ctggttggga ggcaacccaa | 6960 |
| catattttg taaaaatgta gttatttta ttttatgtaa aaaaaaacaa gagggcccaa | 7020 |
| taggtgcaaa tagcaaacag gaggtgcaaa agcaaaggc ccaacaggtg aagacaacaa | 7080 |
| taggaagggt gccaatagca aaactgaagt gggctgcatg aagccgcgcg ctaagcgccc | 7140 |
| aggtatgttt ttaaaatctg atgggcaacc aagggacgct ttccttggtg cgcttagcgg | 7200 |
| ccacatgcgc gctaagcgcg taagtcataa attactggac agttttcgaa actgcccaac | 7260 |
| ccctcagctg cctcctccgc gttattaaat tacaaccatt tcatttcatt atccttcttt | 7320 |
| tctttcgcaa atctacccct ctttgcacct ctgctactgt aaccccctgaa ttcttggtct | 7380 |
| tttcacacaa aacaatcact aacgaaggta aagaattgct ttgtatggat gttgttatga | 7440 |
| atgcacaggt aacagcacgc taagccctgc tcgacgctta gccaatgaag acggattgaa | 7500 |
| ggccataacg acgagctcgt taagcgtgac gaagcacgct aagcaggcgc ctgacaggac | 7560 |
| gagaaagcaa agcgcgcgct tagccggcac ttccgcgcta agcgcgctca tgaacatcac | 7620 |

```
tgaacgcgct aaacgtgtgc cagaggcgct aaacgcgtgc cagaggcgct aaacgcgtgc    7680
attagtcaca gcaggatggt gctaagcgcg gggttgggcc tcagggccca tcaaccctcg    7740
caccttactt gttgcacccc tatttctact attcccactc ccttctaatt tcttttttgca    7800 ccccccttct ttactgactg cacctctatt ttgattactt tttgcacccc ccctgattgc    7860
taacttcaga ctatctttct tgttttttgt tttttggtt ttttggtcag atggcctcct    7920
gtaaacaccg agctgtgccc acacccgggg aagcgtccaa ctgggactct tcacgtttca    7980 cttcgagat tgcttggcac agataccagg atagcattca gctccggaac atccttccag    8040
agaggaatgt agagcttgga ccagggatgt ttgatgagtt cctgcaggaa ctccagaggc    8100
tcagatggga ccaggttctg acccgacttc agagaagtg gattgatgtt gctctggtga    8160
aggagtttta ctccaaccta tatgatccag aggaccacag tccgaagttt tggagtgttc    8220
gaggacaggt tgtgagattt gatgctgaga cgattaatga tttcctcgac accccggtca    8280
tcttggcaga gggagaggat tatccagcct actctcagta cctcagcact cctccagacc    8340
atgatgccat cctttccgct ctgtgtactc caggggacg atttgttctg aatgttgata    8400 gtgcccctg gaagctgctg cggaaggatc tgatgacgct cgcgcagaca tggagtgtgc    8460
tctcttattt taaccttgca ctgactttttc acacttctga tattaatgtt gacagggccc    8520
gactcaatta tggcttggtg atgaagatgg acctggacgt gggcagcctc atttctcttt    8580
agatcagtca gatcgcccag tccatcactt ccaggcttgg gttcccagcg ttgatcacaa    8640
cactgtgtga gattcagggg gttgtctctg ataccctgat ttttgagtca ctcagtcctg    8700
tgatcaacct tgcctacatt aagaagaact gctggaaccc tgccgatcca tctatcacat    8760
ttcaggggac ccgccgcacg cgcaccagag cttcggcgtc ggcatctgag gctcctcttc    8820
catcccagca tccttctcag ccttttttccc agtgaccacg gcctccactt ctatccacct    8880
cagcacctcc atacatgcat ggacagatgc tcaggtcctt gtaccagggt cagcagatca    8940
tcattcagaa cctgtatcga ttgtccctac atttgcagat ggatctgcca ctcatgactc    9000
cggaggccta tcgtcagcag gtcgcctagc taggagacca gccctccact gacaggggg    9060 aagagccttc tggagccgct gctactgagg atcctgccgt tgatgaagac ctcatagctg    9120
acttggctgg cgctgattgg agcccatggg cagacttggg cagaggcagc tgatcttatg    9180
ctttaatgtt ttcttttata ttatgtttgt gttctcttt atgttttatg ttatgttttt    9240
atgtagtctg tttggtaatt aaaaagaggt agtagtaaaa atattagtat ttcagtatgt    9300
gttttctgag taataagtgc atgataactc aagcaatcat aattctttag cttgttcaga    9360
aaggttcaac acttgagatg ccactgatcc ttggagaaac actggttctg gaagcaaaag    9420
tcaggtcaag aaatggaaca tgaatagcac agagtggaaa ggttagcttg atggaacaag    9480
gtcataactg gtacgccgaa tacttgttta agtccctgtg agcatggttg tcaaactcta    9540
gagtcaactc atagactctc atgagtttaa gagtttactt cagtcccgcg agttgactcg    9600
gaagcaaact cgcttttgag caaactcgtg gactcggagt gaactcatgt aaactcgtaa    9660
gagtctacga gttgactcta gagtttgaca accatgcata agtgttcaaa attaaagcat    9720
ttaaataatt aaaaaagca caaatgtctt caaagaagca tgttcaatcc tctaatagga    9780
tcatcttcat gaatatcatc actttcatca tcatctccat ctccatcatc atcatcaagg    9840
tcttcctcag attgtgcatc atcattaggt tccacaaaga ttaaattatc tagatcaaaa    9900
gcttaaaata gatatcaaat atgctatatt agaaatagtt aaaacttaaa ataatacaca    9960
agcaaatttt aaatatgaga aagttcagaa attataccctt ttcttggtgt tattaaagtt    10020
```

```
tcattttatc ttctcttttg cattttccat ctcctcacat atgaaaagca taattctatt    10080
gaatttcagt aacaagtttg atccaactcc aacattgtaa ggtcagttgt tgtgttttgt    10140
aatagactaa tatgaagtat gaagtatgaa ctatgaactt attgtcatct gtttgcaaat    10200
tggtgcattt tgaatatatt tacttattat ccattttttt tttttttacga agtagactct    10260 cacgagtctg cgtagactct cgatatcgat aaccttgccg atgagagtgt gaacttaatt    10320
gtgagagaaa atgcctattt ttaagttcct ggttttgcat cattcttaga cggttagaat    10380
agttacttaa ggtggatatg atcaaggcca tgtttgtttg tttacctact tagccaaaaa    10440
gccaacctaa catagtttta ccccttgcac ccatgattga gccaactgat tattttgaat    10500
taaccttgag ccaattaaac aaaatcctga ccttttagga ttttaagaga gtaaaaatgg    10560
gttataaagg tcttaatttg ggggattttg ggaataggt agccaagaca ataagtacag    10620
cacacaaagt aggacacctt ttacaaacag taggcccaat ttcgaaaaaa aaatgaaaag    10680
aatttaataa agggcagaaa caaagagca agagaggtgt caaagaaaaa gtgttgtggg    10740
gaaataaaag ggctaagtaa aaaggcctag gcagaattgg aaattttgt tctcttttaa    10800 tcctaacttt gaatttccaa gaaaaaccat gattttttgt aagccaggcc ccgatacaag    10860
ccaataaagt ccttagtgat ccaccaaagg taactagaga taactgtaac tgagatgaaa    10920
tgcaaaattt tgaagtgtta cttgcaggtt gttatcaaat tgcaaacact aaactaggca    10980
cttgtgagca gagggaaaca ccagccttgt gaggaaagta aggcaagcca aatttgattg    11040
agttccagat gactaactga ttcaattctt ctgttgtaat gctttcattt taagatgttg    11100
acagatgcag aaaggaccag tgaaagaagg aggaactgag ccattgatag tgttggaata    11160
tttaagaact tgcttgagaa tttacttgtt tttggttttc ttggggacaa gcaaagtttc    11220
atttggggaa ttttgataac tgctaaataa ttgtgaatta atagtaaaga attattcaaa    11280
ttttggcctg aaattaatta tttagcagtt atttgtgatt aaaagttaga aaattaatta    11340
aattgaattt ttggttgcag ataagaaaat tggagttaca ttaagcaaaa aaggcaacaa    11400
aaaatgaagg aaaagaagaa gtctgaagca ggcccagccc aacacgcacg ctaagcgcgt    11460
gtcacgcgct aagcgtgcaa ggcagtacag gcgctaagcg aggcgttaag ctcgaagatg    11520
cagaatccgt tacgcgcgct aagcaagggc cacgcgctaa gcgtgcgatc aacagaaac    11580 acacgctaag cctgcatctc gcgctaagcg cgcgatctga acgcgctaag cgcgaggtgt    11640
cgcgctaagc gcgcttacga aggcccaaaa cccactttag cagctataaa tagagagtca    11700
gtccaaggga aacaacacat ctcgcctcag agcacttccc tcagcattct aagcctaagc    11760 tctcccttt ctcttttgttt ttattatcct cattctttct ttcaccccca gttgtaaagc    11820
cctcaatggc catgagtggc taatctagta gctagggcct ggcaggccta aaaagccaac    11880
gatatatggt gtacttcaag agttatcaat gcaaagaaga ttcattccag gttttttgt    11940 tctaattatt ttcttttat cttgcattca tttcttgaat ttcttttggg ttttatttgc    12000
tcgggagagg gtatttccta ataagggttt aaggattaat gcatgcatca gttttagggg    12060
ttatacgctt gggaaagggt aacacctaat agaacatctt aagaaaagaa tcatcgggtt    12120
agcattgcta ggcatagaat gataactcaa tgcccacgca tttagcaaca tctagaattt    12180
taccttaatg cattttaatt attgagtctt cgcaaaggca tttgggagat aggtagttaa    12240
aataggcttg tcatcgtgag gcatcagggg caagtaaaat taatagatgt gggtagaact    12300
gttacaaatg cattggtaat gaatatcata tttacatgca tcgtaggcca attgggtttg    12360
```

```
tccggtcttg gcatttatat taattgtctt tctaaaacta tttgatctag taatagcaat    12420
ctattcttgc acttactcct gttttctact ttttactctt acaaattgaa aagtattcga    12480
taaagtgcaa taaatccct  gtggaaacga tactcggact tccgaggttt actacttaga    12540
gcgatttggt acacttgcca aagtctcaac a                                   12571

<210> SEQ ID NO 21
<211> LENGTH: 4609
<212> TYPE: DNA
<213> ORGANISM: Glycine max

<400> SEQUENCE: 21
gatctcccat atcctatggt acccaccaag aagaacaagg aacattactt ctgacgtttc      60
ttggaaatat tcaaaggact ggaaatcacc atgccattcg ggaagcctt  acagcagatg     120 cccctctact ccaaatttat gaaggacatc ctcaccaaga aggggaagta tattgacaat     180
gagaatattg tggtaggggg caactgtagt gcaataatac agaggaagct acccaagaag     240
tttaaggacc ccggaagtgt taccatcccg tgcaccatag aaaggaaga  ggtaaacaag     300 gccctcattg atctaggagc aagtatcaat ctaatgccct tgtcaatgtg cagaagaatc     360
aggaatttga agatagatcc caccaagatg acacttcaac tggcagaccg ctcgatcaca     420
agaccataca gggtggtaga agatgtcctg gtcaaggtac accacttcac ttttccggtg     480
gactttgtta tcatggatat cgaagaagac acagagattc cccttatctt aggcagaccc     540
ttcatgctga ttgccaactg tgtggtggat atggggaatg ggaacttgga ggtgagtatt     600
gacaatcaga agatcacctt tgaccttttc aaggcaataa agtacccata ggagggttgg     660
aagtgcttta gaatggagga gattgataag gaagatgtca gtattctcga cacaccacag     720
tcttcgctgg ggaaagcaat ggtaaatgct ttagactgtc taaccagtga agaggaagaa     780
gatctaaagg cttgcttgga agacttggat tgacaagaca gtattcctaa gggagaagcc     840
agatttgaga ctctagaaaa ggaagttccg tccgagaaga agaagataga gttgaagata     900
ttgcccgatc atctgaagta tgtgttcttg gaggaagata aacctgtagt gatcagtaac     960
gtactcacaa cagaggagga aaacaggtta gtagatgtcc tcaagaaaca cagggaatca    1020
attggatggc acacatcgga tctcaaggga attagccctg cttactgcat gcacaggata    1080
atgatggaag aggactacaa gccagtctga caaccccaga ggcggctgaa tccaacaatg    1140
aaggaagagg taagaaaaga ggtactcaag ctcttggagg ttgggctcat atacccatc     1200 tctgacaacg cttgggtaag cccagtacag gtggttccca agaaaggtgg aatgacagtg    1260
gtacaaaatg agaggaatga cttgatacca cacgaacag  tcactggctg gcgaatgtgt    1320
attgactatc acaagctgaa tgaagctaca cggaaggacc atttcccctt acctttcatg    1380
gatcagatgc tggagagact tgcagggcag gcatactact gtttcttgga tggatactcg    1440
ggatacaacc agatcgcggt agaccccata gatcaggaga agacggtctt acatgcccc     1500 tttggcgtct tgcttacag  aaggatgtca ttcgggttat gtaatgtacc agccacattt    1560
cagaggtgca tgctgaccat tttttcagac atggtggaga aaagcatcga ggtatttatg    1620
gacgacttct cggttttggg accctcattt gacagctgtt tgaggaacct agaaatggta    1680
cttcagaggt gcgtagagac taacttggta ctgaattggg aaaagtgtca ttttatggtt    1740
cgagagggca tagtcctagg ccacaagatc tcagctagag ggattgaggt tgatcgggcg    1800
aagatagacg tcatcgagaa gctgccacca ccactgaatg ttaaagggt  tagaagtttc    1860 ttagggcatg caggtttcta taggagggttt atcaaggatt tctcgaagat tgccaggccc    1920
```

```
ttaagcaatc tgctgaataa agacatgatt tttaagtttg atgaagaatg ttcagcagca    1980
tttcagacac tgaaaaataa gctcaccact gcaccggtaa tgattgcacc cgactggaat    2040
aaagattttg aactaatgtg tgatgctagt gattatgcag taggagcagt tttgggacag    2100
aggcacgaca aggtatttca caccatctat tatgctagca aggtcctgaa tgaagcacag    2160
ttgaattatg caaccacaga aaaggagatg ctagccattg tctttgcctt ggagaagttt    2220
aggtcatact agatagggtc gagggtcacc attttcacag atcatgctgc catcaagcac    2280
ctgctcgcca aaacagactc aaagctgagg ttgattagat gggtcatgct attacaagag    2340
tttgacatca ttattaagga caagaaagga tccgagaatg tggtagctga tcatctatct    2400
cgattaaaga atgaagaagt caccaaggaa gaaccagagg taaaaggtga atttcctgat    2460
gagtttcttt tgcaggttac cgctagacct tggtttgcag acatggctaa ctacaaagcc    2520
atgggaatca tcccagagga gtttaattgg agtcagagga agaattttt gcacgatgca     2580
cgcttatatg tgtgggatga tcctcatttg ttcaaggcgg gagcaaataa tttattaagg    2640
agatgcgtca caaggagga agcacgaagc attctttggc actgccacag ttcaccctat    2700
ggcatacatc acagcgagga tagaacaaca gcaaaagtgc tacaatcaag tttttttctag   2760
cccctttattt ttaaagatgc tcacgagttt gtgcattgtt gtgataaatg tcagagaaca   2820
aggggatat ctcgaagaaa tgagatgcct ttgcagaata tcatggaggt agagatcttt     2880
gatagtggg gcatagactt catggggcct cttccttcat catacaggaa tgtctacatc     2940
ttggtagctg tggattacgt ctccaaatgg gtggaagcca tagccacgct gaaggacgat    3000
gccagggtag tgatcaaatt tctgaagaag aacatttttt cccatttcgg agtcccacga    3060
gccttgatta gtgatggggg aacgcacttc tgcaacaatc agttgaagaa agtcctggag    3120
cactataatg tccgacacaa ggtggccaca ccttatcaca ctcagacgaa tggccaagca    3180
gaaatttcta acaggagct caagcgaatc ctggaaaaga cagttgcatc atcaagaaag     3240
gattgggcct tgaagctcga tgatactctc tgggcctata ggacagcgtt caagactccc    3300
atcggcttat caccatttca gctagtatat gggaaggcat gtcatttacc agtagagctg    3360
gagcacaagg catattgggc tctcaagttg ctcaactttg acaacaacgc atgcggggaa    3420
aagaggaagc tacaactgct ggaattagaa gagatgagac tgaatgccta cgagtcatcc    3480
aaaatttaca agcaaaagac aaaggcatat catgacaaga agctacaaag gaaagaattc    3540
cagccagggc agcaggtatt actcgttaac tcaaggctaa ggctattccc aagtaagctg    3600
aagtccaatt ggtcagggcc attcataatc aaagaagtca gacctcacag agcagtagaa    3660
ttggtggacc ctagagaaga gaactttgat aagaaatgga tcatcaatgg acagcgcttg    3720
aagccttata acggaggaca actagagcga ttgacgacca tcatctactt aaatgaccct    3780
tgagaaggcc tactgtcgag ctaaagacaa taaactaagc gctggttggg aggcaaccca    3840
acatattttg taaaaatgta gttatcttca ttctatgtaa aaaaaagcc caacaggtgc     3900
aaataggaaa cacgaggtgc aaaaagcaaa ggcccaacat gtgaagacaa caataggagg    3960
ggtgccaata gcaaaactga agtgggctac acgaagctac gtgcttagct cgcgtccgcg    4020
cgctaagcgc ccagattgca caaaaatagg tgagacttgg aatctggact attgctgtaa    4080
tatcttgcag gtaccattac gctaagccct acacagaggc ttagcgagaa caggcagcat    4140
ggaaaagg aaggagagc gcgctaagcc acaacaagta atagaagaaa acgaagcacg        4200
cgcttagcgg gcactgccgc gctaagcgca ctcttcaaca tcagtgaacg cgctaagcgc    4260
```

-continued

```
gtgccagaag cgctaagcgc gtgtcaccgt caccagcagg aaggcgctaa gcgcgaggtt      4320
gggccttagg gcccatcagc cttcgcgcct tactttttgc acaccccttc tttactaact      4380
gcacccctat tttgatttct tttttgcacc cctctgttta ctaactgcag tttgtttctg      4440
ctgtttcttg tttttgtttc agatggcctc ctgcaaacgc cgagccgtgc ccacacccag      4500
ggaagcgtct aattgggact cttcccgttt cacttcagag attgcatggc acagatatca      4560
ggacaacatt cagctctgga acatcctttc ggagaggaat gtcgagctc              4609
```

<210> SEQ ID NO 22
<211> LENGTH: 9139
<212> TYPE: DNA
<213> ORGANISM: Glycine max

<400> SEQUENCE: 22

```
acctggttgt tgtatgctt gtcttaatgc ggataggttg tcaagtagct ttagtgctaa        60
cactgagaag aatccgaagg aagaatgtaa agttttaatg acaaagagca gaatggaaat       120
tcaagttgat gaagttagag ctgaagagaa ggtggaggga tataaacaac agtcgatagc       180
tgagcctgca ctggaactag tttccgatct tattgaactt gaggaagttt tggaagagga       240
agatgaccaa caggagagag agacaccaat aaaagatagt caagaaggaa taaagatgaa       300
ggaagagcat gaaaagaaa acaaaaaga aaagaagaa atagaaaag aaataataa          360 aaaaaatgaa aataaaaaa agatggttga tgaggagaaa aaaagagca agagtgaggt        420 ttcaagagaa aaaagagag agattacttc agctgaaggc aaggaagtac catatctatt       480
ggtaccttcc aagaaggata agagcaaca cttagccaga tttcttgaca tcttcaagaa       540
actggaaatt actttgcctt ttggagaagc tctccaacag atgccactct atgccaaatt       600
tttaaaagac atgctgacaa agaagaacta gtatatccac agtgacacaa tagttgtgga      660
aggaaattgt agtgctgtca ttcaacacat ccttccccca aatcataagg atcccggaag       720
tgtcactata ttatgttcca ttagcgaggt tgttgtgggt aaagctctca tagacttggg       780
agctagtatc aatttaatgc ctctctcaat gtgtcgacga cttggagaga tagagataat       840
gcccacacgc atgacccttc agttggttga tcactccatc acaagaccat atggagtgat       900
tgaggatatg ttgattcagg tcaagcaact tgtattccct gtagatttcg tggttatgga       960
tatagaggag gatcctgaca ttcccataat cttgggacgt cctttcatgt ccgcgaccaa      1020
ctatatagta gatataggga aaggcaagtt agaattgggt gtggaggatc agaaagtctc      1080
attcgactta tttgaagcaa ataagcatcc aaatgataag aaagcttgct ttgatctaga      1140
caaggtagaa caataaatag aattagctac tatagccatg gtactgaact ctcctttgga      1200
aaaagcattg attaatcatg tagaatgtct tactaaagag gaggaacatg aagtgcaaac      1260
ttgtattaaa gagttggatg gtgcaggaga aaattctgag ggacaggatg catttcaaga      1320
attgaagaat ggtgggcaaa tagaaaaacc aaaagtagaa ttgaagacct tgcctgcaca      1380
tttgaagtat gtatttctcg aagacaatga ctccaaacca gtgattatta gcagctcgtt      1440
gaagaaaata gaagatcaac tggtgaagat tttgaagaga cacaaagctg caattggatg      1500
gcacatatct gacttgcaag gaattagtcc atcttattgc atgcacaaaa tcaatatgga      1560
agctgattac aaaccagtga gagagcctca agaagactg aacccaatca tgaaagaaga      1620
gatgcataag gaggtgctta aattgtagga agcaggcctt attacccct cctcggatag      1680 tgcatgggtt agccttgtgc aggttgtccc caagaaagga ggtatgacag tcattaaaaa      1740
tgataaagat gagttaatat ccataaggac tgtcaccggg tggagaatgt gcattgacta      1800
```

```
tcggaagctg aatgatgcca ctcggaagga ccattatcca cttcctttca tggaccaaat    1860
gcttgaaaga cttgtagggt aatcctatta ttgttttctc gatgagtact ctggctataa    1920
ttagattgtt gttgatccta aagatcaaga gaagactgct ttcacctacc cttttggtgt    1980
attcgcatat cggcacatgc cttttggtct gtgcaatgcc ccagctacat ttcagaggtg    2040
tattatggca attttttctg atatggtgga aaaatgcatc gaagttttca tggatgattt    2100
ctctattttt gggccatcct ttaaggggtg cctattaaat cttgaaagag tattacagag    2160
atgtgaagag tccaatctag ttctcaattg ggagaaattc catttcatgg ttcaagaagg    2220
aatagtgctg gggcataaaa tttcagtaag gggaatagag gtggacaagg caaagattga    2280
tgtaattgag aaacttcctc ctccaatgaa tgccaaagaa gtgagaagtt tcttatgaca    2340
tgcaggattc tacagatgat tcataaaaga tttctcaaaa gtcgcccagc cacttagcaa    2400
tctgttgaat aaagatgttg cttttgtgtt caatcaagag tgcatggaag catttaatga    2460
tctgaaaacc agattagtgt ctgctccagt aagtatagca ccagattggg gacaagaatt    2520
tgagttgatg tgtgatgcaa gtgactatgt cgtaggtgta gtgcttcgac aacggaaggg    2580 aaaactttt catgctatat actacgccaa caaggttcta aatgatgcac aggtgaacta    2640
tgctaccata gaaaagaaa tgctggcaat tgtctatgca cttgaaaagt ttagatctta    2700
tttggtaggt tcaagagtta tcatctacat cgatcacgca gctattaaat atttgctcaa    2760
caaggctgat tccaaaccta gattgataag atggatcttg ttgttgcaag aatttgattt    2820
ggtgattcgg gataaaaagg gatcggaaaa tgttgtagct gaccatttgt ctagattggt    2880
gaatgaggaa gtcacattga agaagcaga agtgagagat gaattccctg atgaatcatt    2940
attcttagtg agtgagagac cttggttttgc cgatatggcc aacttcaaag ctacaagaat    3000
catcccaaag gacttaactt ggtagcagag gaagaaattc ctacatgatg ctcgattcta    3060
tatctgggtt gatcctcatt tgttcaagat aggagctgac aatctcctat gaagatgtgt    3120
gacacaagaa gaggccaaga acatattatg aaattgccac aattctccat gtggcagcca    3180
ttatggtgga gataagacga tgaccaaggt tttgcaatct ggattctttt ggcccatgct    3240
tttcaaagat gctcatcagc atgtgcaaca ctgtgatcaa tgtaagagga tgagggtat    3300 atcaagaaga aatgaaatgc ctctacagaa tattatggag gttgaggtat tcaattgcta    3360
ggggattgat tttgtaggtc ccttcccttc gtcttttggc aatgaatata tactagtggc    3420
gattgactat gtctctaaat tggttgaagc agtggctacc ccgcataatg atgctaagac    3480
tgtggtaaag tttctaaaga aaaacatttt ctcaagattt ggggtgccta gaattctgat    3540
taacgatgga ggcacacact tctgcaataa tcatctatag aaggtgttga agcaatataa    3600
tgtgacacaa agtagcatca ccttatcacc cccagaccaa tgggcaagca gaagtatcaa    3660
acagggaatt gaaaaagatt ttggagaaga ctatagcttc tactagaaaa gactagtcta    3720
tcaaattaga tgatgcttta tgggcataca gaacaacatt caagactccg ataggattat    3780
ctccatttca gatggtgtac ggcaaggctt gtcacttacc agtggagatg gaatataaag    3840
catactaggc cttgaagttt ttgaactttg atgaagccgc atccagagaa caaaggaggc    3900
tgcaactttt ggagttggga gatatgagat taactactta tgaatcttca aggctataca    3960
aagaaagggt caaaaagtat catgacaaga agctgctcaa gaaggacttt cagccaggac    4020
gacaagagtt gcttttcaac tcaagactta aattgttccc tggaaagctt acatcgaaat    4080
ggtctggacc atttaccatc aagaaagtcc gcccatatag agcagtggag ctttgtgatc    4140
```

```
ctcaatctaa agatcctgac aggacatggg tagtgaacgg acaaaggttg aatcaatatc    4200
atggttcatg caatcctacc cctcaagggt attggataga agactccaag aggattgggc    4260
tagagctgct aaagaaggcc ttggggttct catgaacccc agggtaaatt tctgagccca    4320
tggaccaagg ttgggtcctc tcttctttgt aaatattaga ataggttttt ccttcttctc    4380
aggctaagca ccaatatgct tctgtttttc agtcctttga ataaggctaa gcgcagctgc    4440
tgcactaagc ccttgttgtg tgtcaaggag gttgagctaa gcgtgcccta ctgcgctaag    4500
ctcaactatc tcactatttt tgtgttttta tggtcaggct aagcgcgccc tatgtgctaa    4560
gcctaagggt cattctggtg agcgtgagct aagcgcgcca tgctgcacta agcttagacc    4620 ctttttttgtt ttgaaaattt tagacttagg ctaagcccaa catgctacgc taagcctatc    4680
tacagaaaaa tattttgtgt ctttaggcta agctcgagtc tactgcgctt agctcatgag    4740 taatattta taaggcgcgc taagcccagc ctgctgcgct aagtgcccag ttcagttttc    4800
agctttaatt ttttgttttt gatagaaata atcttattta accttgtggt ttgattttat    4860
tctttcagat agcatcaaag aagagaaagg cacctgccac accttcccag gtctgatatg    4920
gccgatcgag gttcacttct cttgtggcct aggaaaggta cactgatatt gtggtaccca    4980
ggaagatact ccctgagtgg aatgtggtaa tctaccacac tgagtttgat gagtttaagg    5040
aagaactaga gagaagaaaa tgggatgagg aattgaccag ttttgatgaa ggcaacattg    5100
atgttgccat tctgaaagag ttttatgata acctctatga ttccgacgat aaatcaccta    5160
agcaggtgag ggtgagaggc catttggtga agtttgatgc agacactctg aacactttct    5220
tgaagacccc tgtgataatt gagagggggg aaaagctgcc tgcctactct agatttgcac    5280
tcttgagtcc tgatcctcaa gagttggctg ctaagctctg catcccaggg agggaatttg    5340
agcttaatgt tgacgacttg ccactaaaga tcctcaggaa gaaaatgacc acactcgctc    5400
agactaggag tgttctttct tactccaact tggtccctac ctcccacact tctcacatca    5460
cactggatcg ggccaagttg atttatggca ttatcatgaa gatggacatg aatttgggct    5520
acctcatctc ccaccagatt tctatcattg cccagcatga ctcctctagg cttggattta    5580
caaccttaat catagctttg tgtaaagcta aaggagtcac attagattcc aaatctttgg    5640
agagtcttag ccctgccatt aacatggcat atataaagaa gaactgttgg aatctagatg    5700
atccaacagt gacattcaga gagccaagga aggccagggg taaaagaatc gaggctcccc    5760
ctacttcagc agcaccaggt gcttctgctc cttcttcatc ttctttacca gatccttcag    5820
caccatccac ttcgactcca catcttccat ggttactagc ttcagctccc actcccttac    5880
cagcttcaat tcagctcctt ctacaggacc ctcctcattc acctctaaga cattatttgc    5940
tatgctgcaa agcctgcaca aaggccagat catcatcata cagaggttgt agagctctgg    6000
ccagaaacca accatgagta tagaggagtt ccttgcacaa gtggcttgcc caggagtcga    6060
gccttctcct tctggagggg gtgaggcctt tgcagcccaa gagccttgcc agcagagaag    6120
cctgtgccag aagcagagga tgagcttgtt cttcctgagc catttgttta tgagattgat    6180
ccagtcgctc aggaggaagc agcagctcag gagcttcctg cacctatttc tgaggatacc    6240
ctgccatctg caccagcatt ggagtaagag cagcctagtt cacaggatcc accagctgct    6300
ccaatgctgg atctgaacga gcatgcagaa gatcagcagt aggatgatca tgagttttaa    6360
attctacata gttttttaaaa ttttgcaaat tatgaatagt ttcttttatc aattatttag    6420
ttcatgtcaa ttatttgttt atgctttatt agtctttaaa tttagtctt ttaaattttt    6480 gttgtttgag tgttgatagc ttgtacaaaa gcatgtttga acagtgaact tattgattat    6540
```

```
gatattcagt ggtgtgattt cttatgaatg aagtgtttgt gaatgacttg aatgagaaaa    6600
tgtatgaatt gagtggactg gaatgattag atgtttgttt tgatcaagct tgtagtcatt    6660
agaagaaaaa gaacatgtga ttagaagtat gactgaaaat gttagtcagt ttgtcaaatt    6720
gattgtgaag gaatgcattg accgtatccc agtgagagtg tgatccttaa attttgagag    6780
aaatgacttt aatttagcac taattttgc acgaatcttt gaagtatgga ttgaatgcat    6840
gaattgagga taatgaaggc catgttttga ttgtgatagc tatttagcca aaaagctgac    6900
cttgtgcttg aatgatttat cccttgcacc cagtttgagc tgaatgaatt attgattgat    6960
tgaaccttga gcctatatag tgttttctcc tgcttccttg tcttaggtta taggagagca    7020
taatccacag aaaagcttgg ttcaaggcaa atttgttcca aatttggggg agacactggg    7080
taaagaaata aaatggtcaa acagagcaa catatacaca ttgttttctg tatgtaaaaa    7140
aaactgtaag tataaataaa aatgtataaa agtgtgtgtg ctgcaaatca aatcaatgaa    7200
agctaagtgc ttaataaaag gcaagtatgg ggtaggaatg aataaaaaaa aaagtaaagg    7260
tttatctatg gatgaatgct ctcgtagaat ctaagctttt gaatcctaga aaaccatga    7320 tttgttggca gcctaacctc attacaagcc tagaaagtcc tttggattca ttttgtgtgt    7380
ttatttctgt atggtatgag atgaaatgca aagttagga cttgtgttag ttgttcatga    7440
tggaatgagc ctaaacactt aagcttgagt gaaacaatga ctgtgaggct ttggttgatg    7500
atttttccct tgatatctgt cattctcact agcttatttt agttgtgact ctaatgcata    7560
tgttcctatc tttgaaaaac tgcatgtttg tgaaagaaa ttggttgaag cattccatga    7620
tattcatttc atatgattga atttctctgt gaggagaaca ccatttggat tgaccactgt    7680
attttgtcac ttgaggacaa gtgaactgtt ctttctttgc ttgaggacaa gcaaaacttt    7740
aaatttgggg gagtatgtta gtcatcttat acgactaact tttgtataga aaaattttc    7800 caaaacttgt atagtttctc caatttatag ttattttgta gggatttgta aataaatctt    7860
gttttattgt tatagttgtc tctagaatat tttccatttg atttaatgat gaaatctgtt    7920
caatttcagg ttaaaagagg ctaagtcttg aagtgctaaa agtgggattt acgctcagct    7980
caccatttgg cctcaacgcg catccaccgc taagcacagc ttcagcgcac ttagtgtgac    8040
agaagaatct ggcagagcat aaatatcaag gccgcttgct aagcaagatg gttgtcttta    8100
gccagactca gcgcatgact ggcgctaagc tcaaatccac taactcgcgc taagcacagg    8160
ggtggcacta agtgcaacgt cgcggattta aagcctattt aaagcctgtc ttgtgcagaa    8220
ttaggtaata tacacacata gaattttagc aagcaataca aaattccaaa gcaaggacac    8280
cacagtgcta atttcgatat agaagctctg gaggcagcaa gaggagaagc tttgcagaga    8340
agcctaggat tcttcaatta gagagagatt agtgagctgt agagtgattg tgaggtgttg    8400
agaagaggag gagggatccc ccttcttgtg taaggaacaa ttatttggta ctctcaaact    8460
catttgtgtt agggttttc tgtaatggct agctaaacac ccttgttggg gatttctaag    8520
gaacaactga tgtaattact ttaatatcta attaattatg ttttatgtgt tcaatgcttc    8580
tttcaatgct taattactgc atgctcttgg tctgatcacc catttgtgtg tattgttagg    8640 tgacttagc attgggaaat gtaccgttgc cttagaactt gatagaagca ggactaaata    8700
actacattac cagggatgga ttatgggtt ttggttttct aaatatgttg tgatgataat    8760
gctatttaag ttaagcctag tcatacaaga gggatctgcg gacgaagctt aggttaaatt    8820
agtataaact tacaagggat cgagatttag tactttaggc tacaacatag aacacaagaa    8880
```

| | |
|---|---:|
| catgattaat tagagaaata tcctcatatg catcaacttg tttgttagaa agacccaacg | 8940 |
| cttttttacct attgttgtca acttttactt acttgcattt tttttttacc atagaagtag | 9000 |
| tttatttctg ttttaaccat caattatcaa tgttgttcca acaatgcctt acttctgaat | 9060 |
| aaaactctgt ctaataagca agttccctaa attcgatact tggatcactc tgttttaatt | 9120 |
| ttaaatactt gacaactca | 9139 |

<210> SEQ ID NO 23
<211> LENGTH: 10482
<212> TYPE: DNA
<213> ORGANISM: Glycine max

<400> SEQUENCE: 23

| | |
|---|---:|
| tgttagtcgt cttatatgac taacttttgt atagaaaaac ctttttcaaa acatgtatag | 60 |
| tttccccaat ttataattct tttgtaggaa tttgtaaata aatcttgata tgttttgata | 120 |
| cctgccatta gagtatcttt agttggagtt aatgagaaaa tttgtacaat ttcaggtcaa | 180 |
| aagaggctaa atcttgaag tgctaaaagg agcagtcgtg ctaaatagag cctgtgggct | 240 |
| cagtgcacat ccaccgctaa gtgcagcttc agcatgctta gcgtgacaag gaacctgaa | 300 |
| agagcacaag aatcaaggtc gcgcgctaag cgagacgttt gtcttttgcc aggctcagcg | 360 |
| cacgactggc gccaagccca aatccactta ctcgcgctaa gcgcgatgtc gcgatttcag | 420 |
| agcctattta agcctgaatt gtcagaatta gggtatgatt ttaagagacc agagctgtat | 480 |
| attttttgcac aaacttcgag aatagtgctc tggaggcagc agagaggcag cagctaagca | 540 |
| gggaagctag ggttcatcac tttgagagat tagagagtgt tttagtgatt gtgaggtgcc | 600 |
| aagaagacga ggagggatcc cccttcctgt gtaagcaaca attgctctgt actttctgtc | 660 |
| tcatttgtat tagggttcct tgtatggctt ggtaaaaacc ctagttgggg atttctaatg | 720 |
| aacagttgat gtaattactt ttcatatcta attaattgtg ttttgtgtgt tcagtgcttc | 780 |
| tttcaatact taattactgc atgctcttgg cctgatcacc ctcttgtgtg tactattagg | 840 |
| tgactttagc attgggaaat gtagtgctgc catagaacat gatagaagca aggctaaata | 900 |
| actgcattac ctaggatgga ttgtgggtt ttagttttct tattatgctg tgatgataat | 960 |
| gttgtttaag ttaagcctag tccaacaaga gggatctgag gatgaagctt gggttaaatt | 1020 |
| agtctaaact tatgagggat cgaggtttag tactttaggc ttcagcatag aacacaagaa | 1080 |
| catgattaat tagagaaata tcttcatatg cattaactcg tttgttagaa agacccaaca | 1140 |
| ctttataccct attgctgtca acttttaat tacttgcatt tactgctttt taacatagca | 1200 |
| tctagtttac ttttgtttat attctcaatt atcaatgttt gttcacacaa tgccatattt | 1260 |
| ctaaataaaa ctttgtctaa taaacaagtt ccctgagttt gatactcgga ttattccgtt | 1320 |
| ttaattttaa atgcttgata acctggtgcg ttttccgata tttcatttcc cttgaatata | 1380 |
| ctgcttgtaa atttgataga aaggaactgt gttgaagggt aaacaaaaat ttgacacaaa | 1440 |
| gcatttatgg cgccgttgtc ggggaactgg attcattaga agagttcagt tcagttttaa | 1500 |
| ggcattgctt tattttgttt tctttaattc attgattctt tttgctaaca ttttagttac | 1560 |
| tgcacatttt attgttcttt ggaattggat aattttgtt ttgtttctt tgtatgcaaa | 1620 |
| ggagatctgt tgtaggtgat ttaattccca tagatttgga gattaatgct acttgcagga | 1680 |
| gacaaaatgc agagagaatt agaaattttt tgcaggactt agaagtagca gcaactctag | 1740 |
| gagagtgacc ctagaagatt actcaagtta aggccacagt ccaagcagct attagatgct | 1800 |
| tctgctgggg gaaaaataaa gttaaagacc cccgaagaag ccatggaact cattgaaaat | 1860 |

-continued

```
atgactgcaa gtgacattac tattttgaga gatagagccc acattccaac aaaaagaagc    1920
ctactagagc tttcatcaca agatgcattg ttggcacaaa acaagttgat gtccaagcaa    1980
ttggaagcat tgaccaaaac actaagtaag tttccagctc aattacattc tgcacaatct    2040
ttaccatcta ctattttgca ggtcacagtg tgtgccatct gtggtggagc tcacgattct    2100
ggttgttgta tccccaatga agaaccaaca actcatgaag tcaattacat gggtaaccaa    2160
cctagaaata attttaatgc aggtggattt cccgaattcc agcatggaca gtaatacaac    2220
caacaacagg gacaatggag gaccaccctg ggaattaatt caatagagac cagggtggac    2280
cgtccacaag gccgtaacaa caagggccta gtctctatga gcgtacaacg aagttggaag    2340
agactctagc tcaatttatg caggtttcta tgtctaacca aaagagcacg gagtttgcca    2400
taaagaattt ggaagtccaa gtgggacagc ttgcaaaaca gttggtggat aggccgtcaa    2460
agagctttag tgctaacact gagaaaaatt cgaaggggga atgtaaagct gtcatgacaa    2520
gaagcagaat ggcaacccat gttgatgaag gaaaagctta agaaggtg gaggagcata     2580 aacaacagtt ggcagctgag ccggcacttg aacccatttc tgattttgtt gaacttgagg    2640
aagttatgga agatgaagat gaccaaaagg aaaagagaaa gaagaagtag aaaaagaaaa    2700
atattagaaa atgaaaaag aaaatgagaa ggttgaggaa agaaagagga gcaagagtga    2760
ggtttcaaga gagaaaaaga gagagattac ttcagctgaa ggcaaggatg taccatatcc    2820
attggtacct tccaagaagg ataaagagcg acacttagcc agatttcttg acatcttcaa    2880
gaagtcggag atcacattgc cttttggaga aactctccaa cagatgccac tctatgccaa    2940 attttttaaaa gacatgctga caaagaaaaa ctggtatatc cacagtgaca cgatagctgt    3000
ggaaggaaat tgtagtgctg tcactcaacg catccttcca ccaaagcata aggatccagg    3060
aagtgtcaca ataccatgtt ctattggtga agttgcagta ggcaaggctc tcattgactt    3120
gggagccagt atcaatttaa tgactctctc catgtgccag caacttggag agttagagat    3180
aatgcccact cgcatgaccc tacagttggc agatcgctcc attgctagac catatggagt    3240
gatcgaggat gtgttgattc aggtcaagca gcttgtattc cctgcaattt gtggttatg    3300 gatatagagg aggatcctaa cattcccata atcttgggac gtcctttcat gtccacgacc    3360
agctgtgtag tagatatggg gaaggcaaa ttagaactgg ttgtggagga tcagaaagtc     3420
tcattcgact tattgaagc aatgaagcat ccaaatgatc aaaaagcttg ctttgatctg     3480
gataaggtag aataggagat agaattagct gctatagcca tggtactgca ctctcatttg    3540
gaaaaagcac gattaatcat gtagaatgtt tgaccaagga ggaggaacat gaagtgtaga    3600
cttgtattaa agagttggat ggtgcaggag aaaattccga gggacatact gcatttgaag    3660
aattgaagaa cagtgggaaa atagaaaaac caaaagtaga attgaagact tgcctgcac    3720 attcgaagta tgtatcttgg aagacaatga ctccaaacca gtgattatta gcagctcttt    3780
gaagaaaaca gaagaagatc agttggtgca gattttgaag aaacataaag ctacaattgg    3840
atggcacata tctgacttga aaggaattag tccatcttat tgcatgcaca aaattattat    3900
ggaagctgat tacaaaccaa tgagacagcc tcaaagaaga ctgaacccaa tcatgaaaga    3960
ggaggtgcgc aaggaggtgc ttaagttgct agaagcaggc ctcacccat ctcagatagt     4020 gcgtgggtta gcccggtgca ggttgttctc aagaagggag gtatgacagt cattaaaaat    4080
gataaagatg aattaatatc cacaaggact gtcaccgggt ggagaatgtg cattgattat    4140
cggaagttga ataatgccac ttggaaagac cattatccac tcccttcat ggaccatatg      4200
```

-continued

```
cttgagagac tcgcaaggca atcatattat tgttttctgg atggatattc tagttacaat    4260
tagattgcta tagatatcaa agatcaagat gtcgcaacct acccttcagt gggagggcga    4320
cgcgtgactt gcgcgtgcat gttccaagaa aggaatacgc gcggagtcgc caccaacgtt    4380
tatttgagga aaacgtcgga aaaccggaa aagacgtgat ctacgaactt taagtgaaag     4440
gttcgggagt tgtatttacg cacggggaag gtattagcac cccacacgtc cgtcacaaga    4500
gatgacaacc tctaatcaaa tgtgcaaata tgacttcaat ttatgttatc ttcccccttt    4560
tttcacgttc ttatgttttt tttatgcctt tttatgtttt tatcttttg tggttgacaa     4620
gggcgtttcc ctttgctcct acgtattcct caattgtgat gagaaaatca aacctacgta    4680
gttcttttgt gaacaaagcg ttttggttaa gttatttttt atccttttt gcaagatatg     4740
ttttattgaa tgaaaggtca tttaaggtgt tggaccatta gacaatcttt cgattctttt    4800
gaaaagtgag aaaacattaa ggcattggac cattaatgat ttctttattt ttgaaagagt    4860
taacaaagtt acatattgat tttaggcttt ttagaaatct acacttaacc aataaaagcg    4920
gaaaagacca tttcaaggcg ttggaccttt gaaaatggc gttttaggc gatgacaaaa       4980
gtttggttta tgaattgatt ttagccttag tttcactttg gttattagtc gattcgattt    5040
aagaaagaga atcccaaag aaaaacgtcc gattgatttt ttgatttatt ttactaaaag     5100
atattttga ttattatatt attatttac ctattttgg ttttcaacgg gttacggcat       5160
gaccgaacag tcggatttca ttttaacaga aattaacgga tgttacaatt taaatgatcg    5220
gtggaaattt attttatttt ttgattaggc gagaaaatga cttaagtaaa tgactaaagc    5280
acgtcaaaag ggggtacgga aagtaaatga aatgaaaata aaagcatgtg aaacaaatga    5340
ggaccactaa gggtacatag aatgaattgt ttgatttcgg gaacttaccg gttgaagatc    5400
gaagaacgac gaagaacgaa cgaagaacgt cgatgaacgg ttgaaaatct cgcaaaatc     5460
acccacggaa acgttacgga agcacctcgg cttggatttt cttcacgaa acaattttc      5520
tcactaattt taagtgaatc tcagatacca ggagggtcga acattttgt tcttccctcc     5580
ttcccttatt tataggaaaa ggaaggagat gcttgccacc cagctcgccc aggcgagcta    5640
ggttgcttcc tccagaagca atcctggaa ggcccaagtg ggcctggttg ctatttgaac     5700
ccccaatttt actaaatata ccccctgcct ttttttggtg attcttttc cgtaaagtta     5760
tggaaactta cgaatttcgt aacgatactt gttttctttc cgtaatgttg tggaaccta    5820
cggattacgt aatcatccct ttttgcctt ccggaacgtt acagaacttt acggattgca    5880
cactaacact tcctttaat tttcggcatg tcacgaacct cacggattgt gctaccacgc     5940
ttttcttttg gcttccgaca tgtctcggaa cttcacaaat tgcctaacca tgggtgccaa    6000
atacctcgaa gtggtcaaac gacggtcgca tcccaacaac ggatggttct cggacgaaat    6060
tagggtatga cacaagagaa gacaactttc actttcccttt tcggtgtatt tgcatatcga    6120
tgcatgcctt tcggtctatg caatgcccta gctacatttc agaggtgtat gatggcaatt    6180
ttttctgata tggtggaaaa atgcattgaa gttttcatgg acgatttctc tgttttgga     6240
ccatctttga tggttgctta tcaaatctgg aaagagtatt ttagagatgt gaagagtcca    6300
acctggtact taattgggaa aatgtcattt catggttcaa gaaggaatag tgctggggca    6360
taaaatatca gtaaggggaa ttgaggtgga taagtgaag attgatgtca ttgagaaact    6420
tcctcctcca atgaatgtca aacgaatgag aagtttctta ggacatgatg gattctatag    6480
gtgacttata aaagattttt caaaagtcgc caaaccactt agcaatttgt tgaacaaaga    6540
tgttgctttt gtgttcaatg gaaagtgtat tgaagcattt aatgatttga aaaccagact    6600
```

```
agtgtctgct ccagtaatta ctacaccaga ttgggggtaa gaatttgagt tgatgtgtga    6660
cgcgagcgat tatgctatag gtgcagtgct tggacaaagg aagggcaaaa tttttcatgc    6720
tatctactac gccagcaaag ttttaaatga tgcacaggtt aactatgcta ccacagaaaa    6780
agaaatgttg gcaattgttt atgcacttga aaagttcaaa tcttatttgg taggctcaaa    6840
agtcatcatc tacattgatc atgcaactat taaatatttt ctcaacaagg ccaattccaa    6900
aaccctgctt aataagatgg attttgctgc tgcaagaatt tgatttggta attcgggata    6960
aaaagggatc ggaaaatgtt gtagctaacc aatttgtcta gattgggaa taagaagtc     7020 atgtcgaaag aagctgaaat tagagatgaa ttccctaatg agtcattatt cttggtgaat    7080
gagagacctt gatttgctga tatggccaac ttcaaagccg caggaatcat tccaaaagac    7140
ctaacttggc agtagaggaa gcaattcctg catgatgctc gatttatat ctgggatgac     7200 ccgcacttgt tcaagattgg agttgacaat cttctccgaa gatgtgtgac acaagaagaa    7260
gccaagaaca tattatggca ctgtcacaat tctccatgtg gcggccatta tggtggagat    7320
aagacgacga ccaaggtttt gcaatctgga ttcttttggc ccacacttttt caaggatgct    7380 catcagaata tgctgcattg tgatcaatgt caaaggatgg ggggcatatc aaaaagaaat    7440
gaaatgcctt tacagaatat tatggaggtt gaggtatttg actgttgggg gattgatttt    7500
gtaggtccct tcccttttgtc ttttggcaat gaatacatac tagtggttgt tgactatgtc    7560
tctaaatggg ttgaagcagt ggctaccctg cataatgatg ctaagattgt ggtaaagttt    7620
ctaaagacga acattttctc cagatttggg gtgcccagag ttttgattag tgatggaagc    7680
acacatttct gcaataataa gatacagaag gtgttgaagc aatataatgt aacacacaag    7740
gtagcatcag cttatcaccc ccaaaccaat gggcaagcag aagtgtcgaa caaggaattg    7800
aaaaagattt tagagaagac tatggcttct actagaaagg actggtccat taaactagat    7860
gatgctttat gggcgtatag gactgcattc aagactccga taggtttatc tccattcag    7920 atggtgtatg gcaagtcttg tcacttacca gtggagatga aatataaaac atattgggcc    7980
ttgaagttgt tgaactttga tgaagccgaa tccagagaac aaaggaggct acaactttgt     8040
gagttggaag agataaaatt aactgcttat gaatcttcac agttgtacaa agaaaaaatt    8100
aaaaagtatc atgataaaaa actgctcaag agggatttt caacaaggaca acaagtgttg     8160 cttttcacct caagacttaa attgtttcct gggaagctta atcgaaatg gtctagacca     8220 tttaccatca agaaagtccg aacatatgga gcagtggagc tttgtgatcc tcatatgggt    8280
ggtgaacgga caaaggctaa agcaatatca tggtggagct attgagagat tgaacactat    8340
tctacacttc aatccaggat aacaggacga tgcgtcaagc taatgacgtt aaccgagcgc     8400
ttacggggag gcaacccagg tctctttta tttctatttt tcttgcattt aatttagtta    8460
gtttaattgc ttgtgattgt aaatgatttc taagcttggt tagtattgag aaaagggttt    8520 caaagttta gtaaagagat ggatagaaaa gacttagaga aaaaattttc agttgtccat     8580
ccgctaagcg cagcccttgt gctaagtgcc atgtcttaat gcactaagca tgtgcttgct    8640
tgcgctaagc actttgacct ttcaccagtt ggctagatgg ttcagctaag cgcacatcac    8700
tgcgctaaac ctaagttctt ctctggattt gaacttcatg acttgggctt agaggagttg    8760
atgcgctaag cgcaactcct tctctgttga aaaattattg taatagcatt aagcttaatt    8820
tcctctctgg aattgaactt tcaggaattg ggcttagcag caggatacgc taagcgccaa    8880
tccttcacta ttttgaaata cttggaattg cgctaagcct ggaaccatca ctgtaagtag    8940
```

-continued

```
agcttgtttt agtgctaagc ctaacatctt aggctaagtg aaaattgcag gaccaatcag      9000
agttgcagac agtgctaagc gcgtgtcctc gcactaagct tgaatacctc tctggaattt      9060
gaaattattg aattaggctt aacgcgagag gtggcgctaa gcgcatgggc cttaaactca      9120
aatgtcatgt tggcatgcta agcgcaacta tgcgctaagt gcgccaaaca aaaatgctaa      9180
ataaaaatag aactaccaat ggcagttacc atttacactt caaagctttt actcccttat      9240
gcttgtgccc acattcgtgc ttttgtgcat tttgctgcct ttgcttcaag ttattcctgc      9300
tttcttgctc tcatcttgca tttccatcac aatccaagta agttttcatg tttattttca      9360
ttttctttta taagcttaaa ccttagggta gatgatttag tgcttttag tttgcaattt        9420 tttttaggtt tagtgttttt aggttagttg ttagttaagg taggtttagg gtttacaatg      9480
taggttttag gttaggtttt tgagccccct aggggcaatg cctgaaaaag gggtgaaaac      9540
ccgtgagtaa tttctagaaa tagcgatgaa cgtgctaagc gcacctgctg tgcttagcca      9600
gttcatcgca acttccttct aatgagtttt aatgatgagc tcgataagcg cgtttgtgcg      9660
ctaagtgaga caagtgtttt agacacttag tatttttttc aattttgtt cagcactaaa       9720 gcctggcttc tcaggctaaa gcacaattct gtctttattt ttcaattgtt ggaataaggc      9780
taagtgcagc ttgttgtgct aagcccatgt tatgtcttag tgaggttgag ctaagcgtgc      9840
cctactgcgc taagctcaat tcctccactg ttttcaaaag tgtggattta ggataagccc      9900
agcttgttgc gctaagccta gtctatggaa aaacattttc tgagtactca cgctaagcgt      9960
gtggctatcg ggcttagccc atgagtaaat tttcataaag cgcgctaagc ccagccttct      0020
gtgctaagca cccagtccta ctttcagttt tatttttttg tttttgttga ataatcctgt     10080
tttaactctg ttgtttgatc taattctttt cagatggcat ctaggaagag aaaggcccat     10140
gcctcaacat cccaggcccg ctatgataga tccagattca catctcagga ggcctgggat     10200
cgttattcta gtgttgtcat tggcaggaaa atattacctg aaagaaatgt catgctctat     10260
tacacagagt ttgatgaatt cactgaagag ttagagagaa gaaacaggca aaggagtta     10320 acaaatttta tggatggcaa cattgatgtt gccattatga aggagttcta tgctaacctc     10380
tatgacccag aggataaatc acctaagcag gtgaggttca gaggtcattt agtgaaattt     10440
gatgcagatg ctctgaacac ttttttttatg accctgtga tc                         10482
```

<210> SEQ ID NO 24
<211> LENGTH: 1857
<212> TYPE: DNA
<213> ORGANISM: Arabidopsis thaliana

<400> SEQUENCE: 24

```
atgagcaatt acagtggcag ttcttctgtt gatcctgact acaacatgga tgagacagaa        60
tcgtcatctt caaggccaga gagagaacag agagaatacg aaagtttcag aaggaaagct       120
gagatagccc gaggaaagag agcgatgaga gagaggtatg agcttataga cgaagatctg       180
gaggacgagt acatgcctga acagactcgc agagctacca aacttctgca caagcccgac       240
atattgcctg ctgaggaata tgttaggctt ttcaagctga atgagttctg tagcacgagg       300
tatccttgct cgacctcact tgcacaactc ggattgttgg aagatgttca gcacctgtac       360
caaagttgtc atctggacac tttgatggct tatccgtatg tagcatatga agatgagaca       420
atacaattcc tctccacact acaagtagag ctctaccaag gtatgacctc tgatgagttg       480
gattgtgaag gattgggatt cttgcgattt tctgtgtatg gtcatgagta caggttatca       540
atcaagcgat tggaaggatt gtttgatttt cccagtggaa cgggatctaa gccaaagtat       600
```

-continued

```
gaaagagaag agttgaaaga cttgtggatc accatcggca gctctgtacc gttgaatgct      660
tccaggtcaa agagcaatca gatacgcagc cctgtcatca ggtacttcca gcgttctgta      720
gccaacgtac tctactcccg agagattaca gggactgtca ctaactctga tatggagatg      780
atcgcaatgg ccctcaaagg aactctccgc caaactaaaa atggcatgtc cctccagggt      840
gaagtcaatg acacacctct ctctatactt cttctgatcc atctgtgtgg atacaaaaac      900
tgggcggtca gcaataaccg caagagagca cgaggcgctc tgtgcatagg tggcgtggtg      960
acacctattc tgatagcttg tggagtccca ctcatttctg ctggactcga gccacgagca     1020
atggatatcg agcacctacg tcactgccaa ttcctggagt ttgcaatggt tgacgatttc     1080
cacaggttca ggtttgagca ctctacagac aggagagcta acatccttct ccctagccct     1140
gaggtcacac ggataatcga gggagataac attgatttta ggcctgagat tggacgcctc     1200
tactatgaga cgctccacc attagatgag acgatcttc ttgaagaagc tgcttcggat     1260
gggatggatg aagatggagc agtaaagttc gacactagca tgtatcactt tgctgaacat     1320
gtacctccag cgaggcagag caagagcttg actgaagctc ataagaatta cagtaaattg     1380
cagaagtggt gcaagaagca ggacaggctg atcgccaagt gtttcaagct tctgacagac     1440
aagctgagtt gctcttcctc caccactgct attccacagg tacaacctcc tatgaaaatg     1500
ccatcgagga gaattaatgc acctgcgcac aggcctgagc ttagcgagca gagagtccca     1560
catgtccagg ctaggcattc gtcattcgaa tcccgggaac acaagagaag aaggaaggct     1620
acactcactc gatctagcag cagatcacgc ctcattcact cgaggagatc actcgaccgt     1680
ggtgctggcc gcagcagaag gagagatgtc gagtttcctc agagcggtgc tggccgccac     1740
agagctgatg aggtcgagta cccatctgct ggagctgata cagaacaagg aggttcgtct     1800
atggcctggg agcaatcgca ggcagccatt gacgagcaac tacgttcatt cttcgac           1857
```

<210> SEQ ID NO 25
<211> LENGTH: 1254
<212> TYPE: DNA
<213> ORGANISM: Pisum sativum

<400> SEQUENCE: 25

```
atggaatcca ggtccggagc ttcgaaaaag agaaagggcg ggaatagttc ccgtcccgtg       60
cccatacaat tcgacaccga caaatttgtc gggccaaagc aagcagtaag atatgttgct      120
ttggaaaagc gaaagatttt gccggaaaag agatttataa tcaaccctga aggcacgaac      180
cgtacattcg ccgggctgat aacagcaaa aagtgggacc ggttaatatc ccccttgaag      240
cattacgaca tcgcaacagt gcgtgagttc tacgcgaacg cactgccgaa cgacgacgag      300
ccattcacat ggacgtctag agtgtccggc cgtcctgttg cgttcgatcg ggatgcaatt      360
aaccgtgtcc tgggtgaacc gctccatctg ggagccaatg agagagacac ttaccaccaa      420
gatttaaggc ttcaccggga taccgattcg atttctactg ccctgctttt ggaagggaaa      480
tcagttgagc tgaacccatc tggggttccg atgagatacc ataggaggga catgattccc      540
ttggctcaac tgatcctttt gttggttctt acaaacatca aacccaagtc tcacacttct      600
accgtgccga tcccagtggc acacttggta cacatcatcc tcacgaatat ccagattgat      660
gtggcaagga ttattgcttt ggagttgaag tccgtgattg aaagcgggct aaagtcgggg      720
gaacgagtga attgtcccct tgctttccct tgtctaatca tggctttgtg ccaacaagcg      780
agggtgaggc taccctccaa gggtcaagta aggatcccgc cggccattga tgaccgatac      840
```

-continued

```
gtggccaagt actgcaaacc gaagaatgta agaagtagtt cagctgctga ggttaccggg      900
gcttctgatg gtcctggtac ttttactcta ggatccgatc ctttccagca ggctgtctgc      960
aactacaact gggattggat ggcggcaact cagcgcgtca tgctcgatat gcacgattct     1020
atgcagctgt tacagttgca gatgcgcgac ccctccggtg agcattctat gatgtcacgt     1080
gagcagtttc tgcagcacgc tagctggcct gtggacaggc tgtgtttgg agagggggcg     1140 ggtgctggtg caactggtgc tggtgctttt tctggtgctg ctgatgatga tgatgatgat     1200
gaggctaccg gttctgaagc cggtagtgat gagggttatg agtccttgga gggc           1254
```

<210> SEQ ID NO 26
<211> LENGTH: 564
<212> TYPE: DNA
<213> ORGANISM: Arabidopsis thaliana

<400> SEQUENCE: 26

```
tgtgattcat gccagagaaa aggcaacatc aatagaagaa atgagatgcc tcagaatcca       60
atcttggaag ttgagatctt tgatgtatgg gggattgatt ttatgggtcc attcccatct      120
tcatacggta ataaatatat actggtcgcc gtagactacg tatcaaagtg ggtcgaagct      180
attgctagtc ctaccaacga tgcaaaagtt gtgctgaagt tgttcaaaac cataatcttc      240
ccaagatttg gagttcccag ggtagtaatc agtgatggcg gaaagcattt catcaacaag      300 gttttttgaga acctcttgaa gaagcatggg gtaaagcagg ttgagatctc caatagggag      360
ataaaaacaa ttctggaaaa gactgttggg attacaagga aagactggtc tgcaaagcta      420
gatgatgcat tatgggctta caggacagct ttcaagaccc ccataggtac aactccttc       480 aatcttctct atggaaaatt atgtcatcta cccgttgagc tcgagtacaa agcaatgtgg      540
gcggtaaaac ttctgaactt tgac                                             564
```

<210> SEQ ID NO 27
<211> LENGTH: 180
<212> TYPE: DNA
<213> ORGANISM: Arabidopsis thaliana

<400> SEQUENCE: 27

```
atcgaggaga tggtggaggt tttcatggac gattttcgg tctatggccc ctcttctcc         60 tcatgtttgt tgaatcttgg cagggtattg actaggtgcg aagagacgaa tcttgttctc      120
aattgggaaa agtgtcattt catggtgaag gaaggcatag tattggacca caagatatca      180
```

<210> SEQ ID NO 28
<211> LENGTH: 192
<212> TYPE: DNA
<213> ORGANISM: Arabidopsis thaliana

<400> SEQUENCE: 28

```
tttgaaatca tgtgtgatgc atcagattac gcagtaggag ctgttctagg ccagaaaata       60
gacaagaagc ttcatgtcat atattacgcc agccgaacgt tggatgacgc tcagggaaga      120
tatgcaacaa ctgagaagga gcttctagct gttgtattcg catttgagaa gttcagaagc      180
tatttggttg ga                                                          192
```

<210> SEQ ID NO 29
<211> LENGTH: 597
<212> TYPE: DNA
<213> ORGANISM: Pisum sativum

<400> SEQUENCE: 29

```
ttggatgcga gaatgattta cccgatctcg gatagtccat gggtcagtcc cgtgcatgtg    60
gttccgaaga aggtggaaaa taccgtcatc cggaatgaca aggatgaatt gatccctacc   120
aaagttgcaa cggggtggag aatgtgtatt gaatataggc ggttgaatac cgcaactcga   180
aaggaccatt ttccactccc gttcatggat caaatgctgg aaagactctc cgggcaacaa   240
tactattgtt tcttggatgg ctattccggg tataaccaaa ttgccgttga cccggccgat   300
cattaaaaga cggctttcac atgtccgttt ggagtgttcg cataccgaaa aatgtccttt   360
gggttgtgca atgcaccgac gacttccaa cgatgtgtgc aagccatttt tgccgacctt   420
aatgagaaaa caatggaagt cttcatggat gacttctcgg tatttggtgt atcctttagt   480
ttatgcttgg caaacttgaa aacggtgctt gaaagatgtg tgaagaccaa tcttgtgctt   540
aattggtaga agtgccactt catggtgacc gaggggatag tgcttggcca taaagtc     597

<210> SEQ ID NO 30
<211> LENGTH: 192
<212> TYPE: DNA
<213> ORGANISM: Pisum sativum

<400> SEQUENCE: 30
tttgagctaa tgtgtgatgc gagcaactat gcaatcggag cggtattagg ccaaagaaaa    60
gagaaaaaat ttcatgcgat acattacgca agtaaagttc ttaatgaggc tcaaattaac   120
tatgccacca ctgaaaaaga attacttgcg atagtgtatg cacttgaaaa gtttaggtct   180
tatcttatag gg                                                       192

<210> SEQ ID NO 31
<211> LENGTH: 581
<212> TYPE: DNA
<213> ORGANISM: Pisum sativum

<400> SEQUENCE: 31
tgtgatagtt gccagagaag cggtgggatt ggtaagagag acgagatgtc tctccaaaac    60
atccaagagg tcgaagtatt tgattgttgg ggcatcgatt ttgtaggacc attccccct   120 cttatggtaa cgagtatatg cttgtcgcag ttgaggcgat tgcctcacct cgggcggatg   180
cgaaaacggt aataattttt ttgaagaaaa acatatttc ccgtttcgga accccccgag   240
tgttgataag tgacggaggg tcacactttt gtaatgcacc gttggaaagc atttttaaaac   300 attacggtgt atcacacaga gtggcaactc cgtatcaccc acaggctaat ggacaagccg   360
aggtctctaa tcgtgagatt aagagaattc tcgaaaaaac tgtgtcaaat tcgaaaaaag   420
agtggtcaca aaaattggat gaagcgttat gggcataccg taccgccttt aaagctccaa   480
ttgggctcac tccttttcaa ttggtgtttg gtaaaacttg ccatttgccg gtcgaattgg   540
agcacaaagc cttgtgggct tgaaaaatta ataattttga a                       581

<210> SEQ ID NO 32
<211> LENGTH: 1362
<212> TYPE: DNA
<213> ORGANISM: Glycine max

<400> SEQUENCE: 32
atggcctcct gtaaacaccg agctgtgccc acacccgggg aagcgtccaa ctgggactct    60
tcacgtttca ctttcgagat tgcttggcac agataccagg atagcattca gctccggaac   120
atccttccag agaggaatgt agagcttgga ccagggatgt tgatgagtt cctgcaggaa   180
```

```
ctccagaggc tcagatggga ccaggttctg acccgacttc cagagaagtg gattgatgtt      240
gctctggtga aggagtttta ctccaaccta tatgatccag aggaccacag tccgaagttt      300
tggagtgttc gaggacaggt tgtgagattt gatgctgaga cgattaatga tttcctcgac      360
accccggtca tcttggcaga gggagaggat tatccagcct actctcagta cctcagcact      420
cctccagacc atgatgccat cctttccgct ctgtgtactc caggggacg atttgttctg       480 aatgttgata gtgcccccctg gaagctgctg cggaaggatc tgatgacgct cgcgcagaca     540
tggagtgtgc tctcttattt taaccttgca ctgacttttc acacttctga tattaatgtt     600
gacagggccc gactcaatta tggcttggtg atgaagatgg aacctggacgt gggcagcctc     660 atttctcttt agatcagtca gatcgcccag tccatcactt ccaggcttgg gttcccagcg      720
ttgatcacaa cactgtgtga gattcagggg ttgtctctg taccctgat ttttgagtca        780 ctcagtcctg tgatcaacct tgcctacatt aagaagaact gctggaaccc tgccgatcca     840
tctatcacat ttcaggggac ccgccgcacg cgcaccagag cttcggcgtc ggcatctgag     900
gctcctcttc catcccagca tccttctcag cctttttccc agtgaccacg gcctccactt     960
ctatccacct cagcacctcc atacatgcat ggacagatgc tcaggtcctt gtaccagggt    1020
cagcagatca tcattcagaa cctgtatcga ttgtccctac atttgcagat ggatctgcca    1080
ctcatgactc cggaggccta tcgtcagcag gtcgcctagc taggagacca gccctccact    1140
gacagggggg aagagccttc tggagccgct gctactgagg atcctgccgt tgatgaagac    1200
ctcatagctg acttggctgg cgctgattgg agcccatggg cagacttggg cagaggcagc    1260
tgatcttatg ctttaatgtt ttcttttata ttatgtttgt gttctctttt atgttttatg    1320
ttatgttttt atgtagtctg tttggtaatt aaaaagaggt ag                       1362

<210> SEQ ID NO 33
<211> LENGTH: 192
<212> TYPE: DNA
<213> ORGANISM: Glycine max

<400> SEQUENCE: 33
tttgagttga tgtgtgacgc gagcgattat gctataggtg cagtgcttgg acaaaggaag       60
ggcaaaattt ttcatgctat ctactacgcc agcaaagttt taaatgatgc acaggttaac      120
tatgctacca cagaaaaaga aatgttggca attgtttatg cacttgaaaa gttcaaatct      180
tatttggtag gc                                                          192

<210> SEQ ID NO 34
<211> LENGTH: 597
<212> TYPE: DNA
<213> ORGANISM: Glycine max

<400> SEQUENCE: 34
ttggaggttg ggctcatata ccccatctct gacaacgctt gggtaagccc agtacaggtg       60
gttcccaaga aggtggaat gacagtggta caaaatgaga ggaatgactt gataccaaca       120
cgaacagtca ctggctggcg aatgtgtatt gactatcaca agctgaatga agctacacgg     180
aaggaccatt tccccttacc tttcatggat cagatgctgg agagacttgc agggcaggca     240
tactactgtt tcttggatgg atactcggga tacaaccaga tcgcggtaga ccccatagat     300
caggagaaga cggtctttac atgcccctt ggcgtctttg cttacagaag gatgtcattc      360
gggttatgta atgtaccagc cacatttcag aggtgcatgc tgaccatttt ttcagacatg     420
gtggagaaaa gcatcgaggt atttatggac gacttctcgg ttttttggacc ctcatttgac    480
```

```
agctgtttga ggaacctaga aatggtactt cagaggtgcg tagagactaa cttggtactg      540
aattgggaaa agtgtcattt tatggttcga gagggcatag tcctaggcca caagatc         597
```

<210> SEQ ID NO 35
<211> LENGTH: 603
<212> TYPE: DNA
<213> ORGANISM: Glycine max

<400> SEQUENCE: 35

```
tgtgataaat gtcagagaac aaggggdata tctcgaagaa atgagatgcc tttgcagaat      60
atcatggagg tagagatctt tgatagttgg ggcatagact tcatgggcc  tcttccttca     120 tcatacagga atgtctacat cttggtagct gtggattacg tctccaaatg gtggaagcc      180 atagccacgc tgaaggacga tgccagggta gtgatcaaat ttctgaagaa gaacattttt     240
tcccatttcg gagtcccacg agccttgatt agtgatgggg gaacgcactt ctgcaacaat     300
cagttgaaga aagtcctgga gcactataat gtccgacaca aggtggccac accttatcac     360
actcagacga atggccaagc agaaatttct aacaggagc  tcaagcgaat cctggaaaag     420
acagttgcat catcaagaaa ggattgggcc ttgaagctcg atgatactct ctgggcctat     480
aggacagcgt tcaagactcc catcggctta tcaccatttc agctagtata tgggaaggca     540
tgtcatttac cagtagagct ggagcacaag gcatattggg ctctcaagtt gctcaacttt     600
gac                                                                   603
```

<210> SEQ ID NO 36
<211> LENGTH: 150
<212> TYPE: DNA
<213> ORGANISM: Glycine max

<400> SEQUENCE: 36

```
cctaaaatac tacaacgaca tgattggtgt tttaggataa ttgactgaaa aacctattat      60
caatttggcg ccgttgccaa ttgggtgttt gtttgttaca tttgagattt cagacttgct     120
tagatcaagt tctttttcaa ttttctttttt                                     150
```

<210> SEQ ID NO 37
<211> LENGTH: 11
<212> TYPE: DNA
<213> ORGANISM: Glycine max

<400> SEQUENCE: 37

```
tggcgccgtt g                                                           11
```

<210> SEQ ID NO 38
<211> LENGTH: 15
<212> TYPE: DNA
<213> ORGANISM: Glycine max

<400> SEQUENCE: 38

```
tggcgccgtt gccgg                                                       15
```

<210> SEQ ID NO 39
<211> LENGTH: 27
<212> TYPE: DNA
<213> ORGANISM: Glycine max

<400> SEQUENCE: 39

```
tttttggcgc cgttgtcggg gattttg                                          27
```

<210> SEQ ID NO 40
<211> LENGTH: 9
<212> TYPE: DNA
<213> ORGANISM: Glycine max

<400> SEQUENCE: 40 tttggggga                                                                                      9

<210> SEQ ID NO 41
<211> LENGTH: 16
<212> TYPE: DNA
<213> ORGANISM: Glycine max

<400> SEQUENCE: 41
tttaatttgg gggatt                                                                              16

<210> SEQ ID NO 42
<211> LENGTH: 775
<212> TYPE: DNA
<213> ORGANISM: Nicotiana tabacum

<400> SEQUENCE: 42
gtgcgtaaag aggttttta actggagatt atcaagtgat tggatgccgg ggttatctac          60
cccatttacg atagttcatg aacttctccg gtgcaatgtg tcccaaagaa ggtggcatga        120
cggtggtcac caatgagaag aatgagttga ttcctacaag aatggtgacc ggttggagag        180
tgtgcatgga ctatcgcaag ctcaacaaac tcacaaggaa ggatcatttc ccatttccat        240
tccttgacca aatgcttgat aggttggcat gtcgtgcttt ctattgcttt ctagatgtat        300
agtcgggcta tagccaaatc tttattgctc cgtaggatca cgagaaaata cctttacatg        360
tccctatggt acttttgcct acaagcggat gccatttggt ttgtgtaatg cactagcgaa        420
cttttatagg tgtatgatgg ctatcttcac ggacatggtg aaggactacc ttaaagtttt        480
catggatgac ttctcgatgg ttggggattc ctttgatgat tgcttggaaa atttggataa        540
agtattggca agatatgaag aaacgaattt ggtactaaat tggagaagt gtcatttcat        600 gatcgaggaa ggcattgttc ttggccacaa gatctcaaat aatggcattg aagtcgacaa        660
ggcaaagatt aaggtgattt ctaaacttac acctccaact ttggtgaaag gcgtgcggag        720
tttcttaggc cacgcggggt tttaccaatt cttcataaaa gatttcacaa aggtt            775

<210> SEQ ID NO 43
<211> LENGTH: 259
<212> TYPE: PRT
<213> ORGANISM: Nicotiana tabacum

<400> SEQUENCE: 43

Val Arg Lys Glu Val Phe Lys Leu Glu Ile Ile Lys Glx Leu Asp Ala
 1               5                  10                  15

Gly Val Ile Tyr Pro Ile Tyr Asp Ser Ser Glx Thr Ser Pro Val Gln
            20                  25                  30

Cys Val Pro Lys Lys Gly Gly Met Thr Val Val Thr Asn Glu Lys Asn
        35                  40                  45

Glu Leu Ile Pro Thr Arg Met Val Thr Gly Trp Arg Val Cys Met Asp
    50                  55                  60

Tyr Arg Lys Leu Asn Lys Leu Thr Arg Lys Asp His Phe Pro Phe Pro
65                  70                  75                  80

Phe Leu Asp Gln Met Leu Asp Arg Leu Ala Cys Arg Ala Phe Tyr Cys

```
                 85                  90                  95
Phe Leu Asp Val Glx Ser Gly Tyr Ser Gln Ile Phe Ile Ala Pro Glx
            100                 105                 110
Asp His Glu Lys Thr Thr Phe Thr Cys Pro Tyr Gly Thr Phe Ala Tyr
            115                 120                 125
Lys Arg Met Pro Phe Gly Leu Cys Asn Ala Leu Ala Asn Phe Tyr Arg
130                 135                 140
Cys Met Met Ala Ile Phe Thr Asp Met Val Lys Asp Tyr Leu Lys Val
145                 150                 155                 160
Phe Met Asp Asp Phe Ser Met Val Gly Asp Ser Phe Asp Cys Leu
            165                 170                 175
Glu Asn Leu Asp Lys Val Leu Ala Arg Tyr Glu Glu Thr Asn Leu Val
            180                 185                 190
Leu Asn Trp Glu Lys Cys His Phe Met Ile Glu Glu Gly Ile Val Leu
            195                 200                 205
Gly His Lys Ile Ser Asn Asn Gly Ile Glu Val Asp Lys Ala Lys Ile
            210                 215                 220
Lys Val Ile Ser Lys Leu Thr Pro Pro Thr Leu Val Lys Gly Val Arg
225                 230                 235                 240
Ser Phe Leu Gly His Ala Gly Phe Tyr Gln Phe Phe Ile Lys Asp Phe
            245                 250                 255
Thr Lys Val

<210> SEQ ID NO 44
<211> LENGTH: 761
<212> TYPE: DNA
<213> ORGANISM: Nicotiana tabacum

<400> SEQUENCE: 44
gtgcgtaaag aggtggtcaa gctgttggat gtcggggttg tgtacccat ctctgatagc      60 tcttggactt cgccggtgca atgtgtacca agaaggttg gcatgactgt ggtgaaaaat     120
tccaaaaatg agttgattcc gacaagaacc atcaccggtt ggagggtatg catggactac    180
cgcaagttga ataaagtgac ctgcaaggat cactttcctt gccatttct ggatcagatg     240 ctagatcgac ttgctgggcg tgccttctat tgcttcttgg atgaatattc tgggtataac    300
caaatcttga ttgctccgga agatccggaa aagaccacat tcacttgtcc gtatggcaca    360
tttgttttct ctaggatgcc ttttaggttg tgtaatgcac cagctacatt tcagcggtgt    420
atgatggcca ttttctccta tatggtgaaa gacatttttg aggtgttcat ggacgatttt    480
agtgttgtgg ggcactcatt tgatgaatgc ttgaagaatc ttgatagggt gttggcccat    540
tgtgaagaaa ccaatcttgt cctcaattgg gagaaatgcc actttatggt agaagaagga    600
atcaatctct ggcataaaat ttcaaaacat ggcattgagg tggataaaca aagatagatg    660
tgatttcaag gctccctccc cctacatccg tcaaggagt ccgatgtttt cttgggcatg     720
cggggttcta ttggagattc ataaagact tctccaaggt t                         761

<210> SEQ ID NO 45
<211> LENGTH: 254
<212> TYPE: PRT
<213> ORGANISM: Nicotiana tabacum

<400> SEQUENCE: 45

Val Arg Lys Glu Val Val Lys Leu Leu Asp Val Gly Val Val Tyr Pro
1               5                  10                  15
```

Ile Ser Asp Ser Ser Trp Thr Ser Pro Val Gln Cys Val Pro Lys Lys
            20                  25                  30

Val Gly Met Thr Val Val Lys Asn Ser Lys Asn Glu Leu Ile Pro Thr
        35                  40                  45

Arg Thr Ile Thr Gly Trp Arg Val Cys Met Asp Tyr Arg Lys Leu Asn
    50                  55                  60

Lys Val Thr Cys Lys Asp His Phe Pro Leu Pro Phe Leu Asp Gln Met
65                  70                  75                  80

Leu Asp Arg Leu Ala Gly Arg Ala Phe Tyr Cys Phe Leu Asp Glu Tyr
                85                  90                  95

Ser Gly Tyr Asn Gln Ile Leu Ile Ala Pro Glu Asp Pro Glu Lys Thr
            100                 105                 110

Thr Phe Thr Cys Pro Tyr Gly Thr Phe Val Phe Ser Arg Met Pro Phe
        115                 120                 125

Arg Leu Cys Asn Ala Pro Ala Thr Phe Gln Arg Cys Met Met Ala Ile
    130                 135                 140

Phe Ser Tyr Met Val Lys Asp Ile Phe Glu Val Phe Met Asp Asp Phe
145                 150                 155                 160

Ser Val Val Gly His Ser Phe Asp Glu Cys Leu Lys Asn Leu Asp Arg
                165                 170                 175

Val Leu Ala His Cys Glu Glu Thr Asn Leu Val Leu Asn Trp Glu Lys
            180                 185                 190

Cys His Phe Met Val Glu Glu Gly Ile Asn Leu Trp His Lys Ile Ser
        195                 200                 205

Lys His Gly Ile Glu Val Asp Lys Ala Lys Ile Asp Val Ile Ser Arg
    210                 215                 220

Leu Pro Pro Pro Thr Ser Val Lys Gly Val Arg Cys Phe Leu Gly His
225                 230                 235                 240

Ala Gly Phe Tyr Trp Arg Phe Ile Lys Asp Phe Ser Lys Val
                245                 250

<210> SEQ ID NO 46
<211> LENGTH: 762
<212> TYPE: DNA
<213> ORGANISM: Nicotiana tabacum

<400> SEQUENCE: 46
gtgcgtaagg aggtgtttaa gttgttggat gttggggttg tgtaccccat ctctgatagc      60
tcttgcattt cgccggtgca atgtgtaccg aagaagggtg gcatgaccgt ggttgcaaat     120
tcgcaaaatg ggttgattcc taccaggatc gtcaccgggt ggaaggtatg catggattac     180
cgaaagttga ataaagtgac ccgcaaggat cactttccat gccttttct tgatcagatg      240
ttagatcgac ttgctgggcg tgccttctac tgtttcttgg atgggtattc tggatacaac     300
caaatcttca ttactccgga agatcaggag aagacaacat tcacttgtcc atatggcacc     360
tttgctttt ctaggatgcc ttttggttg tgtaatgcac cgactacatt ctagcggtat      420
atgatggcca ttttcactga tatggtggaa gatatttgg aggtgttcat ggacgacttt      480
agtgttgtgg gtgattcatt tgatgaatgt ttgaataatc ttgatagagt gttggcccat     540
tgtaaagaaa ccaatcttgt tcttaattgg gagaaatgcc acttcatggt tgaggagggc     600
atagttcttg ggcataaaat tttaaagcat ggtatagagg tggacaaagc aaaaattgat     660
gtgatttcaa ggctccctcc ccctacttct gtcaagggag tgagaagttt cttaggcat      720
gcggggttct accggagatt catcaaagat ttcaccaaag tt                        762

<210> SEQ ID NO 47
<211> LENGTH: 254
<212> TYPE: PRT
<213> ORGANISM: Nicotiana tabacum

<400> SEQUENCE: 47

```
Val Arg Lys Glu Val Phe Lys Leu Leu Asp Val Gly Val Val Tyr Pro
  1               5                  10                  15
Ile Ser Asp Ser Ser Cys Ile Ser Pro Val Gln Cys Val Pro Lys Lys
             20                  25                  30
Gly Gly Met Thr Val Val Ala Asn Ser Gln Asn Gly Leu Ile Pro Thr
         35                  40                  45
Arg Ile Val Thr Gly Trp Lys Val Cys Met Asp Tyr Arg Lys Leu Asn
     50                  55                  60
Lys Val Thr Arg Lys Asp His Phe Pro Leu Pro Phe Leu Asp Gln Met
 65                  70                  75                  80
Leu Asp Arg Leu Ala Gly Arg Ala Phe Tyr Cys Phe Leu Asp Gly Tyr
                 85                  90                  95
Ser Gly Tyr Asn Gln Ile Phe Ile Thr Pro Glu Asp Gln Glu Lys Thr
            100                 105                 110
Thr Phe Thr Cys Pro Tyr Gly Thr Phe Ala Phe Ser Arg Met Pro Phe
        115                 120                 125
Gly Leu Cys Asn Ala Pro Thr Thr Phe Glx Arg Tyr Met Met Ala Ile
    130                 135                 140
Phe Thr Asp Met Val Glu Asp Ile Leu Glu Val Phe Met Asp Asp Phe
145                 150                 155                 160
Ser Val Val Gly Asp Ser Phe Asp Glu Cys Leu Asn Asn Leu Asp Arg
                165                 170                 175
Val Leu Ala His Cys Lys Glu Thr Asn Leu Val Leu Asn Trp Glu Lys
            180                 185                 190
Cys His Phe Met Val Glu Glu Gly Ile Val Leu Gly His Lys Ile Leu
        195                 200                 205
Lys His Gly Ile Glu Val Asp Lys Ala Lys Ile Asp Val Ile Ser Arg
    210                 215                 220
Leu Pro Pro Pro Thr Ser Val Lys Gly Val Arg Ser Phe Leu Arg His
225                 230                 235                 240
Ala Gly Phe Tyr Arg Arg Phe Ile Lys Asp Phe Thr Lys Val
                245                 250
```

<210> SEQ ID NO 48
<211> LENGTH: 760
<212> TYPE: DNA
<213> ORGANISM: Nicotiana tabacum

<400> SEQUENCE: 48

| | | | | | | |
|---|---|---|---|---|---|---|
| gcggaaggag | gtcgtcaagc | tgttggatgt | cggtgttgtg | tacccatat | ttgatagctc | 60 |
| ttggactttg | ccggtgcaat | atgtgccgaa | gaagggtggt | atgaccgtgg | ttaccaatgt | 120 |
| aaaaaatgag | ttgattccta | ccaggactgt | caccgggtgg | agggtgtgca | tggattacca | 180 |
| caaattgaat | aaagtgaccc | gcaaggatca | ctttccatta | ccttttcttg | atcagatgtt | 240 |
| agacagactt | gctgggtgtg | ccttctactg | tttcttggat | gggtattctg | gtgcaacaa | 300 |
| aattttgatt | gcaccaaaag | atcaggagaa | gaccaccttt | acttgtacgt | atggtacctt | 360 |
| tgtcttttct | aggatgtcat | ttgggttgtg | taatgcaccg | actacattct | agaggtgtat | 420 |
| gatggccata | tttacctaca | tggtggagga | cattttggag | gtgtttatgg | atgacttcag | 480 |

```
tgttgttggt gactagtttg atgaatgttt gaaaaatctt gatagagtgt tggcccgttg    540
tgaagaagcc aaccttgtgc ttaattggga gaaatgccac ttcatggttg aggagggcat    600
agtccttagc cataaaattt caaagcatgg tatagaggtg acaaagcaa aaattgaagt    660 gatttcaagg ctccttcccc ctacttctgt caagggagtt agaagttttc ttgggcatgc    720
ggggttctac tggagattca tcaaagactt cacgaaggtt                          760
```

```
<210> SEQ ID NO 49
<211> LENGTH: 253
<212> TYPE: PRT
<213> ORGANISM: Nicotiana tabacum

<400> SEQUENCE: 49
```

```
Arg Lys Glu Val Val Lys Leu Leu Asp Val Gly Val Tyr Pro Ile
 1               5                  10                  15

Phe Asp Ser Ser Trp Thr Leu Pro Val Gln Tyr Val Pro Lys Lys Gly
                20                  25                  30

Gly Met Thr Val Val Thr Asn Val Lys Asn Glu Leu Ile Pro Thr Arg
            35                  40                  45

Thr Val Thr Gly Trp Arg Val Cys Met Asp Tyr His Lys Leu Asn Lys
        50                  55                  60

Val Thr Arg Lys Asp His Phe Pro Leu Pro Phe Leu Asp Gln Met Leu
65                  70                  75                  80

Asp Arg Leu Ala Gly Cys Ala Phe Tyr Cys Phe Leu Asp Gly Tyr Ser
                85                  90                  95

Gly Cys Asn Lys Ile Leu Ile Ala Pro Lys Asp Gln Glu Lys Thr Thr
            100                 105                 110

Phe Thr Cys Thr Tyr Gly Thr Phe Val Phe Ser Arg Met Ser Phe Gly
        115                 120                 125

Leu Cys Asn Ala Pro Thr Thr Phe Glx Arg Cys Met Met Ala Ile Phe
    130                 135                 140

Thr Tyr Met Val Glu Asp Ile Leu Glu Val Phe Met Asp Asp Phe Ser
145                 150                 155                 160

Val Val Gly Asp Glx Phe Asp Glu Cys Leu Lys Asn Leu Asp Arg Val
                165                 170                 175

Leu Ala Arg Cys Glu Glu Ala Asn Leu Val Leu Asn Trp Glu Lys Cys
            180                 185                 190

His Phe Met Val Glu Glu Gly Ile Val Leu Ser His Lys Ile Ser Lys
        195                 200                 205

His Gly Ile Glu Val Asp Lys Ala Lys Ile Glu Val Ile Ser Arg Leu
    210                 215                 220

Leu Pro Pro Thr Ser Val Lys Gly Val Arg Ser Phe Leu Gly His Ala
225                 230                 235                 240

Gly Phe Tyr Trp Arg Phe Ile Lys Asp Phe Thr Lys Val
                245                 250
```

```
<210> SEQ ID NO 50
<211> LENGTH: 762
<212> TYPE: DNA
<213> ORGANISM: Oryza sativa

<400> SEQUENCE: 50
gtgcgtaagg aggtgtttaa gttcctgtat gccaggatta tttatctcgt accatacagc    60
gagtgggtta gcccagttca ggtcgtgcca agaagggag gaatgacggc cgttgcaaat    120
```

```
gctcaaaatg aactaatccc gcaacgaacc gtaaccggat ggagaatgtg catcgattac    180
aggaaactta acaaggctac aaaaaaggat catttcccgc tacccttcat tgatgaaatg    240
ttggaacggc tggcaaatca ttccttcttc tgtttccttg atgggtattc aggatatcat    300
caaattccca tccatccgga ggaccagagt aagactacgt tcacatgtcc atatggcacc    360
tatgcgtatc gtaggatgcc ctttggactg tgcaacactc ctgcatcttt ccaaggtgt    420 atgatgtcta ttttctcgga catgatcgag gatatcatgg aagtcttcat ggatgacttc    480
tcggtctatg gaaagacttt gggtcattgt ctgcagaatc tagacaaagt cttacaacga    540
tgccaagaaa aggacctagt gcttaactgg gaaaagtgcc atttcatggt ctgtgaaggg    600
atagttcttg gcatcgagt gtccgaacga ggagtcgaag ttgatcgtgc taaaattgat    660
gtgatagatc agcttcctcc acccgtgaac atcaaaggaa tccgcagctt ctttggtcac    720
gctggctttt atagaaggtt catcaaggac ttcacaaaag tt    762
```

<210> SEQ ID NO 51
<211> LENGTH: 254
<212> TYPE: PRT
<213> ORGANISM: Oryza sativa

<400> SEQUENCE: 51

```
Val Arg Lys Glu Val Phe Lys Phe Leu Tyr Ala Arg Ile Ile Tyr Leu
  1               5                  10                  15

Val Pro Tyr Ser Glu Trp Val Ser Pro Val Gln Val Val Pro Lys Lys
             20                  25                  30

Gly Gly Met Thr Ala Val Ala Asn Ala Gln Asn Glu Leu Ile Pro Gln
         35                  40                  45

Arg Thr Val Thr Gly Trp Arg Met Cys Ile Asp Tyr Arg Lys Leu Asn
     50                  55                  60

Lys Ala Thr Lys Lys Asp His Phe Pro Leu Pro Phe Ile Asp Glu Met
 65                  70                  75                  80

Leu Glu Arg Leu Ala Asn His Ser Phe Phe Cys Phe Leu Asp Gly Tyr
                 85                  90                  95

Ser Gly Tyr His Gln Ile Pro Ile His Pro Glu Asp Gln Ser Lys Thr
            100                 105                 110

Thr Phe Thr Cys Pro Tyr Gly Thr Tyr Ala Tyr Arg Arg Met Pro Phe
        115                 120                 125

Gly Leu Cys Asn Thr Pro Ala Ser Phe Gln Arg Cys Met Met Ser Ile
    130                 135                 140

Phe Ser Asp Met Ile Glu Asp Ile Met Glu Val Phe Met Asp Asp Phe
145                 150                 155                 160

Ser Val Tyr Gly Lys Thr Leu Gly His Cys Leu Gln Asn Leu Asp Lys
                165                 170                 175

Val Leu Gln Arg Cys Gln Glu Lys Asp Leu Val Leu Asn Trp Glu Lys
            180                 185                 190

Cys His Phe Met Val Cys Glu Gly Ile Val Leu Gly His Arg Val Ser
        195                 200                 205

Glu Arg Gly Val Glu Val Asp Arg Ala Lys Ile Asp Val Ile Asp Gln
    210                 215                 220

Leu Pro Pro Val Asn Ile Lys Gly Ile Arg Ser Phe Phe Gly His
225                 230                 235                 240

Ala Gly Phe Tyr Arg Arg Phe Ile Lys Asp Phe Thr Lys Val
                245                 250
```

<210> SEQ ID NO 52
<211> LENGTH: 761
<212> TYPE: DNA
<213> ORGANISM: Oryza sativa

<400> SEQUENCE: 52

```
gtgcgcaagg aggttttgaa attgctgcat gccaggatta tctatcccgt accatacagt      60
gagagggtta gcccagtcca ggttgtgcca agaagggag gaatggcggt cgttgcaaat      120
gctcagaatg aactaattac gcaacaaacc gtaaccggat ggaggatgtg tatcgattac     180
aggaaactca acaaggctac aaaaaaggat catttcccgc taccttcat tgttgaaatg      240
ttggaacggc tggcaaatca ttccttcttt tgtttccttg atggatattt cggatatcat     300
caaattccca tccatccgga ggactagagt aagactacgt tcacatgtcc atatggcacc     360
tatgcgtatc ataggatgtc ctttggactg tgcaacgctc ctgcatcttt ccaaggtgta     420
tgatgtctat tttctcggac atgatcgagg atatcatgga agtcttcatg gatgacttct     480
cggtctatgg aaagactttc ggtcattgtc tgcaaaatct agacaaagtc ttacaacgat     540
gccaagaaaa ggacctggtg cttaactggg aaaagtgaca tttcatggtc cgtgaaggga     600
tagttcttgg gcatcgagtg ttcgaacaag gaatcgaagt tgatcatgct aaaattgatg     660
tgatagatca gcttcctcct cccgtgaaca tcaaaggtat ccgcagcttc ttgggtcatg     720
tcggctttta tagaaggttc atcaaggact tcactaaagt t                         761
```

<210> SEQ ID NO 53
<211> LENGTH: 254
<212> TYPE: PRT
<213> ORGANISM: Oryza sativa

<400> SEQUENCE: 53

```
Val Arg Lys Glu Val Leu Lys Leu Leu His Ala Arg Ile Ile Tyr Pro
 1               5                   10                  15

Val Pro Tyr Ser Glu Arg Val Ser Pro Val Gln Val Val Pro Lys Lys
            20                  25                  30

Gly Gly Met Ala Val Val Ala Asn Ala Gln Asn Glu Leu Ile Thr Gln
        35                  40                  45

Gln Thr Val Thr Gly Trp Arg Met Cys Ile Asp Tyr Arg Lys Leu Asn
    50                  55                  60

Lys Ala Thr Lys Lys Asp His Phe Pro Leu Pro Phe Ile Val Glu Met
65                  70                  75                  80

Leu Glu Arg Leu Ala Asn His Ser Phe Phe Cys Phe Leu Asp Gly Tyr
                85                  90                  95

Phe Gly Tyr His Gln Ile Pro Ile His Pro Glu Asp Glx Ser Lys Thr
            100                 105                 110

Thr Phe Thr Cys Pro Tyr Gly Thr Tyr Ala Tyr His Arg Met Ser Phe
        115                 120                 125

Gly Leu Cys Asn Ala Pro Ala Ser Phe Gln Arg Cys Met Met Ser Ile
    130                 135                 140

Phe Ser Asp Met Ile Glu Asp Ile Met Glu Val Phe Met Asp Asp Phe
145                 150                 155                 160

Ser Val Tyr Gly Lys Thr Phe Gly His Cys Leu Gln Asn Leu Asp Lys
                165                 170                 175

Val Leu Gln Arg Cys Gln Glu Lys Asp Leu Val Leu Asn Trp Glu Lys
            180                 185                 190

Glx His Phe Met Val Arg Glu Gly Ile Val Leu Gly His Arg Val Phe
        195                 200                 205
```

```
Glu Gln Gly Ile Glu Val Asp His Ala Lys Ile Asp Val Ile Asp Gln
    210                 215                 220

Leu Pro Pro Val Asn Ile Lys Gly Ile Arg Ser Phe Leu Gly His
225                 230                 235                 240

Val Gly Phe Tyr Arg Arg Phe Ile Lys Asp Phe Thr Lys Val
                245                 250
```

<210> SEQ ID NO 54
<211> LENGTH: 762
<212> TYPE: DNA
<213> ORGANISM: Oryza sativa

<400> SEQUENCE: 54

```
gtgcggaaag aggtttttaa gctcctgcat gccgggatta tttataccgt tccatgcagt     60
gagtgggtca gcacagtcca ggttgggccg aagatgggat gaatgacggt cgttgcaaat    120
gctcaaaata aacttatccc gcaaccaacc ataaccggat ggaggatgtg catagactac    180
aggaaactca acaaggctac aaaagaggat cattttccgc tacccttcat tgatgaaatg    240
ttggaacgga tgacaaatca ttccttcttc tgtttccttg atgggtattc cggatatcat    300
caaattccca tccgtccaga ggaccagagt aagactacgt tcacatgtcc atatggcacc    360
tatgcgtatc gtaggatgtc cttcggactg tgcaacgctc ctgcatcttt ccaaggtgt     420
atgttgtcta ttttctcgga catgatcgaa gatatcatga agtcttcat ggatgacttc     480
tcagtttatg gaaagacttt cggtcattgt ctgtagaatc tagacaaagt cttacaacga    540
tgccaagaaa atgacctagt gtttaattgg gaaaagtgcc atttatggt ccgtgaaggg     600
atagttcttg ggcatcgagt atccgaatga ggaatcgaag ttgatcgtgc taaaatcgat    660
gttatagatc aaattcgtcc tcctgcgaat atcaaaggaa tccgcagctt cttgggacat    720
gccggctttt atagaaggtt cctcaaggac ttcacaaaag tt                       762
```

<210> SEQ ID NO 55
<211> LENGTH: 254
<212> TYPE: PRT
<213> ORGANISM: Oryza sativa

<400> SEQUENCE: 55

```
Val Arg Lys Glu Val Phe Lys Leu Leu His Ala Gly Ile Ile Tyr Thr
 1               5                  10                  15

Val Pro Cys Ser Glu Trp Val Ser Thr Val Gln Val Gly Pro Lys Met
                20                  25                  30

Gly Glx Met Thr Val Val Ala Asn Ala Gln Asn Lys Leu Ile Pro Gln
            35                  40                  45

Pro Thr Ile Thr Gly Trp Arg Met Cys Ile Asp Tyr Arg Lys Leu Asn
    50                  55                  60

Lys Ala Thr Lys Glu Asp His Phe Pro Leu Pro Phe Ile Asp Glu Met
65                  70                  75                  80

Leu Glu Arg Met Thr Asn His Ser Phe Phe Cys Phe Leu Asp Gly Tyr
                85                  90                  95

Ser Gly Tyr His Gln Ile Pro Ile Arg Pro Glu Asp Gln Ser Lys Thr
            100                 105                 110

Thr Phe Thr Cys Pro Tyr Gly Thr Tyr Ala Tyr Arg Arg Met Ser Phe
        115                 120                 125

Gly Leu Cys Asn Ala Pro Ala Ser Phe Gln Arg Cys Met Leu Ser Ile
    130                 135                 140
```

-continued

Phe Ser Asp Met Ile Glu Asp Ile Met Lys Val Phe Met Asp Asp Phe
145                 150                 155                 160

Ser Val Tyr Gly Lys Thr Phe Gly His Cys Leu Glx Asn Leu Asp Lys
            165                 170                 175

Val Leu Gln Arg Cys Gln Glu Asn Asp Leu Val Phe Asn Trp Glu Lys
        180                 185                 190

Cys His Phe Met Val Arg Glu Gly Ile Val Leu Gly His Arg Val Ser
            195                 200                 205

Glu Glx Gly Ile Glu Val Asp Arg Ala Lys Ile Asp Val Ile Asp Gln
        210                 215                 220

Ile Arg Pro Pro Ala Asn Ile Lys Gly Ile Arg Ser Phe Leu Gly His
225                 230                 235                 240

Ala Gly Phe Tyr Arg Arg Phe Leu Lys Asp Phe Thr Lys Val
            245                 250

<210> SEQ ID NO 56
<211> LENGTH: 762
<212> TYPE: DNA
<213> ORGANISM: Oryza sativa

<400> SEQUENCE: 56
gtgcgtaagg aggtcttgaa gctcttgcat gccgagatta tttatcccgt accatataga      60
gagtgggtta gcccggtcta ggttatgccg aagaagggac gaatgacggt cattgcaaat     120
gctcaaaatg aacttattcc gcaacgaaca gtaaccggat ggaggatgtg catagattac     180
atgaaactta caaggctac gaaaaaggat catttcccac tacccttcat tgatgaaatg      240
ttggaacggc tggcaaatca ttctttcttc cgtttccttg atgggtattc taggtatgat     300
caaattccca tccatccgga ggaccaaagt aagactacgt tcacatgttc gtatgatacc     360
tatgcttatc gtaggatgtc cttcggactg tgcaacgctc ctgcatcttt ccaaaggtgt     420
atgatgtcta ttttctccga catgattaag gacattatgg aagtcttcat gcatgacttc     480
tctatttatg gaaagaccct cggtcattgt ctacaaaatt tagacaaaat tttgcaacga     540
tgccaagaga aggacctggt acttaattgg gaaaagtgtc atttcatggt ccgtgaaggg     600
atagttctta gtcatcgagt gtccgaataa ggaatcgaag ttgatcgtgc taaaaactat     660
gtaatagatt agcttccttc tcctgtgaac attaagggga tccgcaattt tttgggacat     720
gctggctttt atagaaggtt catcaaagac ttcacaaagg tt                        762

<210> SEQ ID NO 57
<211> LENGTH: 254
<212> TYPE: PRT
<213> ORGANISM: Oryza sativa

<400> SEQUENCE: 57

Val Arg Lys Glu Val Leu Lys Leu Leu His Ala Glu Ile Ile Tyr Pro
1               5                   10                  15

Val Pro Tyr Arg Glu Trp Val Ser Pro Val Glx Val Met Pro Lys Lys
            20                  25                  30

Gly Arg Met Thr Val Ile Ala Asn Ala Gln Asn Glu Leu Ile Pro Gln
        35                  40                  45

Arg Thr Val Thr Gly Trp Arg Met Cys Ile Asp Tyr Met Lys Leu Asn
    50                  55                  60

Lys Ala Thr Lys Lys Asp His Phe Pro Leu Pro Phe Ile Asp Glu Met
65                  70                  75                  80

Leu Glu Arg Leu Ala Asn His Ser Phe Phe Arg Phe Leu Asp Gly Tyr

```
                    85                  90                  95
Ser Arg Tyr Asp Gln Ile Pro Ile His Pro Glu Asp Gln Ser Lys Thr
                100                 105                 110

Thr Phe Thr Cys Ser Tyr Asp Thr Tyr Ala Tyr Arg Arg Met Ser Phe
            115                 120                 125

Gly Leu Cys Asn Ala Pro Ala Ser Phe Gln Arg Cys Met Met Ser Ile
    130                 135                 140

Phe Ser Asp Met Ile Lys Asp Ile Met Glu Val Phe Met His Asp Phe
145                 150                 155                 160

Ser Ile Tyr Gly Lys Thr Ser Gly His Cys Leu Gln Asn Leu Asp Lys
                165                 170                 175

Ile Leu Gln Arg Cys Gln Glu Lys Asp Leu Val Leu Asn Trp Glu Lys
            180                 185                 190

Cys His Phe Met Val Arg Glu Gly Ile Val Leu Ser His Arg Val Ser
        195                 200                 205

Glu Glx Gly Ile Glu Val Asp Arg Ala Lys Asn Tyr Val Ile Asp Glx
210                 215                 220

Leu Pro Ser Pro Val Asn Ile Lys Gly Ile Arg Asn Phe Leu Gly His
225                 230                 235                 240

Ala Gly Phe Tyr Arg Arg Phe Ile Lys Asp Phe Thr Lys Val
                245                 250

<210> SEQ ID NO 58
<211> LENGTH: 762
<212> TYPE: DNA
<213> ORGANISM: Hordeum vulgare

<400> SEQUENCE: 58
gtgcgcaagg aggtttagaa gttcctggaa gcaggtatca tctatcgtgt tgctcatagt      60
gattggttga gtcgggtgca ttgtgtccct aagaagggag gcattaccgt tgtccctaat     120
gataaggatg aattgatccc acagaggact attactggct ataggatggt gattgatttt     180
aggaaattga ataaagccac taggaaagat cattaccctt tgccttttat cgaccaaatg     240
cgagaaaggc tgtctaaaca cacacacttc tgctttctaa acggttattt tggtttctcc     300
caaataccag ttgcacaatc tgatcaggag aaaaccactt tcacctgccc ttttggtaca     360
tttgcttata gacgtatgac ttttggctta tgtaatgcac ctgcctcctt tcaaagatgt     420
atgatggcta tattccctga cttttgtgaa aagattgttg aggttttcat ggatgacttc     480
tccatttacg gatcttcctt tgatgattgc ctcagcaacc ttgatcgagt cttgcagaga     540
tgtaaagaca ccaatctttt cttgaattgg aagaagtgcc actttatggt taatgacggc     600
atcgtcttag gacataaatt ttctgaaaga ggtattgaag tcgataaggc taaggttgat     660
ggaatcgaga aaatgccata ccccacagat atcaagggaa taagaagttt ccttggtcat     720
gctggtttct atagaaggtt cataaaagac ttcactaagg tt                        762

<210> SEQ ID NO 59
<211> LENGTH: 254
<212> TYPE: PRT
<213> ORGANISM: Hordeum vulgare

<400> SEQUENCE: 59

Val Arg Lys Glu Val Glx Lys Phe Leu Glu Ala Gly Ile Ile Tyr Arg
1               5                   10                  15

Val Ala His Ser Asp Trp Leu Ser Arg Val His Cys Val Pro Lys Lys
                20                  25                  30
```

```
Gly Gly Ile Thr Val Val Pro Asn Asp Lys Asp Glu Leu Ile Pro Gln
            35                  40                  45

Arg Thr Ile Thr Gly Tyr Arg Met Val Ile Asp Phe Arg Lys Leu Asn
 50                  55                  60

Lys Ala Thr Arg Lys Asp His Tyr Pro Leu Pro Phe Ile Asp Gln Met
65                  70                  75                  80

Arg Glu Arg Leu Ser Lys His Thr His Phe Cys Phe Leu Asn Gly Tyr
                85                  90                  95

Phe Gly Phe Ser Gln Ile Pro Val Ala Gln Ser Asp Gln Glu Lys Thr
            100                 105                 110

Thr Phe Thr Cys Pro Phe Gly Thr Phe Ala Tyr Arg Arg Met Thr Phe
            115                 120                 125

Gly Leu Cys Asn Ala Pro Ala Ser Phe Gln Arg Cys Met Met Ala Ile
            130                 135                 140

Phe Pro Asp Phe Cys Glu Lys Ile Val Glu Val Phe Met Asp Asp Phe
145                 150                 155                 160

Ser Ile Tyr Gly Ser Ser Phe Asp Asp Cys Leu Ser Asn Leu Asp Arg
                165                 170                 175

Val Leu Gln Arg Cys Lys Asp Thr Asn Leu Phe Leu Asn Trp Lys Lys
            180                 185                 190

Cys His Phe Met Val Asn Asp Gly Ile Val Leu Gly His Lys Phe Ser
            195                 200                 205

Glu Arg Gly Ile Glu Val Asp Lys Ala Lys Val Asp Gly Ile Glu Lys
            210                 215                 220

Met Pro Tyr Pro Thr Asp Ile Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 60
<211> LENGTH: 762
<212> TYPE: DNA
<213> ORGANISM: Hordeum vulgare

<400> SEQUENCE: 60
gtgcgtaaag aggtcctaaa gttcctggaa gcgggtatta tctatcctgt tgctcacaac      60
gattgggtga gtccggtgca ttgcgtccct aagaagggat gcattaccgt tgtccctaat     120
gataaggatg aattgatccc acataggatt attactggct ataggatggt gatcgatttt     180
aggaaaatga ataaagccac taggaaagaa cattacccct tgccttttag cgaccaaatg     240
ctagaaaggt tgtctaaaca cacacacttc tgctttctag acggttattc tagtttctcc     300
caaatactag ttgcacaatc tgatcaggag aaaaccactt tcacctaccc gttcggtacc     360
tttgcttata gacgtatgcc ttttggctta tgtaatgcac ctgccacctt tcaaagatgt     420
atgatggcta tattctctga cttttgtgaa agtttgtcg aggttttcat ggatgacttt     480
tccgtttacg gatcttcctt tgatgattgc ctcaacaacc ttgatcgggt cttgcagaga     540
tgtaaagata ctaatcttgt cttgaattgg gagaagtgcc actttatggt taatgaaggc     600
atcgtcttag gacataaaat ttccgaaaga ggtattgaat tcgataaggc taaggttggt     660
gcaatcaaga aaatgccata ccccacagat atcaaggta taagaagttt cttggtccat     720
gctggtttct atagaaggtt catcaaggac tttacaaagg tt                        762

<210> SEQ ID NO 61
```

<211> LENGTH: 254
<212> TYPE: PRT
<213> ORGANISM: Hordeum vulgare

<400> SEQUENCE: 61

```
Val Arg Lys Glu Val Leu Lys Phe Leu Glu Ala Gly Ile Ile Tyr Pro
 1               5                  10                  15
Val Ala His Asn Asp Trp Val Ser Pro Val His Cys Val Pro Lys Lys
             20                  25                  30
Gly Cys Ile Thr Val Val Pro Asn Asp Lys Asp Glu Leu Ile Pro His
         35                  40                  45
Arg Ile Ile Thr Gly Tyr Arg Met Val Ile Asp Phe Arg Lys Met Asn
     50                  55                  60
Lys Ala Thr Arg Lys Glu His Tyr Pro Leu Pro Phe Ser Asp Gln Met
 65                  70                  75                  80
Leu Glu Arg Leu Ser Lys His Thr His Phe Cys Phe Leu Asp Gly Tyr
                 85                  90                  95
Ser Ser Phe Ser Gln Ile Leu Val Ala Gln Ser Asp Gln Glu Lys Thr
            100                 105                 110
Thr Phe Thr Tyr Pro Phe Gly Thr Phe Ala Tyr Arg Arg Met Pro Phe
        115                 120                 125
Gly Leu Cys Asn Ala Pro Ala Thr Phe Gln Arg Cys Met Met Ala Ile
    130                 135                 140
Phe Ser Asp Phe Cys Glu Lys Phe Val Glu Val Phe Met Asp Asp Phe
145                 150                 155                 160
Ser Val Tyr Gly Ser Ser Phe Asp Asp Cys Leu Asn Asn Leu Asp Arg
                165                 170                 175
Val Leu Gln Arg Cys Lys Asp Thr Asn Leu Val Leu Asn Trp Glu Lys
            180                 185                 190
Cys His Phe Met Val Asn Glu Gly Ile Val Leu Gly His Lys Ile Ser
        195                 200                 205
Glu Arg Gly Ile Glu Phe Asp Lys Ala Lys Val Gly Ala Ile Lys Lys
    210                 215                 220
Met Pro Tyr Pro Thr Asp Ile Lys Gly Ile Arg Ser Phe Leu Val His
225                 230                 235                 240
Ala Gly Phe Tyr Arg Arg Phe Ile Lys Asp Phe Thr Lys Val
                245                 250
```

<210> SEQ ID NO 62
<211> LENGTH: 757
<212> TYPE: DNA
<213> ORGANISM: Hordeum vulgare

<400> SEQUENCE: 62

```
gaaaagaggt tgtgaagctc ctggatgaag gtattatcta tcatgttgct catagcgatt      60
gggtgagtcc ggtgcatagc gttcctaaga agggaggcat taccgttgtc cctaatgata     120
aggatgaatt gatcccgcag aggattatca ctggctatag gatggtgatc gatttcagga     180
aactgaataa agccactagg aaagatcatt accctttgcc ttttatcgac catatgctag     240
aaaggttgtc caaactcaca cacttctgct ttctagacgg ttattctagt ttctcccaaa     300
taccagttgc acaatctgat caggagaaaa ccactttcac ctgcccttc ggtacctttg      360
cttatagacg tatgccttt ggcttatgta atgcacctgc cacctttcaa agatgtatga      420
tggctatatt ctctaacttt tgtgaaaata ttgtcgaggt tttcatggat gacttttccg     480
tttacgggtc ttcttttgat gattgcctca gcaaccttga tcgagtctta cagagatgta     540
```

-continued

```
aagacaccaa tcttgtcttg aatggggaga agtgccactt tatggttaat gaaggcatcg    600
tcttaggaca taaaatttct gaaagaggta ttgaagtcga taaggctaag gttgatgcaa    660
tcgacaaaat gccatacccc acagatatca aggtataag  aagtttcctt ggtcatggtg    720
gtttctatag aaggtttatc aaagatttca caaggt                              757
```

<210> SEQ ID NO 63
<211> LENGTH: 251
<212> TYPE: PRT
<213> ORGANISM: Hordeum vulgare

<400> SEQUENCE: 63

```
Lys Glu Val Val Lys Leu Leu Asp Glu Gly Ile Ile Tyr His Val Ala
  1               5                  10                  15

His Ser Asp Trp Val Ser Pro Val His Ser Val Pro Lys Lys Gly Gly
             20                  25                  30

Ile Thr Val Val Pro Asn Asp Lys Asp Glu Leu Ile Pro Gln Arg Ile
         35                  40                  45

Ile Thr Gly Tyr Arg Met Val Ile Asp Phe Arg Lys Leu Asn Lys Ala
     50                  55                  60

Thr Arg Lys Asp His Tyr Pro Leu Pro Phe Ile Asp His Met Leu Glu
 65                  70                  75                  80

Arg Leu Ser Lys Leu Thr His Phe Cys Phe Leu Asp Gly Tyr Ser Ser
                 85                  90                  95

Phe Ser Gln Ile Pro Val Ala Gln Ser Asp Gln Glu Lys Thr Thr Phe
            100                 105                 110

Thr Cys Pro Phe Gly Thr Phe Ala Tyr Arg Arg Met Pro Phe Gly Leu
        115                 120                 125

Cys Asn Ala Pro Ala Thr Phe Gln Arg Cys Met Met Ala Ile Phe Ser
130                 135                 140

Asn Phe Cys Glu Asn Ile Val Glu Val Phe Met Asp Asp Phe Ser Val
145                 150                 155                 160

Tyr Gly Ser Ser Phe Asp Asp Cys Leu Ser Asn Leu Asp Arg Val Leu
                165                 170                 175

Gln Arg Cys Lys Asp Thr Asn Leu Val Leu Asn Gly Glu Lys Cys His
            180                 185                 190

Phe Met Val Asn Glu Gly Ile Val Leu Gly His Lys Ile Ser Glu Arg
        195                 200                 205

Gly Ile Glu Val Asp Lys Ala Lys Val Asp Ala Ile Asp Lys Met Pro
    210                 215                 220

Tyr Pro Thr Asp Ile Lys Gly Ile Arg Ser Phe Leu Gly His Gly Gly
225                 230                 235                 240

Phe Tyr Arg Arg Phe Ile Lys Asp Phe Thr Lys
                245                 250
```

<210> SEQ ID NO 64
<211> LENGTH: 740
<212> TYPE: DNA
<213> ORGANISM: Hordeum vulgare

<400> SEQUENCE: 64

```
gtgcgtaaag aggtgattaa attcctagaa gaaggtatta tctatcctgt tgctcacagc    60
gattgggtga gtccggtgca ttgcattcct aagaaggag  gcattaccgt tgtccctaat   120
gataaggatg aattgatccc atagaggatt attactggct ataggatggt gattgatttt   180
```

```
aggaagttga ataaagccac taggaaagat cattacccttt tgccttttat cgaccaaatg    240
ctagaaaggc tgtctaaaca cacacacttc ttgtttctgg acggttatac tggtttctcc    300
caaataccag ttgcacaatt tgatcaggag aaaaccactt taacctgaca tttcggtacc    360
tttgcttata tacgtatgcc ttttggcttg tgtaatgcac ctgccaccctt tcaaagatgt    420 atgatggcta tattctccga cttctgtgaa aagattgtca atgttttcat ggataacttc    480
tccgtttacg ggtgttcctt tgatgattgc ctcaacaacg ttgatcgagt cttacagaga    540
tgtaaggaca ccaatgttgt cttgaattgg gagaagtgtc actttatggt taatgaaggc    600
atcgtcttag gacataagat ttctgaaaga ggtattaaag ttgataaggc taaggttgat    660
gcaatcgaga aaatgccata tccacagata tcaaaggtat aagaagtttc cttggtcatg    720
ctggtttcta tagaaggttc                                                740
```

\<210\> SEQ ID NO 65
\<211\> LENGTH: 247
\<212\> TYPE: PRT
\<213\> ORGANISM: Hordeum vulgare

\<400\> SEQUENCE: 65

```
Val Arg Lys Glu Val Ile Lys Phe Leu Glu Glu Gly Ile Ile Tyr Pro
 1               5                  10                  15

Val Ala His Ser Asp Trp Val Ser Pro Val His Cys Ile Pro Lys Lys
            20                  25                  30

Gly Gly Ile Thr Val Val Pro Asn Asp Lys Asp Glu Leu Ile Pro Glx
        35                  40                  45

Arg Ile Ile Thr Gly Tyr Arg Met Val Ile Asp Phe Arg Lys Leu Asn
    50                  55                  60

Lys Ala Thr Arg Lys Asp His Tyr Pro Leu Pro Phe Ile Asp Gln Met
65                  70                  75                  80

Leu Glu Arg Leu Ser Lys His Thr His Phe Leu Phe Leu Asp Gly Tyr
                85                  90                  95

Thr Gly Phe Ser Gln Ile Pro Val Ala Gln Phe Asp Gln Glu Lys Thr
            100                 105                 110

Thr Leu Thr Glx His Phe Gly Thr Phe Ala Tyr Ile Arg Met Pro Phe
        115                 120                 125

Gly Leu Cys Asn Ala Pro Ala Thr Phe Gln Arg Cys Met Met Ala Ile
    130                 135                 140

Phe Ser Asp Phe Cys Glu Lys Ile Val Asn Val Phe Met Asp Asn Phe
145                 150                 155                 160

Ser Val Tyr Gly Cys Ser Phe Asp Asp Cys Leu Asn Asn Val Asp Arg
                165                 170                 175

Val Leu Gln Arg Cys Lys Asp Thr Asn Val Val Leu Asn Trp Glu Lys
            180                 185                 190

Cys His Phe Met Val Asn Glu Gly Ile Val Leu Gly His Lys Ile Ser
        195                 200                 205

Glu Arg Gly Ile Lys Val Asp Lys Ala Lys Val Asp Ala Ile Glu Lys
    210                 215                 220

Met Pro Tyr Pro Thr Asp Ile Lys Gly Ile Arg Ser Phe Leu Gly His
225                 230                 235                 240

Ala Gly Phe Tyr Arg Arg Phe
                245
```

\<210\> SEQ ID NO 66

<211> LENGTH: 762
<212> TYPE: DNA
<213> ORGANISM: Avena sativa

<400> SEQUENCE: 66

```
gtgcgaaagg aggttttcaa gctcatggat gctggtatta tttaccctat tgctgatagt    60
gaatgggtta gtcatgttca ttgtgttcct aaaaagggag gtattaccgt tgtccctaat   120
gataatgatg agcttattcc tcaaagaata gtggtaggct ataggatgtg catcgatttt   180
aggaaagtca ataaagttac taagaaagat cactacccgc ttccttttat tgatcaaatg   240
ttggaaagat tttctaaaaa gacccatttt tgttttcttg atggttattc tggtttctct   300
caaattgttg ttaaacaaca agatcaagaa aaaactactt ttacttgccc ttatggaact   360
tatgcttata gatgtatgcc ttttggttta tgtaatgctc cttctacttt cctaaggtgc   420
atgtctgcta tctttcatgg ttttttgtgag gaaattgtag aagtgttcat ggacgacttt   480
tctgtctacg gaacttcttt tgataattgt ctgcacaacc ttgataaagt tttacagaga   540
tgtgaaggaa ctaatcttgt tcttaattgg gagaaatgcc acttcatggt taatgaaggg   600
attgttcttg ggcataaagt ttctaaaaga ggcatagaag ttgatagagc taaggttgag   660
gcaattgaga agatgccatg tccaagagac atcaaggta ttcgtagtat ccttggtcat   720
gctggtttct ataggaggtt catcaaagac ttcacaaagg tt                     762
```

<210> SEQ ID NO 67
<211> LENGTH: 254
<212> TYPE: PRT
<213> ORGANISM: Avena sativa

<400> SEQUENCE: 67

```
Val Arg Lys Glu Val Phe Lys Leu Met Asp Ala Gly Ile Ile Tyr Pro
 1               5                  10                  15

Ile Ala Asp Ser Glu Trp Val Ser His Val His Cys Val Pro Lys Lys
             20                  25                  30

Gly Gly Ile Thr Val Val Pro Asn Asp Asn Asp Glu Leu Ile Pro Gln
         35                  40                  45

Arg Ile Val Val Gly Tyr Arg Met Cys Ile Asp Phe Arg Lys Val Asn
     50                  55                  60

Lys Val Thr Lys Lys Asp His Tyr Pro Leu Pro Phe Ile Asp Gln Met
 65                  70                  75                  80

Leu Glu Arg Phe Ser Lys Lys Thr His Phe Cys Phe Leu Asp Gly Tyr
                 85                  90                  95

Ser Gly Phe Ser Gln Ile Val Val Lys Gln Gln Asp Gln Glu Lys Thr
            100                 105                 110

Thr Phe Thr Cys Pro Tyr Gly Thr Tyr Ala Tyr Arg Cys Met Pro Phe
        115                 120                 125

Gly Leu Cys Asn Ala Pro Ser Thr Phe Leu Arg Cys Met Ser Ala Ile
    130                 135                 140

Phe His Gly Phe Cys Glu Glu Ile Val Glu Val Phe Met Asp Asp Phe
145                 150                 155                 160

Ser Val Tyr Gly Thr Ser Phe Asp Asn Cys Leu His Asn Leu Asp Lys
                165                 170                 175

Val Leu Gln Arg Cys Glu Gly Thr Asn Leu Val Leu Asn Trp Glu Lys
            180                 185                 190

Cys His Phe Met Val Asn Glu Gly Ile Val Leu Gly His Lys Val Ser
        195                 200                 205
```

-continued

Lys Arg Gly Ile Glu Val Asp Arg Ala Lys Val Glu Ala Ile Glu Lys
210                 215                 220

Met Pro Cys Pro Arg Asp Ile Lys Gly Ile Arg Ser Ile Leu Gly His
225                 230                 235                 240

Ala Gly Phe Tyr Arg Arg Phe Ile Lys Asp Phe Thr Lys Val
                245                 250

<210> SEQ ID NO 68
<211> LENGTH: 762
<212> TYPE: DNA
<213> ORGANISM: Avena sativa

<400> SEQUENCE: 68

```
gtgcgcaaag aggtctttaa gttccttgat gctggtatta tttaccctat tgctgatagt     60
caatgggtta gccttgttca ttgtgtcccc aagaaagggg gaataactgt tgtgcctaat    120
gaagataatg agcttatacc ccaaagagta gtggttgtgt atagaatgtg cattgatttt    180
agaaggatta ataaagttac taggaaagat cattatcctt gccctttat tgatcaaatg     240
cttgagaggt tgtccaaaaa gactcacttt tgttttcttg atggtcattc tgggttttct    300
caaattgttg tgaaagcaca agaccaagag aaaactactt tcacttgtcc ttatggtact    360
tatgattata ggcgtatgcc ttttggttta tgtaatgctc ctgctacctt tcagagatgt    420
atgtctgcta tatttcatgg ttttttgtgaa gaaattgtgg aggttttcat ggacgatttt    480
tctgtctatg gaacttcttt tgataactgt ttgcacaacc ttgataaatt tttgcagaga    540
tttgaagaaa ccaaccttgt tcttaattgg gagaaatgcc atttcatggt taatgaaggg    600
attgttcttg gacacaagat ctcagaaaga ggcattgaag ttgacagagc caaaattgaa    660
gcaattgaga acatgccttg ccctagagat attaaaggta ttcgtagtat ccttggtcat    720
gctggtttct atagtaggtt catcaaagac tttacaaaag tt                        762
```

<210> SEQ ID NO 69
<211> LENGTH: 254
<212> TYPE: PRT
<213> ORGANISM: Avena sativa

<400> SEQUENCE: 69

Val Arg Lys Glu Val Phe Lys Phe Leu Asp Ala Gly Ile Ile Tyr Pro
1               5                   10                  15

Ile Ala Asp Ser Gln Trp Val Ser Leu Val His Cys Val Pro Lys Lys
                20                  25                  30

Gly Gly Ile Thr Val Val Pro Asn Glu Asp Asn Glu Leu Ile Pro Gln
            35                  40                  45

Arg Val Val Val Tyr Arg Met Cys Ile Asp Phe Arg Arg Ile Asn
        50                  55                  60

Lys Val Thr Arg Lys Asp His Tyr Pro Leu Pro Phe Ile Asp Gln Met
65                  70                  75                  80

Leu Glu Arg Leu Ser Lys Lys Thr His Phe Cys Phe Leu Asp Gly His
                85                  90                  95

Ser Gly Phe Ser Gln Ile Val Val Lys Ala Gln Asp Gln Glu Lys Thr
            100                 105                 110

Thr Phe Thr Cys Pro Tyr Gly Thr Tyr Asp Tyr Arg Arg Met Pro Phe
        115                 120                 125

Gly Leu Cys Asn Ala Pro Ala Thr Phe Gln Arg Cys Met Ser Ala Ile
    130                 135                 140

Phe His Gly Phe Cys Glu Glu Ile Val Glu Val Phe Met Asp Asp Phe

```
                145                 150                 155                 160
Ser Val Tyr Gly Thr Ser Phe Asp Asn Cys Leu His Asn Leu Asp Lys
                    165                 170                 175

Phe Leu Gln Arg Phe Glu Glu Thr Asn Leu Val Leu Asn Trp Glu Lys
                180                 185                 190

Cys His Phe Met Val Asn Glu Gly Ile Val Leu Gly His Lys Ile Ser
                195                 200                 205

Glu Arg Gly Ile Glu Val Asp Arg Ala Lys Ile Glu Ala Ile Glu Asn
        210                 215                 220

Met Pro Cys Pro Arg Asp Ile Lys Gly Ile Arg Ser Ile Leu Gly His
225                 230                 235                 240

Ala Gly Phe Tyr Ser Arg Phe Ile Lys Asp Phe Thr Lys Val
                245                 250

<210> SEQ ID NO 70
<211> LENGTH: 696
<212> TYPE: DNA
<213> ORGANISM: Avena sativa

<400> SEQUENCE: 70
gttagtcttg ttcattgtgt tcctaaaaag ggaggtatta ccgttgttcc taatgataat      60
gatgagctta ttcctcaaag aatagtggta ggctatagga tgtgcataga ttttaggaaa     120
gttaataaag ttactaagaa agatcactac ccgcttcctt ttattgatca aatgttggaa     180
aggttgtcta aaaagaccca ttttttgtttt cttgatggtt actctagctt ctctcaaatt    240
gctgttaaac aacaagatca agaaaaaact acttttactt gcccttatgg aacttttgct    300
tatagacgta tgcctattgg tttatgtaat gctcctgcta cttttcaaag gtgtatgtct    360
gctatatttc atggtttttg tgaggaaatt gtagaagtgt tcatggatga cttttctgtc    420
tatggaactt cttttgataa ttgcctgcac aaccttgata agttttgca gagatgtgaa    480 gaaactaata ttgttcttaa ttgggagaaa ttccacttca tggttaatga agggattgtc    540
cttgggcata agtttctaa agaggcata aagttgata gagctaaggt tgaggcaatt    600
gagaagatgc catgcccaag agacatcaaa ggtatacgta gtatccttgg tcatgctggt    660
ttctatagaa ggtttatcaa agacttcaca aaggtt                              696

<210> SEQ ID NO 71
<211> LENGTH: 252
<212> TYPE: PRT
<213> ORGANISM: Avena sativa

<400> SEQUENCE: 71

Lys Glu Val Phe Lys Leu Leu Asp Val Gly Ile Ile Tyr Pro Ile Ala
1               5                   10                  15

Asp Ser Glu Trp Val Ser Leu Val His Cys Val Pro Lys Lys Gly Gly
                20                  25                  30

Ile Thr Val Val Pro Asn Asp Asn Asp Glu Leu Ile Pro Gln Arg Ile
            35                  40                  45

Val Val Gly Tyr Arg Met Cys Ile Asp Phe Arg Lys Val Asn Lys Val
        50                  55                  60

Thr Lys Lys Asp His Tyr Pro Leu Pro Phe Ile Asp Gln Met Leu Glu
65                  70                  75                  80

Arg Leu Ser Lys Lys Thr His Phe Cys Phe Leu Asp Gly Tyr Ser Ser
                85                  90                  95

Phe Ser Gln Ile Ala Val Lys Gln Gln Asp Gln Glu Lys Thr Thr Phe
```

```
                100             105             110
Thr Cys Pro Tyr Gly Thr Phe Ala Tyr Arg Arg Met Pro Ile Gly Leu
        115                 120                 125

Cys Asn Ala Pro Ala Thr Phe Gln Arg Cys Met Ser Ala Ile Phe His
    130                 135                 140

Gly Phe Cys Glu Glu Ile Val Glu Val Phe Met Asp Asp Phe Ser Val
145                 150                 155                 160

Tyr Gly Thr Ser Phe Asp Asn Cys Leu His Asn Leu Asp Lys Val Leu
                165                 170                 175

Gln Arg Cys Glu Glu Thr Asn Ile Val Leu Asn Trp Glu Lys Phe His
        180                 185                 190

Phe Met Val Asn Glu Gly Ile Val Leu Gly His Lys Val Ser Lys Arg
            195                 200                 205

Gly Ile Glu Val Asp Arg Ala Lys Val Glu Ala Ile Glu Lys Met Pro
    210                 215                 220

Cys Pro Arg Asp Ile Lys Gly Ile Arg Ser Ile Leu Gly His Ala Gly
225                 230                 235                 240

Phe Tyr Arg Arg Phe Ile Lys Asp Phe Thr Lys Val
                245                 250

<210> SEQ ID NO 72
<211> LENGTH: 748
<212> TYPE: DNA
<213> ORGANISM: Secale cereale

<400> SEQUENCE: 72
gtgcggaaag aggtctttaa actcctagag gcaggtatta actatcccat tgctgatagc      60
cagcgggtaa gtcatgtcca ttgtgttcct aagaaaggag gtatgactgt cgtccctaag     120
gataaagatg aatttatccc gcaaagaata gttacaggtt ataggatggt aattgatttt     180
cgtaagttaa ataaagctac tatgaaagat cattacccct tgccatttat tgatcaaatg     240
ccagacaggt tatccaaaca tactcatttc tgctttctag atggttattc tggtttctct     300
caaataccct tgtcaagggg ggatcaagaa agaccaccct ttacttgtcc tttcggtacc     360
tttgcttata gaggtatgcc ttttggttta tgtaatgcac ctgctacctt tcaaagatgt     420
atgatcgtta tattctctgt ctttttttgaa aagattgttg aggtattcat ggatgatttc     480
tccgtttatg gaacttcttt tgatgattgc ttaagcaacc ttgatcgagt tttgcagaga     540
tgtgaagata ctaaccttgt cttgaattgg gagaagtgcc actttatggt taatgaaggc     600
attttcttgg gacataaaat ttctgaaaga ggtactgaag ttgagaaagc taaagtggat     660
gctattgaaa agatgccatg ccctaaggat atgaaaggta tacgaagttt ccttggtcac     720
gctgggtttt ataggaggtt cataaaag                                        748

<210> SEQ ID NO 73
<211> LENGTH: 249
<212> TYPE: PRT
<213> ORGANISM: Secale cereale

<400> SEQUENCE: 73

Val Arg Lys Glu Val Phe Lys Leu Leu Glu Ala Gly Ile Asn Tyr Pro
 1               5                  10                  15

Ile Ala Asp Ser Gln Arg Val Ser His Val His Cys Val Pro Lys Lys
            20                  25                  30

Gly Gly Met Thr Val Val Pro Lys Asp Lys Asp Glu Phe Ile Pro Gln
        35                  40                  45
```

```
-continued

Arg Ile Val Thr Gly Tyr Arg Met Val Ile Asp Phe Arg Lys Leu Asn
            50                  55                  60

Lys Ala Thr Met Lys Asp His Tyr Pro Leu Pro Phe Ile Asp Gln Met
 65                  70                  75                  80

Pro Asp Arg Leu Ser Lys His Thr His Phe Cys Phe Leu Asp Gly Tyr
                85                  90                  95

Ser Gly Phe Ser Gln Ile Pro Leu Ser Lys Gly Asp Gln Glu Lys Thr
            100                 105                 110

Thr Phe Thr Cys Pro Phe Gly Thr Phe Ala Tyr Arg Gly Met Pro Phe
            115                 120                 125

Gly Leu Cys Asn Ala Pro Ala Thr Phe Gln Arg Cys Met Ile Val Ile
            130                 135                 140

Phe Ser Val Phe Glu Lys Ile Val Glu Val Phe Met Asp Asp Phe
145                 150                 155                 160

Ser Val Tyr Gly Thr Ser Phe Asp Asp Cys Leu Ser Asn Leu Asp Arg
                165                 170                 175

Val Leu Gln Arg Cys Glu Asp Thr Asn Leu Val Leu Asn Trp Glu Lys
            180                 185                 190

Cys His Phe Met Val Asn Glu Gly Ile Phe Leu Gly His Lys Ile Ser
            195                 200                 205

Glu Arg Gly Thr Glu Val Glu Lys Ala Lys Val Asp Ala Ile Glu Lys
            210                 215                 220

Met Pro Cys Pro Lys Asp Met Lys Gly Ile Arg Ser Phe Leu Gly His
225                 230                 235                 240

Ala Gly Phe Tyr Arg Arg Phe Ile Lys
                245

<210> SEQ ID NO 74
<211> LENGTH: 762
<212> TYPE: DNA
<213> ORGANISM: Secale cereale

<400> SEQUENCE: 74
gtgcggaagg aggtcgttaa gcttccagag gcaggtatta tctatcccgt tgctgatagc      60
cagtgggtaa gtcatgtcca ttgtgtccct aagaagggag gtatgactgt cgttcctaat     120
gacaaacatg aattgatccc gcaaagaata gttacaggtt ataggatggt aattgatttc     180
cgtaagttaa ataaagctac taagaaagat cattaccccct tgccatttat tgatcaaatg    240
ctagacaggt tatccaaaca tactcatttt tgctttctag atggttatta tggtttctct    300
caaatacctg tgtcaaaagg ggatcaagaa agaccacttt tcacttgtcc tttcggtacc    360
tttgcttata gacgtatgcc ttttggttta tgtaatgcac ctgctacctt tcaaagatgt    420
atgatggcta tattatctga ttttttgagaa aagattgttg aggttttcat ggatgatttc    480
tccgtttacg gaacttcttt tgatgactac ttaagcaaca atgatcgagt tttgcagaga    540
tgtgaagaca ctaatcttgt tttgaattgg gagaagtgcc actttatggt taatgaaggc    600
attgtcttgg gacaaaaaat ttctgaaaga ggtattgaag ttgacaaagc taaagtcgat    660
gctgttgaaa agatgccatg ccccaaggac atcaaggta tacgaagttt cctcggtcat    720
gttgggtttt ataggaggtt catcaaagac ttcacgaaag tt                        762

<210> SEQ ID NO 75
<211> LENGTH: 254
<212> TYPE: PRT
<213> ORGANISM: Secale cereale
```

<400> SEQUENCE: 75

| | | | | | | | | | | | | |
|---|---|---|---|---|---|---|---|---|---|---|---|---|
| Val | Arg | Lys | Glu | Val | Lys | Leu | Pro | Glu | Ala | Gly | Ile | Ile | Tyr | Pro |
| 1 | | | | 5 | | | | | 10 | | | | | 15 |
| Val | Ala | Asp | Ser | Gln | Trp | Val | Ser | His | Val | His | Cys | Val | Pro | Lys | Lys |
| | | | 20 | | | | | 25 | | | | | 30 | | |
| Gly | Gly | Met | Thr | Val | Val | Pro | Asn | Asp | Lys | His | Glu | Leu | Ile | Pro | Gln |
| | | | 35 | | | | | 40 | | | | | 45 | | |
| Arg | Ile | Val | Thr | Gly | Tyr | Arg | Met | Val | Ile | Asp | Phe | Arg | Lys | Leu | Asn |
| | | | 50 | | | | | 55 | | | | | 60 | | |
| Lys | Ala | Thr | Lys | Lys | Asp | His | Tyr | Pro | Leu | Pro | Phe | Ile | Asp | Gln | Met |
| 65 | | | | | 70 | | | | | 75 | | | | | 80 |
| Leu | Asp | Arg | Leu | Ser | Lys | His | Thr | His | Phe | Cys | Phe | Leu | Asp | Gly | Tyr |
| | | | | 85 | | | | | 90 | | | | | 95 | |
| Tyr | Gly | Phe | Ser | Gln | Ile | Pro | Val | Ser | Lys | Gly | Asp | Gln | Glu | Lys | Thr |
| | | | | 100 | | | | | 105 | | | | | 110 | |
| Thr | Phe | Thr | Cys | Pro | Phe | Gly | Thr | Phe | Ala | Tyr | Arg | Arg | Met | Pro | Phe |
| | | | | 115 | | | | | 120 | | | | | 125 | |
| Gly | Leu | Cys | Asn | Ala | Pro | Ala | Thr | Phe | Gln | Arg | Cys | Met | Met | Ala | Ile |
| | | | 130 | | | | | 135 | | | | | 140 | | |
| Leu | Ser | Asp | Phe | Glx | Glu | Lys | Ile | Val | Glu | Val | Phe | Met | Asp | Asp | Phe |
| 145 | | | | | 150 | | | | | 155 | | | | | 160 |
| Ser | Val | Tyr | Gly | Thr | Ser | Phe | Asp | Asp | Tyr | Leu | Ser | Asn | Asn | Asp | Arg |
| | | | | 165 | | | | | 170 | | | | | 175 | |
| Val | Leu | Gln | Arg | Cys | Glu | Asp | Thr | Asn | Leu | Val | Leu | Asn | Trp | Glu | Lys |
| | | | | 180 | | | | | 185 | | | | | 190 | |
| Cys | His | Phe | Met | Val | Asn | Glu | Gly | Ile | Val | Leu | Gly | Gln | Lys | Ile | Ser |
| | | | | 195 | | | | | 200 | | | | | 205 | |
| Glu | Arg | Gly | Ile | Glu | Val | Asp | Lys | Ala | Lys | Val | Asp | Ala | Val | Glu | Lys |
| | | | 210 | | | | | 215 | | | | | 220 | | |
| Met | Pro | Cys | Pro | Lys | Asp | Ile | Lys | Gly | Ile | Arg | Ser | Phe | Leu | Gly | His |
| 225 | | | | | 230 | | | | | 235 | | | | | 240 |
| Val | Gly | Phe | Tyr | Arg | Arg | Phe | Ile | Lys | Asp | Phe | Thr | Lys | Val |
| | | | | 245 | | | | | 250 | | | | |

<210> SEQ ID NO 76
<211> LENGTH: 762
<212> TYPE: DNA
<213> ORGANISM: Secale cereale

<400> SEQUENCE: 76

```
gtgcgtaagg aggtggttaa gctcctagaa gcaggtatta tctatccagt tgctgatagt      60
cagtgggtaa gtcatgtcca ttatgttcct aagaaaggag gtatgactgt tgtccctaat     120
gataaagatg aattgatccc gcaaagaata gttacaggtt ataggatggt aagtgatttc     180
cgtaagttga ataaagccac taagaaagat cattacccct tgccatttat tgatcaaatg     240
ctagaaaggt tatccaaaca tactcatttc ttctttctag atggttattc tggtttctct     300
caaatacctg tgtcaaaagg ggatcaagaa agaccacct ttacttgtac tttcggtacc      360
tttgcttata gacgtatgcc ttttggttta tgtaatgcac ctgctacctt tcaaagatgc     420
atgatggcta tattctctga cttttgtgaa aagattgttg aggtattcat ggatgatttc     480
tccgtttacg gaacttcttt tgatgattgc ttaagcaacc ttgatcgagt tttgcagaga     540
tgtgaagaca ctaaccttgt cttgaattgc gagaagtgcc actttatggt taatgaaggc     600
```

-continued

```
attgtcttgg gacataaaat ttctgaaata ggtattgaag ttgacaaagc taaagttgat      660
gctattgaaa agatgccatg cgcaaaggac atcaaaggta tacggagttt ccttggtcat      720
gccgggtttt ataggaggtt catcaaagat ttctcaaagg tt                        762
```

<210> SEQ ID NO 77
<211> LENGTH: 254
<212> TYPE: PRT
<213> ORGANISM: Secale cereale

<400> SEQUENCE: 77

```
Val Arg Lys Glu Val Val Lys Leu Leu Glu Ala Gly Ile Ile Tyr Pro
  1               5                  10                  15

Val Ala Asp Ser Gln Trp Val Ser His Val His Tyr Val Pro Lys Lys
             20                  25                  30

Gly Gly Met Thr Val Val Pro Asn Asp Lys Asp Glu Leu Ile Pro Gln
         35                  40                  45

Arg Ile Val Thr Gly Tyr Arg Met Val Ser Asp Phe Arg Lys Leu Asn
     50                  55                  60

Lys Ala Thr Lys Asp His Tyr Pro Leu Pro Phe Ile Asp Gln Met
 65                  70                  75                  80

Leu Glu Arg Leu Ser Lys His Thr His Phe Phe Leu Asp Gly Tyr
                 85                  90                  95

Ser Gly Phe Ser Gln Ile Pro Val Ser Lys Gly Asp Gln Glu Lys Thr
            100                 105                 110

Thr Phe Thr Cys Thr Phe Gly Thr Phe Ala Tyr Arg Arg Met Pro Phe
        115                 120                 125

Gly Leu Cys Asn Ala Pro Ala Thr Phe Gln Arg Cys Met Met Ala Ile
    130                 135                 140

Phe Ser Asp Phe Cys Glu Lys Ile Val Glu Val Phe Met Asp Asp Phe
145                 150                 155                 160

Ser Val Tyr Gly Thr Ser Phe Asp Asp Cys Leu Ser Asn Leu Asp Arg
                165                 170                 175

Val Leu Gln Arg Cys Glu Asp Thr Asn Leu Val Leu Asn Cys Glu Lys
            180                 185                 190

Cys His Phe Met Val Asn Glu Gly Ile Val Leu Gly His Lys Ile Ser
        195                 200                 205

Glu Ile Gly Ile Glu Val Asp Lys Ala Lys Val Asp Ala Ile Glu Lys
    210                 215                 220

Met Pro Cys Ala Lys Asp Ile Lys Gly Ile Arg Ser Phe Leu Gly His
225                 230                 235                 240

Ala Gly Phe Tyr Arg Arg Phe Ile Lys Asp Phe Ser Lys Val
                245                 250
```

<210> SEQ ID NO 78
<211> LENGTH: 759
<212> TYPE: DNA
<213> ORGANISM: Secale cereale

<400> SEQUENCE: 78

```
gtgcgcaagg aagtttttaa gtttctagag gcaggtataa tctatccagt tgctgatagc      60
cagtgggtaa gtcctgtcca ttgtgtccct aagaagggag gtatgactgt agttcctaat     120
gataaagatg aattgatctc gcaaagaatt gttacaggtt ataggatggt aattgatttt     180
cgcaaattaa ataagccac taagaaagat caatacccctt tgcctttat tgatcaaatg     240 ctagaaaggt tatccaaaca cacccatttt tgctttctag atggttattc tagtttctct     300
```

```
caaataccta tgtcaaaagg ggataaagaa aagaccactt ttacttgtcc ctttggtact    360
ttgcttatag acgtatgcct tttggtttat gtaatgcatc tgctacctttt caaacatgca   420 tgatggctat actctatgat ttttgtgaaa gaatgttgat gttttcatgg atgattttttg  480 tatttacgaa acttcttttg atgattgctt gagcaacctt gatcgagttt tgcagagatg   540
tgaagaaact aatcttgtct tgaactggga aaagtccac tttatggtta atgaaggcat    600
tgcttgggac ataaaatttc tgaaagaggt accgaagttg acaaagctaa agttgatgct   660
gttgaaaaga tgccatgtcc caaggacatc aaaggtataa gaagtttcct tggtcatgcc   720
gggttttata ggaggtttat caaggacttc accaaggtt                          759
```

<210> SEQ ID NO 79
<211> LENGTH: 254
<212> TYPE: PRT
<213> ORGANISM: Secale cereale

<400> SEQUENCE: 79

```
Val Arg Lys Glu Val Phe Lys Phe Leu Glu Ala Gly Ile Ile Tyr Pro
  1               5                  10                  15

Val Ala Asp Ser Gln Trp Val Ser Pro Val His Cys Val Pro Lys Lys
             20                  25                  30

Gly Gly Met Thr Val Val Pro Asn Asp Lys Asp Glu Leu Ile Ser Gln
         35                  40                  45

Arg Ile Val Thr Gly Tyr Arg Met Val Ile Asp Phe Arg Lys Leu Asn
     50                  55                  60

Lys Ala Thr Lys Lys Asp Gln Tyr Pro Leu Pro Phe Ile Asp Gln Met
 65                  70                  75                  80

Leu Glu Arg Leu Ser Lys His Thr His Phe Cys Phe Leu Asp Gly Tyr
                 85                  90                  95

Ser Ser Phe Ser Gln Ile Pro Met Ser Lys Gly Asp Lys Glu Lys Thr
            100                 105                 110

Thr Phe Thr Cys Pro Phe Gly Thr Phe Ala Tyr Arg Arg Met Pro Phe
        115                 120                 125

Gly Leu Cys Asn Ala Ser Ala Thr Phe Gln Thr Cys Met Met Ala Ile
    130                 135                 140

Leu Tyr Asp Phe Cys Glu Arg Ile Val Asp Val Phe Met Asp Asp Phe
145                 150                 155                 160

Cys Ile Tyr Glu Thr Ser Phe Asp Asp Cys Leu Ser Asn Leu Asp Arg
                165                 170                 175

Val Leu Gln Arg Cys Glu Glu Thr Asn Leu Val Leu Asn Trp Glu Lys
            180                 185                 190

Ser His Phe Met Val Asn Glu Gly Ile Val Leu Gly His Lys Ile Ser
        195                 200                 205

Glu Arg Gly Thr Glu Val Asp Lys Ala Lys Val Asp Ala Val Glu Lys
    210                 215                 220

Met Pro Cys Pro Lys Asp Ile Lys Gly Ile Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 80
<211> LENGTH: 761
<212> TYPE: DNA
<213> ORGANISM: Triticum aestivum

```
<400> SEQUENCE: 80
gtgcgtaagg aggttctcaa gtttctggag gtaggtataa tttatcccgt tgctgatagt      60
cagtgggtaa gtcctgtcca ttgtgtccct aagaagggag gtattactgt tgtccctaat     120
gataaagatg aattgattcc tcaaagaatt attacggtta taggatggta attgatttcc     180
gcaaattaaa taaagccact aagagagatc attacccctt acctttatt gatcaaattc      240
tagaaagatt atgcaaacat acacattatt gcttccaaga tggttatcct ggttttctc      300
aaatacctgt gtcggctaaa gatcaatcaa agactacttt tacatgccct tttggtactt     360
ttgcttatag atgtatgcct tttggtttat gtaatgcacc tgctacctt caaagatgca      420
tgatggctat attctctgat ttttgtgaaa agatttgtga ggttttcatg gatgactttt     480
ccgtctatgg ttcctctttt gatgattgct tgagcaatct tgatcgagtt ttgcagagat     540
gtgaagaaac taatcttgtc ttgaattggg aaaagtgtca ctttatggtt aatgaaggta     600
ttgtcttggg gcacaaagtt tctgaaagag gtattgaagt tgataaagcc aaggttgaca     660
ctattgaaaa gataccatgt cccaaggaca tcaaggtac aagaagtttc cttggtcacg      720
ccggatttta taggaggttc ataaaagatt tcacaaaggt t                        761

<210> SEQ ID NO 81
<211> LENGTH: 254
<212> TYPE: PRT
<213> ORGANISM: Triticum aestivum

<400> SEQUENCE: 81
```

Val Arg Lys Glu Val Leu Lys Phe Leu Glu Val Gly Ile Ile Tyr Pro
1               5                   10                  15

Val Ala Asp Ser Gln Trp Val Ser Pro Val His Cys Val Pro Lys Lys
            20                  25                  30

Gly Gly Ile Thr Val Val Pro Asn Asp Lys Asp Glu Leu Ile Pro Gln
        35                  40                  45

Arg Ile Ile Thr Gly Tyr Arg Met Val Ile Asp Phe Arg Lys Leu Asn
    50                  55                  60

Lys Ala Thr Lys Arg Asp His Tyr Pro Leu Pro Phe Ile Asp Gln Ile
65                  70                  75                  80

Leu Glu Arg Leu Cys Lys His Thr His Tyr Cys Phe Gln Asp Gly Tyr
                85                  90                  95

Pro Gly Phe Ser Gln Ile Pro Val Ser Ala Lys Asp Gln Ser Lys Thr
            100                 105                 110

Thr Phe Thr Cys Pro Phe Gly Thr Phe Ala Tyr Arg Cys Met Pro Phe
        115                 120                 125

Gly Leu Cys Asn Ala Pro Ala Thr Phe Gln Arg Cys Met Met Ala Ile
    130                 135                 140

Phe Ser Asp Phe Cys Glu Lys Ile Cys Glu Val Phe Met Asp Asp Phe
145                 150                 155                 160

Ser Val Tyr Gly Ser Ser Phe Asp Asp Cys Leu Ser Asn Leu Asp Arg
                165                 170                 175

Val Leu Gln Arg Cys Glu Glu Thr Asn Leu Val Leu Asn Trp Glu Lys
            180                 185                 190

Cys His Phe Met Val Asn Glu Gly Ile Val Leu Gly His Lys Val Ser
        195                 200                 205

Glu Arg Gly Ile Glu Val Asp Lys Ala Lys Val Asp Thr Ile Glu Lys
    210                 215                 220

Ile Pro Cys Pro Lys Asp Ile Lys Gly Thr Arg Ser Phe Leu Gly His

```
                    225                 230                 235                 240
Ala Gly Phe Tyr Arg Arg Phe Ile Lys Asp Phe Thr Lys Val
                245                 250

<210> SEQ ID NO 82
<211> LENGTH: 780
<212> TYPE: DNA
<213> ORGANISM: Triticum aestivum

<400> SEQUENCE: 82
gtgcggaagg aggtgtttaa gctccttgag gcaggtataa tttatcccgt tgctgatagt       60
aagtgggtaa ttcctgtcca ttaagtgatc gtgattactg ttgttcctaa gaagggaggt      120
attaccgttg ttcctaatga taaagatgaa ttgattcctc aaagaaccat tactggttat      180
aggatggtaa ttgatttccg caaattaaat aaggctacta aaaaatatca ttacccctta      240 cctttatcg atcaaatgct agaaagatta tccaaacata cacattttg ctttctagat        300 ggttactctg gtttctctca aatacctgtg tcagccaaag atcaatcaaa gactacttt       360 acatgccctt ttggtacttt tgcttataga cgtatgcctt ttggtttatg taatgcacct      420
gctacctttc aaagatacat gatggctata ttatctgact tttgtgaaaa gatttgtgag      480
gttttcatgg acgactcttc catctatgga tcttcttttg atgattgctt gagcaacctt      540
gatcgagttt tgcagagatg tgaagaaact tatcttgtct tgaattggga aaagtgccaa      600
tttatggtta atgaaggtat tgtcctgggg cataaagttt ctgaaagagg tattcgagtt      660
gataaagcca aggttgatgc tattgaaaag atgccatgtc ccatggacat caaaggtata      720
agaagtttcc ttggtcatgc cggttttat aggaggttca taaaagactt cacgaaggtt      780

<210> SEQ ID NO 83
<211> LENGTH: 260
<212> TYPE: PRT
<213> ORGANISM: Triticum aestivum

<400> SEQUENCE: 83

Val Arg Lys Glu Val Phe Lys Leu Leu Glu Ala Gly Ile Ile Tyr Pro
  1               5                  10                  15

Val Ala Asp Ser Lys Trp Val Ile Pro Val His Glx Val Ile Val Ile
                 20                  25                  30

Thr Val Pro Lys Lys Gly Gly Ile Thr Val Pro Asn Asp Lys
             35                  40                  45

Asp Glu Leu Ile Pro Gln Arg Thr Ile Thr Gly Tyr Arg Met Val Ile
     50                  55                  60

Asp Phe Arg Lys Leu Asn Lys Ala Thr Lys Lys Tyr His Tyr Pro Leu
 65                  70                  75                  80

Pro Phe Ile Asp Gln Met Leu Glu Arg Leu Ser Lys His Thr His Phe
                 85                  90                  95

Cys Phe Leu Asp Gly Tyr Ser Gly Phe Ser Gln Ile Pro Val Ser Ala
            100                 105                 110

Lys Asp Gln Ser Lys Thr Thr Phe Thr Cys Pro Phe Gly Thr Phe Ala
        115                 120                 125

Tyr Arg Arg Met Pro Phe Gly Leu Cys Asn Ala Pro Ala Thr Phe Gln
    130                 135                 140

Arg Tyr Met Met Ala Ile Leu Ser Asp Phe Cys Glu Lys Ile Cys Glu
145                 150                 155                 160

Val Phe Met Asp Asp Ser Ser Ile Tyr Gly Ser Ser Phe Asp Asp Cys
                165                 170                 175
```

-continued

```
Leu Ser Asn Leu Asp Arg Val Leu Gln Arg Cys Glu Glu Thr Tyr Leu
            180                 185                 190
Val Leu Asn Trp Glu Lys Cys Gln Phe Met Val Asn Glu Gly Ile Val
            195                 200                 205
Leu Gly His Lys Val Ser Glu Arg Gly Ile Arg Val Asp Lys Ala Lys
            210                 215                 220
Val Asp Ala Ile Glu Lys Met Pro Cys Pro Met Asp Ile Lys Gly Ile
225                 230                 235                 240
Arg Ser Phe Leu Gly His Ala Gly Phe Tyr Arg Arg Phe Ile Lys Asp
                245                 250                 255
Phe Thr Lys Val
            260
```

<210> SEQ ID NO 84
<211> LENGTH: 762
<212> TYPE: DNA
<213> ORGANISM: Triticum aestivum

<400> SEQUENCE: 84

| | | |
|---|---|---|
| gtgcgtaagg aggtattcaa gcttctggag gcaggtataa tttatcccgt tgttgatagt | 60 |
| caatgggtaa gtcctgtcca ttgtgtcctt aagaagggag gtattactgt tgtccctaat | 120 |
| gataaagatg aattgattcc gcaaagaatt atcacaggtt ataggatggt aattgatttc | 180 |
| cgtaagttaa ataaagctac taagaaagat cattacccct tacctttat tgatcaaatg | 240 |
| ttagaaagat tatgcaaaca tacacattat tgctttctag atggttattc tggtttctct | 300 |
| caaatacctg tgtcagctaa ggatcaatca agactactt ttacatgccc ttttggtact | 360 |
| tttggttata gacgtatgcc tttcgattta tgtaatgcac ctgctacctt tcaaatatgc | 420 |
| atgatggcta tattctctga cttttgcgaa aagatttgtg aggttttcat ggacgacttt | 480 |
| tccgtctatg gttcctctta tgatgattgc ttgagcaatc ttaatcgagt tttgcagaga | 540 |
| tgtgaagaaa ctaatcttgt cttgaattgg gaaaagtgcc actttatggt taatgaaggt | 600 |
| attgtcttgg ggcacaaagt ttctgaacga ggtattgaag ttgataaggc caaggttgat | 660 |
| gctattgaaa agatgacatg tcccaaggac atcaaggta taagaagttt ccttggtcac | 720 |
| gccagatttt ataggaggtt cataaaagac ttcacaaagg tt | 762 |

<210> SEQ ID NO 85
<211> LENGTH: 254
<212> TYPE: PRT
<213> ORGANISM: Triticum aestivum

<400> SEQUENCE: 85

```
Val Arg Lys Glu Val Phe Lys Leu Leu Glu Ala Gly Ile Ile Tyr Pro
1               5                   10                  15
Val Val Asp Ser Gln Trp Val Ser Pro Val His Cys Val Leu Lys Lys
            20                  25                  30
Gly Gly Ile Thr Val Val Pro Asn Asp Lys Asp Glu Leu Ile Pro Gln
        35                  40                  45
Arg Ile Ile Thr Gly Tyr Arg Met Val Ile Asp Phe Arg Lys Leu Asn
    50                  55                  60
Lys Ala Thr Lys Lys Asp His Tyr Pro Leu Pro Phe Ile Asp Gln Met
65                  70                  75                  80
Leu Glu Arg Leu Cys Lys His Thr His Tyr Cys Phe Leu Asp Gly Tyr
                85                  90                  95
```

-continued

```
Ser Gly Phe Ser Gln Ile Pro Val Ser Ala Lys Asp Gln Ser Lys Thr
                100                 105                 110

Thr Phe Thr Cys Pro Phe Gly Thr Phe Gly Tyr Arg Met Pro Phe
            115                 120                 125

Asp Leu Cys Asn Ala Pro Ala Thr Phe Gln Ile Cys Met Met Ala Ile
    130                 135                 140

Phe Ser Asp Phe Cys Glu Lys Ile Cys Glu Val Phe Met Asp Phe
145                 150                 155                 160

Ser Val Tyr Gly Ser Ser Tyr Asp Asp Cys Leu Ser Asn Leu Asn Arg
                165                 170                 175

Val Leu Gln Arg Cys Glu Glu Thr Asn Leu Val Leu Asn Trp Glu Lys
            180                 185                 190

Cys His Phe Met Val Asn Glu Gly Ile Val Leu Gly His Lys Val Ser
                195                 200                 205

Glu Arg Gly Ile Glu Val Asp Lys Ala Lys Val Asp Ala Ile Glu Lys
            210                 215                 220

Met Thr Cys Pro Lys Asp Ile Lys Gly Ile Arg Ser Phe Leu Gly His
225                 230                 235                 240

Ala Arg Phe Tyr Arg Arg Phe Ile Lys Asp Phe Thr Lys Val
                245                 250
```

```
<210> SEQ ID NO 86
<211> LENGTH: 762
<212> TYPE: DNA
<213> ORGANISM: Triticum aestivum

<400> SEQUENCE: 86
gtgcggaaag aggtgctcaa gcttctggag gcaggtataa tttatcccgt tgctgagagt        60
cagtgggtaa gtcctgtcca ttgtgtccct aagaagggag gtattactgt tgtccctaat       120
gataaagatg aattgattcc tcaaagaatt attacaggtt ataggatggt aattgatttc       180
cgcaaattaa ataaagccac caagaaagat cattacccct tacctttat tgatcaaatg        240 ctagaaagat tatgcaaaca tacacattat tgcttcctag atggttattc tggtttctct       300
caaatacctg tgtcggctaa agatcaatca aagactactt ttacatgccc ttttggtact       360
tttgcttata gacgtatgcc ttttggttta tgtaatgcac cttctacctt tcaaagatgc       420
atgatggcta tattctctga ttttttgtgaa aagatttgtg aggttttcat ggacgaattt       480
tccgtctatg gttcctcttt tgatgattgc ttgagcaatc ctgatcgagt tttgcagaga       540
tgtgaagaaa ctaatcttgt cttgaattgg gaaaagtgcc actttatggt taatgaaggt       600
attgtcttgg ggcacaaagt ttctgaaaga ggtattgaag ttgataaagc caaggttgac       660
gctattgaaa agatgccatg tcccaaggac atcaaaggta taagaagttt ccttggtcac       720
gccggatttt ataggaggtt cataaaagac ttcacaaagg tt                          762

<210> SEQ ID NO 87
<211> LENGTH: 254
<212> TYPE: PRT
<213> ORGANISM: Triticum aestivum

<400> SEQUENCE: 87

Val Arg Lys Glu Val Leu Lys Leu Leu Glu Ala Gly Ile Ile TyrPro
  1               5                  10                  15

Val Ala Glu Ser Gln Trp Val Ser Pro Val His Cys Val ProLysLys
                 20                  25                  30
```

```
Gly Gly Ile Thr Val Pro Asn Asp Lys Asp Glu Leu Ile Pro Gln
            35                  40                  45
Arg Ile Ile Thr Gly Tyr Arg Met Val Ile Asp Phe Arg Lys Leu Asn
        50                  55                  60
Lys Ala Thr Lys Lys Asp His Tyr Pro Leu Pro Phe Ile Asp Gln Met
65                  70                  75                  80
Leu Glu Arg Leu Cys Lys His Thr His Tyr Cys Phe Leu Asp Gly Tyr
                85                  90                  95
Ser Gly Phe Ser Gln Ile Pro Val Ser Ala Lys Asp Gln Ser Lys Thr
            100                 105                 110
Thr Phe Thr Cys Pro Phe Gly Thr Phe Ala Tyr Arg Arg Met Pro Phe
        115                 120                 125
Gly Leu Cys Asn Ala Pro Ser Thr Phe Gln Arg Cys Met Met Ala Ile
    130                 135                 140
Phe Ser Asp Phe Cys Glu Lys Ile Cys Glu Val Phe Met Asp Glu Phe
145                 150                 155                 160
Ser Val Tyr Gly Ser Ser Phe Asp Asp Cys Leu Ser Asn Pro Asp Arg
                165                 170                 175
Val Leu Gln Arg Cys Glu Glu Thr Asn Leu Val Leu Asn Trp Glu Lys
            180                 185                 190
Cys His Phe Met Val Asn Glu Gly Ile Val Leu Gly His Lys Val Ser
        195                 200                 205
Glu Arg Gly Ile Glu Val Asp Lys Ala Lys Val Asp Ala Ile Glu Lys
    210                 215                 220
Met Pro Cys Pro Lys Asp Ile Lys Gly Ile Arg Ser Phe Leu Gly His
225                 230                 235                 240
Ala Gly Phe Tyr Arg Arg Phe Ile Lys Asp Phe Thr Lys Val
                245                 250

<210> SEQ ID NO 88
<211> LENGTH: 762
<212> TYPE: DNA
<213> ORGANISM: Triticum aestivum

<400> SEQUENCE: 88
gtgcgtaagg aggttttcaa gttccttgag gcaggtatta cttatcccgt tgctgatagt      60
gaatgggtaa gccctctcca ttgtgttcct aaaaagggag gtattaccgt tgttcttaat     120
gataaagatg aattgatccc gcaaataatt attacaggtt ataggatggt aattgatttc     180
cataagttaa ataaagctac taagaaagat cattacccct tacctcttat tgatcaaatt     240
ctagaaagac tatccaaaca cacacatttc tgctttctag atggttatac tggtttctct     300
caaatacctg tgtcagtgaa ggatcaatct aaaactactt ttacttgccc ttttggtact     360
tttgcttata gacttatgcc ttttggttta tgtaatgcac ctacttcctt tcaaagatgc     420
atgatggcta tattctctgt tttttgtgaa aatatttgtg aggtattcat ggatgatttc     480
```

```
tccgtttatg gatcctcttt tgatgattgt ttgagcaacc ttgatcgagt tttgcagaga      540
tgcgaagaca ctagtctcat cctgaattgg gaaaagtgtc actttatggt taatgaaggc      600
attgtcttgg ggcataagat ttccgagaga ggtattgaag ttgacaaagc caaagttgat      660
gctattgaaa agattccatg tcccaaggac ataaaggta taagaagttt ccttggtcat       720
gctggttttt ataggaggtt catcaaagac ttctcaaagg tt                         762
```

<210> SEQ ID NO 89
<211> LENGTH: 254
<212> TYPE: PRT
<213> ORGANISM: Triticum aestivum

<400> SEQUENCE: 89

```
Val Arg Lys Glu Val Phe Lys Phe Leu Glu Ala Gly Ile Thr Tyr Pro
  1               5                  10                  15

Val Ala Asp Ser Glu Trp Val Ser Pro Leu His Cys Val Pro Lys Lys
                 20                  25                  30

Gly Gly Ile Thr Val Val Leu Asn Asp Lys Asp Glu Leu Ile Pro Gln
             35                  40                  45

Ile Ile Ile Thr Gly Tyr Arg Met Val Ile Asp Phe His Lys Leu Asn
         50                  55                  60

Lys Ala Thr Lys Lys Asp His Tyr Pro Leu Pro Leu Ile Asp Gln Ile
 65                  70                  75                  80

Leu Glu Arg Leu Ser Lys His Thr His Phe Cys Phe Leu Asp Gly Tyr
                 85                  90                  95

Thr Gly Phe Ser Gln Ile Pro Val Ser Val Lys Asp Gln Ser Lys Thr
            100                 105                 110

Thr Phe Thr Cys Pro Phe Gly Thr Phe Ala Tyr Arg Leu Met Pro Phe
        115                 120                 125

Gly Leu Cys Asn Ala Pro Thr Ser Phe Gln Arg Cys Met Met Ala Ile
    130                 135                 140

Phe Ser Val Phe Cys Glu Asn Ile Cys Glu Val Phe Met Asp Asp Phe
145                 150                 155                 160

Ser Val Tyr Gly Ser Ser Phe Asp Asp Cys Leu Ser Asn Leu Asp Arg
                165                 170                 175

Val Leu Gln Arg Cys Glu Asp Thr Ser Leu Ile Leu Asn Trp Glu Lys
            180                 185                 190

Cys His Phe Met Val Asn Glu Gly Ile Val Leu Gly His Lys Ile Ser
        195                 200                 205

Glu Arg Gly Ile Glu Val Asp Lys Ala Lys Val Asp Ala Ile Glu Lys
    210                 215                 220

Ile Pro Cys Pro Lys Asp Ile Lys Gly Ile Arg Ser Phe Leu Gly His
225                 230                 235                 240

Ala Gly Phe Tyr Arg Arg Phe Ile Lys Asp Phe Ser Lys Val
                245                 250
```

<210> SEQ ID NO 90
<211> LENGTH: 791
<212> TYPE: DNA
<213> ORGANISM: Gossypium hirsutum

<400> SEQUENCE: 90

```
gtgcgcaagg aggttttaaa gctacttgat gacgggatga tctatcccat atctaacagt       60
aattgggtta gcccagtaca catagtacca aaaaagacca gtgcaaccgt aatcgagaat      120
```

```
tcggcaggtg agatagttcc cactcgggtc caaaacgggt ggagagtatg catcgattac    180
aggaagttga attccttaac tcggaaggat cactttccac ttcctttat tgaccagatg     240 ttagaacgtt tagctggaaa gtctcattat ttagaacgtt tagctggaaa gtctcattat    300
tgttgtttgg atggttacta aggtttttc cagatcccag tggcaccgga ggatcaagaa     360
agacaatgtt tacgtgccca tttggcacgt tttcttacag acggatgccg ttcggactct    420
gtaatgcacc agccagtttt cataggtgca tggtaagtat attttcagac tacgtcgata    480
aaattatcga ggtgttcatg gacgactta ctgtatatgg tgagtccttc gaggtaagtc     540
tgacgaacct tgcaaaaatt ttggaaagat gcttagaatt taatcttgtt ctaaattatg    600
agaaatgcca ttttatggta gacaagggat tagttctagg tcatattatt tctgctgatg    660
gaatttctgt tgataaagca aaaatcaaca tcattaactc actaccatac cccacaactg    720
tgagggagat tggtctttc cttggtcatg caggtttcta caagtggttc atcaaagact     780
tttcaaaagt t                                                          791
```

<210> SEQ ID NO 91
<211> LENGTH: 264
<212> TYPE: PRT
<213> ORGANISM: Gossypium hirsutum

<400> SEQUENCE: 91

```
Val Arg Lys Glu Val Leu Lys Leu Leu Asp Asp Gly Met Ile Tyr Pro
  1               5                  10                  15

Ile Ser Asn Ser Asn Trp Val Ser Pro Val His Ile Val Pro Lys Lys
             20                  25                  30

Thr Ser Ala Thr Val Ile Glu Asn Ser Ala Gly Glu Ile Val Pro Thr
         35                  40                  45

Arg Val Gln Asn Gly Trp Arg Val Cys Ile Asp Tyr Arg Lys Leu Asn
     50                  55                  60

Ser Leu Thr Arg Lys Asp His Phe Pro Leu Pro Phe Ile Asp Gln Met
 65                  70                  75                  80

Leu Glu Arg Leu Ala Gly Lys Ser His Tyr Leu Glu Arg Leu Ala Gly
                 85                  90                  95

Lys Ser His Tyr Cys Cys Leu Asp Gly Tyr Glx Gly Phe Phe Gln Ile
            100                 105                 110

Pro Val Ala Pro Glu Asp Gln Glu Lys Thr Met Phe Thr Cys Pro Phe
        115                 120                 125

Gly Thr Phe Ser Tyr Arg Arg Met Pro Phe Gly Leu Cys Asn Ala Pro
    130                 135                 140

Ala Ser Phe His Arg Cys Met Val Ser Ile Phe Ser Asp Tyr Val Asp
145                 150                 155                 160

Lys Ile Ile Glu Val Phe Met Asp Asp Phe Thr Val Tyr Gly Glu Ser
                165                 170                 175

Phe Glu Val Ser Leu Thr Asn Leu Ala Lys Ile Leu Glu Arg Cys Leu
            180                 185                 190

Glu Phe Asn Leu Val Leu Asn Tyr Glu Lys Cys His Phe Met Val Asp
        195                 200                 205

Lys Gly Leu Val Leu Gly His Ile Ile Ser Ala Asp Gly Ile Ser Val
    210                 215                 220

Asp Lys Ala Lys Ile Asn Ile Asn Ser Leu Pro Tyr Pro Thr Thr
225                 230                 235                 240

Val Arg Glu Ile Trp Ser Phe Leu Gly His Ala Gly Phe Tyr Lys Trp
                245                 250                 255
```

Phe Ile Lys Asp Phe Ser Lys Val
            260

<210> SEQ ID NO 92
<211> LENGTH: 763
<212> TYPE: DNA
<213> ORGANISM: Gossypium hirsutum

<400> SEQUENCE: 92

| | | | | | |
|---|---|---|---|---|---|
| gtgcgtaaag | aggtcgtaaa | gctacttgat | tccgggatga | tctatcccat | atctgacaat | 60 |
| aattgggtta | gtccagtcca | catagtaccc | aaaaagaccg | gtgtaaccgt | aattgagaat | 120 |
| tcagcaggtg | agatggttcc | cacttaagtc | cgaaacggtc | ggagagtatg | catcgattac | 180 |
| aggaagttga | attccttaac | tcggaaagat | cactttccac | ttcttttat | tgatcagatg | 240 |
| ttagaacatt | tagccagaaa | gtctcattat | tgttgtctgg | atggttactc | aggttttttc | 300 |
| cagatcccaa | tggcactaaa | ggatcaagaa | aagatgacat | ttacgtgccc | atttggcatg | 360 |
| ttcgcttata | gaaggatgtc | gtttcagact | ttgcaatgca | ccaaccatgt | ttcagaggtg | 420 |
| catgataagt | atattttttg | actatgttaa | gaaaataatt | gaggtgttca | tggacgaatt | 480 |
| tactgtatat | agtgagtcct | tcgaggtata | tttgtcaaat | ctagaaaaat | ttttggaaag | 540 |
| atgcttagaa | tttaatcttg | ttctaaatta | tgagaattgc | tatttaatgg | tagacaaggg | 600 |
| attagttcta | ggtcatatca | tttctgctaa | gggaatttct | gtcgataaag | taaaaattaa | 660 |
| catcataagc | tcaataccat | accccacaac | tgtgagggag | attcgttctt | tccttagtca | 720 |
| tataggtttc | tataggcgat | tcatcaagga | cttttcaaaa | gtt | | 763 |

<210> SEQ ID NO 93
<211> LENGTH: 254
<212> TYPE: PRT
<213> ORGANISM: Gossypium hirsutum

<400> SEQUENCE: 93

Val Arg Lys Glu Val Val Lys Leu Leu Asp Ser Gly Met Ile Tyr Pro
 1               5                  10                  15

Ile Ser Asp Asn Asn Trp Val Ser Pro Val His Ile Val Pro Lys Lys
            20                  25                  30

Thr Gly Val Thr Val Ile Glu Asn Ser Ala Gly Glu Met Val Pro Thr
        35                  40                  45

Glx Val Arg Asn Gly Arg Arg Val Cys Ile Asp Tyr Arg Lys Leu Asn
    50                  55                  60

Ser Leu Thr Arg Lys Asp His Phe Pro Leu Leu Phe Ile Asp Gln Met
65                  70                  75                  80

Leu Glu His Leu Ala Arg Lys Ser His Tyr Cys Cys Leu Asp Gly Tyr
                85                  90                  95

Ser Gly Phe Phe Gln Ile Pro Met Ala Leu Lys Asp Gln Glu Lys Met
            100                 105                 110

Thr Phe Thr Cys Pro Phe Gly Met Phe Ala Tyr Arg Arg Met Ser Phe
        115                 120                 125

Arg Leu Cys Asn Ala Pro Thr Met Phe Gln Arg Cys Met Ile Ser Ile
    130                 135                 140

Phe Phe Asp Tyr Val Lys Lys Ile Ile Glu Val Phe Met Asp Glu Phe
145                 150                 155                 160

Thr Val Tyr Ser Glu Ser Phe Glu Val Tyr Leu Ser Asn Leu Glu Lys
                165                 170                 175

```
Phe Leu Glu Arg Cys Leu Glu Phe Asn Leu Val Leu Asn Tyr Glu Asn
            180                 185                 190

Cys Tyr Leu Met Val Asp Lys Gly Leu Val Leu Gly His Ile Ile Ser
        195                 200                 205

Ala Lys Gly Ile Ser Val Asp Lys Val Lys Ile Asn Ile Ile Ser Ser
    210                 215                 220

Ile Pro Tyr Pro Thr Thr Val Arg Glu Ile Arg Ser Phe Leu Ser His
225                 230                 235                 240

Ile Gly Phe Tyr Arg Arg Phe Ile Lys Asp Phe Ser Lys Val
                245                 250

<210> SEQ ID NO 94
<211> LENGTH: 723
<212> TYPE: DNA
<213> ORGANISM: Gossypium hirsutum

<400> SEQUENCE: 94
gtgcgtaagg aggttttgaa attgttggat gctggaatga tatactcgat ctttgacagt    60
gattgggtta gctgggttca tgtcgtgcca agaaaactg gcgtgacagt ggtgaaaaac   120
tcatcaggag agctagtccc tacccgagtc cagaatcgat ggagggtttg catcgattac   180
aggaagttga acgcagctac ccgaaatgac cattttccac ttcccttcat tgatcaaatg   240
ctcgagcgat tagctaataa gacccattat tgttgtctcg atgggtactc aggacttttc   300
caaattccgg tggcacctga ggatcaagac aaaacaactt tcacgtgccc ctttggaacg   360
tttgcgtata agaatgtc gtttggactc tgtaatgctc cggccacttt ccagagatgt   420
atggtgagca tattctctga ttatgtcgag aaaatcattg aattcttcat ggatgacttc   480
acggtgtacg gtaactcttt taacgaatgt ctcgataatc ttgctaagat attacagaga   540
tgcctagaat ttaatcttgt tttaaattat gaaaaatgcc acttcatggt tgacaaagga   600
ttaattttgg gtcatatagt ttcttcagaa ggtattgagg tcaataaagc aaaaacgaat   660
attattgact cattacctta ccccagattt tacagacgat tcataaagga cttcacaaaa   720
gtt                                                                723

<210> SEQ ID NO 95
<211> LENGTH: 241
<212> TYPE: PRT
<213> ORGANISM: Gossypium hirsutum

<400> SEQUENCE: 95

Val Arg Lys Glu Val Leu Lys Leu Leu Asp Ala Gly Met Ile Tyr Ser
1               5                   10                  15

Ile Phe Asp Ser Asp Trp Val Ser Trp Val His Val Val Pro Lys Lys
            20                  25                  30

Thr Gly Val Thr Val Val Lys Asn Ser Ser Gly Glu Leu Val Pro Thr
        35                  40                  45

Arg Val Gln Asn Arg Trp Arg Val Cys Ile Asp Tyr Arg Lys Leu Asn
    50                  55                  60

Ala Ala Thr Arg Asn Asp His Phe Pro Leu Pro Phe Ile Asp Gln Met
65                  70                  75                  80

Leu Glu Arg Leu Ala Asn Lys Thr His Tyr Cys Cys Leu Asp Gly Tyr
                85                  90                  95

Ser Gly Leu Phe Gln Ile Pro Val Ala Pro Glu Asp Gln Asp Lys Thr
            100                 105                 110

Thr Phe Thr Cys Pro Phe Gly Thr Phe Ala Tyr Arg Arg Met Ser Phe
```

-continued

```
                115                 120                 125
Gly Leu Cys Asn Ala Pro Ala Thr Phe Gln Arg Cys Met Val Ser Ile
    130                 135                 140

Phe Ser Asp Tyr Val Glu Lys Ile Ile Glu Phe Phe Met Asp Asp Phe
145                 150                 155                 160

Thr Val Tyr Gly Asn Ser Phe Asn Glu Cys Leu Asp Asn Leu Ala Lys
                165                 170                 175

Ile Leu Gln Arg Cys Leu Glu Phe Asn Leu Val Leu Asn Tyr Glu Lys
                180                 185                 190

Cys His Phe Met Val Asp Lys Gly Leu Ile Leu Gly His Ile Val Ser
                195                 200                 205

Ser Glu Gly Ile Glu Val Asn Lys Ala Lys Thr Asn Ile Ile Asp Ser
    210                 215                 220

Leu Pro Tyr Pro Arg Phe Tyr Arg Arg Phe Ile Lys Asp Phe Thr Lys
225                 230                 235                 240

Val
```

```
<210> SEQ ID NO 96
<211> LENGTH: 762
<212> TYPE: DNA
<213> ORGANISM: Lycopersicon esculentum

<400> SEQUENCE: 96
gtgcggaaag aggttgtgaa gctgttagat acgggtattg tctagccaat ttcggacaac    60
aagtaggtta gtccagtaca atgtgaacct aaaaagggag acataacggt gatcactaat   120
gaaaaaaatg agttgatccc aaccatgata gtcacataat ggagaatatg catggattac   180
aggaaattga atgaagccac caggaaggac cattacccgg tccctttttat tgatcagatg   240
ttggaccggt tggctgggga ataatattat tgttttctta atggctattt acggtacaac   300
caaattgtga tttcaccaaa ggattaagag aaaaccactt tcacttgccc gtatggtaca   360
tatgctttca aaagatacc ttttgggtta tgaaatgcct cggctacttt ccaatgatgc   420
atgatggcta tttttcatga tatggttgaa gattttgttg agatattcat gaatgatttc   480
tcagtgtttg gggattcttt tgatatgtgc ttggagaatt tggacagtgt gttggctagt   540
tgtgaagaaa ctaatctttt cctaaactgg aataatagc aatttctagt aaaggaaggg   600
attatgctag gacataaggt gtcaaagaga ggtatggaag ttgatagtgc caaagtggag   660
gttattgaaa agcttccccc tcctatatct gttaaaggga tgcaaagttt tctgggtcat   720
gttgggttct ataggagatt cataaaagac ttcacaaagg tt                     762
```

```
<210> SEQ ID NO 97
<211> LENGTH: 254
<212> TYPE: PRT
<213> ORGANISM: Lycopersicon esculentum

<400> SEQUENCE: 97

Val Arg Lys Glu Val Val Lys Leu Leu Asp Thr Gly Ile Val Glx Pro
  1               5                  10                  15

Ile Ser Asp Asn Lys Glx Val Ser Pro Val Gln Cys Glu Pro Lys Lys
                 20                  25                  30

Gly Asp Ile Thr Val Ile Thr Asn Glu Lys Asn Glu Leu Ile Pro Thr
             35                  40                  45

Met Ile Val Thr Glx Trp Arg Ile Cys Met Asp Tyr Arg Lys Leu Asn
    50                  55                  60
```

Glu Ala Thr Arg Lys Asp His Tyr Pro Val Pro Phe Ile Asp Gln Met
65                  70                  75                  80

Leu Asp Arg Leu Ala Gly Glu Glx Tyr Tyr Cys Phe Leu Asn Gly Tyr
                85                  90                  95

Leu Arg Tyr Asn Gln Ile Val Ile Ser Pro Lys Asp Glx Glu Lys Thr
            100                 105                 110

Thr Phe Thr Cys Pro Tyr Gly Thr Tyr Ala Phe Lys Lys Ile Pro Phe
        115                 120                 125

Gly Leu Glx Asn Ala Ser Ala Thr Phe Gln Glx Cys Met Met Ala Ile
    130                 135                 140

Phe His Asp Met Val Glu Asp Phe Val Glu Ile Phe Met Asn Asp Phe
145                 150                 155                 160

Ser Val Phe Gly Asp Ser Phe Asp Met Cys Leu Glu Asn Leu Asp Ser
                165                 170                 175

Val Leu Ala Ser Cys Glu Glu Thr Asn Leu Phe Leu Asn Trp Glu Glx
            180                 185                 190

Glx Gln Phe Leu Val Lys Glu Gly Ile Met Leu Gly His Lys Val Ser
        195                 200                 205

Lys Arg Gly Met Glu Val Asp Ser Ala Lys Val Glu Val Ile Glu Lys
    210                 215                 220

Leu Pro Pro Ile Ser Val Lys Gly Met Gln Ser Phe Leu Gly His
225                 230                 235                 240

Val Gly Phe Tyr Arg Arg Phe Ile Lys Asp Phe Thr Lys Val
                245                 250

<210> SEQ ID NO 98
<211> LENGTH: 689
<212> TYPE: DNA
<213> ORGANISM: Lycopersicon esculentum

<400> SEQUENCE: 98
cgaaaggagg tggtgaaact ggaaattatc aagtagttgg atgctagagt aatctatcca      60
atcgccgata gtagttgggt atgcctagtt cagtgtgtac caaagaaagg gggaatgact     120
gtggtcccca acgaaaagaa tgaacttgtt cgaatgagac cggttactgg atggagggtg     180
tgcatggatt accgtaaact gaactcatag actgaaaaag actattttca tatgcccttc     240
atggatcaga tgttggatag acttgccgga aaagggtggt attgttttct tgatgggtat     300
tcggggtata atcagatttc tattgcacca gaagatcaag agaaaaccac tttcacttgt     360
ccatacggga cttttgcatt cagaagaatg tcgtttgggt tgtgcaatgc acccgcaacc     420
tttcagagat ggatgatgtc aatatttcct gacatgatgg aggatactat agaggttttt     480
atggatgatt tttctgtggt tggtgattca ttcgagcggt gcttgtccaa tttatctgag     540
gttcttaaga gatgtgaaga ctgcaatttg gtactaaact gggaaaagtg tcatttcatg     600
gtgaaagagg gtattgtgtt gggtcatcgc atttcagaaa agggcatgca tgttttact      660
ggtgattcat caaagacttc acaaaggtt                                        689

<210> SEQ ID NO 99
<211> LENGTH: 229
<212> TYPE: PRT
<213> ORGANISM: Lycopersicon esculentum

<400> SEQUENCE: 99

Arg Lys Glu Val Val Lys Leu Glu Ile Ile Lys Glx Leu Asp Ala Arg
1               5                   10                  15

Val Ile Tyr Pro Ile Ala Asp Ser Ser Trp Val Cys Leu Val Gln Cys
            20                  25                  30

Val Pro Lys Lys Gly Met Thr Val Val Pro Asn Glu Lys Asn Glu
        35                  40                  45

Leu Val Arg Met Arg Pro Val Thr Gly Trp Arg Val Cys Met Asp Tyr
    50                  55                  60

Arg Lys Leu Asn Ser Glx Thr Glu Lys Asp Tyr Phe His Met Pro Phe
65                  70                  75                  80

Met Asp Gln Met Leu Asp Arg Leu Ala Gly Lys Gly Trp Tyr Cys Phe
                85                  90                  95

Leu Asp Gly Tyr Ser Gly Tyr Asn Gln Ile Ser Ile Ala Pro Glu Asp
            100                 105                 110

Gln Glu Lys Thr Thr Phe Thr Cys Pro Tyr Gly Thr Phe Ala Phe Arg
            115                 120                 125

Arg Met Ser Phe Gly Leu Cys Asn Ala Pro Ala Thr Phe Gln Arg Trp
    130                 135                 140

Met Met Ser Ile Phe Ser Asp Met Met Glu Asp Thr Ile Glu Val Phe
145                 150                 155                 160

Met Asp Asp Phe Ser Val Val Gly Asp Ser Phe Glu Arg Cys Leu Ser
                165                 170                 175

Asn Leu Ser Glu Val Leu Lys Arg Cys Glu Asp Cys Asn Leu Val Leu
            180                 185                 190

Asn Trp Glu Lys Cys His Phe Met Val Lys Glu Gly Ile Val Leu Gly
    195                 200                 205

His Arg Ile Ser Glu Lys Gly Met His Val Phe Thr Gly Asp Ser Ser
    210                 215                 220

Lys Thr Ser Gln Arg
225

<210> SEQ ID NO 100
<211> LENGTH: 760
<212> TYPE: DNA
<213> ORGANISM: Lycopersicon esculentum

<400> SEQUENCE: 100
gtgcgtaagg aggtgtttaa gcttctagat gcgggtattg tctacccaat taggacaaca      60
agtgggttag tctagtacaa tgtgtaccta aaaagggagg catggcaatg attactaatg     120
aaaacaatga gtttatccca accagcacag tcacaagatg gcgaatatgc atgaattaca     180
cgaagttaat gaagccacta ggaagaatca ttacccaatt cttttttattg attatatgtt     240
ggaccggtta gctgggcaag aatattattg ttttttggat tactaatcag ggtacaacta     300
aattttgatt gcaccagagg atcaagagaa acaactttc acttgcccgt atggtacata     360
tgctttcaag aggatacctt tgggttatg caatgctctg tctaatttcc aaagatgcat     420
gatgactatt tttcatgata tggttgaata ttttgaggat atattcatgg atgatttctt     480
agtgttttgg gagtcttttg atagatgctt ggagaatttg aacaggttgt tagctaggtg     540
cgaacaaact aatcttgtcc tgaactggga aaaatgtcat ttttttagtaa aggaagggaa     600
ttttcgggg cataaggtgt aaaagatagg gctggaagtt gatcatgaca aagtggaagt     660
aattgaaaag atctcctctc ccattttgt gaaacgggtg agaagtttac taggtcatgc     720
tgagttttac aggatattca tcaaggactt ctcaaaggtt                           760

<210> SEQ ID NO 101
<211> LENGTH: 254
<212> TYPE: PRT
<213> ORGANISM: Lycopersicon esculentum

<400> SEQUENCE: 101

```
Val Arg Lys Glu Val Phe Lys Leu Leu Asp Ala Gly Ile Val Tyr Pro
 1               5                  10                  15
Ile Ser Asp Asn Lys Trp Val Ser Leu Val Gln Cys Val Pro Lys Lys
            20                  25                  30
Gly Gly Met Ala Met Ile Thr Asn Glu Asn Asn Glu Phe Ile Pro Thr
        35                  40                  45
Ser Thr Val Thr Arg Trp Arg Ile Cys Met Asn Tyr Thr Lys Leu Asn
50                  55                  60
Glu Ala Thr Arg Lys Asn His Tyr Pro Ile Leu Phe Ile Asp Tyr Met
65                  70                  75                  80
Leu Asp Arg Leu Ala Gly Gln Glu Tyr Tyr Cys Phe Leu Asp Tyr Glx
                85                  90                  95
Ser Gly Tyr Asn Glx Ile Leu Ile Ala Pro Glu Asp Gln Glu Lys Thr
            100                 105                 110
Thr Phe Thr Cys Pro Tyr Gly Thr Tyr Ala Phe Lys Arg Ile Pro Phe
        115                 120                 125
Gly Leu Cys Asn Ala Leu Ser Asn Phe Gln Arg Cys Met Met Thr Ile
130                 135                 140
Phe His Asp Met Val Glu Tyr Phe Glu Asp Ile Phe Met Asp Asp Phe
145                 150                 155                 160
Leu Val Phe Trp Glu Ser Phe Asp Arg Cys Leu Glu Asn Leu Asn Arg
                165                 170                 175
Leu Leu Ala Arg Cys Glu Gln Thr Asn Leu Val Leu Asn Trp Glu Lys
            180                 185                 190
Cys His Phe Leu Val Lys Glu Gly Asn Phe Ser Gly His Lys Val Glx
        195                 200                 205
Lys Ile Gly Leu Glu Val Asp His Asp Lys Val Glu Val Ile Glu Lys
210                 215                 220
Ile Ser Ser Pro Ile Phe Val Lys Arg Val Arg Ser Leu Leu Gly His
225                 230                 235                 240
Ala Glu Phe Tyr Arg Ile Phe Ile Lys Asp Phe Ser Lys Val
                245                 250
```

<210> SEQ ID NO 102
<211> LENGTH: 776
<212> TYPE: DNA
<213> ORGANISM: Lycopersicon esculentum

<400> SEQUENCE: 102

```
gtgcggaaag aagtgtttaa actggaatca ttaaatggtt ggatgctgga gtaatatatc      60
cgatctccga tagtagttgg gtatgcccta ttcagtgtgt acctaagaaa gggggaatga     120
ctgtggtccc caataagaaa atgaacttg ttctaatgag accggttact ggagggtggg     180
tgtgtatgga ttaccgtaaa ttaaatgcat ggactgaaaa agaccatttt cctatgccct     240
tcatggatca gatgttggat agacttgccg aaaaagggtg gtactgtttt cttgatggat     300
agtcaggta taattagatt tctattgcac cagaagatca agagaaaacc acatttactt     360
gtccatatgg gaccttttgca ttgaagagaa tgtcgtttgg gttgtgcaat gcacccgcca     420
catttcacag atgtaaaaat gttgatattc ttcgacatgg tggatgatac tattgatgct     480
```

```
tttatggatg attttctct tgttggtgaa tcattcgaga ggtgtttgaa ccatttatct      540
gatgtcctta agagatgtga agactgcaat ttagtactaa attgggaaaa atgccacttc    600
atggtgaaaa aaggtattgt tttgggtcat cgcattccag aaaagggcat agaggttgat    660
cgagctaaag tagaggtaat agagagactt cccccactat ctctgtaaaa ggtgtgagaa    720
gctttcttgg gcatgcaagt ttttaccgga gattcatcaa agacttcaca aaagtt        776
```

<210> SEQ ID NO 103
<211> LENGTH: 258
<212> TYPE: PRT
<213> ORGANISM: Lycopersicon esculentum

<400> SEQUENCE: 103

```
Ala Glu Arg Ser Val Glx Thr Gly Ile Ile Lys Trp Leu Asp Ala Gly
 1               5                  10                  15
Val Ile Tyr Pro Ile Ser Asp Ser Ser Trp Val Cys Pro Ile Gln Cys
            20                  25                  30
Val Pro Lys Lys Gly Gly Met Thr Val Val Pro Asn Lys Lys Asn Glu
        35                  40                  45
Leu Val Leu Met Arg Pro Val Thr Gly Gly Trp Val Cys Met Asp Tyr
    50                  55                  60
Arg Lys Leu Asn Ala Trp Thr Glu Lys Asp His Phe Pro Met Pro Phe
65                  70                  75                  80
Met Asp Gln Met Leu Asp Arg Leu Ala Glu Lys Gly Trp Tyr Cys Phe
                85                  90                  95
Leu Asp Gly Glx Ser Gly Tyr Asn Glx Ile Ser Ile Ala Pro Glu Asp
            100                 105                 110
Gln Glu Lys Thr Thr Phe Thr Cys Pro Tyr Gly Thr Phe Ala Leu Lys
        115                 120                 125
Arg Met Ser Phe Gly Leu Cys Asn Ala Pro Ala Thr Phe His Arg Cys
    130                 135                 140
Lys Met Leu Ile Phe Phe Asp Met Val Asp Asp Thr Ile Asp Ala Phe
145                 150                 155                 160
Met Asp Asp Phe Ser Leu Val Gly Glu Ser Phe Glu Arg Cys Leu Asn
                165                 170                 175
His Leu Ser Asp Val Leu Lys Arg Cys Glu Asp Cys Asn Leu Val Leu
            180                 185                 190
Asn Trp Glu Lys Cys His Phe Met Val Lys Lys Gly Ile Val Leu Gly
        195                 200                 205
His Arg Ile Pro Glu Lys Gly Ile Glu Val Asp Arg Ala Lys Val Glu
    210                 215                 220
Val Ile Glu Arg Leu Pro Pro Pro Ile Ser Val Lys Gly Val Arg Ser
225                 230                 235                 240
Phe Leu Gly His Ala Ser Phe Tyr Arg Arg Phe Ile Lys Asp Phe Thr
                245                 250                 255
Lys Val
```

<210> SEQ ID NO 104
<211> LENGTH: 761
<212> TYPE: DNA
<213> ORGANISM: Solanum tuberosum

<400> SEQUENCE: 104

```
gtgcggaagg aggtacttaa attgttggat gcacggattg tgtacccaat atcagacagt    60
```

-continued

| | |
|---|---|
| aaatgggtaa gtccagtaaa gtgtgtgccc aagaagggca gaatgacggt gttgactaat | 120 |
| gagaagaatg aggtaatccc cacaagaaca gtgactgggt gacggatttg catggactac | 180 |
| atgaagttga acgacgccac cagaaaggac cattatccgg tacctttcat tgataaaata | 240 |
| ttggataggt tggcaggaca tgagtactat tgttttcttg gtgtctactc agggtacaat | 300 |
| cagattgtta ttgcaataga ggactaggtg aaaaccacct tcacctgttc gtatggcaca | 360 |
| tatgcgttca agcacatgcc attcggcttg tgcaatgccc tggccacatt tcagagatgc | 420 |
| atgttggcaa tcttccatga tatggtggag gattttgttg aagttttcat ggatgacttc | 480 |
| ttggtgtttg gtgagtcttt tgaactttgt ttgactaatt ttgacagatt tcttgctagg | 540 |
| tgtgaagaga cgaatctggt gataaactga tagaagtgtc actttctggt tcgagaggga | 600 |
| attgtgttgg gacacaagat ctccaaaaat gggctgaaag ttgacaaagc caacgtagag | 660 |
| gttattgaga aattgccacc cccatcacag tgaaggtaat taaaagctta ctaggacatg | 720 |
| cttggtttta tacgaggttc atcaaagact tcacaaaggt t | 761 |

<210> SEQ ID NO 105
<211> LENGTH: 254
<212> TYPE: PRT
<213> ORGANISM: Solanum tuberosum

<400> SEQUENCE: 105

```
Val Arg Lys Glu Val Leu Lys Leu Leu Asp Ala Arg Ile Val Tyr Pro
 1               5                  10                  15
Ile Ser Asp Ser Lys Trp Val Ser Pro Val Lys Cys Val Pro Lys Lys
            20                  25                  30
Gly Arg Met Thr Val Leu Thr Asn Glu Lys Asn Glu Val Ile Pro Thr
        35                  40                  45
Arg Thr Val Thr Gly Glx Arg Ile Cys Met Asp Tyr Met Lys Leu Asn
    50                  55                  60
Asp Ala Thr Arg Lys Asp His Tyr Pro Val Pro Phe Ile Asp Lys Ile
65                  70                  75                  80
Leu Asp Arg Leu Ala Gly His Glu Tyr Tyr Cys Phe Leu Gly Val Tyr
                85                  90                  95
Ser Gly Tyr Asn Gln Ile Val Ile Ala Ile Glu Asp Glx Val Lys Thr
            100                 105                 110
Thr Phe Thr Cys Ser Tyr Gly Thr Tyr Ala Phe Lys His Met Pro Phe
        115                 120                 125
Gly Leu Cys Asn Ala Leu Ala Thr Phe Gln Arg Cys Met Leu Ala Ile
    130                 135                 140
Phe His Asp Met Val Glu Asp Phe Val Glu Val Phe Met Asp Asp Phe
145                 150                 155                 160
Leu Val Phe Gly Glu Ser Phe Glu Leu Cys Leu Thr Asn Phe Asp Arg
                165                 170                 175
Phe Leu Ala Arg Cys Glu Glu Thr Asn Leu Val Ile Asn Glx Glx Lys
            180                 185                 190
Cys His Phe Leu Val Arg Glu Gly Ile Val Leu Gly His Lys Ile Ser
        195                 200                 205
Lys Asn Gly Leu Lys Val Asp Lys Ala Asn Val Glu Val Ile Glu Lys
    210                 215                 220
Leu Pro Pro Pro Ile Thr Val Lys Val Ile Lys Ser Leu Leu Gly His
225                 230                 235                 240
Ala Trp Phe Tyr Thr Arg Phe Ile Lys Asp Phe Thr Lys Val
                245                 250
```

<210> SEQ ID NO 106
<211> LENGTH: 760
<212> TYPE: DNA
<213> ORGANISM: Solanum tuberosum

<400> SEQUENCE: 106

```
gtgcgtaaag aggttttcaa actgctagat gtcggtattg tatatccgat ttcagaaagc     60
aaatgggtca gcccagttta gtgtgtgcct aaaaaaagag gcatgccggt gatcaccaat    120
gaaaaaaatg agttgattcc aaccaggaca gtgacagggt ggcgaatatg catggattat    180
aggaaattga atgaggccac cagaaaggat cactgcccgg ttcctttttat tgatcagatg    240
ctggacaggt tagttgggca agaatattat tgtttcctgg aaggctattc aggatacaac    300
caaattgtga ttgcaccaga ggaccaggag aaaactacat tcacttgtct gtatgggaca    360
tatgctttca gtgactgcc gtttgggcta tgcaatgctc cagccacctt ccaaagatga    420
atgatggcta tctttcatga tatggttgaa gattttgtgg agatattcat ggatgacttc    480
tcagtcttta gggagtcttt tgataggtgt ttggagaatt gggacagggt gctggctaga    540
tgcgaggaaa ctaatctcat cctaaactgg aaaaaatgtc atttcctagt aaatgaaggg    600
attgtattgg ccataaggt gtcaaagaga gggctggaag ttgatcgtgc caaagtggaa    660
gttattgaaa aactacctcc tccaatctgt taaagggggtg agaagctttc tgggtcatgc    720
tggttttac aggagattta taaggactt cacaaaggtt                             760
```

<210> SEQ ID NO 107
<211> LENGTH: 254
<212> TYPE: PRT
<213> ORGANISM: Solanum tuberosum

<400> SEQUENCE: 107

```
Val Arg Lys Glu Val Phe Lys Leu Leu Asp Val Gly Ile Val Tyr Pro
  1               5                  10                  15

Ile Ser Glu Ser Lys Trp Val Ser Pro Val Glx Cys Val Pro Lys Lys
                 20                  25                  30

Arg Gly Met Pro Val Ile Thr Asn Glu Lys Asn Glu Leu Ile Pro Thr
             35                  40                  45

Arg Thr Val Thr Gly Trp Arg Ile Cys Met Asp Tyr Arg Lys Leu Asn
         50                  55                  60

Glu Ala Thr Arg Lys Asp His Cys Pro Val Pro Phe Ile Asp Gln Met
 65                  70                  75                  80

Leu Asp Arg Leu Val Gly Gln Glu Tyr Tyr Cys Phe Leu Glu Gly Tyr
                 85                  90                  95

Ser Gly Tyr Asn Gln Ile Val Ile Ala Pro Glu Asp Gln Glu Lys Thr
            100                 105                 110

Thr Phe Thr Cys Leu Tyr Gly Thr Tyr Ala Phe Lys Glx Leu Pro Phe
        115                 120                 125

Gly Leu Cys Asn Ala Pro Ala Thr Phe Gln Arg Glx Met Met Ala Ile
    130                 135                 140

Phe His Asp Met Val Glu Asp Phe Val Glu Ile Phe Met Asp Asp Phe
145                 150                 155                 160

Ser Val Phe Arg Glu Ser Phe Asp Arg Cys Leu Glu Asn Trp Asp Arg
                165                 170                 175

Val Leu Ala Arg Cys Glu Glu Thr Asn Leu Ile Leu Asn Trp Lys Lys
            180                 185                 190
```

Cys His Phe Leu Val Asn Glu Gly Ile Val Leu Gly His Lys Val Ser
        195                 200                 205

Lys Arg Gly Leu Glu Val Asp Arg Ala Lys Val Glu Val Ile Glu Lys
        210                 215                 220

Leu Pro Pro Ile Ser Val Lys Gly Val Arg Ser Phe Leu Gly His
225                 230                 235                 240

Ala Gly Phe Tyr Arg Arg Phe Ile Lys Asp Phe Thr Lys Val
                245                 250

<210> SEQ ID NO 108
<211> LENGTH: 761
<212> TYPE: DNA
<213> ORGANISM: Solanum tuberosum

<400> SEQUENCE: 108

| | | | | | |
|---|---|---|---|---|---|
| gtgcgtaaag | aggttttcaa | gctctggatg | caggtattgt | ctatccaatt | tcagacagca | 60 |
| agtgggtcag | tccagttcag | tgtgtgccta | aaaagggagg | catgacggtg | atcactaatg | 120 |
| aaaaaaatga | gttgattcca | accaggacag | tgacaggatg | gcgaatatgc | atggattaca | 180 |
| gaaaattaaa | tgaagctacc | agaaaggatc | actacccggt | tccttttatt | gatcagatgc | 240 |
| tggacaggtt | ggctggacaa | gaatattatt | gtttcttgga | tggttattca | ggatacaacc | 300 |
| aaatagtgat | tgcaccagag | gaccagggga | aaactacatt | cacttgcttg | tatgggacat | 360 |
| atgtttccaa | gagaatgtcg | tttgggctat | gcaatgctcc | atccattttc | caaagatgca | 420 |
| tgatggccat | cttccatgat | aaggttgaag | attttatgga | atattcatg | gatgacttct | 480 |
| cagtatttgg | ggagtctttt | gacaggtgct | tggagaattt | agacagagtg | ttggctagat | 540 |
| gcgaggaaac | taattttgtc | ctaaactggg | aaaaatgtca | tttcctagtg | aaggaaggga | 600 |
| ttgtgttggg | tcataaggtg | tcaaagagag | ggctggaagt | tgatcgtgcc | agagtggaaa | 660 |
| taatcaaaaa | gctacctccc | ccaatttctg | ttaaaggggg | cgaagtttt | ttgggtcatg | 720 |
| ttagtttcta | cgaaagattc | ataaaggact | tcaccaaggt | t | | 761 |

<210> SEQ ID NO 109
<211> LENGTH: 254
<212> TYPE: PRT
<213> ORGANISM: Solanum tuberosum

<400> SEQUENCE: 109

Val Arg Lys Glu Val Phe Lys Leu Leu Asp Ala Gly Ile Val Tyr Pro
1               5                   10                  15

Ile Ser Asp Ser Lys Trp Val Ser Pro Val Gln Cys Val Pro Lys Lys
            20                  25                  30

Gly Gly Met Thr Val Ile Thr Asn Glu Lys Asn Glu Leu Ile Pro Thr
        35                  40                  45

Arg Thr Val Thr Gly Trp Arg Ile Cys Met Asp Tyr Arg Lys Leu Asn
    50                  55                  60

Glu Ala Thr Arg Lys Asp His Tyr Pro Val Pro Phe Ile Asp Gln Met
65                  70                  75                  80

Leu Asp Arg Leu Ala Gly Gln Glu Tyr Tyr Cys Phe Leu Asp Gly Tyr
                85                  90                  95

Ser Gly Tyr Asn Gln Ile Val Ile Ala Pro Glu Asp Gln Gly Lys Thr
            100                 105                 110

Thr Phe Thr Cys Leu Tyr Gly Thr Tyr Val Ser Lys Arg Met Ser Phe
        115                 120                 125

```
Gly Leu Cys Asn Ala Pro Ser Ile Phe Gln Arg Cys Met Met Ala Ile
    130                 135                 140

Phe His Asp Lys Val Glu Asp Phe Met Glu Ile Phe Met Asp Asp Phe
145                 150                 155                 160

Ser Val Phe Gly Glu Ser Phe Asp Arg Cys Leu Glu Asn Leu Asp Arg
                165                 170                 175

Val Leu Ala Arg Cys Glu Glu Thr Asn Phe Val Leu Asn Trp Glu Lys
            180                 185                 190

Cys His Phe Leu Val Lys Glu Gly Ile Val Leu Gly His Lys Val Ser
        195                 200                 205

Lys Arg Gly Leu Glu Val Asp Arg Ala Arg Val Glu Ile Ile Lys Lys
    210                 215                 220

Leu Pro Pro Pro Ile Ser Val Lys Gly Val Arg Ser Phe Leu Gly His
225                 230                 235                 240

Val Ser Phe Tyr Glu Arg Phe Ile Lys Asp Phe Thr Lys Val
                245                 250
```

<210> SEQ ID NO 110
<211> LENGTH: 762
<212> TYPE: DNA
<213> ORGANISM: Solanum tuberosum

<400> SEQUENCE: 110

```
gtgcgtaagg aggtcctcaa gctgtctgat gcaggaattg tgtaccccat ttatgatata      60
aagtggatca gcccagttca ctgtgtgccg aaaaagggag gcatgacgat tattactaat     120
gaaaagaagg agttgatttc agctagaacg gtgatagagt ggcacatatg aatggactat     180
aggagactaa atgaggcaac tagaaaggaa cactacccag ttcctttcat tgatcaaatg     240
ttggacaggt ttattgggca agagtattat tgtttcctag atggctattc aggatataat     300
caaattgtga ttgcgccata agataaagag aaaactacat ttacttctct atatgggaca     360
tatgccttca agagaatgtc gtttgggccg tgcaatgctc caaccacatt ccaaagatgc     420
atgacagcca tttttcatga tatggtcaaa tattttgtgg agatattcat ggatgaattc     480
ttagtctttg gggagtcttt tgacacgtgt ctagaatatt tggacaatgt gcttgccaga     540
tgtgaggaaa ctaatcccgt cctcaactgg gaaaaatgtc attttctagt gaagaagggg     600
attgtactag gccacaaggt ttcagaggaa ggactggaag ttgatcgtgg aaaagtagag     660
gtaatttaaa agctacccc tcaagtcttc gttaaggggg tgagaaggtt ccttggtcat     720
tctaggttcg aaatgagatt cataaaagac ttcacaaaag tt                        762
```

<210> SEQ ID NO 111
<211> LENGTH: 254
<212> TYPE: PRT
<213> ORGANISM: Solanum tuberosum

<400> SEQUENCE: 111

```
Val Arg Lys Glu Val Leu Lys Leu Ser Asp Ala Gly Ile Val Tyr Pro
1               5                   10                  15

Ile Tyr Asp Ile Lys Trp Ile Ser Pro Val His Cys Val Pro Lys Lys
            20                  25                  30

Gly Gly Met Thr Ile Ile Thr Asn Glu Lys Lys Glu Leu Ile Ser Ala
        35                  40                  45

Arg Thr Val Ile Glu Trp His Ile Glx Met Asp Tyr Arg Arg Leu Asn
    50                  55                  60

Glu Ala Thr Arg Lys Glu His Tyr Pro Val Pro Phe Ile Asp Gln Met
```

|   |   |   | 65 |   |   |   | 70 |   |   |   | 75 |   |   |   | 80 |
|---|---|---|---|---|---|---|---|---|---|---|---|---|---|---|---|

Leu Asp Arg Phe Ile Gly Gln Glu Tyr Tyr Cys Phe Leu Asp Gly Tyr
            85                  90                  95

Ser Gly Tyr Asn Gln Ile Val Ile Ala Pro Glx Asp Lys Glu Lys Thr
             100                 105                 110

Thr Phe Thr Ser Leu Tyr Gly Thr Tyr Ala Phe Lys Arg Met Ser Phe
             115                 120                 125

Gly Pro Cys Asn Ala Pro Thr Thr Phe Gln Arg Cys Met Thr Ala Ile
             130                 135                 140

Phe His Asp Met Val Lys Tyr Phe Val Glu Ile Phe Met Asp Glu Phe
145                  150                 155                 160

Leu Val Phe Gly Glu Ser Phe Asp Thr Cys Leu Glu Tyr Leu Asp Asn
             165                 170                 175

Val Leu Ala Arg Cys Glu Glu Thr Asn Pro Val Leu Asn Trp Glu Lys
             180                 185                 190

Cys His Phe Leu Val Lys Lys Gly Ile Val Leu Gly His Lys Val Ser
             195                 200                 205

Glu Glu Gly Leu Glu Val Asp Arg Gly Lys Val Glu Val Ile Glx Lys
         210                 215                 220

Leu Pro Pro Gln Val Phe Val Lys Gly Val Arg Arg Phe Leu Gly His
225                  230                 235                 240

Ser Arg Phe Glu Met Arg Phe Ile Lys Asp Phe Thr Lys Val
             245                 250

<210> SEQ ID NO 112
<211> LENGTH: 762
<212> TYPE: DNA
<213> ORGANISM: Solanum tuberosum

<400> SEQUENCE: 112

| gtgcggaagg aggtttttaa gctgctggat gcgggtattg tataccagat tcagatagc | 60 |
| aaagggtct acccgattta gtttgtgcct aaaaaatgca gcatgacagt gatcaccaat | 120 |
| gaaaagaatg agctgattcc aaccaggaca gtgacagggt ggcgaatatg catggattat | 180 |
| atgaagttga atgaggccac cagaaaggat cactacccga ttcatttat tgatcagatg | 240 |
| ttggacaagt tagctgagta aaatattat tgtttcttgg cttgttattc aagatacaac | 300 |
| caatttctca ttgcaccaca ggaccaggag gaaactacat tcacttgtcc ttatgggaca | 360 |
| tatgctttca agcgaatgtc gtttgggcta tgcaatgctc caaccacctt ccaaagatgc | 420 |
| ataagggcta tctttcatga tatggttgaa gattttgtgg agatattcat ggatgacttc | 480 |
| tcagtctttg ggtagtcttt tgagaggtgt ctggaaaatt ttgacagggt gctggctgta | 540 |
| tgcgaggaaa ctaattttt cctaaactgg gaaaaatgtc attttctagt gaaggaaggg | 600 |
| attgtattgg gacataaggt gtcaaagtga aggcttgaag ttgatcgtgc caaagtggaa | 660 |
| gtcgttgaaa acctaccttc cccattctct gttaaagggg tgagaagttt tttgggtcat | 720 |
| gctggtttct ataggagatt tatcaaagac ttcactaagg tt | 762 |

<210> SEQ ID NO 113
<211> LENGTH: 254
<212> TYPE: PRT
<213> ORGANISM: Solanum tuberosum

<400> SEQUENCE: 113

Val Arg Lys Glu Val Phe Lys Leu Leu Asp Ala Gly Ile Val Tyr Gln
1               5                   10                  15

Ile Ser Asp Ser Lys Gly Val Tyr Pro Ile Glx Phe Val Pro Lys Lys
              20                  25                  30

Cys Ser Met Thr Val Ile Thr Asn Glu Lys Asn Glu Leu Ile Pro Thr
          35                  40                  45

Arg Thr Val Thr Gly Trp Arg Ile Cys Met Asp Tyr Met Lys Leu Asn
      50                  55                  60

Glu Ala Thr Arg Lys Asp His Tyr Pro Ile His Phe Ile Asp Gln Met
65                  70                  75                  80

Leu Asp Lys Leu Ala Glu Glx Lys Tyr Tyr Cys Phe Leu Ala Cys Tyr
                  85                  90                  95

Ser Arg Tyr Asn Gln Phe Leu Ile Ala Pro Gln Asp Gln Glu Glu Thr
              100                 105                 110

Thr Phe Thr Cys Pro Tyr Gly Thr Tyr Ala Phe Lys Arg Met Ser Phe
          115                 120                 125

Gly Leu Cys Asn Ala Pro Thr Thr Phe Gln Arg Cys Ile Arg Ala Ile
      130                 135                 140

Phe His Asp Met Val Glu Asp Phe Val Glu Ile Phe Met Asp Asp Phe
145                 150                 155                 160

Ser Val Phe Gly Glx Ser Phe Glu Arg Cys Leu Glu Asn Phe Asp Arg
                  165                 170                 175

Val Leu Ala Val Cys Glu Glu Thr Asn Phe Phe Leu Asn Trp Glu Lys
              180                 185                 190

Cys His Phe Leu Val Lys Glu Gly Ile Val Leu Gly His Lys Val Ser
          195                 200                 205

Lys Glx Arg Leu Glu Val Asp Arg Ala Lys Val Glu Val Val Glu Asn
      210                 215                 220

Leu Pro Ser Pro Phe Ser Val Lys Gly Val Arg Ser Phe Leu Gly His
225                 230                 235                 240

Ala Gly Phe Tyr Arg Arg Phe Ile Lys Asp Phe Thr Lys Val
                  245                 250

<210> SEQ ID NO 114
<211> LENGTH: 793
<212> TYPE: DNA
<213> ORGANISM: Solanum tuberosum

<400> SEQUENCE: 114 aactttgtg aagtctttaa tgaaggatgt tgtcagagaa gaagtcatca agtggctgga      60
tacagggatt gtgtacccaa tatctgacaa taaatgggca agtccagtgc agtgtgtgcc     120
taaaaaggga ggaatgacag ttgtgaccaa tgagaaaaat gagttgatcc ccacaagaac     180
agtaactggg tggaggctat gcatggacta cagaaaactc aatgaagcca ccaggaagga     240
ccactattcg gtaccgttca ttgatcaaat gttagacagg ttggctggcc aagagtatta     300
ctgtttcctt gatggttatt caaggtataa ttagatcgtc attgcacctg aggatcaaga     360
gaatacgaca ttcacttgcc catatggcac gtatgcattc aaacgcttgc cattcggctt     420
gtgcaatgcc ccaaccctat ttcagagatg tatgatggca atcttccatg atatggtgga     480
agattttgtt aaagtataca tggacgattt ctcggtgttt ggtgagtcgt tcgaactttg     540
tttatctaat cgtgatagag ttcttactag gtgtgaggag accaatttgg tgctgaactg     600
ggagaagtgt cactttctgg tcagagaagg aattatgttg gggcagaaga tctccaaaag     660
tgggctagaa gtagacaagg cgaaggtgga agtgattgag aagttgccac caccaatata     720
agtaaaggga gtgcgaagct tccttggaca tgctggtttt tacaagaggt tcataaagga     780

<210> SEQ ID NO 115
<211> LENGTH: 264
<212> TYPE: PRT
<213> ORGANISM: Solanum tuberosum

<400> SEQUENCE: 115

```
Thr Phe Val Lys Ser Leu Met Lys Asp Val Arg Glu Glu Val Ile
1               5                   10                  15

Lys Trp Leu Asp Thr Gly Ile Val Tyr Pro Ile Ser Asp Asn Lys Trp
            20                  25                  30

Ala Ser Pro Val Gln Cys Val Pro Lys Lys Gly Gly Met Thr Val Val
        35                  40                  45

Thr Asn Glu Lys Asn Glu Leu Ile Pro Thr Arg Thr Val Thr Gly Trp
    50                  55                  60

Arg Leu Cys Met Asp Tyr Arg Lys Leu Asn Glu Ala Thr Arg Lys Asp
65                  70                  75                  80

His Tyr Ser Val Pro Phe Ile Asp Gln Met Leu Asp Arg Leu Ala Gly
                85                  90                  95

Gln Glu Tyr Tyr Cys Phe Leu Asp Gly Tyr Ser Arg Tyr Asn Glx Ile
            100                 105                 110

Val Ile Ala Pro Glu Asp Gln Glu Asn Thr Thr Phe Thr Cys Pro Tyr
        115                 120                 125

Gly Thr Tyr Ala Phe Lys Arg Leu Pro Phe Gly Leu Cys Asn Ala Pro
    130                 135                 140

Thr Leu Phe Gln Arg Cys Met Met Ala Ile Phe His Asp Met Val Glu
145                 150                 155                 160

Asp Phe Val Lys Val Tyr Met Asp Asp Phe Ser Val Phe Gly Glu Ser
                165                 170                 175

Phe Glu Leu Cys Leu Ser Asn Arg Asp Arg Val Leu Thr Arg Cys Glu
            180                 185                 190

Glu Thr Asn Leu Val Leu Asn Trp Glu Lys Cys His Phe Leu Val Arg
        195                 200                 205

Glu Gly Ile Met Leu Gly Gln Lys Ile Ser Lys Ser Gly Leu Glu Val
    210                 215                 220

Asp Lys Ala Lys Val Glu Val Ile Glu Lys Leu Pro Pro Pro Ile Glx
225                 230                 235                 240

Val Lys Gly Val Arg Ser Phe Leu Gly His Ala Gly Phe Tyr Lys Arg
                245                 250                 255

Phe Ile Lys Asp Phe Ser Lys Val
            260
```

<210> SEQ ID NO 116
<211> LENGTH: 761
<212> TYPE: DNA
<213> ORGANISM: Platanus occidentalis

<400> SEQUENCE: 116

```
gtgcgtaagg aggttttcaa acttcttaaa gtttgagtga tttatcctat ttaggatagg      60
aattgggtca gcccggttca gtggttcct  aaaaagattg gaataaccgt tgtgaaaaat     120
tagaatgatg agttggttcc taccagtgtt cagaatgggt ggagggttgt atagattata    180
gaaaattgaa tgttgtaacc cgcaaggatc acttcccttt accttttatt gatcaaatgc    240
ttgaaaggtt agttggtcat tcttactatt gtttcctaga tggttattca agttatttcc    300
```

```
agattgtaat tactccagag gattaagaaa agacaacttt tacatgtcca tttgggactt    360
ttgcatatcg ttgcatgccc tttggccttt gcaatgcccc aaccactttc caaggtgta    420 tggttagcat atttcatat tacattgaga atatcataga agtttttatg gatgatttca    480
tagtttatgg agactccttt aataattttc tgcataacct tacacttgtt cttcaaagat    540
gcatagaaac taaccttgtg ttaaattatg aaaaatgtca ttttatggtt gaacaaggta    600
tagttttggg tcatgttatt tcatctaaag gaattgaggt agataaagct aaagttgata    660
ttattcaatc tttaccttat ctcattagta tgcggaaagt tcattctttt cttggacatg    720
caggtttcta ccgaagattc attaaagact ttacaaaggt t                        761
```

<210> SEQ ID NO 117
<211> LENGTH: 254
<212> TYPE: PRT
<213> ORGANISM: Platanus occidentalis

<400> SEQUENCE: 117

```
Val Arg Lys Glu Val Phe Lys Leu Leu Lys Val Glx Val Ile Tyr Pro
 1               5                  10                  15

Ile Glx Asp Arg Asn Trp Val Ser Pro Val Gln Val Pro Lys Lys
            20                  25                  30

Ile Gly Ile Thr Val Val Lys Asn Glx Asn Asp Glu Leu Val Pro Thr
        35                  40                  45

Ser Val Gln Asn Gly Trp Arg Val Cys Ile Asp Tyr Arg Lys Leu Asn
    50                  55                  60

Val Val Thr Arg Lys Asp His Phe Pro Leu Pro Phe Ile Asp Gln Met
65                  70                  75                  80

Leu Glu Arg Leu Val Gly His Ser Tyr Tyr Cys Phe Leu Asp Gly Tyr
                85                  90                  95

Ser Ser Tyr Phe Gln Ile Val Ile Thr Pro Glu Asp Glx Glu Lys Thr
            100                 105                 110

Thr Phe Thr Cys Pro Phe Gly Thr Phe Ala Tyr Arg Cys Met Pro Phe
        115                 120                 125

Gly Leu Cys Asn Ala Pro Thr Thr Phe Gln Arg Cys Met Val Ser Ile
    130                 135                 140

Phe Ser Tyr Tyr Ile Glu Asn Ile Ile Glu Val Phe Met Asp Asp Phe
145                 150                 155                 160

Ile Val Tyr Gly Asp Ser Phe Asn Asn Phe Leu His Asn Leu Thr Leu
                165                 170                 175

Val Leu Gln Arg Cys Ile Glu Thr Asn Leu Val Leu Asn Tyr Glu Lys
            180                 185                 190

Cys His Phe Met Val Glu Gln Gly Ile Val Leu Gly His Val Ile Ser
        195                 200                 205

Ser Lys Gly Ile Glu Val Asp Lys Ala Lys Val Asp Ile Ile Gln Ser
    210                 215                 220

Leu Pro Tyr Leu Ile Ser Met Arg Lys Val His Ser Phe Leu Gly His
225                 230                 235                 240

Ala Gly Phe Tyr Arg Arg Phe Ile Lys Asp Phe Thr Lys Val
                245                 250
```

<210> SEQ ID NO 118
<211> LENGTH: 762
<212> TYPE: DNA
<213> ORGANISM: Platanus occidentalis

```
<400> SEQUENCE: 118
gtgcgtaagg aagttttcaa gcttcttgaa gttggagtga tttatcttat ttcgaatagc      60
aattgggtta gcccagttca agtggctcct aaaaagactg gaataaccgt tgtgaaaaat     120
cagaatgatg agttagttcc tacccatgtt cagaatgggt ggtgggtttg tataaattat     180
agaaaattaa atgttataac ctgcaaggat cacttccctt tacctttat tgataaaatg      240 cttgaaaggt tagctggtca ttcttactat tgtttccttg atggttattt aggttatttt     300
caaattgcaa ttacttcgga ggatcaagaa aagatgattt ttaagtgccc attcgggact     360
tttgcatatc gtcacatgcc ctttggcctt tgcaatgccc caaccacttt ctaaaggtgt     420
atggttagca tattttcaga ttacattgag aatatcatag aagtctttat ggatgatttc     480
acagtttatg gagactcctt tgataattgt ctgcataacc ttacacttgt tattcaaaga     540
tgcatagaaa ctaacctagt gttaaattct taaaaatgtc attttatggt tgaacaaggt     600
atagttttgg gtcatgttgt ttcatctagg ggaattgagg tagataaacc taagttgat      660 attattcaaa ctttacctta ttccactagt gtgcgagaag ttcgttcttt tcttggacat     720
gtaggttttt actgaagatt cataaaagac ttcacaaagg tt                        762

<210> SEQ ID NO 119
<211> LENGTH: 254
<212> TYPE: PRT
<213> ORGANISM: Platanus occidentalis

<400> SEQUENCE: 119

Val Arg Lys Glu Val Phe Lys Leu Leu Glu Val Gly Val Ile Tyr Leu
  1               5                  10                  15

Ile Ser Asn Ser Asn Trp Val Ser Pro Val Gln Val Ala Pro Lys Lys
                 20                  25                  30

Thr Gly Ile Thr Val Val Lys Asn Gln Asn Asp Glu Leu Val Pro Thr
             35                  40                  45

His Val Gln Asn Gly Trp Trp Val Cys Ile Asn Tyr Arg Lys Leu Asn
         50                  55                  60

Val Ile Thr Cys Lys Asp His Phe Pro Leu Pro Ile Asp Lys Met
 65                  70                  75                  80

Leu Glu Arg Leu Ala Gly His Ser Tyr Tyr Cys Phe Leu Asp Gly Tyr
                 85                  90                  95

Leu Gly Tyr Phe Gln Ile Ala Ile Thr Ser Glu Asp Gln Glu Lys Met
            100                 105                 110

Ile Phe Lys Cys Pro Phe Gly Thr Phe Ala Tyr Arg His Met Pro Phe
        115                 120                 125

Gly Leu Cys Asn Ala Pro Thr Thr Phe Glx Arg Cys Met Val Ser Ile
    130                 135                 140

Phe Ser Asp Tyr Ile Glu Asn Ile Ile Glu Val Phe Met Asp Asp Phe
145                 150                 155                 160

Thr Val Tyr Gly Asp Ser Phe Asp Asn Cys Leu His Asn Leu Thr Leu
                165                 170                 175

Val Ile Gln Arg Cys Ile Glu Thr Leu Val Leu Asn Ser Glx Lys
            180                 185                 190

Cys His Phe Met Val Glu Gln Gly Ile Val Leu Gly His Val Val Ser
        195                 200                 205

Ser Arg Gly Ile Glu Val Asp Lys Pro Lys Val Asp Ile Ile Gln Thr
    210                 215                 220

Leu Pro Tyr Ser Thr Ser Val Arg Glu Val Arg Ser Phe Leu Gly His
```

```
                225                 230                 235                 240
Val Gly Phe Tyr Glx Arg Phe Ile Lys Asp Phe Thr Lys Val
                245                 250
```

<210> SEQ ID NO 120
<211> LENGTH: 759
<212> TYPE: DNA
<213> ORGANISM: Platanus occidentalis

<400> SEQUENCE: 120

```
gtgcggaaag aggttttaa gcttttggat gtagggatta tatacccaat tttttatagt      60
aattaggtaa gtcccactca agtggaccca agaattctgg tgtgactgta gttaaaaatg    120
caaatgatga attgattcca aatagactca ctattggttg gcgtgtatgc attaactata    180
agaagttgaa ctcagtgact aggaaggacc atttccctt accattcatg actaaatcct    240
agaaagggta gctggtcaca aatttttatta tttcctatat ggttattcta gatataacta    300
aatagagatt gcacctgagg actaagaaaa taccactttt acatgtccat ttggcactt    360
tgcttatcga aggatgtcat ttggattatg taatgctctt gccacgttct aaagatgcat    420
gttgagtata tttagtgata tggtagaaca ttttcttgag gtgtttatgg atttttttg    480
tttttggtaa ttcatttgat gattgtttgc ataatttgaa aaaagtgtta aatagatgtg    540
aaggaaaaaa acatcatttt gaattgagag aagtgtcatt tcatggtctc taaaagaatt    600
gtacttggtc acattgtctc ctcccaagga attaaagtgg tcaaagccaa aattgaattg    660
atagtcaatt tgcctagccc aaagactctt aaagacattc gatctttct aggtcatgca    720
ggatttaaca aaaggttcat caaagacttc acgaaagtt                           759
```

<210> SEQ ID NO 121
<211> LENGTH: 254
<212> TYPE: PRT
<213> ORGANISM: Platanus occidentalis

<400> SEQUENCE: 121

```
Val Arg Lys Glu Val Phe Lys Leu Leu Asp Val Gly Ile Ile Tyr Pro
  1               5                  10                  15
Ile Phe Tyr Ser Asn Glx Val Ser Pro Thr Gln Val Pro Lys Asn
                 20                  25                  30
Ser Gly Val Thr Val Val Lys Asn Ala Asn Asp Glu Leu Ile Pro Asn
             35                  40                  45
Arg Leu Thr Ile Gly Trp Arg Val Cys Ile Asn Tyr Lys Lys Leu Asn
         50                  55                  60
Ser Val Thr Arg Lys Asp His Phe Pro Leu Pro Phe Met Asp Glx Ile
 65                  70                  75                  80
Leu Glu Arg Val Ala Gly His Lys Phe Tyr Tyr Phe Leu Tyr Gly Tyr
                 85                  90                  95
Ser Arg Tyr Asn Glx Ile Glu Ile Ala Pro Glu Asp Glx Glu Asn Thr
                100                 105                 110
Thr Phe Thr Cys Pro Phe Gly Thr Phe Ala Tyr Arg Arg Met Ser Phe
            115                 120                 125
Gly Leu Cys Asn Ala Leu Ala Thr Phe Glx Arg Cys Met Leu Ser Ile
        130                 135                 140
Phe Ser Asp Met Val Glu His Phe Leu Glu Val Phe Met Asp Asp Phe
145                 150                 155                 160
Phe Val Phe Gly Asn Ser Phe Asp Asp Cys Leu His Asn Leu Lys Lys
                165                 170                 175
```

```
Val Leu Asn Arg Cys Glu Glu Lys Asn Ile Ile Leu Asn Glx Glu Lys
                180                 185                 190

Cys His Phe Met Val Ser Lys Arg Ile Val Leu Gly His Ile Val Ser
            195                 200                 205

Ser Gln Gly Ile Lys Val Lys Ala Lys Ile Glu Leu Ile Val Asn
        210                 215                 220

Leu Pro Ser Pro Lys Thr Leu Lys Asp Ile Arg Ser Phe Leu Gly His
225                 230                 235                 240

Ala Gly Phe Asn Lys Arg Phe Ile Lys Asp Phe Thr Lys Val
                245                 250

<210> SEQ ID NO 122
<211> LENGTH: 761
<212> TYPE: DNA
<213> ORGANISM: Platanus occidentalis

<400> SEQUENCE: 122
tgcgtaaaga ggtggtcaag cttcttgaag ttggagtgat ttatcctatt tcggatagca      60
attgggttag cccggttcaa gtggttccta aaaagactgg aataaccgtt gtgaaaaatc     120
aaaatgatga gttagttcct acccgtgttc agaatgggtg gcaggtttgt atagattata     180
taaaattaaa tgttgtaacc cgcaaggatc acttcccttt accttttatt gatcaaatgt     240
ttgaaaggtt agctggtcat tcttactatt gtttccttga tggatattca tgttattttt     300
agattgcaat tactccagag gatcaagaaa agacgacttt tacgtgccca ttcgggactt     360
tttcatatcg ttgcatgccc tttggccttt gcaacgcccc agccactttc caaaggtgta     420
tggttagcat attttcagat tacattgaga atatcataga agtctttatg gatgatttca     480
tagtttatga agactccttt gataattgtc tgcataacct tacacttgtt ttttaaagat     540
gcatagaaac taaccttgtg ttaaattttg aaaaatgtca tgttatggtt gaataaggta     600
tagttttggg tcatgttgtt tcatctatgg gaattgaggg agataaagtt aaagttgata     660
ttattcaatc tttaccttat cccattagtg tgcaggaagt tcgttctttt cttggacatg     720
cgggttttta ccaaagattc attaaagact tcacgaaagt t                        761

<210> SEQ ID NO 123
<211> LENGTH: 253
<212> TYPE: PRT
<213> ORGANISM: Platanus occidentalis

<400> SEQUENCE: 123

Arg Lys Glu Val Val Lys Leu Leu Glu Val Gly Val Ile Tyr Pro Ile
1               5                   10                  15

Ser Asp Ser Asn Trp Val Ser Pro Val Gln Val Pro Lys Lys Thr
            20                  25                  30

Gly Ile Thr Val Val Lys Asn Gln Asn Asp Glu Leu Val Pro Thr Arg
        35                  40                  45

Val Gln Asn Gly Trp Gln Val Cys Ile Asp Tyr Ile Lys Leu Asn Val
    50                  55                  60

Val Thr Arg Lys Asp His Phe Pro Leu Pro Phe Ile Asp Gln Met Phe
65                  70                  75                  80

Glu Arg Leu Ala Gly His Ser Tyr Tyr Cys Phe Leu Asp Gly Tyr Ser
                85                  90                  95

Cys Tyr Phe Glx Ile Ala Ile Thr Pro Glu Asp Gln Glu Lys Thr Thr
            100                 105                 110

Phe Thr Cys Pro Phe Gly Thr Phe Ser Tyr Arg Cys Met Pro Phe Gly
```

-continued

```
            115                 120                   125
Leu Cys Asn Ala Pro Ala Thr Phe Gln Arg Cys Met Val Ser Ile Phe
    130                 135                 140

Ser Asp Tyr Ile Glu Asn Ile Ile Glu Val Phe Met Asp Asp Phe Ile
145                 150                 155                 160

Val Tyr Glu Asp Ser Phe Asp Asn Cys Leu His Asn Leu Thr Leu Val
                165                 170                 175

Phe Glx Arg Cys Ile Glu Thr Asn Leu Val Leu Asn Phe Glu Lys Cys
            180                 185                 190

His Val Met Val Glu Glx Gly Ile Val Leu Gly His Val Ser Ser
        195                 200                 205

Met Gly Ile Glu Val Asp Lys Val Lys Val Asp Ile Ile Gln Ser Leu
    210                 215                 220

Pro Tyr Pro Ile Ser Val Gln Glu Val Arg Ser Phe Leu Gly His Ala
225                 230                 235                 240

Gly Phe Tyr Gln Arg Phe Ile Lys Asp Phe Thr Lys Val
            245                 250
```

<210> SEQ ID NO 124
<211> LENGTH: 761
<212> TYPE: DNA
<213> ORGANISM: Sorghum bicolor

<400> SEQUENCE: 124

```
gtgcgtaaag aggtcttcaa gctctatcat gctgggatta tttatcctgt gccgcatagt      60
gagtgggtta gccctgttca agtagtgcca agaaaggag gaatgacggt cgttaggaat     120
gagaagaatg aactcatccc tcaacgaatt gtcactgggt ggcgtatgtg tattgactat     180
caaaaactca acacggctac aaagaaagat aactttccgt tacccttcat tgatgaaatg     240
ttggaacggc ttgcaaacca ctctttcttc tgtttccttg atggttattc tggatatcac     300
caaatcccaa tccacccaga tgaccaagaa aagactacct tacatgccc gtatggaact     360
tatgcataac gacgaatgtc gttcggactg tgcaatgctc cagcttcttt ccaacggtgc     420
atgatgtcta ttttctcgga catgattgag aagatcatgg aggttttcat ggatgatttt     480
accgtctatg gtaaaacctt cgatcattgt ttggagaatt tagatagagt cttgcagcga     540
tgtgaagaaa agcacttaat cctgaactgg agaaatgcc attttatggt tcaggaagga     600
atagtgctag acataaagt gtccgaacgt ggtatagagg tggacaaagc aaagattgaa     660
gttattgaaa aacttccacc tcccacgaat gtgaaggat ccgtagcttc ttgggacatg     720
cagggttcta tagatgcttc ataaaagact tcacaaaggt t                        761
```

<210> SEQ ID NO 125
<211> LENGTH: 254
<212> TYPE: PRT
<213> ORGANISM: Sorghum bicolor

<400> SEQUENCE: 125

```
Val Arg Lys Glu Val Phe Lys Leu Tyr His Ala Gly Ile Ile Tyr Pro
1               5                   10                  15

Val Pro His Ser Glu Trp Val Ser Pro Val Gln Val Val Pro Lys Lys
            20                  25                  30

Gly Gly Met Thr Val Val Arg Asn Glu Lys Asn Glu Leu Ile Pro Gln
        35                  40                  45

Arg Ile Val Thr Gly Trp Arg Met Cys Ile Asp Tyr Gln Lys Leu Asn
    50                  55                  60
```

Thr Ala Thr Lys Lys Asp Asn Phe Pro Leu Pro Phe Ile Asp Glu Met
65                  70                  75                  80

Leu Glu Arg Leu Ala Asn His Ser Phe Phe Cys Phe Leu Asp Gly Tyr
            85                  90                  95

Ser Gly Tyr His Gln Ile Pro Ile His Pro Asp Asp Gln Glu Lys Thr
                100                 105                 110

Thr Phe Thr Cys Pro Tyr Gly Thr Tyr Ala Glx Arg Arg Met Ser Phe
            115                 120                 125

Gly Leu Cys Asn Ala Pro Ala Ser Phe Gln Arg Cys Met Met Ser Ile
        130                 135                 140

Phe Ser Asp Met Ile Glu Lys Ile Met Glu Val Phe Met Asp Asp Phe
145                 150                 155                 160

Thr Val Tyr Gly Lys Thr Phe Asp His Cys Leu Glu Asn Leu Asp Arg
                165                 170                 175

Val Leu Gln Arg Cys Glu Glu Lys His Leu Ile Leu Asn Trp Glu Lys
            180                 185                 190

Cys His Phe Met Val Gln Glu Gly Ile Val Leu Gly His Lys Val Ser
        195                 200                 205

Glu Arg Gly Ile Glu Val Asp Lys Ala Lys Ile Glu Val Ile Glu Lys
    210                 215                 220

Leu Pro Pro Pro Thr Asn Val Lys Gly Ile Arg Ser Phe Leu Gly His
225                 230                 235                 240

Ala Gly Phe Tyr Arg Cys Phe Ile Lys Asp Phe Thr Lys Val
                245                 250

<210> SEQ ID NO 126
<211> LENGTH: 762
<212> TYPE: DNA
<213> ORGANISM: Sorghum bicolor

<400> SEQUENCE: 126
gtgcggaagg aggtccttaa attgctgcat gcagggatta tatatcctgt gccgcacagt      60
gagtgggtga gcccagtaca agttgtgcct aaaaaaggag gcatgactgt tattataaat     120
gaaaagaacg agctaattcc gcaacgcacc gtcacaggat ggcagatgtg catagactat     180
agaaaactaa acaaagccac gagaaaggat cactttcctt tacctttat agatgagatg      240
ctagagcggt tagcaaacca ttcgttcttc tgtttcttag atggatattc agggtatcat     300
cagatcccga tccatcccga tgatcaaagc aaaaccactt ttacatgccc ttatggaact     360
tatgcttacc gtagaatgtc ttttgggtta tgtaatgcac cagcttcttt tcaaagatgc     420
atgatgtcta tattttctga tatgattgaa gagattatgg aagttttcat ggatgatttc     480
tctgtttatg gaaaagcttt tgatagttgt cttgaaaact agacaaggt tttgcaaagt      540
tgtgaagaaa agcacttaat ccttaattgg gaaaatgtc attttatggt tagggaagga     600
atagtgctag gacacttagt gtctgaaagg ggtattgagg tagacaaagc tgaaattgaa     660
gtaattgaac aactacctcc acctgtgaat ataaaggaa ttcgaagctt tcttggccat      720
gctggttttt atcgtagatt catcaaagat ttcacgaaag tt                        762

<210> SEQ ID NO 127
<211> LENGTH: 254
<212> TYPE: PRT
<213> ORGANISM: Sorghum bicolor

<400> SEQUENCE: 127

```
Val Arg Lys Glu Val Leu Lys Leu Leu His Ala Gly Ile Ile Tyr Pro
 1               5                  10                  15

Val Pro His Ser Glu Trp Val Ser Pro Val Gln Val Pro Lys Lys
            20                  25                  30

Gly Gly Met Thr Val Ile Ile Asn Glu Lys Asn Glu Leu Ile Pro Gln
            35                  40                  45

Arg Thr Val Thr Gly Trp Gln Met Cys Ile Asp Tyr Arg Lys Leu Asn
 50                  55                  60

Lys Ala Thr Arg Lys Asp His Phe Pro Leu Pro Phe Ile Asp Glu Met
65                   70                  75                  80

Leu Glu Arg Leu Ala Asn His Ser Phe Phe Cys Phe Leu Asp Gly Tyr
                 85                  90                  95

Ser Gly Tyr His Gln Ile Pro Ile His Pro Asp Asp Gln Ser Lys Thr
             100                 105                 110

Thr Phe Thr Cys Pro Tyr Gly Thr Tyr Ala Tyr Arg Arg Met Ser Phe
             115                 120                 125

Gly Leu Cys Asn Ala Pro Ala Ser Phe Gln Arg Cys Met Met Ser Ile
         130                 135                 140

Phe Ser Asp Met Ile Glu Ile Met Glu Val Phe Met Asp Asp Phe
145                 150                 155                 160

Ser Val Tyr Gly Lys Ala Phe Asp Ser Cys Leu Glu Asn Leu Asp Lys
                 165                 170                 175

Val Leu Gln Ser Cys Glu Glu Lys His Leu Ile Leu Asn Trp Glu Lys
             180                 185                 190

Cys His Phe Met Val Arg Glu Gly Ile Val Leu Gly His Leu Val Ser
         195                 200                 205

Glu Arg Gly Ile Glu Val Asp Lys Ala Glu Ile Glu Val Ile Glu Gln
         210                 215                 220

Leu Pro Pro Pro Val Asn Ile Lys Gly Ile Arg Ser Phe Leu Gly His
225                 230                 235                 240

Ala Gly Phe Tyr Arg Arg Phe Ile Lys Asp Phe Thr Lys Val
                 245                 250
```

<210> SEQ ID NO 128
<211> LENGTH: 762
<212> TYPE: DNA
<213> ORGANISM: Sorghum bicolor

<400> SEQUENCE: 128

```
gtgcggaagg aagtcttaaa gcttttacac actaggatta tttatctcgt tcctcatagt    60
gagtgggtta gcacggtaca agttgtgcca agaaaggag gaatgtcggt tgttaggaat    120
gagaagaacg aattcatccc tcaacaaact gtcactgggt ggcgtatgtg cattgactac   180
caaaaactca acaaggccac aaggaaagat cacttcccgt tacctttcat tgatgaaatg   240
ttgtaatggc ttacaaatca ctcgttcttt tgtttccttg aagggtattc cagatatcat   300
caaatcccga tccaccacga tgaccaaagt aagactactt tcacatgacc ctatggaact   360
tacgcatacc gacgaatgtc gttcaggtta tgtaatgctc cagcttcttt tcaacggtgc   420
atgatgtcta ttttttccaa tatgattgag aaaatcatgg aggtattcac ggatgatttt   480
accgtatatg gcaaaacctt tgatgattgt ttagagaatt tggacaaagt cttacaattg   540
tgtgaaggaa agcacttaat cgtaaactag gagaaatgcc attttatggt ccgagaagga   600
atagtgctag gcacaaggt gtccgaacgt gggatagagg tggatagagc caagattgaa   660
gttattgaaa aacttccacc tcccacaaat gtgaaagaca tccgcagttt tcttggacat   720
```

```
gcagggttct ataggcgctt catcaaagat ttcaccaagg tt                762
```

<210> SEQ ID NO 129
<211> LENGTH: 254
<212> TYPE: PRT
<213> ORGANISM: Sorghum bicolor

<400> SEQUENCE: 129

| | | | | | | | | | | | | | | | |
|---|---|---|---|---|---|---|---|---|---|---|---|---|---|---|---|
| Val | Arg | Lys | Glu | Val | Leu | Lys | Leu | Leu | His | Thr | Arg | Ile | Ile | Tyr | Leu |
| 1 | | | | 5 | | | | | 10 | | | | | 15 | |
| Val | Pro | His | Ser | Glu | Trp | Val | Ser | Thr | Val | Gln | Val | Val | Pro | Lys | Lys |
| | | | 20 | | | | | 25 | | | | | 30 | | |
| Gly | Gly | Met | Ser | Val | Val | Arg | Asn | Glu | Lys | Asn | Glu | Phe | Ile | Pro | Gln |
| | | | | 35 | | | | | 40 | | | | | 45 | |
| Gln | Thr | Val | Thr | Gly | Trp | Arg | Met | Cys | Ile | Asp | Tyr | Gln | Lys | Leu | Asn |
| | 50 | | | | | 55 | | | | | 60 | | | | |
| Lys | Ala | Thr | Arg | Lys | Asp | His | Phe | Pro | Leu | Pro | Phe | Ile | Asp | Glu | Met |
| 65 | | | | | 70 | | | | | 75 | | | | | 80 |
| Leu | Glx | Trp | Leu | Thr | Asn | His | Ser | Phe | Phe | Cys | Phe | Leu | Glu | Gly | Tyr |
| | | | | 85 | | | | | 90 | | | | | 95 | |
| Ser | Arg | Tyr | His | Gln | Ile | Pro | Ile | His | His | Asp | Asp | Gln | Ser | Lys | Thr |
| | | | 100 | | | | | 105 | | | | | 110 | | |
| Thr | Phe | Thr | Glx | Pro | Tyr | Gly | Thr | Tyr | Ala | Tyr | Arg | Arg | Met | Ser | Phe |
| | | | | 115 | | | | | 120 | | | | | 125 | |
| Arg | Leu | Cys | Asn | Ala | Pro | Ala | Ser | Phe | Gln | Arg | Cys | Met | Met | Ser | Ile |
| | 130 | | | | | 135 | | | | | 140 | | | | |
| Phe | Ser | Asn | Met | Ile | Glu | Lys | Ile | Met | Glu | Val | Phe | Thr | Asp | Asp | Phe |
| 145 | | | | | 150 | | | | | 155 | | | | | 160 |
| Thr | Val | Tyr | Gly | Lys | Thr | Phe | Asp | Asp | Cys | Leu | Glu | Asn | Leu | Asp | Lys |
| | | | | 165 | | | | | 170 | | | | | 175 | |
| Val | Leu | Gln | Leu | Cys | Glu | Gly | Lys | His | Leu | Ile | Val | Asn | Glx | Glu | Lys |
| | | | 180 | | | | | 185 | | | | | 190 | | |
| Cys | His | Phe | Met | Val | Arg | Glu | Gly | Ile | Val | Leu | Gly | His | Lys | Val | Ser |
| | | | | 195 | | | | | 200 | | | | | 205 | |
| Glu | Arg | Gly | Ile | Glu | Val | Asp | Arg | Ala | Lys | Ile | Glu | Val | Ile | Glu | Lys |
| | 210 | | | | | 215 | | | | | 220 | | | | |
| Leu | Pro | Pro | Pro | Thr | Asn | Val | Lys | Asp | Ile | Arg | Ser | Phe | Leu | Gly | His |
| 225 | | | | | 230 | | | | | 235 | | | | | 240 |
| Ala | Gly | Phe | Tyr | Arg | Arg | Phe | Ile | Lys | Asp | Phe | Thr | Lys | Val | | |
| | | | | 245 | | | | | 250 | | | | | | |

<210> SEQ ID NO 130
<211> LENGTH: 761
<212> TYPE: DNA
<213> ORGANISM: Sorghum bicolor

<400> SEQUENCE: 130

```
gtgcgtaagg aggtttttaa gctgctgcat gcagagatta tatatcatgt gccgcacagt    60
gagtgggtaa gcccagttca agttgtgcct aaaaagggag gcatgattgt tgttacgaat   120
gaaaagaacg agctaattcc gcaacgcacc gtcacagggt ggcggatgtg catagactat   180
agaaaactaa acaaagccac gagaaaggat cattttcctt tacctttcat agatgagatg   240
ctagagcgat tagcaaacca ttcgttcttc tgtttcttag atggataatt agggtatcac   300
cagatcccaa tcaatcttga tgatcaaagc aaaaccactt ttccatgccc acatggaact   360
```

```
tatgcttacc gtagaatgtc ttttgggtta tgtaatgcac cagcttcttt tcaaagatgc    420
atgatgtctg tattttctaa tatgattgaa gagattatgg aattttcatg gatgatttct    480
ctgtttatgg aaaaactttt gatagttgtc ttgaaaactt agacagggtt ttgcaaagat    540
gtgaagaaaa gtacttagtc cttaattgga aaaaatgtca ttttatggtt agggaaggaa    600
tagtgctggg acacctagtg tctgaaagag gtattgaggt cgacaaagct aaaattgaag    660
taattgaaca actacctcca cctttgaata taaaaggaat tcgaagcttt cttggccatg    720
ctggttttta tcgtagattc attaaggact ttacaaaggt t                        761
```

```
<210> SEQ ID NO 131
<211> LENGTH: 254
<212> TYPE: PRT
<213> ORGANISM: Sorghum bicolor

<400> SEQUENCE: 131
```

Val Arg Lys Glu Val Phe Lys Leu Leu His Ala Glu Ile Ile Tyr His
1               5                   10                  15

Val Pro His Ser Glu Trp Val Ser Pro Val Gln Val Val Pro Lys Lys
            20                  25                  30

Gly Gly Met Ile Val Val Thr Asn Glu Lys Asn Glu Leu Ile Pro Gln
        35                  40                  45

Arg Thr Val Thr Gly Trp Arg Met Cys Ile Asp Tyr Arg Lys Leu Asn
    50                  55                  60

Lys Ala Thr Arg Lys Asp His Phe Pro Leu Pro Phe Ile Asp Glu Met
65                  70                  75                  80

Leu Glu Arg Leu Ala Asn His Ser Phe Phe Cys Phe Leu Asp Gly Glx
                85                  90                  95

Leu Gly Tyr His Gln Ile Pro Ile Asn Leu Asp Asp Gln Ser Lys Thr
            100                 105                 110

Thr Phe Pro Cys Pro His Gly Thr Tyr Ala Tyr Arg Arg Met Ser Phe
        115                 120                 125

Gly Leu Cys Asn Ala Pro Ala Ser Phe Gln Arg Cys Met Met Ser Val
    130                 135                 140

Phe Ser Asn Met Ile Glu Glu Ile Met Glu Ile Phe Met Asp Asp Phe
145                 150                 155                 160

Ser Val Tyr Gly Lys Thr Phe Asp Ser Cys Leu Glu Asn Leu Asp Arg
                165                 170                 175

Val Leu Gln Arg Cys Glu Glu Lys Tyr Leu Val Leu Asn Trp Lys Lys
            180                 185                 190

Cys His Phe Met Val Arg Glu Gly Ile Val Leu Gly His Leu Val Ser
        195                 200                 205

Glu Arg Gly Ile Glu Val Asp Lys Ala Lys Ile Glu Val Ile Glu Gln
    210                 215                 220

Leu Pro Pro Pro Leu Asn Ile Lys Gly Ile Arg Ser Phe Leu Gly His
225                 230                 235                 240

Ala Gly Phe Tyr Arg Arg Phe Ile Lys Asp Phe Thr Lys Val
                245                 250

```
<210> SEQ ID NO 132
<211> LENGTH: 763
<212> TYPE: DNA
<213> ORGANISM: Sorghum bicolor

<400> SEQUENCE: 132
gtgcggaaag aggtcgtcaa gctctatcat gctgggatta tttatcctgt gccacatagt    60
```

```
gagtgggtta gccctgttca agtagtgcca agaaagaag gaatgacggt cgttaggaat      120
gagaagaatg aactcatccc tcaacaaatt gtcactagat ggcgtatgtg tattgactat      180
cgaaaactca acaaagctac aaagaaagat cactttccgt tacccttcat tgatgaaatg      240
ttggaatggc ttgcaaacca ctctttcttc tgtttccttg atggttattc tggatatcac      300
caaatcccaa tccacccaga tgaccaagaa aagactacct ttacatgccc gtattgaact      360
tatgcatact gacgaatgtc gttcggattg tgcaatgctc tagcttcttt tccagcggtg      420
catgatgtct attttctcgg acatgattga aagatcatg gaggttttca tggatgattt       480
taccgtctat ggcaaaacct tcgatcattg tttggagaat ttagatagag tcttgcagcg      540
atgtgaggaa atcacttaa tcttgaactg ggagaaatgt cattttatgg ttcaggaagg       600
aatagtgcta ggacataaag tgtccgaacg tggtatagat gtggacaaag caaagattaa      660
agttattgaa aaacttccac ctcacacgaa tgtgaaagga atccatagct ttttgggaca      720
tgcagggttc tatagacgct tcatcaagga tttcacaaag gtt                        763
```

<210> SEQ ID NO 133
<211> LENGTH: 254
<212> TYPE: PRT
<213> ORGANISM: Sorghum bicolor

<400> SEQUENCE: 133

```
Val Arg Lys Glu Val Val Lys Leu Tyr His Ala Gly Ile Ile Tyr Pro
 1               5                  10                  15

Val Pro His Ser Glu Trp Val Ser Pro Val Gln Val Val Pro Lys Lys
                20                  25                  30

Glu Gly Met Thr Val Val Arg Asn Glu Lys Asn Glu Leu Ile Pro Gln
            35                  40                  45

Gln Ile Val Thr Arg Trp Arg Met Cys Ile Asp Tyr Arg Lys Leu Asn
        50                  55                  60

Lys Ala Thr Lys Lys Asp His Phe Pro Leu Pro Phe Ile Asp Glu Met
 65                  70                  75                  80

Leu Glu Trp Leu Ala Asn His Ser Phe Phe Cys Phe Leu Asp Gly Tyr
                85                  90                  95

Ser Gly Tyr His Gln Ile Pro Ile His Pro Asp Asp Gln Glu Lys Thr
            100                 105                 110

Thr Phe Thr Cys Pro Tyr Glx Thr Tyr Ala Tyr Glx Arg Met Ser Phe
        115                 120                 125

Gly Leu Cys Asn Ala Leu Ala Ser Phe Gln Arg Cys Met Met Ser Ile
    130                 135                 140

Phe Ser Asp Met Ile Glu Lys Ile Met Glu Val Phe Met Asp Asp Phe
145                 150                 155                 160

Thr Val Tyr Gly Lys Thr Phe Asp His Cys Leu Glu Asn Leu Asp Arg
                165                 170                 175

Val Leu Gln Arg Cys Glu Glu Asn His Leu Ile Leu Asn Trp Glu Lys
            180                 185                 190

Cys His Phe Met Val Gln Glu Gly Ile Val Leu Gly His Lys Val Ser
        195                 200                 205

Glu Arg Gly Ile Asp Val Asp Lys Ala Lys Ile Lys Val Ile Glu Lys
    210                 215                 220

Leu Pro Pro His Thr Asn Val Lys Gly Ile His Ser Phe Leu Gly His
225                 230                 235                 240

Ala Gly Phe Tyr Arg Arg Phe Ile Lys Asp Phe Thr Lys Val
                245                 250
```

<210> SEQ ID NO 134
<211> LENGTH: 756
<212> TYPE: DNA
<213> ORGANISM: Sorghum bicolor

<400> SEQUENCE: 134

```
aaggaggttt tcaagttgct gcatgcaggg attatatatc ttgtgccgca tagtgagtgg      60
gtaagcccag ttcaagttgt gcctaaaaag ggaggcatga ctattattat gaatgaaaag     120
aacgagctaa ttccgcaacg caccgttaca gtatggcgga tgtgcataga ctatagaaaa     180
ctaaacaaag ccacgagaga ggatcacttt cctttacctt tcatagatga gatgctagag     240
tggttagcaa accattcgtt cttctgtttc ttagatggat attgagggta tcatcagatc     300
ccgatccatc ccgatgatca aagcaaaacc acttttacat gcccatatgg aacttatgct     360
taccgtagaa tgtcttttgg gttatgtaat gcactagctc cttttcaaag atgcatgatg     420
tctatatttt ctgatatgat tgaagagatt atggaagttt tcatggatga tttctctgtt     480
tatggaaaaa cttttgatag ttgtcttaaa aacttagaca aggttttgca agatgtgaa      540
gaaaagcact tagtccttaa ttgggaaaaa tgtcatttca tggttaggga aggaatagtg     600
ctgggacact tagtgtctga aagagctatt gaggtagata aagctaaaat tgaagtaatt     660
gaacaactac gtccacctgt gaacataaaa ggaatttgaa gctttcttgg ccatgctggt     720
tttcatcgta gattcataaa agactttaca aaggtt                               756
```

<210> SEQ ID NO 135
<211> LENGTH: 252
<212> TYPE: PRT
<213> ORGANISM: Sorghum bicolor

<400> SEQUENCE: 135

```
Lys Glu Val Phe Lys Leu Leu His Ala Gly Ile Ile Tyr Leu Val Pro
  1               5                  10                  15
His Ser Glu Trp Val Ser Pro Val Gln Val Val Pro Lys Lys Gly Gly
             20                  25                  30
Met Thr Ile Ile Met Asn Glu Lys Asn Glu Leu Ile Pro Gln Arg Thr
         35                  40                  45
Val Thr Val Trp Arg Met Cys Ile Asp Tyr Arg Lys Leu Asn Lys Ala
     50                  55                  60
Thr Arg Glu Asp His Phe Pro Leu Pro Phe Ile Asp Glu Met Leu Glu
 65                  70                  75                  80
Trp Leu Ala Asn His Ser Phe Phe Cys Phe Leu Asp Gly Tyr Glx Gly
                 85                  90                  95
Tyr His Gln Ile Pro Ile His Pro Asp Asp Gln Ser Lys Thr Thr Phe
            100                 105                 110
Thr Cys Pro Tyr Gly Thr Tyr Ala Tyr Arg Arg Met Ser Phe Gly Leu
        115                 120                 125
Cys Asn Ala Leu Ala Ser Phe Gln Arg Cys Met Met Ser Ile Phe Ser
    130                 135                 140
Asp Met Ile Glu Glu Ile Met Glu Val Phe Met Asp Asp Phe Ser Val
145                 150                 155                 160
Tyr Gly Lys Thr Phe Asp Ser Cys Leu Lys Asn Leu Asp Lys Val Leu
                165                 170                 175
Gln Arg Cys Glu Glu Lys His Leu Val Leu Asn Trp Glu Lys Cys His
            180                 185                 190
```

Phe Met Val Arg Glu Gly Ile Val Leu Gly His Leu Val Ser Glu Arg
                195                 200                 205

Ala Ile Glu Val Asp Lys Ala Lys Ile Glu Val Ile Glu Gln Leu Arg
        210                 215                 220

Pro Pro Val Asn Ile Lys Gly Ile Glx Ser Phe Leu Gly His Ala Gly
225                 230                 235                 240

Phe His Arg Arg Phe Ile Lys Asp Phe Thr Lys Val
                245                 250

<210> SEQ ID NO 136
<211> LENGTH: 762
<212> TYPE: DNA
<213> ORGANISM: Glycine max

<400> SEQUENCE: 136
gtgcgtaagg aggttgtcaa gcttttggag gttgggctca tatacctcat ctctgacagc      60
gcttgggtaa gcctagtaca ggtggctccc aagaaatgcg gaatgacagt ggtacaaaat     120
gagaggaatg acttgatacc aacacgaact gtcactggct agcggatgtg tatcgactac     180
tgcaagttga atgaagccac acggaaggac catttcccct acctttcat ggatcagatg      240 ctggagaggc ttgcagggca ggcatactac tgtttcttgg atagatattc aggatacaac     300
caaatcgcgg tagaccccag agatcaggag aagatggcct tacatgccc ctttggcgtc      360 tttgcttaca gaaggatgtc attcaggtta tgtaacgcac cagccacatt tcagaggtgc     420
gtgctggcca ttttttcaga catggtggag aagagcatcg aggtatttat ggatgaattc     480 tcgattttg accettatt tgacagttgc ttaaggaact tagagatggt actacagagg      540
tgcgtataga ctaacttggt actaaattag gaaaaatgtc atttcatggt tcgagaggga     600
atagtgatgg accacaatat ctcagctaga gggattgagg ttgatcaggc aaagatagac     660
gtcattgaga agttgccacc accactgaat gttaaaggcg tcagaagttt cttagggcat     720
gcaggtttct acaggaggtt tatcaaggac ttcaccaagg tt                        762

<210> SEQ ID NO 137
<211> LENGTH: 254
<212> TYPE: PRT
<213> ORGANISM: Glycine max

<400> SEQUENCE: 137

Val Arg Lys Glu Val Val Lys Leu Leu Glu Val Gly Leu Ile Tyr Leu
  1               5                  10                  15

Ile Ser Asp Ser Ala Trp Val Ser Leu Val Gln Val Ala Pro Lys Lys
                20                  25                  30

Cys Gly Met Thr Val Val Gln Asn Glu Arg Asn Asp Leu Ile Pro Thr
            35                  40                  45

Arg Thr Val Thr Gly Glx Arg Met Cys Ile Asp Tyr Cys Lys Leu Asn
        50                  55                  60

Glu Ala Thr Arg Lys Asp His Phe Pro Leu Pro Phe Met Asp Gln Met
65                  70                  75                  80

Leu Glu Arg Leu Ala Gly Gln Ala Tyr Tyr Cys Phe Leu Asp Arg Tyr
                85                  90                  95

Ser Gly Tyr Asn Gln Ile Ala Val Asp Pro Arg Asp Gln Glu Lys Met
            100                 105                 110

Ala Phe Thr Cys Pro Phe Gly Val Phe Ala Tyr Arg Arg Met Ser Phe
        115                 120                 125

```
Arg Leu Cys Asn Ala Pro Ala Thr Phe Gln Arg Cys Val Leu Ala Ile
    130                 135                 140
Phe Ser Asp Met Val Glu Lys Ser Ile Glu Val Phe Met Asp Glu Phe
145                 150                 155                 160
Ser Ile Phe Gly Pro Leu Phe Asp Ser Cys Leu Arg Asn Leu Glu Met
                165                 170                 175
Val Leu Gln Arg Cys Val Glx Thr Asn Leu Val Leu Asn Glx Glu Lys
            180                 185                 190
Cys His Phe Met Val Arg Glu Gly Ile Val Met Asp His Asn Ile Ser
        195                 200                 205
Ala Arg Gly Ile Glu Val Asp Gln Ala Lys Ile Asp Val Ile Glu Lys
    210                 215                 220
Leu Pro Pro Pro Leu Asn Val Lys Gly Val Arg Ser Phe Leu Gly His
225                 230                 235                 240
Ala Gly Phe Tyr Arg Arg Phe Ile Lys Asp Phe Thr Lys Val
                245                 250
```

<210> SEQ ID NO 138
<211> LENGTH: 763
<212> TYPE: DNA
<213> ORGANISM: Glycine max

<400> SEQUENCE: 138

```
gtgcgtaagg aggtctttaa gttcttggag gctgggctca tatatcccat ctctaatagc      60
acttaggtaa gcccagtaca ggtggttccc aagaaaggtg aatgacagt agtacagaat     120
gagaagaatg acttgatacc aacacgaact gtcactagct ggcgaatatg catcgattat     180
cgcaagctga atgaggccac ccggaaggac cacttccctc tacctttcat ggatcagatg     240
ttggagagac ttgcagggca ggcgtattat tgtttcttgg atggatactc gagatataat     300
cagattgcgg tggaccctag agaccaagag aagacgacct tcacatgccc ttttggcgt      360
ctttgcttac agaaggatgc cattcgggtt atgtaatgca ccagccacat ttcagaggtg     420
catgctggcc atttttcag acatggtgga gaaaaatatc gaggtattca tggatgactt       480
ttcagttttt gggccctcat tgacagttg tttgaggaac ctagagatgg tactttagag      540
gtgcgtagag actaatttag tgctgaactg ggagaagtgt cattttatgg ttcgagaggg     600
catagtcctg agccacaaga tctcagctag agggattgag gttgaccggg caaagataga     660
cgtcatagag aagctgccac caccattgaa tattaaaggt gtcagaagtt cttagggca      720
tgcaggattc tacaggagat tcataaagga ctttacaaag gtt                       763
```

<210> SEQ ID NO 139
<211> LENGTH: 254
<212> TYPE: PRT
<213> ORGANISM: Glycine max

<400> SEQUENCE: 139

```
Val Arg Lys Glu Val Phe Lys Phe Leu Glu Ala Gly Leu Ile Tyr Pro
1               5                   10                  15
Ile Ser Asn Ser Thr Glx Val Ser Pro Val Gln Val Pro Lys Lys
            20                  25                  30
Gly Gly Met Thr Val Val Gln Asn Glu Lys Asn Asp Leu Ile Pro Thr
        35                  40                  45
Arg Thr Val Thr Ser Trp Arg Ile Cys Ile Asp Tyr Arg Lys Leu Asn
    50                  55                  60
Glu Ala Thr Arg Lys Asp His Phe Pro Leu Pro Phe Met Asp Gln Met
```

```
                65                  70                  75                  80
Leu Glu Arg Leu Ala Gly Gln Ala Tyr Tyr Cys Phe Leu Asp Gly Tyr
                    85                  90                  95

Ser Arg Tyr Asn Gln Ile Ala Val Asp Pro Arg Asp Gln Glu Lys Thr
                    100                 105                 110

Thr Phe Thr Cys Pro Phe Gly Val Phe Ala Tyr Arg Arg Met Pro Phe
                    115                 120                 125

Gly Leu Cys Asn Ala Pro Ala Thr Phe Gln Arg Cys Met Leu Ala Ile
            130                 135                 140

Phe Ser Asp Met Val Glu Lys Asn Ile Glu Val Phe Met Asp Asp Phe
145                 150                 155                 160

Ser Val Phe Gly Pro Ser Phe Asp Ser Cys Leu Arg Asn Leu Glu Met
                    165                 170                 175

Val Leu Glx Arg Cys Val Glu Thr Asn Leu Val Leu Asn Trp Glu Lys
                    180                 185                 190

Cys His Phe Met Val Arg Glu Gly Ile Val Leu Ser His Lys Ile Ser
                    195                 200                 205

Ala Arg Gly Ile Glu Val Asp Arg Ala Lys Ile Asp Val Ile Glu Lys
            210                 215                 220

Leu Pro Pro Pro Leu Asn Ile Lys Gly Val Arg Ser Phe Leu Gly His
225                 230                 235                 240

Ala Gly Phe Tyr Arg Arg Phe Ile Lys Asp Phe Thr Lys Val
                    245                 250

<210> SEQ ID NO 140
<211> LENGTH: 762
<212> TYPE: DNA
<213> ORGANISM: Glycine max

<400> SEQUENCE: 140
gtgcgcaagg aggttttgaa gcttctagag gttgggctta tctaccccat ctccgacagc    60
gcttgggtaa gcccagtctt ggtggtgtcg aagaaagagg gcatgacagt cattcgaaat   120
gaaaagaatg acctgatacc aacacgaact gtcactagtt ggaaattatg catcgattac   180
cgcaagctca acgaagccac aaggaaagac catttccctc tacccttcat ggatcagatg   240
ttggagagac ttgcaggaca cgcttattat tgcttcttgg atgcatactt tggatataat   300
cagattgttg tagaccccaa ggatcaggag aagatggcct tcacatgccc ttttggtgtc   360
tttgcctata cgggattcc atttggggtg tgcaatgcac ctaccacatt ccaaatgtgc   420
atgttggcca ttttgcaga tatagtggag aaaagcatcg aagtattcat ggatgacttt   480
tcagtatttg tgccctcatt agaaagttgt ttgaagaagt tggagatggt actacaaaga   540
tgcgtggaaa caaacttagt actaaattgg gagaagtgtc acttcatggt tcgagaaggc   600
atagtcttag ccataaaat tcgacccga ggaattgagg tagaccaaac aaagattgat   660
gtcattgaaa agttgccacc accatcaaat gttaaaggca tcaggagctt cctaggacaa   720
gccaggttct acagaagatt catcaaggac ttcacaaaag tt                      762

<210> SEQ ID NO 141
<211> LENGTH: 254
<212> TYPE: PRT
<213> ORGANISM: Glycine max

<400> SEQUENCE: 141

Val Arg Lys Glu Val Leu Lys Leu Leu Glu Val Gly Leu Ile Tyr Pro
1               5                   10                  15
```

Ile Ser Asp Ser Ala Trp Val Ser Pro Val Leu Val Ser Lys Lys
            20                  25                  30

Glu Gly Met Thr Val Ile Arg Asn Glu Lys Asn Asp Leu Ile Pro Thr
             35                  40                  45

Arg Thr Val Thr Ser Trp Lys Leu Cys Ile Asp Tyr Arg Lys Leu Asn
 50                  55                  60

Glu Ala Thr Arg Lys Asp His Phe Pro Leu Pro Phe Met Asp Gln Met
 65                  70                  75                  80

Leu Glu Arg Leu Ala Gly His Ala Tyr Tyr Cys Phe Leu Asp Ala Tyr
                 85                  90                  95

Phe Gly Tyr Asn Gln Ile Val Val Asp Pro Lys Asp Gln Glu Lys Met
            100                 105                 110

Ala Phe Thr Cys Pro Phe Gly Val Phe Ala Tyr Arg Arg Ile Pro Phe
            115                 120                 125

Gly Leu Cys Asn Ala Pro Thr Thr Phe Gln Met Cys Met Leu Ala Ile
130                 135                 140

Phe Ala Asp Ile Val Glu Lys Ser Ile Glu Val Phe Met Asp Asp Phe
145                 150                 155                 160

Ser Val Phe Val Pro Ser Leu Glu Ser Cys Leu Lys Lys Leu Glu Met
                165                 170                 175

Val Leu Gln Arg Cys Val Glu Thr Asn Leu Val Leu Asn Trp Glu Lys
            180                 185                 190

Cys His Phe Met Val Arg Glu Gly Ile Val Leu Gly His Lys Ile Ser
            195                 200                 205

Thr Arg Gly Ile Glu Val Asp Gln Thr Lys Ile Asp Val Ile Glu Lys
210                 215                 220

Leu Pro Pro Pro Ser Asn Val Lys Gly Ile Arg Ser Phe Leu Gly Gln
225                 230                 235                 240

Ala Arg Phe Tyr Arg Arg Phe Ile Lys Asp Phe Thr Lys Val
                245                 250

<210> SEQ ID NO 142
<211> LENGTH: 762
<212> TYPE: DNA
<213> ORGANISM: Glycine max

<400> SEQUENCE: 142
gtgcggaagg aggttattaa gttgctagag gcagggctca tttacctaat ctcagatagt      60
tcataggtta gtcctgttca tgttgctctg aaaaagggag gtatgacagt gataaagaat     120
gatagagatg agttaattcc tacaagaata gttactggat ggaggatggg tattgattac     180
aagaagctaa atgaagccac caggaaagac cattacccgc ttcccttcat ggatcaaatg     240
cttgagagac ttgcagggca atcttcctac tatttattag atggatactc gggctacaat     300
caaattgcag tggatcctca ggaccaagaa agacagctt tcacatgtcc ttttggtgta      360
tttgcttatc gccgcatgtc gttcggttta tgtaatgccc caactacttt ccagagatgt     420
atgatggcaa ttttttgctga catggtaaag aaatgtattg aagtttttat ggacgatttc    480
tctgtctttg gtgcatcttt tgaaaattgc ctagcaaatt tagagaaagt gttacaacgc    540
tatgaagaat ctaatttggt gctcaactgg gaaaaatgtc actttatggt tcaagaaggt    600
atcatgctgg gacacaagat ttctagaaga ggaattaagg tggataaggc aaagattgag    660
gttattgata aacttccacc tctagttaat gttagaggca tacgaagttt tttgggtcat    720
gctagattct atcgatgatt tatcaaggac ttcaccaaag tt                        762

<210> SEQ ID NO 143
<211> LENGTH: 254
<212> TYPE: PRT
<213> ORGANISM: Glycine max

<400> SEQUENCE: 143

| | | | | | | | | | | | | | | |
|---|---|---|---|---|---|---|---|---|---|---|---|---|---|---|
| Val | Arg | Lys | Glu | Val | Ile | Lys | Leu | Leu | Glu | Ala | Gly | Leu | Ile | Tyr | Leu |
| 1 | | | | 5 | | | | | 10 | | | | | 15 | |
| Ile | Ser | Asp | Ser | Ser | Glx | Val | Ser | Pro | Val | His | Val | Ala | Leu | Lys | Lys |
| | | | 20 | | | | | 25 | | | | | 30 | | |
| Gly | Gly | Met | Thr | Val | Ile | Lys | Asn | Asp | Arg | Asp | Glu | Leu | Ile | Pro | Thr |
| | | | 35 | | | | | 40 | | | | | 45 | | |
| Arg | Ile | Val | Thr | Gly | Trp | Arg | Met | Gly | Ile | Asp | Tyr | Lys | Lys | Leu | Asn |
| | | 50 | | | | | 55 | | | | | 60 | | | |
| Glu | Ala | Thr | Arg | Lys | Asp | His | Tyr | Pro | Leu | Pro | Phe | Met | Asp | Gln | Met |
| 65 | | | | | 70 | | | | | 75 | | | | | 80 |
| Leu | Glu | Arg | Leu | Ala | Gly | Gln | Ser | Ser | Tyr | Tyr | Leu | Leu | Asp | Gly | Tyr |
| | | | | 85 | | | | | 90 | | | | | 95 | |
| Ser | Gly | Tyr | Asn | Gln | Ile | Ala | Val | Asp | Pro | Gln | Asp | Gln | Glu | Lys | Thr |
| | | | 100 | | | | | 105 | | | | | 110 | | |
| Ala | Phe | Thr | Cys | Pro | Phe | Gly | Val | Phe | Ala | Tyr | Arg | Arg | Met | Ser | Phe |
| | | | 115 | | | | | 120 | | | | | 125 | | |
| Gly | Leu | Cys | Asn | Ala | Pro | Thr | Thr | Phe | Gln | Arg | Cys | Met | Met | Ala | Ile |
| | | 130 | | | | | 135 | | | | | 140 | | | |
| Phe | Ala | Asp | Met | Val | Lys | Lys | Cys | Ile | Glu | Val | Phe | Met | Asp | Asp | Phe |
| 145 | | | | | 150 | | | | | 155 | | | | | 160 |
| Ser | Val | Phe | Gly | Ala | Ser | Phe | Glu | Asn | Cys | Leu | Ala | Asn | Leu | Glu | Lys |
| | | | | 165 | | | | | 170 | | | | | 175 | |
| Val | Leu | Gln | Arg | Tyr | Glu | Glu | Ser | Asn | Leu | Val | Leu | Asn | Trp | Glu | Lys |
| | | | 180 | | | | | 185 | | | | | 190 | | |
| Cys | His | Phe | Met | Val | Gln | Glu | Gly | Ile | Met | Leu | Gly | His | Lys | Ile | Ser |
| | | 195 | | | | | 200 | | | | | 205 | | | |
| Arg | Arg | Gly | Ile | Lys | Val | Asp | Lys | Ala | Lys | Ile | Glu | Val | Ile | Asp | Lys |
| | 210 | | | | | 215 | | | | | 220 | | | | |
| Leu | Pro | Pro | Leu | Val | Asn | Val | Arg | Gly | Ile | Arg | Ser | Phe | Leu | Gly | His |
| 225 | | | | | 230 | | | | | 235 | | | | | 240 |
| Ala | Arg | Phe | Tyr | Arg | Glx | Phe | Ile | Lys | Asp | Phe | Thr | Lys | Val | | |
| | | | | 245 | | | | | 250 | | | | | | |

<210> SEQ ID NO 144
<211> LENGTH: 761
<212> TYPE: DNA
<213> ORGANISM: Glycine max

<400> SEQUENCE: 144

| | | |
|---|---|---|
| gtgcggaagg aggtctttaa gttgctggaa gcaggcctta tttatcccat ttcggatagt | 60 |
| gcatgggtta gccctatgca agttgtccct aagaaaggag gtatgacagt cattaagaat | 120 |
| gataaagatg agttgatatc cacaaggacc gtcaccgggt ggagaatgtg cattgactat | 180 |
| cgaaagctga atgatgcacc cggaaggacc attatccact cccttcatg ggccatatgc | 240 |
| ttgaaagact tgttgggcaa tcctattatt gttttctaga tggatattat ggttataatc | 300 |
| agattgttgt agatcccaaa gatcaagaga agacagcttt cacctaccct tttggtgtat | 360 |
| tcgcatatca gtgcatgcct tttggtctat gcaatgcccc agctacattt cagaggtgta | 420 |

```
tgatggctat ttttctgat atggtggaaa tatgcattga agttttcatg gacgatttct    480
ctatttttgg gccatccttt gaagggtgct tatcaaatct tgaaaaagta ttaaagagat   540
gtgaagagtc caatctagtt ctcaattgga gaaatgcca tttcatggtt caagaaggaa    600
taatgttggg gcataaaatt tcagtaagag ggatagaggg ggacaaggca agattgatg    660 taattgagaa actacttgct cccatgaatg tcaagggaat aagaagcttc ttaggacatg   720
cagggttcta caggcgattc ataaaagact tcaccaaagt t                       761
```

<210> SEQ ID NO 145
<211> LENGTH: 254
<212> TYPE: PRT
<213> ORGANISM: Glycine max

<400> SEQUENCE: 145

```
Val Arg Lys Glu Val Phe Lys Leu Leu Glu Ala Gly Leu Ile Tyr Pro
 1               5                  10                  15

Ile Ser Asp Ser Ala Trp Val Ser Pro Met Gln Val Pro Lys Lys
                20                  25                  30

Gly Gly Met Thr Val Ile Lys Asn Asp Lys Asp Glu Leu Ile Ser Thr
            35                  40                  45

Arg Thr Val Thr Gly Trp Arg Met Cys Ile Asp Tyr Arg Lys Leu Asn
        50                  55                  60

Asp Ala Thr Arg Lys Asp His Tyr Pro Leu Pro Phe Met Gly His Met
    65                  70                  75                  80

Leu Glu Arg Leu Val Gly Gln Ser Tyr Tyr Cys Phe Leu Asp Gly Tyr
                85                  90                  95

Tyr Gly Tyr Asn Gln Ile Val Val Asp Pro Lys Asp Gln Glu Lys Thr
            100                 105                 110

Ala Phe Thr Tyr Pro Phe Gly Val Phe Ala Tyr Gln Cys Met Pro Phe
        115                 120                 125

Gly Leu Cys Asn Ala Pro Ala Thr Phe Gln Arg Cys Met Met Ala Ile
    130                 135                 140

Phe Ser Asp Met Val Glu Ile Cys Ile Glu Val Phe Met Asp Asp Phe
145                 150                 155                 160

Ser Ile Phe Gly Pro Ser Phe Glu Gly Cys Leu Ser Asn Leu Glu Lys
                165                 170                 175

Val Leu Lys Arg Cys Glu Glu Ser Asn Leu Val Leu Asn Trp Lys Lys
            180                 185                 190

Cys His Phe Met Val Gln Glu Gly Ile Met Leu Gly His Lys Ile Ser
        195                 200                 205

Val Arg Gly Ile Glu Val Asp Lys Ala Lys Ile Asp Val Ile Glu Lys
    210                 215                 220

Leu Leu Ala Pro Met Asn Val Lys Gly Ile Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 146
<211> LENGTH: 762
<212> TYPE: DNA
<213> ORGANISM: Glycine max

<400> SEQUENCE: 146

```
gtgcgtaagg aggtggtcaa gttgcttgaa gtaggactaa tttatccaat ctctgatagt   60
gcttgggtga gttcgaacta ggtggtgcct aagaaaggtg gtatgacggt gatccacaat  120
```

-continued

```
gataagaatg atcttattcc tacacagaca atcattaggt ggcaaatgtg tattgactat      180
cacaagttga atgatgtcac caagaaggac catttttcctc tgccattcat ggaccaaatg     240
ttagagaggt tagctggcca agcttttttat tgttttttgg atggttattc tgggtataac    300
caaatagcgg tgcatcttaa agatcaagag aagactacta tcatatgccc atttggtgtc    360
tttgcttaca gacaaatgtc atttgaactg tgtaatgccc ctaccacctt ctagagattc    420
atgatggcca ttttttgctga ccttgtggag aaatgcatag aggtgttcat gaatgatttc   480 tctatttttcg gctcttcctt ttatcattgt ttatccaacc tggaattagt gttacaacgg   540
tgtgcggaaa ccaatttgtt gatgaactgg gagaaatgtc atttcatggt ccaagagggg    600
attgtcttag gccacaagat ctcttccaga gggttggaag tggacaaggc aaaaattgat    660
gttattgaga agttgcctcc acctatgaat gtgaaaggca tccgaagttt tctcgaatat    720
gttggatttt ataggaggtt catcaaagac ttcacgaaag tt                       762
```

<210> SEQ ID NO 147
<211> LENGTH: 254
<212> TYPE: PRT
<213> ORGANISM: Glycine max

<400> SEQUENCE: 147

```
Val Arg Lys Glu Val Val Lys Leu Leu Glu Val Gly Leu Ile Tyr Pro
  1               5                  10                  15

Ile Ser Asp Ser Ala Trp Val Ser Ser Asn Glx Val Val Pro Lys Lys
             20                  25                  30

Gly Gly Met Thr Val Ile His Asn Asp Lys Asn Asp Leu Ile Pro Thr
         35                  40                  45

Gln Thr Ile Ile Arg Trp Gln Met Cys Ile Asp Tyr His Lys Leu Asn
     50                  55                  60

Asp Val Thr Lys Lys Asp His Phe Pro Leu Pro Phe Met Asp Gln Met
 65                  70                  75                  80

Leu Glu Arg Leu Ala Gly Gln Ala Phe Tyr Cys Phe Leu Asp Gly Tyr
                 85                  90                  95

Ser Gly Tyr Asn Gln Ile Ala Val His Leu Lys Asp Gln Glu Lys Thr
            100                 105                 110

Thr Ile Ile Cys Pro Phe Gly Val Phe Ala Tyr Arg Gln Met Ser Phe
        115                 120                 125

Glu Leu Cys Asn Ala Pro Thr Thr Phe Glx Arg Phe Met Met Ala Ile
    130                 135                 140

Phe Ala Asp Leu Val Glu Lys Cys Ile Glu Val Phe Met Asn Asp Phe
145                 150                 155                 160

Ser Ile Phe Gly Ser Ser Phe Tyr His Cys Leu Ser Asn Leu Glu Leu
                165                 170                 175

Val Leu Gln Arg Cys Ala Glu Thr Asn Leu Leu Met Asn Trp Glu Lys
            180                 185                 190

Cys His Phe Met Val Gln Glu Gly Ile Val Leu Gly His Lys Ile Ser
        195                 200                 205

Ser Arg Gly Leu Glu Val Asp Lys Ala Lys Ile Asp Val Ile Glu Lys
    210                 215                 220

Leu Pro Pro Pro Met Asn Val Lys Gly Ile Arg Ser Phe Leu Glu Tyr
225                 230                 235                 240

Val Gly Phe Tyr Arg Arg Phe Ile Lys Asp Phe Thr Lys Val
                245                 250
```

<210> SEQ ID NO 148
<211> LENGTH: 762
<212> TYPE: DNA
<213> ORGANISM: Glycine max

<400> SEQUENCE: 148

```
gtgcgtaagg aggttctcaa gcttttggag gttgggctca tatacctcat ctctgacagc      60
gcttgggtaa gcctagtaca ggtggctccc aagaaatgcg gaatgacagt ggtacaaaat     120
gagaggaatg acttgatacc aacacgaact gtcactggct agcggatgtg tatcgactac     180
tgcaagttga atgaagccac acggaaggac catttcccct tacctttcat ggatcagatg     240
ctggagaggc ttgcagggca ggcatactac tgtttcttgg atagatattc aggatacaac     300
caaatcgcgg tagaccccag agatcaggag aagatggcct tacatgccc ctttggcgtc      360
tttgcttaca gaaggatgtc attcaggtta tgtaacgcac cagccacatt tcagaggtgc     420
atgctggcca ttttttcaga catggtggag aagagcatcg aggtatttat ggatgaattc     480
tcgattttg acccttatt tgacagttgc ttaaggaact tagagatggt actacagagg        540
tgcgtataga ctaacttggt actaaattag gaaaaatgtc atttcatggt tcgagaggga     600
atagtgatgg ccacaatat ctcagctaga gggattgagg ttgatcagac aaagatagac       660
gtcattgaga agttgccacc accactgaat gttaaaggcg tcagaagttt cttagggcat     720
gcaggtttct acaggaggtt cataaaagac ttcacaaagg tt                        762
```

<210> SEQ ID NO 149
<211> LENGTH: 254
<212> TYPE: PRT
<213> ORGANISM: Glycine max

<400> SEQUENCE: 149

```
Val Arg Lys Glu Val Leu Lys Leu Leu Glu Val Gly Leu Ile Tyr Leu
  1               5                  10                  15

Ile Ser Asp Ser Ala Trp Val Ser Leu Val Gln Val Ala Pro Lys Lys
             20                  25                  30

Cys Gly Met Thr Val Val Gln Asn Glu Arg Asn Asp Leu Ile Pro Thr
         35                  40                  45

Arg Thr Val Thr Gly Glx Arg Met Cys Ile Asp Tyr Cys Lys Leu Asn
     50                  55                  60

Glu Ala Thr Arg Lys Asp His Phe Pro Leu Pro Phe Met Asp Gln Met
 65                  70                  75                  80

Leu Glu Arg Leu Ala Gly Gln Ala Tyr Tyr Cys Phe Leu Asp Arg Tyr
                 85                  90                  95

Ser Gly Tyr Asn Gln Ile Ala Val Asp Pro Arg Asp Gln Glu Lys Met
            100                 105                 110

Ala Phe Thr Cys Pro Phe Gly Val Phe Ala Tyr Arg Arg Met Ser Phe
        115                 120                 125

Arg Leu Cys Asn Ala Pro Ala Thr Phe Gln Arg Cys Met Leu Ala Ile
    130                 135                 140

Phe Ser Asp Met Val Glu Lys Ser Ile Glu Val Phe Met Asp Glu Phe
145                 150                 155                 160

Ser Ile Phe Gly Pro Leu Phe Asp Ser Cys Leu Arg Asn Leu Glu Met
                165                 170                 175

Val Leu Gln Arg Cys Val Glx Thr Asn Leu Val Leu Asn Glx Glu Lys
            180                 185                 190

Cys His Phe Met Val Arg Glu Gly Ile Val Met Gly His Asn Ile Ser
```

```
                    195                 200                 205
Ala Arg Gly Ile Glu Val Asp Gln Thr Lys Ile Asp Val Ile Glu Lys
    210                 215                 220

Leu Pro Pro Leu Asn Val Lys Gly Val Arg Ser Phe Leu Gly His
225                 230                 235                 240

Ala Gly Phe Tyr Arg Arg Phe Ile Lys Asp Phe Thr Lys Val
                245                 250

<210> SEQ ID NO 150
<211> LENGTH: 761
<212> TYPE: DNA
<213> ORGANISM: Glycine max

<400> SEQUENCE: 150
gtgcgtaagg aggtttttaa gttgctggaa gcaggtctta tttatcccat ttcggatagt      60
gcatgggtta gccctgtgca ggttgtcccc aagaaagaag gtaagacagt cattaaggat     120
gaaaaggatg agttgatatc cacaaggact atcaccgggt ggagaatgtg cattgactat     180
cagaagctga atgatgccac ccggaaggac cattatccac tcccttttcat ggaccaaatg    240 cttgaaagac ttgccgggca atcttattat tgttttctgg atggatattc tggttataat    300
cagattgatg tagatcccaa ggatcaagag aagactgctt tcacctaccc ttttggtgta    360
ttcgcctatc ggcgcatgcc ctttggtttg tgcaatgccc cagctacatt tcagaggtgt    420
atgatgacta ttttttctga tatggtggaa aaatgaattg aagttttcat ggacgatttc    480 tctattttg ggccatcttt tgaagggtgc ttatcaaatc ttgaaagagt attaaagaga     540
cgtgaagagt ccaaactagt tctcaattgg gagaaatgcc atttcatggt tcaagaagga    600
atagtgtggg gcataaaatt tcagtaagag ggatagaggg ggacaaggca agattgatg     660 taatagagaa actacctcct cccatgaatg tcaagggaat aagaagcttc ctaggacatg    720
cagggttcta caagcgattc atcaaagatt tcacaaaggt t                        761

<210> SEQ ID NO 151
<211> LENGTH: 254
<212> TYPE: PRT
<213> ORGANISM: Glycine max

<400> SEQUENCE: 151

Val Arg Lys Glu Val Phe Lys Leu Leu Glu Ala Gly Leu Ile Tyr Pro
 1               5                  10                  15

Ile Ser Asp Ser Ala Trp Val Ser Pro Val Gln Val Val Pro Lys Lys
            20                  25                  30

Glu Gly Lys Thr Val Ile Lys Asp Glu Lys Asp Glu Leu Ile Ser Thr
        35                  40                  45

Arg Thr Ile Thr Gly Trp Arg Met Cys Ile Asp Tyr Gln Lys Leu Asn
    50                  55                  60

Asp Ala Thr Arg Lys Asp His Tyr Pro Leu Pro Phe Met Asp Gln Met
65                  70                  75                  80

Leu Glu Arg Leu Ala Gly Gln Ser Tyr Tyr Cys Phe Leu Asp Gly Tyr
                85                  90                  95

Ser Gly Tyr Asn Gln Ile Asp Val Asp Pro Lys Asp Gln Glu Lys Thr
            100                 105                 110

Ala Phe Thr Tyr Pro Phe Gly Val Phe Ala Tyr Arg Arg Met Pro Phe
        115                 120                 125

Gly Leu Cys Asn Ala Pro Ala Thr Phe Gln Arg Cys Met Met Thr Ile
    130                 135                 140
```

```
Phe Ser Asp Met Val Glu Lys Glx Ile Glu Val Phe Met Asp Asp Phe
145                 150                 155                 160

Ser Ile Phe Gly Pro Ser Phe Glu Gly Cys Leu Ser Asn Leu Glu Arg
            165                 170                 175

Val Leu Lys Arg Arg Glu Ser Lys Leu Val Leu Asn Trp Glu Lys
        180                 185                 190

Cys His Phe Met Val Gln Glu Gly Ile Val Leu Gly His Lys Ile Ser
            195                 200                 205

Val Arg Gly Ile Glu Val Asp Lys Ala Lys Ile Asp Val Ile Glu Lys
        210                 215                 220

Leu Pro Pro Met Asn Val Lys Gly Ile Arg Ser Phe Leu Gly His
225                 230                 235                 240

Ala Gly Phe Tyr Lys Arg Phe Ile Lys Asp Phe Thr Lys Val
            245                 250
```

<210> SEQ ID NO 152
<211> LENGTH: 762
<212> TYPE: DNA
<213> ORGANISM: Glycine max

<400> SEQUENCE: 152

```
gtgcggaaag aggtattcaa gttactagag gcagggctca tctacccaat ttcagatagc    60
tcctgggtta gtccggttca agttgttcca aaaaaggag ggatgacagt ggtaaaaaat   120
gatagaaatg agctaattcc tacaagaaga gtcaccagat ggagaatgtg tattgattat   180
aggaagctca atgaagccac aagaaaagac cattacccac ttcccttcat ggatcaaatg   240
cttaagagac ttgcaaggca atccttctac cgtttcttgg acggatactc aggttacaat   300
cagattgcag tggatcctca ggatcaagaa aaaacagctt ttacatgtcc tttcagtgtt   360
tttgcttatc gccgcatgcc gttcggttta tgtaatgcct ctactacttt tcagagatgt   420
atgatggcaa ttttttgatga catggtagag aaatgtattg aagtctttat ggatgatttt   480
tcgttctttg gtgcatcttt tggaaattgc ttagcaaatt tagagaaagt gttcaacgt    540
tgtgaaaaat ctaatttggt gcttaactgg gaaaaatgtc actttatggt acaagaaggt   600
attgtgctag gacacaaaat ctctaaaaga ggaattgagg tggttaaaga aaaactagat   660
gttattgata aacttccacc cccagttaat gtaaaaggca tacacagttt tttgggtcat   720
gttggatttt atcggcgatt cataaaggac ttcaccaaag tt                     762
```

<210> SEQ ID NO 153
<211> LENGTH: 254
<212> TYPE: PRT
<213> ORGANISM: Glycine max

<400> SEQUENCE: 153

```
Val Arg Lys Glu Val Phe Lys Leu Leu Glu Ala Gly Leu Ile Tyr Pro
1               5                   10                  15

Ile Ser Asp Ser Ser Trp Val Ser Pro Val Gln Val Val Pro Lys Lys
            20                  25                  30

Gly Gly Met Thr Val Val Lys Asn Asp Arg Asn Glu Leu Ile Pro Thr
        35                  40                  45

Arg Arg Val Thr Arg Trp Arg Met Cys Ile Asp Tyr Arg Lys Leu Asn
    50                  55                  60

Glu Ala Thr Arg Lys Asp His Tyr Pro Leu Pro Phe Met Asp Gln Met
65                  70                  75                  80
```

```
Leu Lys Arg Leu Ala Arg Gln Ser Phe Tyr Arg Phe Leu Asp Gly Tyr
                85                  90                  95

Ser Gly Tyr Asn Gln Ile Ala Val Asp Pro Gln Asp Gln Glu Lys Thr
               100                 105                 110

Ala Phe Thr Cys Pro Phe Ser Val Phe Ala Tyr Arg Arg Met Pro Phe
               115                 120                 125

Gly Leu Cys Asn Ala Ser Thr Thr Phe Gln Arg Cys Met Met Ala Ile
               130                 135                 140

Phe Asp Asp Met Val Glu Lys Cys Ile Glu Val Phe Met Asp Asp Phe
145                 150                 155                 160

Ser Phe Phe Gly Ala Ser Phe Gly Asn Cys Leu Ala Asn Leu Glu Lys
               165                 170                 175

Val Leu Gln Arg Cys Glu Lys Ser Asn Leu Val Leu Asn Trp Glu Lys
               180                 185                 190

Cys His Phe Met Val Gln Glu Gly Ile Val Leu Gly His Lys Ile Ser
               195                 200                 205

Lys Arg Gly Ile Glu Val Val Lys Glu Lys Leu Asp Val Ile Asp Lys
               210                 215                 220

Leu Pro Pro Val Asn Val Lys Gly Ile His Ser Phe Leu Gly His
225                 230                 235                 240

Val Gly Phe Tyr Arg Arg Phe Ile Lys Asp Phe Thr Lys Val
               245                 250
```

<210> SEQ ID NO 154
<211> LENGTH: 761
<212> TYPE: DNA
<213> ORGANISM: Glycine max

<400> SEQUENCE: 154

```
gtgcgtaaag aagttttgaa gctgctagaa gcagacctta tttatcccat ttcggatagt      60
acatgggtta gccctgtgca agttgtcccc gagaaaggag gtatgacagt cattaagaat     120
gataaagatg agttgatatc cacaaggact gtcaccgggt gagaatgtgc attgactatc     180
ggaagctgaa tgatgccacc cagaaggacc attattcact cccttcatg accagatgc       240
ttgaaagact gccggacaa tcctattatt gttttctgaa tggatactct ggctataatc     300
agattgtggt agatcccaaa gatcaggaga aaactgcttt cacctgcctt tttggtgtat     360
ttgcatacaa gcgtatgcat tttggcttgt gtaatgctcc aactacgtgt cagaggtgta     420
tgatgactat tttttctggt atcgtggaaa aatgcattga acttttcatg gacgatttct     480
ctatttttgg gccatctttt gaaggctact atcaaacct tgaaagagta ttacagagat      540
gtgaagagtc taatctagtt ctcaattggg agaaatgcca tttcatggtt caagaaggaa     600
tagtgctggg gcataaaatt tcagtaagag ggatagaggt ggacaaggca agattgatg      660
taattgagaa actacctcct cccatgattg tcaagggaat aagaagcctc ctaggacatg     720
tagggttcta caggcgattc atcaaagact tcacaaaggt t                         761
```

<210> SEQ ID NO 155
<211> LENGTH: 254
<212> TYPE: PRT
<213> ORGANISM: Glycine max

<400> SEQUENCE: 155

```
Val Arg Lys Glu Val Leu Lys Leu Leu Glu Ala Asp Leu Ile Tyr Pro
1               5                   10                  15

Ile Ser Asp Ser Thr Trp Val Ser Pro Val Gln Val Val Pro Glu Lys
```

```
                    20                  25                  30
Gly Gly Met Thr Val Ile Lys Asn Asp Lys Asp Glu Leu Ile Ser Thr
        35                  40                  45
Arg Thr Val Thr Gly Trp Arg Met Cys Ile Asp Tyr Arg Lys Leu Asn
50                  55                  60
Asp Ala Thr Gln Lys Asp His Tyr Ser Leu Pro Phe Met Asp Gln Met
65                  70                  75                  80
Leu Glu Arg Leu Ala Gly Gln Ser Tyr Tyr Cys Phe Leu Asn Gly Tyr
                85                  90                  95
Ser Gly Tyr Asn Gln Ile Val Val Asp Pro Lys Asp Gln Glu Lys Thr
            100                 105                 110
Ala Phe Thr Cys Leu Phe Gly Val Phe Ala Tyr Lys Arg Met His Phe
        115                 120                 125
Gly Leu Cys Asn Ala Pro Thr Thr Cys Gln Arg Cys Met Met Thr Ile
        130                 135                 140
Phe Ser Gly Ile Val Glu Lys Cys Ile Glu Leu Phe Met Asp Asp Phe
145                 150                 155                 160
Ser Ile Phe Gly Pro Ser Phe Glu Gly Tyr Leu Ser Asn Leu Glu Arg
                165                 170                 175
Val Leu Gln Arg Cys Glu Glu Ser Asn Leu Val Leu Asn Trp Glu Lys
            180                 185                 190
Cys His Phe Met Val Gln Gly Ile Val Leu Gly His Lys Ile Ser
        195                 200                 205
Val Arg Gly Ile Glu Val Asp Lys Ala Lys Ile Asp Val Ile Glu Lys
        210                 215                 220
Leu Pro Pro Pro Met Ile Val Lys Gly Ile Arg Ser Leu Leu Gly His
225                 230                 235                 240
Val Gly Phe Tyr Arg Arg Phe Ile Lys Asp Phe Thr Lys Val
                245                 250
```

<210> SEQ ID NO 156
<211> LENGTH: 762
<212> TYPE: DNA
<213> ORGANISM: Glycine max

<400> SEQUENCE: 156

| | | | | | |
|---|---|---|---|---|---|
| gtgcgtaagg | aggtttttaa | gttgctggaa | gcaggtctta | tttatcccat | ttcggatagt | 60 |
| gcatgggtta | gccctgtgca | ggttgtcccc | aagaaagaag | gtaagacagt | cattaaggat | 120 |
| gaaaaagatg | agttgatatc | cacaaggact | atcaccgggt | ggagaatgtg | cattgactat | 180 |
| cagaagctga | atgatgccac | ccggaaggac | cattatccac | tccctttcat | ggaccaaatg | 240 |
| cttgaaagac | ttgccgggca | atcttattat | tgttttctgg | atggatattc | tggttataat | 300 |
| cagattgatg | tagatcccaa | ggatcaagag | aagactgctt | tcacctaccc | ttttggtgta | 360 |
| ttcgcctatc | ggcgcatgcc | ctttggtttg | tgcaatgccc | cagctacatt | tcagaggtgt | 420 |
| atgatgacta | ttttttctga | tatggtggaa | aaatgaattg | aagttttcat | ggacgatgtc | 480 |
| tctattttg | ggccatcttt | tgaagggtgc | ttatcaaatc | ttgaaagagt | attaaagaga | 540 |
| cgtgaagagt | ccaaactagt | tctcaattgg | gagaaatgcc | atttcatggt | tcaagaagga | 600 |
| atagtgttgg | ggcataaaat | ttcagtaaga | gggatagagg | tggacaaggc | aaagattgat | 660 |
| gtaatagaga | aactacctcc | tcccatgaat | gtcaagggaa | taagaagctt | cctaggacat | 720 |
| gcagggttct | acaagcgatt | catcaaagac | ttctcaaaag | tt | | 762 |

<210> SEQ ID NO 157
<211> LENGTH: 254
<212> TYPE: PRT
<213> ORGANISM: Glycine max

<400> SEQUENCE: 157

```
Val Arg Lys Glu Val Phe Lys Leu Leu Glu Ala Gly Leu Ile Tyr Pro
 1               5                  10                  15
Ile Ser Asp Ser Ala Trp Val Ser Pro Val Gln Val Pro Lys Lys
            20                  25                  30
Glu Gly Lys Thr Val Ile Lys Asp Glu Lys Asp Glu Leu Ile Ser Thr
        35                  40                  45
Arg Thr Ile Thr Gly Trp Arg Met Cys Ile Asp Tyr Gln Lys Leu Asn
    50                  55                  60
Asp Ala Thr Arg Lys Asp His Tyr Pro Leu Pro Phe Met Asp Gln Met
65                  70                  75                  80
Leu Glu Arg Leu Ala Gly Gln Ser Tyr Tyr Cys Phe Leu Asp Gly Tyr
                85                  90                  95
Ser Gly Tyr Asn Gln Ile Asp Val Asp Pro Lys Asp Gln Glu Lys Thr
            100                 105                 110
Ala Phe Thr Tyr Pro Phe Gly Val Phe Ala Tyr Arg Arg Met Pro Phe
        115                 120                 125
Gly Leu Cys Asn Ala Pro Ala Thr Phe Gln Arg Cys Met Met Thr Ile
    130                 135                 140
Phe Ser Asp Met Val Glu Lys Glx Ile Glu Val Phe Met Asp Asp Val
145                 150                 155                 160
Ser Ile Phe Gly Pro Ser Phe Glu Gly Cys Leu Ser Asn Leu Glu Arg
                165                 170                 175
Val Leu Lys Arg Arg Glu Glu Ser Lys Leu Val Leu Asn Trp Glu Lys
            180                 185                 190
Cys His Phe Met Val Gln Glu Gly Ile Val Leu Gly His Lys Ile Ser
        195                 200                 205
Val Arg Gly Ile Glu Val Asp Lys Ala Lys Ile Asp Val Ile Glu Lys
    210                 215                 220
Leu Pro Pro Pro Met Asn Val Lys Gly Ile Arg Ser Phe Leu Gly His
225                 230                 235                 240
Ala Gly Phe Tyr Lys Arg Phe Ile Lys Asp Phe Ser Lys Val
                245                 250
```

<210> SEQ ID NO 158
<211> LENGTH: 761
<212> TYPE: DNA
<213> ORGANISM: Glycine max

<400> SEQUENCE: 158

```
gtgcggaagg aggttcttaa gctcctggaa gcagggctca tctatcttat ctcagatagt    60
gttgggtgag tccagtgcat gtggttccca agaagggtgg gaagactgtg gtgagaaatg   120
gaaaaatga cctcattcta acccgaactg tcacaggatg gagaatgtgc atagattatc   180
gaagttgaa tgatgccatc aagaaggatc acttccctct accattcata gatcagatgc   240
tgagaggtt agcaagccag tctttctatt atttcttgga tgaatattct agatacaatc   300
gattgctat acatcccaag gaccaagaga agattgcatt tacatgccca tttggtgtct   360
tgcctatag aaggatgcca tttgaactat gcaatgctcc agctaccttt tagaggcata   420
gctagccat attcgctaac atggtggaga aatgcatcga agtgttcata gatgattttt   480
```

```
ggtgtttgg tccatccttt gtttgttgtt tgaccaattt agagctagtg ttgaagtact      540 tgaggagac aaatttagta ttgaattggg agaaatgtca tttcatggtc caagaaggaa      600 tatgttggg gcataaaatt tttgctagag gtattgaggt ggacaaggcc aaaattgatg      660 tattgaaaa gctgcctcca ccagtcaatg taaaaggcat caggagtttt cttggacaca      720 tggtttctt caggcgtttc atcaaggact tcacaaaagt t                         761
```

```
<210> SEQ ID NO 159
<211> LENGTH: 254
<212> TYPE: PRT
<213> ORGANISM: Glycine max

<400> SEQUENCE: 159
```

Val Arg Lys Glu Val Leu Lys Leu Leu Glu Ala Gly Leu Ile Tyr Leu
 1               5                  10                  15

Ile Ser Asp Ser Ala Trp Val Ser Pro Val His Val Pro Lys Lys
            20                  25                  30

Gly Gly Lys Thr Val Val Arg Asn Glu Lys Asn Asp Leu Ile Leu Thr
        35                  40                  45

Arg Thr Val Thr Gly Trp Arg Met Cys Ile Asp Tyr Arg Lys Leu Asn
     50                  55                  60

Asp Ala Ile Lys Lys Asp His Phe Pro Leu Pro Phe Ile Asp Gln Met
 65                  70                  75                  80

Leu Glu Arg Leu Ala Ser Gln Ser Phe Tyr Tyr Phe Leu Asp Glu Tyr
                 85                  90                  95

Ser Arg Tyr Asn Gln Ile Ala Ile His Pro Lys Asp Gln Glu Lys Ile
            100                 105                 110

Ala Phe Thr Cys Pro Phe Gly Val Phe Ala Tyr Arg Arg Met Pro Phe
        115                 120                 125

Glu Leu Cys Asn Ala Pro Ala Thr Phe Glx Arg His Met Leu Ala Ile
    130                 135                 140

Phe Ala Asn Met Val Glu Lys Cys Ile Glu Val Phe Ile Asp Asp Phe
145                 150                 155                 160

Ser Val Phe Gly Pro Ser Phe Val Cys Cys Leu Thr Asn Leu Glu Leu
                165                 170                 175

Val Leu Lys Tyr Cys Glu Glu Thr Asn Leu Val Leu Asn Trp Glu Lys
            180                 185                 190

Cys His Phe Met Val Gln Glu Gly Ile Met Leu Gly His Lys Ile Phe
        195                 200                 205

Ala Arg Gly Ile Glu Val Asp Lys Ala Lys Ile Asp Val Ile Glu Lys
    210                 215                 220

Leu Pro Pro Pro Val Asn Val Lys Gly Ile Arg Ser Phe Leu Gly His
225                 230                 235                 240

Thr Gly Phe Phe Arg Arg Phe Ile Lys Asp Phe Thr Lys Val
                245                 250

```
<210> SEQ ID NO 160
<211> LENGTH: 762
<212> TYPE: DNA
<213> ORGANISM: Pisum sativum

<400> SEQUENCE: 160
gtgcgcaagg aagtactcaa gttgttagat tcgggaatga tttacccat ttctgacagc      60 tcgtgggtaa gtccagtgca cgtggtacca agaaaggag gaacctcagt aattttaaat     120
```

-continued

```
gaaaagaatg aactgatccc aactcgcaca gtgacagggt ggcgagtatg catcgatcac    180
agaagactga acacagcaac aagaaaggat cattttcctc tccctttat tgatcaaatg     240 ttagaaagac ttgcaggtca tgagtattat tgctttctgg atggatattc gggatacaat    300
caaattgttg tagccccgga agatcaggaa aaaactgcat tacatgtcc ttatggtatt     360 ttcgcttaca acggatgcc atttgggcta tgcaatgccc cagctacttt tcagaggtgt     420
atgacatcta tattctccga catgcttgaa agtatatga aggtgtttat ggatgatttc     480
tctgtgtttg gttcttcttt tgataattgt ttagctaact tgtctcttgt tttgcaaaga    540
tgtcaggaaa ctaaccttgt tctcaattgg gagaaatgtc atttcatggt gcaggaagga    600
attgtgctag gacacaaaat tcccacaaa ggaattgaag tggacaaagc caaagtggag     660
gttatagcta acctcccacc tccggtgaat gaaaaaggga taaggagttt tttgggtcat    720
gcaggttttt atcgcaggtt catcaaagac ttcacaaagg tt                       762
```

```
<210> SEQ ID NO 161
<211> LENGTH: 254
<212> TYPE: PRT
<213> ORGANISM: Pisum sativum

<400> SEQUENCE: 161

Val Arg Lys Glu Val Leu Lys Leu Leu Asp Ser Gly Met Ile Tyr Pro
  1               5                  10                  15

Ile Ser Asp Ser Ser Trp Val Ser Pro Val His Val Pro Lys Lys
                 20                  25                  30

Gly Gly Thr Ser Val Ile Leu Asn Glu Lys Asn Glu Leu Ile Pro Thr
             35                  40                  45

Arg Thr Val Thr Gly Trp Arg Val Cys Ile Asp His Arg Arg Leu Asn
     50                  55                  60

Thr Ala Thr Arg Lys Asp His Phe Pro Leu Pro Phe Ile Asp Gln Met
 65                  70                  75                  80

Leu Glu Arg Leu Ala Gly His Glu Tyr Tyr Cys Phe Leu Asp Gly Tyr
                 85                  90                  95

Ser Gly Tyr Asn Gln Ile Val Val Ala Pro Glu Asp Gln Glu Lys Thr
            100                 105                 110

Ala Phe Thr Cys Pro Tyr Gly Ile Phe Ala Tyr Arg Arg Met Pro Phe
        115                 120                 125

Gly Leu Cys Asn Ala Pro Ala Thr Phe Gln Arg Cys Met Thr Ser Ile
    130                 135                 140

Phe Ser Asp Met Leu Glu Lys Tyr Met Lys Val Phe Met Asp Asp Phe
145                 150                 155                 160

Ser Val Phe Gly Ser Ser Phe Asp Asn Cys Leu Ala Asn Leu Ser Leu
                165                 170                 175

Val Leu Gln Arg Cys Gln Glu Thr Asn Leu Val Leu Asn Trp Glu Lys
            180                 185                 190

Cys His Phe Met Val Gln Glu Gly Ile Val Leu Gly His Lys Ile Ser
        195                 200                 205

His Lys Gly Ile Glu Val Asp Lys Ala Lys Val Glu Val Ile Ala Asn
    210                 215                 220

Leu Pro Pro Pro Val Asn Glu Lys Gly Ile Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 162
<211> LENGTH: 762
<212> TYPE: DNA
<213> ORGANISM: Pisum sativum

<400> SEQUENCE: 162

```
gtgcgtaagg aggtctttaa actattggat gcgggaatga tttacccgat ctcggatagt      60
ccgtgggtta gtcccgtgca cgtggttccg aagaagggtg gaatgaccgt aatccgtaat     120
gacaaagacg aattgatccc gactaaagtt gcaacggggt ggagaatatg tatagattat     180
agacagttga ataccgcgac tcgaaaggac cattttccac tcccatttat ggatcaaatg     240
cttgaaagac tatcgggcca acaatactat tgtttcttgg acggctactc cgggtacaac     300
caaattgcgg ttgacccggt tgatcatgag aagacggctt tcacgtgtcc gtttggagtg     360
ttcgcataca gaaaaatgcc ctttgggctg tgcaatgcac cggcgacttt ccaacgatgc     420
gtcctagcca ttttgccga tctaatagag aaaacaatgg acgtcttcat ggatgacttc     480
tcggtatttg gtgggacgtt tagtctatgc ttggcaaatt gaagacggt gttggaaagg     540
tgtgtgaaga ccaatttggt gctaaattgg gaaagtgtc acttcatggt gaccgagggg     600
atcgtgctag gccacaaagt ctctaaaagg gggcttgaag tggatagagc taaggttgaa     660
gtaattgaaa aattacccccc tccggtgaat gtgaaaggca tccgtagctt tttggggcac     720
gcggggtttt accggcgctt cattaaagac ttctcaaaag tt                        762
```

<210> SEQ ID NO 163
<211> LENGTH: 254
<212> TYPE: PRT
<213> ORGANISM: Pisum sativum

<400> SEQUENCE: 163

```
Val Arg Lys Glu Val Phe Lys Leu Leu Asp Ala Gly Met Ile Tyr Pro
  1               5                  10                  15

Ile Ser Asp Ser Pro Trp Val Ser Val His Val Val Pro Lys Lys
             20                  25                  30

Gly Gly Met Thr Val Ile Arg Asn Asp Lys Asp Glu Leu Ile Pro Thr
         35                  40                  45

Lys Val Ala Thr Gly Trp Arg Ile Cys Ile Asp Tyr Arg Gln Leu Asn
 50                  55                  60

Thr Ala Thr Arg Lys Asp His Phe Pro Leu Pro Phe Met Asp Gln Met
 65                  70                  75                  80

Leu Glu Arg Leu Ser Gly Gln Gln Tyr Tyr Cys Phe Leu Asp Gly Tyr
                 85                  90                  95

Ser Gly Tyr Asn Gln Ile Ala Val Asp Pro Val Asp His Glu Lys Thr
            100                 105                 110

Ala Phe Thr Cys Pro Phe Gly Val Phe Ala Tyr Arg Lys Met Pro Phe
        115                 120                 125

Gly Leu Cys Asn Ala Pro Ala Thr Phe Gln Arg Cys Val Leu Ala Ile
    130                 135                 140

Phe Ala Asp Leu Ile Glu Lys Thr Met Asp Val Phe Met Asp Asp Phe
145                 150                 155                 160

Ser Val Phe Gly Gly Thr Phe Ser Leu Cys Leu Ala Asn Leu Lys Thr
                165                 170                 175

Val Leu Glu Arg Cys Val Lys Thr Asn Leu Val Leu Asn Trp Glu Lys
            180                 185                 190

Cys His Phe Met Val Thr Glu Gly Ile Val Leu Gly His Lys Val Ser
        195                 200                 205
```

```
Lys Arg Gly Leu Glu Val Asp Arg Ala Lys Val Glu Val Ile Glu Lys
        210                 215                 220

Leu Pro Pro Val Asn Val Lys Gly Ile Arg Ser Phe Leu Gly His
225                 230                 235                 240

Ala Gly Phe Tyr Arg Arg Phe Ile Lys Asp Phe Ser Lys Val
                245                 250

<210> SEQ ID NO 164
<211> LENGTH: 762
<212> TYPE: DNA
<213> ORGANISM: Pisum sativum

<400> SEQUENCE: 164
gtgcggaagg aggtctttaa attgttggat gcggggatga tttacccgat ctcggatagt     60
ccatgggtta gtcctgtgca cgttgttccg aagaagggg ggattaccgt aatccggaat    120
gacaaggatg aattgatccc cactaaagtt gaaacgggt ggagaatgtg tattgattat    180
aggcggttga ataccgcgac tcgaaaagac cattttccac tcccatttat ggatcaaatg    240
ctcgaaagac tatcgggcca acaatattat tgttttttgg acggctactc cgggtacaac    300
caaattgcgg ttgacccggc cgatcatgag aagacggctt tcacatgtcc gtttggagtg    360
ttcgcatacc gaaaaatgcc ctttgggctg tgcaatgcac cggcgacctt ccaacgatgt    420
gtccaagcca tttttgtcga tctgatagag aaaacaatgg aagtcttcat ggatgacttc    480
tcggtatttg gtgggtcttt tagtctatgc ttggcgaact tgaaaacggt gttggagaga    540
tgtgtgaaga ccaatttggt gcttaattgg agaagtgtc acttcatggt gaccgagggg    600
atcgtgctag ccacaaagt ctctagaagg gggcttgaag tggatagagc taaggttgaa    660
gtgatagaaa aattacctcc tccggtgaat gtgaagggca tccgaagctt tttggggcac    720
gccgggttct accggcgctt cattaaagat ttcacaaagg tt                       762

<210> SEQ ID NO 165
<211> LENGTH: 254
<212> TYPE: PRT
<213> ORGANISM: Pisum sativum

<400> SEQUENCE: 165

Val Arg Lys Glu Val Phe Lys Leu Leu Asp Ala Gly Met Ile Tyr Pro
1               5                   10                  15

Ile Ser Asp Ser Pro Trp Val Ser Pro Val His Val Val Pro Lys Lys
                20                  25                  30

Gly Gly Ile Thr Val Ile Arg Asn Asp Lys Asp Glu Leu Ile Pro Thr
            35                  40                  45

Lys Val Glu Thr Gly Trp Arg Met Cys Ile Asp Tyr Arg Arg Leu Asn
    50                  55                  60

Thr Ala Thr Arg Lys Asp His Phe Pro Leu Pro Phe Met Asp Gln Met
65                  70                  75                  80

Leu Glu Arg Leu Ser Gly Gln Gln Tyr Tyr Cys Phe Leu Asp Gly Tyr
                85                  90                  95

Ser Gly Tyr Asn Gln Ile Ala Val Asp Pro Ala Asp His Glu Lys Thr
            100                 105                 110

Ala Phe Thr Cys Pro Phe Gly Val Phe Ala Tyr Arg Lys Met Pro Phe
        115                 120                 125

Gly Leu Cys Asn Ala Pro Ala Thr Phe Gln Arg Cys Val Gln Ala Ile
    130                 135                 140
```

```
Phe Val Asp Leu Ile Glu Lys Thr Met Glu Val Phe Met Asp Asp Phe
145                 150                 155                 160

Ser Val Phe Gly Gly Ser Phe Ser Leu Cys Leu Ala Asn Leu Lys Thr
                165                 170                 175

Val Leu Glu Arg Cys Val Lys Thr Asn Leu Val Leu Asn Trp Glu Lys
            180                 185                 190

Cys His Phe Met Val Thr Glu Gly Ile Val Leu Gly His Lys Val Ser
        195                 200                 205

Arg Arg Gly Leu Glu Val Asp Arg Ala Lys Val Glu Val Ile Glu Lys
    210                 215                 220

Leu Pro Pro Val Asn Val Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 166
<211> LENGTH: 23
<212> TYPE: DNA
<213> ORGANISM: Artificial Sequence
<220> FEATURE:
<223> OTHER INFORMATION: Synthetically generated
<220> FEATURE:
<221> NAME/KEY: misc_feature
<222> LOCATION: 6, 15, 16, 18
<223> OTHER INFORMATION: N= A, T, C or G

<400> SEQUENCE: 166
gtgcgnaarg argtnntnaa ryt                                        23

<210> SEQ ID NO 167
<211> LENGTH: 8
<212> TYPE: PRT
<213> ORGANISM: Consensus sequence

<400> SEQUENCE: 167

Val Arg Lys Glu Val Leu Lys Leu
1               5

<210> SEQ ID NO 168
<211> LENGTH: 24
<212> TYPE: DNA
<213> ORGANISM: Artificial Sequence
<220> FEATURE:
<223> OTHER INFORMATION: Synthetically generated
<220> FEATURE:
<221> NAME/KEY: misc_feature
<222> LOCATION: 7
<223> OTHER INFORMATION: n= A,T, C or G

<400> SEQUENCE: 168
aacyttngwr aartcyttda traa                                       24

<210> SEQ ID NO 169
<211> LENGTH: 8
<212> TYPE: PRT
<213> ORGANISM: Consensus sequence

<400> SEQUENCE: 169

Val Lys Ser Phe Asp Lys Ile Phe
1               5

<210> SEQ ID NO 170
<211> LENGTH: 20
<212> TYPE: DNA
```

```
<213> ORGANISM: Artificial Sequence
<220> FEATURE:
<223> OTHER INFORMATION: Primer

<400> SEQUENCE: 170
gggatccgca attagaatct                                                      20

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
cgaattcggt ccacttcgga                                                      20

<210> SEQ ID NO 172
<211> LENGTH: 24
<212> TYPE: DNA
<213> ORGANISM: Artificial Sequence
<220> FEATURE:
<223> OTHER INFORMATION: Primer

<400> SEQUENCE: 172
ccacaagatt ctaattgcgg attc                                                 24

<210> SEQ ID NO 173
<211> LENGTH: 24
<212> TYPE: DNA
<213> ORGANISM: Artificial Sequence
<220> FEATURE:
<223> OTHER INFORMATION: Primer

<400> SEQUENCE: 173
ccgaaatgga ccgaacccga catc                                                 24

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
tttccaggct cttgacgaga tttg                                                 24

<210> SEQ ID NO 175
<211> LENGTH: 22
<212> TYPE: DNA
<213> ORGANISM: Artificial Sequence
<220> FEATURE:
<223> OTHER INFORMATION: Primer

<400> SEQUENCE: 175
cgactcgagc tccatagcga tg                                                   22

<210> SEQ ID NO 176
<211> LENGTH: 24
<212> TYPE: DNA
<213> ORGANISM: Artificial Sequence
<220> FEATURE:
<223> OTHER INFORMATION: Primer

<400> SEQUENCE: 176
cggattgggc cgaaatggac cgaa                                                 24
```

<210> SEQ ID NO 177
<211> LENGTH: 18
<212> TYPE: DNA
<213> ORGANISM: Arabidopsis thaliana

<400> SEQUENCE: 177
gaggacttgg ggggcaaa                                                    18

<210> SEQ ID NO 178
<211> LENGTH: 13
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 2, 3, 5, 6, 7, 9, 10, 11, 12
<223> OTHER INFORMATION: Xaa=any amino acid

<400> SEQUENCE: 178

Cys Xaa Xaa Cys Xaa Xaa Xaa His Xaa Xaa Xaa Xaa Cys
 1               5                  10

<210> SEQ ID NO 179
<211> LENGTH: 6
<212> TYPE: PRT
<213> ORGANISM: Artificial Sequence
<220> FEATURE:
<223> OTHER INFORMATION: Consensus

<400> SEQUENCE: 179

Leu Ile Glu Leu Gly Ala
 1               5

<210> SEQ ID NO 180
<211> LENGTH: 4
<212> TYPE: PRT
<213> ORGANISM: Artificial Sequence
<220> FEATURE:
<223> OTHER INFORMATION: Consensus

<400> SEQUENCE: 180

Lys Thr Ala Phe
 1

<210> SEQ ID NO 181
<211> LENGTH: 8
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 2
<223> OTHER INFORMATION: Xaa= Pro or Ser

<400> SEQUENCE: 181

Met Xaa Phe Gly Leu Cys Asn Ala
 1               5

<210> SEQ ID NO 182
<211> LENGTH: 10
<212> TYPE: PRT
<213> ORGANISM: Artificial Sequence
<220> FEATURE:
<223> OTHER INFORMATION: Consensus
<220> FEATURE:

```
<221> NAME/KEY: VARIANT
<222> LOCATION: 1
<223> OTHER INFORMATION: Xaa= Val, Ile or Met
<220> FEATURE:
<221> NAME/KEY: VARIANT
<222> LOCATION: 9
<223> OTHER INFORMATION: Xaa= Ser or Trp
<220> FEATURE:
<221> NAME/KEY: VARIANT
<222> LOCATION: 10
<223> OTHER INFORMATION: Xaa= Val or Ile

<400> SEQUENCE: 182

Xaa Glu Val Phe Met Asp Asp Phe Xaa Xaa
 1               5                  10

<210> SEQ ID NO 183
<211> LENGTH: 19
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 12
<223> OTHER INFORMATION: Xaa= Ile or Val

<400> SEQUENCE: 183

Phe Glu Leu Met Cys Asp Ala Ser Asp Tyr Ala Xaa Gly Ala Val Leu
 1               5                  10                  15

Gly Gln Arg

<210> SEQ ID NO 184
<211> LENGTH: 27
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 4
<223> OTHER INFORMATION: Xaa=Thr or Ile
<220> FEATURE:
<221> NAME/KEY: VARIANT
<222> LOCATION: 8
<223> OTHER INFORMATION: Xaa=Leu or Met
<220> FEATURE:
<221> NAME/KEY: VARIANT
<222> LOCATION: 13
<223> OTHER INFORMATION: Xaa=Phe or Tyr
<220> FEATURE:
<221> NAME/KEY: VARIANT
<222> LOCATION: 15
<223> OTHER INFORMATION: Leu or Phe
<220> FEATURE:
<221> NAME/KEY: VARIANT
<222> LOCATION: 19
<223> OTHER INFORMATION: Xaa=Arg or Lys
<220> FEATURE:
<221> NAME/KEY: VARIANT
<222> LOCATION: 23
<223> OTHER INFORMATION: Xaa=Ile or Val
<220> FEATURE:
<221> NAME/KEY: VARIANT
<222> LOCATION: 26
<223> OTHER INFORMATION: Xaa=Arg or Lys

<400> SEQUENCE: 184

Tyr Ala Thr Xaa Glu Lys Glu Xaa Leu Ala Ile Val Xaa Ala Xaa Glu
 1               5                  10                  15

Lys Phe Xaa Ser Tyr Leu Xaa Gly Ser Xaa Val
             20                  25
```

```
<210> SEQ ID NO 185
<211> LENGTH: 46
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 4, 6, 7, 11-40, 43
<223> OTHER INFORMATION: Xaa=any amino acids

<400> SEQUENCE: 185

His Cys His Xaa Ser Xaa Xaa Gly Gly His Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Asp Xaa Cys Gln Arg
        35                  40                  45

<210> SEQ ID NO 186
<211> LENGTH: 8
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 6
<223> OTHER INFORMATION: Xaa=Ile, Val, or Met

<400> SEQUENCE: 186

Trp Gly Ile Asp Phe Xaa Gly Pro
 1               5

<210> SEQ ID NO 187
<211> LENGTH: 11
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 7, 10
<223> OTHER INFORMATION: Xaa=Ala or Val

<400> SEQUENCE: 187

Phe Tyr His Pro Gln Thr Xaa Gly Gln Xaa Glu
 1               5                  10

<210> SEQ ID NO 188
<211> LENGTH: 13
<212> TYPE: DNA
<213> ORGANISM: Artificial Sequence
<220> FEATURE:
<223> OTHER INFORMATION: Consensus
<220> FEATURE:
<221> NAME/KEY: misc_feature
<222> LOCATION: 11, 12
<223> OTHER INFORMATION: n=any nucleotide

<400> SEQUENCE: 188
atttggggra nnt                                                          13

<210> SEQ ID NO 189
<211> LENGTH: 9
<212> TYPE: PRT
<213> ORGANISM: Artificial Sequence
```

```
<220> FEATURE:
<223> OTHER INFORMATION: Consensus
<220> FEATURE:
<221> NAME/KEY: VARIANT
<222> LOCATION: 5, 8
<223> OTHER INFORMATION: Xaa=Arg or Lys

<400> SEQUENCE: 189

Gln Met Ala Ser Xaa Lys Arg Xaa Ala
  1               5

<210> SEQ ID NO 190
<211> LENGTH: 6
<212> TYPE: PRT
<213> ORGANISM: Pisum sativum

<400> SEQUENCE: 190

Ala Ser Lys Lys Arg Lys
  1               5

<210> SEQ ID NO 191
<211> LENGTH: 11
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 2, 3, 11
<223> OTHER INFORMATION: Xaa=Val or Ile
<220> FEATURE:
<221> NAME/KEY: VARIANT
<222> LOCATION: 4, 5, 6, 7, 8
<223> OTHER INFORMATION: Xaa=any amino acid
<220> FEATURE:
<221> NAME/KEY: VARIANT
<222> LOCATION: 9
<223> OTHER INFORMATION: Xaa=Asp or Glu

<400> SEQUENCE: 191

Thr Xaa Xaa Xaa Xaa Xaa Xaa Xaa Xaa Leu Xaa
  1               5                  10

<210> SEQ ID NO 192
<211> LENGTH: 4
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 1, 2
<223> OTHER INFORMATION: Xaa=Arg or Lys

<400> SEQUENCE: 192

Xaa Xaa Asp His
  1

<210> SEQ ID NO 193
<211> LENGTH: 5
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 3
<223> OTHER INFORMATION: Xaa=Asp or Glu

<400> SEQUENCE: 193
```

```
Met Leu Xaa Arg Leu
  1               5

<210> SEQ ID NO 194
<211> LENGTH: 7
<212> TYPE: PRT
<213> ORGANISM: Artificial Sequence
<220> FEATURE:
<223> OTHER INFORMATION: Consensus

<400> SEQUENCE: 194

Cys Phe Leu Asp Gly Tyr Ser
  1               5

<210> SEQ ID NO 195
<211> LENGTH: 4
<212> TYPE: PRT
<213> ORGANISM: Artificial Sequence
<220> FEATURE:
<223> OTHER INFORMATION: Consensus

<400> SEQUENCE: 195

Phe Thr Cys Pro
  1

<210> SEQ ID NO 196
<211> LENGTH: 7
<212> TYPE: PRT
<213> ORGANISM: Artificial Sequence
<220> FEATURE:
<223> OTHER INFORMATION: Consensus

<400> SEQUENCE: 196

Phe Gly Leu Cys Asn Ala Pro
  1               5

<210> SEQ ID NO 197
<211> LENGTH: 5
<212> TYPE: PRT
<213> ORGANISM: Artificial Sequence
<220> FEATURE:
<223> OTHER INFORMATION: Consensus

<400> SEQUENCE: 197

Phe Met Asp Asp Phe
  1               5

<210> SEQ ID NO 198
<211> LENGTH: 12
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 2, 12
<223> OTHER INFORMATION: Xaa=Val or Ile

<400> SEQUENCE: 198

Leu Xaa Leu Asn Trp Glu Lys Cys His Phe Met Xaa
  1               5                  10

<210> SEQ ID NO 199
<211> LENGTH: 10
<212> TYPE: PRT
<213> ORGANISM: Artificial Sequence
<220> FEATURE:
<223> OTHER INFORMATION: Consensus
```

```
<220> FEATURE:
<221> NAME/KEY: VARIANT
<222> LOCATION: 2
<223> OTHER INFORMATION: Xaa=Val or Ile

<400> SEQUENCE: 199

Leu Xaa Leu Asn Trp Glu Lys Cys His Phe
 1               5                   10

<210> SEQ ID NO 200
<211> LENGTH: 6
<212> TYPE: PRT
<213> ORGANISM: Artificial Sequence
<220> FEATURE:
<223> OTHER INFORMATION: Consensus
<220> FEATURE:
<221> NAME/KEY: VARIANT
<222> LOCATION: 2
<223> OTHER INFORMATION: Xaa=Leu or Ile

<400> SEQUENCE: 200

Gly Xaa Val Leu Gly His
 1               5
```